(12) United States Patent
Flores et al.

(10) Patent No.: US 7,919,493 B2
(45) Date of Patent: Apr. 5, 2011

(54) ANITITUMORAL ECTEINASCIDIN DERIVATIVES

(75) Inventors: Maria Flores, Madrid (ES); Andres Francesh, Madrid (ES); Pilar Gallego, Madrid (ES); Jose Luis Chicharro, Madrid (ES); Maria Zarzuelo, Madrid (ES); Carolina Fernandez, Madrid (ES); Ignacio Manzanares, Madrid (ES)

(73) Assignee: Pharma Mar, S.A. (ES)

( * ) Notice: Subject to any disclaimer, the term of this patent is extended or adjusted under 35 U.S.C. 154(b) by 193 days.

(21) Appl. No.: 11/733,606

(22) Filed: Apr. 10, 2007
(Under 37 CFR 1.47)

(65) Prior Publication Data

US 2008/0146580 A1    Jun. 19, 2008

Related U.S. Application Data

(63) Continuation-in-part of application No. 10/240,963, filed as application No. PCT/GB01/01667 on Apr. 12, 2001, now Pat. No. 7,202,361.

(51) Int. Cl.
C07D 241/36 (2006.01)
A61K 31/495 (2006.01)
A01N 43/60 (2006.01)

(52) U.S. Cl. .................................. 514/250; 544/338
(58) Field of Classification Search .................. 544/338; 514/250
See application file for complete search history.

(56) References Cited

U.S. PATENT DOCUMENTS

| | | | |
|---|---|---|---|
| 5,089,273 A | 2/1992 | Rinehart et al. | |
| 5,149,804 A | 9/1992 | Rinehart et al. | |
| 5,256,663 A | 10/1993 | Rinehart et al. | |
| 5,478,932 A | 12/1995 | Rinehart et al. | |
| 5,654,426 A | 8/1997 | Rinehart et al. | |
| 5,721,362 A | 2/1998 | Corey et al. | |
| 5,985,876 A | 11/1999 | Rinehart et al. | |
| 6,124,292 A | 9/2000 | Corey | |
| 6,124,293 A | 9/2000 | Rinehart | |
| 6,316,214 B1 | 11/2001 | Rinehart | |
| 6,348,467 B1 | 2/2002 | Corey | |
| 6,544,560 B1 | 4/2003 | Bullent | |
| 6,569,859 B1 | 5/2003 | Corey | |
| 6,686,470 B2 | 2/2004 | Danishefsky et al. | |
| 6,712,023 B2 | 3/2004 | Targotay | |
| 6,815,544 B2 | 11/2004 | Corey | |
| 6,867,334 B2 | 3/2005 | Rinehart | |
| 7,115,743 B2 | 10/2006 | Rinehart | |
| 7,202,361 B2 * | 4/2007 | Flores et al. .................. | 544/338 |
| 7,241,892 B1 | 7/2007 | Cuevas | |
| 7,247,629 B2 | 7/2007 | Manzanares | |
| 7,410,969 B2 | 8/2008 | Manzanares | |
| 7,420,051 B2 | 9/2008 | Francesch | |
| 7,524,956 B2 | 4/2009 | Cuevas | |
| 2003/0216397 A1 | 11/2003 | Flores | |
| 2004/0002602 A1 | 1/2004 | Francesch | |
| 2004/0019056 A1 | 1/2004 | Manzanares et al. | |
| 2008/0234279 A1 | 9/2008 | Rinehart | |

FOREIGN PATENT DOCUMENTS

| | | |
|---|---|---|
| EP | 0 309 477 B1 | 11/1991 |
| JP | 59-225189 | 12/1984 |
| JP | 60-84288 | 5/1985 |
| WO | WO 87/07610 | 12/1987 |
| WO | WO 92/09607 | 6/1992 |
| WO | WO 98/12198 | 3/1998 |
| WO | WO 98/46080 | 10/1998 |
| WO | WO 99/58125 | 11/1999 |
| WO | WO 00/18233 | 4/2000 |
| WO | WO 00/69862 | 11/2000 |
| WO | WO 01/77115 | 10/2001 |
| WO | WO 01/87894 | 11/2001 |
| WO | WO 01/87895 | 11/2001 |
| WO | WO 2009/050303 | 4/2009 |
| WO | WO 2009/138509 | 11/2009 |
| WO | WO 2009/140675 | 11/2009 |

OTHER PUBLICATIONS

Pinedo et al., "Translational Research . . . ", TheOncologist 2000,, 5 (suppl1): 1-2 (www.The Oncologist.com).*
McMahon, Gerald, "VEGF Receptor Signaling in Tumor Angiogenesis", the Oncologist 2000; 5(suppl 1): 3-10 (www.TheOncologist.com).*
Pinedo et al., "Translational Research . . . ", The Oncologist 2000,, 5 (suppl1): 1-2 (www.The Oncologist .com).*
McMahon, Gerald, "VEGF Receptor Signaling in Tumor Angiogenesis", The Oncologist 2000; 5(suppl 1): 3-10 (www.TheOncologist.com).*
Pommier, Yves et al., "DNA Sequence- and Structure-Selective Alkylation of Guanine N2 in the DNA Minor Groove by Ecteinascidin 743, a Potent Antitumor Compound from the Caribbean Tunicate Ecteinascidia Turbinata", *Biochemistry*, vol. 35, pp. 13303-13309 (1996).

(Continued)

*Primary Examiner* — Paul V. Ward
(74) *Attorney, Agent, or Firm* — Kenneth H. Sonnenfeld; King & Spalding LLP

(57) ABSTRACT

This invention relates to antitumoral ecteinascidin derivatives that contain a fused ecteinascidin five ring system with a 1,4-bridge having the structure of formula (VIa) or (VIb) as described herein and compounds in which the —$NH_2$ or —OH of the 1,4-bridge is derivatized, and related pharmaceutical compositions and methods. Such ecteinascidin derivatives include, but are not limited to, those compounds having formula (XVIIb):

(XVIIb)

in which $R^1$ and $R^4$ together form a group of formula (VIa) or (VIb) as described herein, and $R^5$, $R^7$, $R^8$, $R^{14a}$, $R^{14b}$, $R^{15}$, and $R^{21}$ are as defined herein.

47 Claims, No Drawings

OTHER PUBLICATIONS

Pretsch et al., *Tables of Spectral Data for Structure Determination of Organic Compounds*, pp. H125 (1983).
Reid, Joel M. et al., "Preclinical pharmacology of ecteinascidin 729, a marine natural product with potent antitumor activity", *Cancer Chemotherapy and Pharmacology*, vol. 38, No. 4, pp. 329-334 (1996).
Remers, William A., "Saframycins, Renieramycins, and Safracins", *The Chemistry of Antitumor Antibiotics*, vol. 2, pp. 93-119 (1988).
Rinehart et al., "Novel Bioactive Natural Products from Marine Organisms", *Topics in Pharmaceutical Sciences 1989*, pp. 613-626, D.D. Breimer, D.J.A. Cromwelin, K.K. Midha, Eds., Amsterdam Medical Press B.V. Noordwijk, The Netherlands (1989).
Rinehart, Kenneth L. et al., "Applications of High-Resolution Tandem FAB Mass Spectrometry", *Biological Mass Spectrometry*, eds. Burlingame et al., Elsevier Amsterdam, pp. 233-258 (1990).
Rinehart, Kenneth L. et al., "Biologically active natural products", *Pure and Applied Chemistry*, vol. 62, No. 7, pp. 1277-1280 (1990).
Rinehart, Kenneth L. et al., "Bioactive Compounds from Aquatic and Terrestrial Sources", *Journal of Natural Products*, vol. 53, No. 4, pp. 771-792 (1990).
Rinehart, Kenneth L., "Antitumor Compounds from Tunicates", *Medicinal Research Reviews*, vol. 20, No. 1, pp. 1-27 (2000).
Rinehart, Kenneth L. et al., "Ecteinascidins 729, 743, 759A, 759B, and 770: Potent Antitumor Agents from the Caribbean Tunicate Exteinascidia Turbinata", *The Journal of Organic Chemistry*, vol. 55, No. 15, pp. 4512-4515 (1990).
Saito, Naoki et al., "Synthesis of Saframycins. 3. Preparation of a Key Tricyclic Lactam Intermediate to Saframycin A", *The Journal of Organic Chemistry*, vol. 54, No. 22, pp. 5391-5395 (1989).
Sakai, Ryuichi et al., "Ecteinascidins: Putative Biosynthetic Precursors and Absolute Stereochemistry", *Journal of the American Chemical Society*, vol. 118, No. 38, pp. 9017-9023 (1996).
Sakai, Ryuichi et al., "Additional antitumor ecteinascidins from a Caribbean tunicate: Crystal structures and activities in vivo", *Proceedings of the National Academy of Sciences*, vol. 89, No. 23, pp. 11456-11460 (1992).
Shamma, Maurice et al., *Carbon-13 NMR Shift Assignments of Amines and Alkaloids*, pp. 206 (1979).
Still, W. Clark et al., "Rapid Chromatographic Technique for Preparative Separations with Moderate Resolution", *Journal of Organic Chemistry*, vol. 43, No. 14, pp. 2923-2925 (1978).
Takahaski, Katsuhiro, "New Antibiotics, Saframycins A, B, C, D and E", *The Journal of Antibiotics*, vol. XXX, No. 11, pp. 1015-1018 (1977).
Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", *The Journal of Antibiotics*, vol. XXXV, No. 2, pp. 196-202 (1982).
Trowitzsch-Kienast, Wolfram et al., "Isolierung und Strukturaufklarung der Saframycine Mx 1 und Mx 2, neue antitumoraktive Antibiotika aus Myxococcus xanthus", *Liebigs Ann. Chem.*, vol. XXXV, pp. 475-481 (1988).
Valoti et al., "Ecteinascidin-743, a New Marine Natural Product with Potent Antitumor Activity on Human Ovarian Carcinoma Xenografts", Clin. Cancer Res. 4 (8): 1977-83, 1998.
Witten, Jane L. et al., "Structures of Two Cockroach Neuropeptides Assigned by Fast Atom bombardment Mass Spectrometry", *Biochemical and Biophysical Research Communications*, vol. 124, No. 2, pp. 350-358 (1984).
Wright, Amy E. et al., "Antitumor Tetrahydroisoquinoline Alkaloids from the Colonial Ascidian Ecteinascidia Turbinata", *The Journal of Organic Chemistry*, vol. 55, No. 15, pp. 4508-4512 (1990).
Yazawa, Katsukiyo et al., "Bioconversions of Saframycin a Specific to some Genera of Actinomycetes", *The Journal of Antibiotics*, vol. XXXV, No. 7, pp. 915-917 (1982).
Yazawa, Katsukiyo et al., "Isolation and Structural Elucidation of New Saframycins Y3, Yd-1, Yd-2, Ad-1, Y2b and Y2b-d", *The Journal of Antibiotics*, vol. XXXIX, No. 12, pp. 1639-1650 (1986).
Zmijewski, Milton J., Jr. et al., "The in vitro Interaction of Naphthyridinomycin with Deoxyribonucleic Acids", *Chemico-Biological Interactions*, vol. 52, No. 3, pp. 361-375 (1985).

Suggitt et al., "50 Years of Preclinical Anticancer Drug Screening: Empirical to Target-Driven Approaches," Clinical Cancer Research, vol. 11, Feb. 1, 2005, pp. 971-981.
U.S. Appl. No. 10/485,536, filed May 18, 2005, Pilar Gallego.
U.S. Appl. No. 10/503,106, filed Jun. 8, 2005, Valentin Martinez Barrasa.
U.S. Appl. No. 12/273,919, filed Nov. 19, 2008, Valentin Martinez Barrasa.
U.S. Appl. No. 11/769,873, filed Jun. 28, 2007, Esteban Cvitkovich.
U.S. Appl. No. 10/738,973, filed Dec. 17, 2003, Elias J. Corey.
U.S. Appl. No. 10/484,060, filed Mar. 2, 2005, Valentin Martinez Barrasa.
U.S. Appl. No. 11/645,356, filed Dec. 22, 2006, Ignacio Manzanares.
U.S. Appl. No. 12/091,540, filed Jun. 4, 2008, Pilar Calvo Salve.
Arai, T. et al., "The Structure of a Novel Antitumor Antibiotic, Saframycin A", *Experientia*, vol. 36, pp. 1025-1027 (1980).
Arai, Tadashi et al., "Increased Production of Saframycin A and Isolation of Saframycin S", *The Journal of Antibiotics*, vol. XXXIII, No. 9, pp. 951-960 (1980).
Arai, Tadashi et al., "Directed Biosynthesis of New Saframycin Derivatives with Resting Cells of *Streptomyces lavendulae*", *Antimicrobial Agents and Chemotherapy*, vol. 28, No. 1, pp. 5-11 (1985).
Arai, Tadashi et al., "Isoquinolineinones from Actinomycetes and Sponges", *The Alkaloids Chemistry and Pharmacology*, vol. XXI, pp. 56-100 (1983).
Arai, Tadashi et al., "New Antibiotics, Safraycins A, B, C, D and E", *The Journal of Antibiotics*, vol. XXX, No. 11, pp. 1015-1018 (1977).
Asaoka, Takemitsu et al., "A New Saframycin, Saframycin R", *The Journal of Antibiotics*, vol. XXXV, No. 12, pp. 1708-1710 (1982).
Barton, Derek H.R. et al, "Synthesis and Properties of a Series of Sterically Hindered Guanidine Bases[1]", *Journal of the Chemical Society Perkin Transactions I*, No. 9, pp. 2085-2090 (1982).
Brown, "NCI's Anticancer Drug Screening Program May Not Be Selecting for Clinically Active Compounds", Oncol. Res., 1997; 9 (5), pp. 213-215.
Cable, Karl M. et al., "The Biosynthesis of Tuberin from Tyrosine and Glycine; Observations on the Stereochemistry Associated with the Conversion of Glycine through Methylenetetrahydrofolate into Methenyltetrahydrofolate", *Journal of the Chemical Society Perkins Transactions I*, No. 7, pp. 1593-1598 (1987).
Calabresi et al., "Chemotherapy of Neoplastic Diseases", Goodman & Gillman's the Pharmacological Basis of Therapeutics, 9th ed. New York: McGraw-Hill, 1996, pp. 1225-1229.
Cecil Textbook of Medicine (Bennet, J.C. and Plum, F., eds.) 20th Edition, vol. 1, pp. 1004-1010, 1996.
Cooper, Raymond et al., "Structure of the Quinone Antibiotic EM5519 and the Behavior of Quinones in Fast Atom Bombardment Mass Spectrometry", *The Journal of Antibiotics*, vol. XXXVIII, No. 1, pp. 24-30 (1985).
Corey, E.J. et al., "Enantioselective Total Synthesis of Ecteinascidin 743", *Journal of the American Chemical Society*, vol. 118, No. 38, pp. 9202-9203 (1996).
Cuevas et al., "Synthesis of ecteinascidin ET-743 and phthalascidin Pt-650 from cyanosafracin B", Organic Letters, Aug. 10, 2000;2(16):2545-8.
Draetta et al., "Annual Reports in Medicinal Chemistry", vol. 31, 1996, Academic Press, pp. 241-246.
Eckhardt, S.G. et al. "Activity of ecteinascidin, a novel marine cytotoxic, against primary human tumor colony-forming units", *Proceedings of the American Association for Cancer Research*, vol. 37, #2791, pp. 409 (1996).
Faircloth, G. et al., "Ecteinascidin-743 (ET743): in vitro (IVT) and in vivo (INV) Results in Tumor Models", *The European Journal of Cancer*, vol. 32A, Supp. 1, #24 O, pp. S5 (1996).
Flam, Faye, "Chemical Prospectors Scour the Seas for Promising Drugs", *Science*, vol. 266, pp. 1324-1325 (1994).
Frincke, James M. et al., "Antimicrobial Metabolites of the Sponge Reniera sp.", *Journal of the American Chemical Society*, vol. 104, pp. 265-269 (1982).
Fukuyama, Tohru et al., "Total Synthesis of (±)-Saframycin A", *Journal of American Chemical Society*, vol. 112, pp. 3712-3713 (1990).

Fukuyama, Tohru et al., "Stereocontrolled Total Synthesis of (±)-Saframycin B", *Journal of American Chemical Society*, vol. 104, pp. 4957-4958 (1982).

Garcia-Rocha, M. et al., "Characterisation of antimitotic products from marine organisms that disorganize the microtubule network: ecteinascidin 743, isohomohalichondrin-B and LL-15", *British Journal of Cancer*, vol. 73, pp. 875-883 (1996).

Goldwasser, F, et al. "Characterization of ecteinascidin 743-induced DNA damages in cells", *Proceedings of the American Association for Cancer Research*, vol. 39, #4066, pp. 598 (1998).

Guan, Yue et al., "Molecular and Crystal Structures of Ecteinascidins: Potent Antitumor Compounds from the Caribbean Tunicate Ecteinascidia Turbinata", *Journal of Biomolecular Structure & Dynamics*, vol. 10, No. 5, pp. 793-818 (1993).

Gulavita, Nanda K., et al., "Antimicrobial Constituents of a Sponge-Nudibranch Pair from Sri Lanka", *Bioactive Compounds from Marine Organisms*, Oxford & IBH Publishing Co. Pvt. Ltd., pp. 229-233 (1991).

He, Hai-yin et al., "Renieramycins E and F from the Sponge Reniera sp.: Reassignment of the Stereochemistry of the Renieramycins", *The Journal of Organic Chemistry*, vol. 54, No. 24, pp. 5822-5824 (1989).

Hendriks, H.R. et al., "High antitumor activity of ET743 in human tumor xenograft models", *Proceedings of the American Association for Cancer Research*, vol. 37, #2653, pp. 389 (1996).

Ikeda, Yoshifumi et al., "Safracins, New Antitumor Antibiotics I. Producing Organism, Fermentation and Isolation", *The Journal of Antibiotics*, vol. XXXVI, No. 10, pp. 1279-1283 (1983).

Ikeda, Yoshifumi et al., "Safracins, New Antitumor Antibiotics I. Producing Organism, Fermentation and Isolation", *The Journal of Antibiotics*, vol. XXXVI, No. 10, pp. 1284-1289 (1983).

Ito, Yoichiro, "High-Speed Countercurrent Chromatography", *Critical Reviews in Analytical Chemistry*, vol. 17, No. 1, pp. 65-143 (1986).

Kania, "The First Enantioselective Total Synthesis of Dolabellatrienone and Ecteinascidin 743", Harvard University, Sep. 1997, pp. 1-225.

Koenig, Karl E., "The Applicability of Asymmetric Homogeneous Catalytic Hodrogenation", *Asymmetric Synthesis*, Ed. Morrison, Academic Press, Inc., Orlando, FL, vol. 5, pp. 71 (1985).

Kofron, William G. et al., "A Convenient Method for Estimation of Alkyllithium Concentrations", *The Journal of Organic Chemistry*, vol. 41, No. 10, pp. 1879-1880 (1976).

Kubo, Akinori et al., "Structure of Saframycin D, A New Dimeric Isoquinolinequinone Antibiotic", *Chem. Pharm. Bull.*, vol. 35, No. 1, pp. 440-442 (1987).

Kuffel, M.J. et al., "Cytochrome P450 catalyzed metabolism of Ecteinascidin 743 by rat and human liver microsomes", *Proceedings of the American Association for Cancer Research*, vol. 38, #4003, pp. 596 (1997).

Lichter, W. et al., "Biological Activities Exerted by Extracts of Ecteinascidia Turbinata", *Food and Drugs from the Sea Proceedings*, pp. 117-127 (1972).

Lown, J. William et al., "Structure and Confirmation of Saframycin R Determined by High Field $^1$H and $^{13}$C NMR and its Interactions with DNA in Soloution", *The Journal of Antibiotics*, vol. XXXVI, No. 9, pp. 1184-1194 (1983).

Lown, J. William et al., "Molecular Mechanisms of Binding and Single-Strand Scission of Deoxyribonucleic Acid by the Antitumor Antibiotics Saframycins A and C", *Biochemistry*, vol. 21, No. 3, pp. 419-428 (1982).

Martinez, Eduardo J. et al., "Phthalascidin, a synthetic antitumor agent with potency and mode of action comparable to ecteinascidin 743", *Proc. Natl. Acad. Sci. USA*, vol. 96, pp. 3496-3501 (1999).

Martinez et al., "Enantioselective Synthesis of Saframycin A and Evaluation of Antitumor Activity Relative to Ecteinascidin/Saframycin Hybirds", Organic Letters, 1(7):75-77 (1999).

Martinez et al., "A New, More Efficient, and Effective Process for the Synthesis of a Key Pentacyclic Intermediate for Production of Ecteinascidin and Phthalascidin Antitumor Agents", Organic Letters, 2(7):993-996 (2000).

Mikami, Yuzuru et al., "Structural Studies on Minor Components of Saframycin Group Antibiotics Saframycins F, G and H", *The Journal of Antibiotics*, vol. XII, No. 6, pp. 734-740 (1988).

Mirsalis, J.C. et al., "Toxicity of Ecteinascidin 743 in female Fischer-344 rats administered i.v. in a multiple-dose regimen", *Proceedings of the American Association for Cancer Research*, vol. 38, #2073, pp. 309 (1997).

Moore, B.M. et al., "The NMR model of an ecteinascidin 743-DNA adduct", *Proceedings of the American Association for Cancer Research*, vol. 38, #2105, pp. 314 (1997).

Myers et al., "A Concise, Stereocontrolled Syntheis of (−)-Saframycin A by the Directed Condensation of α-Amino Aldehyde Precursors", J. Am. Chem. Soc., 121:10828-10829 (1999).

Nakagawa, Masako et al., "Total Synthesis of (−)-Eudistomin L and (−)-Debromoeudistomin L", *Journal of the American Chemical Society*, vol. 111, No. 7, pp. 2721-2722 (1989).

Parulekar, A.H. et al., "Bioactivity and Chemical Ecology of Some Interdial Animals", *Bioactivity and Chemical Ecology*, pp. 29-35.

* cited by examiner

ANITITUMORAL ECTEINASCIDIN DERIVATIVES

CROSS REFERENCE TO RELATED APPLICATIONS

This application is a continuation-in-part of U.S. application Ser. No. 10/240,963, filed on Mar. 19, 2003, now U.S. Pat. No. 7,202,361, which is the National Stage of International Application No.: PCT/GB01/01667, filed on Apr. 12, 2001, and which claims the benefit under 35 U.S.C. §119 of Great Britain Application No.: 0009043.1, filed on Apr. 12, 2000; International Application No.: PCT/GB00/01852, filed on May 15, 2000; and Great Britain Application No.: 0022644.9, filed on Sep. 14, 2000. Each of these prior applications is incorporated herein by reference in its entirety.

TECHNICAL FIELD

This invention relates to antitumoral ecteinascidin derivatives.

BACKGROUND OF THE INVENTION

The ecteinascidins are exceedingly potent antitumour agents isolated from the marine tunicate *Ecteinascidia turbinata*. Several ecteinascidins have been reported previously in the patent and scientific literature.

U.S. Pat. No. 5,256,663 describes pharmaceutical compositions comprising matter extracted from the tropical marine invertebrate, *Ecteinascidia turbinata*, and designated therein as ecteinascidins, and the use of such compositions as antibacterial, anti-viral, and/or antitumour agents in mammals.

U.S. Pat. No. 5,089,273 describes novel compositions of matter extracted from the tropical marine invertebrate, *Ecteinascidia turbinata*, and designated therein as ecteinascidins 729, 743, 745, 759A, 759B and 770. These compounds are useful as antibacterial and/or antitumour agents in mammals.

U.S. Pat. No. 5,478,932 describes ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

U.S. Pat. No. 5,654,426 describes several ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

U.S. Pat. No. 5,721,362 describes a synthetic process for the formation of ecteinascidin compounds and related structures.

WO 00/69862, from which the present application claims priority, describes the synthesis of ecteinascidin compounds from cyanosafracin B.

The interested reader is also referred to: Corey, E. J., J. Am. Chem. Soc., 1996, 118 pp. 9202-9203; Rinehart, et al., Journal of National Products, 1990, "Bioactive Compounds from Aquatic and Terrestrial Sources", vol. 53, pp. 771-792; Rinehart et al., Pure and Appl. Chem., 1990, "Biologically active natural products", vol 62, pp. 1277-1280; Rinehart, et al., J. Org. Chem., 1990, "Ecteinascidins 729, 743, 745, 759A, 759B, and 770: Potent Antitumour Agents from the Caribbean Tunicate *Ecteinascidia turbinata*", vol. 55, pp. 4512-4515; Wright et al., J. Org. Chem., 1990, "Antitumour Tetrahydroisoquinoline Alkaloids from the Colonial Ascidian *Ecteinascidia turbinata*", vol. 55, pp. 4508-4512; Sakai et al., Proc. Natl. Acad. Sci. USA 1992, "Additional antitumour ecteinascidins from a Caribbean tunicate: Crystal structures and activities in vivo", vol. 89, 11456-11460; Science 1994, "Chemical Prospectors Scour the Seas for Promising Drugs", vol. 266, pp. 1324; Koenig, K. E., "Asymmetric Synthesis", ed. Morrison, Academic Press, Inc., Orlando, Fla., vol. 5, 1985, p. 71; Barton, et al., J. Chem Soc. Perkin Trans., 1, 1982, "Synthesis and Properties of a Series of Sterically Hindered Guanidine Bases", pp. 2085; Fukuyama et al., J. Am. Chem. Soc., 1982, "Stereocontrolled Total Synthesis of (+)—Saframycin B", vol. 104, pp. 4957; Fukuyama et al., J. Am Chem Soc., 1990, "Total Synthesis of (+)—Saframycin A", vol. 112, p. 3712; Saito, et al., J. Org. Chem., 1989, "Synthesis of Saframycins. Preparation of a Key Tricyclic Lactam Intermediate to Saframycin A", vol. 54, 5391; Still, et al., J. Org. Chem., 1978, "Rapid Chromatographic Technique for Preparative Separations with Moderate Resolution", vol. 43, p. 2923; Kofron, W. G.; Baclawski, L. M., J. Org. Chem., 1976, vol. 41, 1879; Guan et al., J. Biomolec. Struc. & Dynam., vol. 10 pp. 793-817 (1993); Shamma et al., "Carbon-13 NMR Shift Assignments of Amines and Alkaloids", p. 206 (1979); Lown et al., Biochemistry, 21, 419-428 (1982); Zmijewski et al., Chem. Biol. Interactions, 52, 361-375 (1985); Ito, CRC CRIT. Rev. Anal. Chem., 17, 65-143 (1986); Rinehart et al., "Topics in Pharmaceutical Sciences 1989" pp. 613-626, D. D. Breimer, D. J. A. Cromwelin, K. K. Midha, Eds., Amsterdam Medical Press B. V., Noordwijk, The Netherlands (1989); Rinehart et al., "Biological Mass Spectrometry," 233-258 eds. Burlingame et al., Elsevier Amsterdam (1990); Guan et al., Jour. Biomolec. Struct. & Dynam., vol. 10 pp. 793-817 (1993); Nakagawa et al., J. Amer. Chem. Soc., 111: 2721-2722 (1989); Lichter et al., "Food and Drugs from the Sea Proceedings" (1972), Marine Technology Society, Washington, D.C. 1973, 117-127; Sakai et al., J. Amer. Chem. Soc. 1996, 118, 9017; García-Rocha et al., Brit. J. Cancer, 1996, 73: 875-883; and Pommier et al., Biochemistry, 1996, 35: 13303-13309; Rinehart, K. L., Med. Res. Rev., 2000, 20, 1-27 and I. Manzanares et al, Org. Lett., 2000, 2(16), 2545-2548.

The most promising ecteinascidin is ecteinascidin 743, which is undergoing clinical trials for treatment of cancers. Et 743 has a complex tris(tetrahydroisoquinolinephenol) structure of the following formula (I):

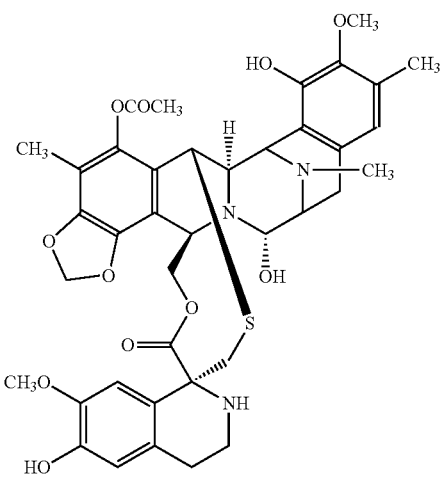

It is currently prepared by isolation from extracts of the marine tunicate *Ecteinascidin turbinata*. The yield is low, and alternative preparative processes have been sought.

The ecteinascidins include a fused system of five rings (A) to (E) as shown in the following structure of formula (XIV):

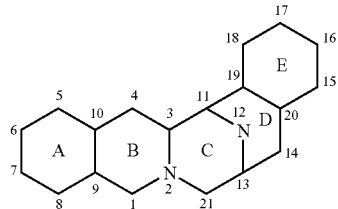

In ecteinascidin 743, the 1,4 bridge has the structure of formula (IV):

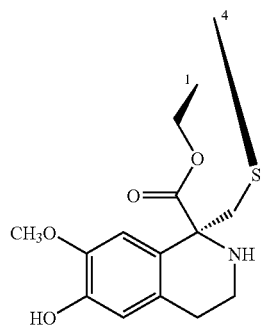

Other known ecteinascidins include compounds with a different bridged cyclic ring system, such as occurs in ecteinascidin 722 and 736, where the bridge has the structure of formula (V):

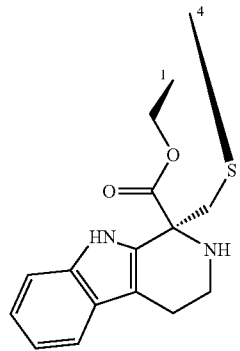

ecteinascidins 583 and 597, where the bridge has the structure of formula (VI):

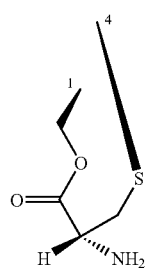

and ecteinascidin 594 and 596, where the bridge has the structure of formula (VII):

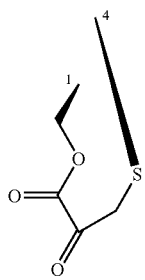

The complete structure for these and related compounds is given in J. Am. Chem. Soc. (1996) 118, 9017-9023.

Further compounds are known with the fused five ring system. In general, they lack the bridged cyclic ring system which is present in the ecteinascidins. They include the bis (tetrahydroisoquinolinequinone) antitumor-antimicrobial antibiotics safracins and saframycins, and the marine natural products renieramicins and xestomycin isolated from cultured microbes or sponges. They all have a common dimeric tetrahydroisoquinoline carbon framework. These compounds can be classified into four types, types I to IV, with respect to the oxidation pattern of the aromatic rings.

Type I, dimeric isoquinolinequinones, is a system of formula (VIII) most commonly occurring in this class of compounds, see the following table I.

TABLE I

Structure of Type I Saframycin Antibiotics

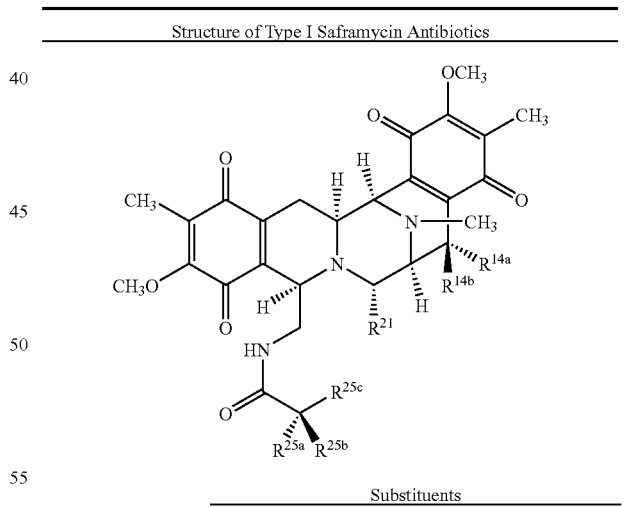

| Compound | R$^{14a}$ | R$^{14b}$ | R$^{21}$ | R$^{25a}$ | R$^{25b}$ | R$^{25c}$ |
|---|---|---|---|---|---|---|
| saframycin A | H | H | CN | O | O | CH$_3$ |
| saframycin B | H | H | H | O | O | CH$_3$ |
| saframycin C | H | OCH$_3$ | H | O | O | CH$_3$ |
| saframycin G | H | OH | CN | O | O | CH$_3$ |
| saframycin H | H | H | CN | OH | CH$_2$COCH$_3$ | CH$_3$ |
| saframycin S | H | H | OH | O | O | CH$_3$ |
| saframycin Y$_3$ | H | H | CN | NH$_2$ | H | CH$_3$ |
| saframycin Yd$_1$ | H | H | CN | NH$_2$ | H | C$_2$H$_5$ |
| saframycin Ad$_1$ | H | H | CN | O | O | C$_2$H$_5$ |
| saframycin Yd$_2$ | H | H | CN | NH$_2$ | H | H |

TABLE I-continued

Structure of Type I Saframycin Antibiotics

| Compound | Substituents | | | | | |
|---|---|---|---|---|---|---|
| | $R^{14a}$ | $R^{14b}$ | $R^{21}$ | $R^{25a}$ | $R^{25b}$ | $R^{25c}$ |
| saframycin $Y_{2b}$ | H | $Q^b$ | CN | $NH_2$ | H | $CH_3$ |
| saframycin $Y_{2b-d}$ | H | $Q^b$ | CN | $NH_2$ | H | $C_2H_5$ |
| saframycin $AH_2$ | H | H | CN | $H^a$ | $OH^a$ | $CH_3$ |
| saframycin $AH_2Ac$ | H | H | CN | H | OAc | $CH_3$ |
| saframycin $AH_1$ | H | H | CN | $OH^a$ | $H^a$ | $CH_3$ |
| saframycin $AH_1Ac$ | H | H | CN | OAc | H | $CH_3$ |
| saframycin $AR_3$ | H | H | H | H | OH | $CH_3$ |

$^a$assignments are interchangeable.
$^b$where the group Q is of formula (IX):

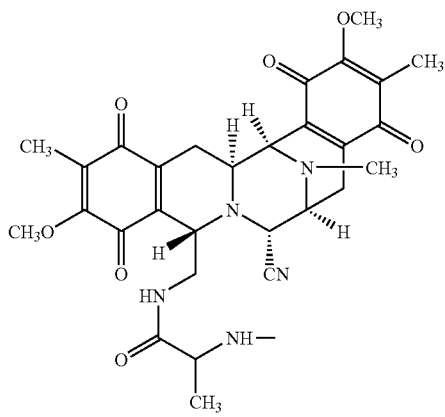

Type I aromatic rings are seen in saframycins A, B and C; G and H; and S isolated from *Streptomyces lavendulae* as minor components. A cyano derivative of saframycin A, called cyanoquinonamine, is known from Japanese Kokai JP-A2 59/225189 and 60/084,288. Saframycins $Y_3$, $Yd_1$, $Ad_1$ and $Yd_2$ were produced by *S. lavendulae* by directed biosynthesis, with appropriate supplementation of the culture medium. Saframycins $Y_{2b}$ and $Y_{2b-d}$ dimers formed by linking the nitrogen on the C-25 of one unit to the C-14 of the other, have also been produced in supplemented culture medium of *S. lavendulae*. Saframycins $AR_1$ (=$AH_2$), a microbial reduction product of saframycin A at C-25 produced by *Rhodococcus amidophilus*, is also prepared by nonstereoselective chemical reduction of saframycin A by sodium borohydride as a 1:1 mixture of epimers followed by chromatographic separation (the other isomer $AH_1$ is less polar). The further reduction product saframycin $AR_3$, 21-decyano-25-dihydro-saframycin A, (=25-dihydrosaframycin B) was produced by the same microbial conversion. Another type of microbial conversion of saframycin A using a *Nocardia* species produced saframycin B and further reduction by a Mycobacterium species produced saframycin $AH^1Ac$. The 25-O-acetates of saframycin $AH_2$ and $AH_1$ have also been prepared chemically for biological studies.

Type I compounds of formula (X) have also been isolated from marines sponges, see Table II.

TABLE II

Structures of Type I Compounds from Marine Sponges

| | Substituents | | | |
|---|---|---|---|---|
| | $R^{14a}$ | $R^{14b}$ | $R^{21}$ | R |
| renieramycin A | OH | H | H | $-C(CH_3)=CH-CH_3$ |
| renieramycin B | $OC_2H_5$ | H | H | $-C(CH_3)=CH-CH_3$ |
| renieramycin C | OH | O | O | $-C(CH_3)=CH-CH_3$ |
| renieramycin D | $OC_2H_5$ | O | O | $-C(CH_3)=CH-CH_3$ |
| renieramycin E | H | H | OH | $-C(CH_3)=CH-CH_3$ |
| renieramycin F | $OCH_3$ | H | OH | $-C(CH_3)=CH-CH_3$ |
| xestomycin | $OCH_3$ | H | H | $-CH_3$ |

Renieramycins A-D were isolated from the antimicrobial extract of a sponge, a *Reniera* species collected in Mexico, along with the biogenetically related monomeric isoquinolines renierone and related compounds. The structure of renieramycin A was initially assigned with inverted stereochemistry at C-3, C-11, and C-13. However, careful examination of the $^1H$ NMR data for new, related compounds renierarycins E and F, isolated from the same sponge collected in Palau, revealed that the ring junction of renieramycins was identical to that of saframycins. This result led to the conclusion that the formerly assigned stereochemistry of renieramycins A to D must be the same as that of saframycins.

Xestomycin was found in a sponge, a *Xestospongia* species collected from Sri Lankan waters.

Type II compounds of formula (XI) with a reduced hydroquinone ring include saframycins D and F, isolated from *S. Lavendulae*, and saframycins Mx-1 and Mx-2, isolated from *Myxococcus xanthus*. See table III.

TABLE III

Type II Compounds

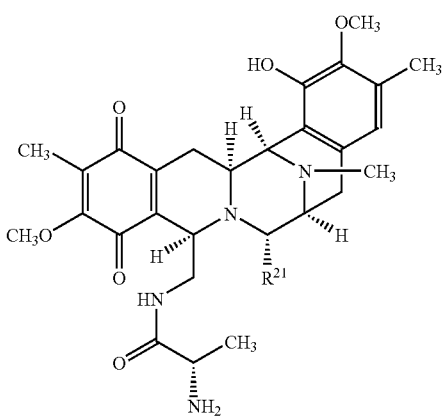

| Compound | $R^{14a}$ | $R^{14b}$ | $R^{21}$ | $R^{25a}$ | $R^{25b}$ | $R^{25c}$ |
|---|---|---|---|---|---|---|
| saframycin D | O | O | H | O | O | $CH_3$ |
| saframycin F | O | O | CN | O | O | $CH_3$ |
| saframycin Mx-1 | H | $OCH_3$ | OH | H | $CH_3$ | $NH_2$ |
| saframycin Mx-2 | H | $OCH_3$ | H | H | $CH_3$ | $NH_2$ |

The type III skeleton is found in the antibiotics safracins A and B, isolated from cultured *Pseudomonas fluorescens*. These antibiotics of formula (XII) consist of a tetrahydroisoquinoline-quinone subunit and a tetrahydroisoquinolinephenol subunit.

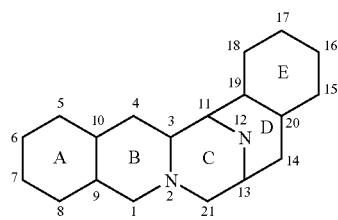

Where $R^{21}$ is —H in safracin A and is —OH in safracin B.

Saframycin R, the only compound classified as the Type IV skeleton, was also isolated from *S. lavendulae*. This compound of formula (XIII), consisting of a hydroquinone ring with a glycolic ester side chain on one of the phenolic oxygens, is conceivably a pro-drug of saframycin A because of its moderate toxicity.

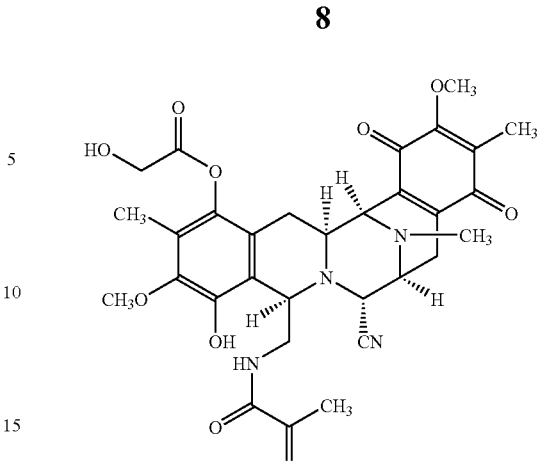

These known compounds include the fused system of five rings of the formula (XIV):

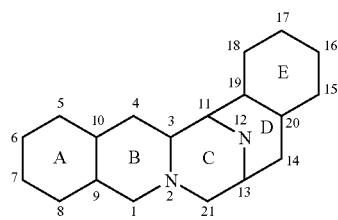

In this text, we refer to this ring structure as the fused ecteinascidin five ring system, though it will be appreciated that the rings A and E are phenolic in the ecteinascidins and some other compounds, while in other compounds, notably the saframycins, the rings A and E are quinolic. In the compounds, the rings B and D are tetrahydro, while ring C is perhydro.

SUMMARY OF THE INVENTION

The present invention provides compounds having the fused ecteinascidin five ring system and related to ecteinascidins 583 and 597. In ecteinascidins 583 and 597 the 1,4 bridge has the structure of formula (VIa):

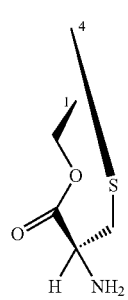

VIa

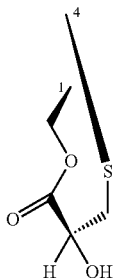

Certain compounds of this invention have the fused five ring system of ecteinascidins and the bridge structure of formula (VIa), with the —NH₂ optionally derivatised. These compounds can be acylated on the —CHNH₂— group present in the formula (VI). Other derivative compounds of this invention comprise those where this —CHNH₂— group is replaced by a group —CHNHX₁ or —C(X₂)₂— where X₁ or X₂ are as defined. The remaining substituents on the fused ecteinascidin five ring system can be the same as those on natural compounds, particularly natural ecteinascidins, or different.

Other compounds of this invention have the fused five ring system of ecteinascidins and the bridge structure of formula (VIb) in which the —NH₂ group on the bridge has been replaced with an —OH group which may be optionally derivatised. These compounds can be acylated on the —CHOH— group present in the formula (VIb). Other derivative compounds of this invention comprise those where this —CHOH— group is replaced by a group —CHOX₁ or —C(X₂)₂— where X₁ or X₂ are as defined. The remaining substituents on the fused ecteinascidin five ring system can be the same as those on natural compounds, particularly natural ecteinascidins, or different.

In the compounds of this invention, the stereochemistry of the bridgehead carbon atom bearing the —OH or —NH₂ group (or substituted derivatives thereof) can be the same as that of the natural compounds, particularly natural ecteinascidins, or different.

In the compounds of this invention, the fused system of five rings (A) to (E) of formula (XIV) can be as in the ecteinascidins, or may be as in other related compounds. Thus the rings A and E can be phenolic or quinolic; the rings B and D are tetrahydro, and ring C is perhydro.

Compounds of this invention exhibit antitumor activity, and the invention provides pharmaceutical compositions of the compounds, along with methods for preparing the compositions and methods of treatment using the compounds or compositions.

The invention also provides new hemisynthetic and synthetic routes to the compounds of this invention.

In one aspect, this invention features a compound having a fused ecteinascidin five ring system with a 1, 4 bridge having the structure of formula (VIa or VIb) as described herein and compounds in which the —NH₂ or —OH of the 1, 4 bridge is derivatised; with the exception of ecteinascidin 583 or 597, and with the exception of compounds 14, 15 or 47 of U.S. Pat. No. 5,721,362.

The fused ecteinascidin five ring system can be as in the ecteinascidins, the ring system being of the formula (XIV) as described herein, in which the rings A and E are phenolic; the rings B and D are tetrahydro, and ring C is perhydro.

The substituents at positions 5, 6, 7, 8, 12, 16, 17, 18 and 21 can be as in a known ecteinascidin. The substituents at positions 5, 6, 7, 8, 12, 16, 17 and 18 can be as in a known ecteinascidin. The known ecteinascidin can be ecteinascidin 743. The —NH₂ or —OH of the 1, 4 bridge can be derivatised. The group —CHNH₂— in the 1, 4 bridge can be replaced by a group —C(X₂)₂—, where X₂ is OX₁ or N(X₁)₂ wherein the or each X₁ is independently H, C(═O)R', substituted or unsubstituted C₁-C₁₈ alkyl, substituted or unsubstituted C₂-C₁₈ alkenyl, substituted or unsubstituted C₂-C₁₈ alkynyl, substituted or unsubstituted aryl, or two X₁ groups may together form a cyclic substituent on the nitrogen atom.

In one aspect, this invention features a pharmaceutical composition, which includes a compound having a fused ecteinascidin five ring system with a 1, 4 bridge having the structure of formula (VIa or VIb) as described herein and compounds in which the —NH₂ or —OH of the 1, 4 bridge is derivatised; with the exception of ecteinascidin 583 or 597, together with a pharmaceutically acceptable carrier.

In one aspect, this invention features the use of a compound having a fused ecteinascidin five ring system with a 1, 4 bridge having the structure of formula (VIa or VIb) as described herein and compounds in which the —NH₂ or —OH of the 1, 4 bridge is derivatised; with the exception of ecteinascidin 583 or 597, in the preparation of a medicament for use in the treatment of a tumour.

In one aspect, this invention features a method of treating a tumour which includes administration of an effective amount of a compound having a fused ecteinascidin five ring system with a 1, 4 bridge having the structure of formula (VIa or VIb) as described herein and compounds in which the —NH₂ or —OH of the 1,4 bridge is dervatised; with the exception of ecteinacidin 583 or 597.

In one aspect, this invention features a compound of the formula:

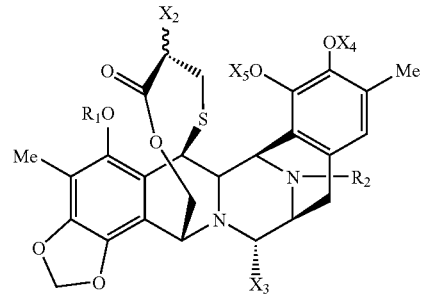

wherein:
the substituent groups defined by R₁, R₂ are each independently selected of H, C(═O)R', C₁-C₁₈ alkyl, C₂-C₁₈ alkenyl, C₂-C₁₈ alkynyl, or aryl;
each of the R' groups is independently selected from the group consisting of H; OH; NO₂; NH₂; SH; CN; halogen; ═O; C(═O)H; C(═O)CH₃; CO₂H; or C₁-C₁₈ alkyl, C₂-C₁₈ alkenyl, or C₂-C₁₈ alkynyl, each of which, independently, may be substituted with one or more substituents selected from the group consisting of halogen, cyano, hydroxy, nitro, azido; alkanoyl, carboxamido, alkyl, alkenyl, alkynyl, aryloxy, alkoxy, alkylthio, alkylsulfinyl, alkylsulfonyl, carbocylic aryl having 6 or more carbons, and aralkyl; or unsubstituted aryl;
X₂ is OX₁ or N(X₁)₂ wherein each X₁ is independently H, C(═O)R' where R' is as defined, unsubstituted C₁-C₁₈ alkyl, C₂-C₁₈ alkenyl, C₂-C₁₈ alkynyl, aryl, alkoxy, heterocyclyl, or two X₁ groups together form a cyclic substituent on the nitrogen atom, or X₁ is SO₂CH₃ when X₂ is OX₁, or N(X₁)₂ is NHCOalkylCOOH, NHbiotin, NH(aa)$_y$ where aa is amino acid acyl and y is 1, 2 or 3 optionally with a amide terminal group, protected NHCOCH(NH$_2$)CH$_2$SH, NHCOalkenylaryl substituted with CF$_3$, or m-methoxycarbonylbenzoylNH; wherein N(X$_1$)$_2$ is not NH$_2$;

X$_3$ is selected of OR$_1$ where R$^1$ is as defined, CN, (=O), or H;

X$_4$ is —H or C$_1$-C$_{18}$ alkyl; and

X$_5$ is selected of H, or R$_1$ where R$_1$ is as defined;

with the exception of compounds 14 and 47 of U.S. Pat. No. 5,721,362. The compound can be a salt (e.g., a pharmaceutically acceptable salt) thereof.

In another aspect, this invention features a compound of formula (XVIIb):

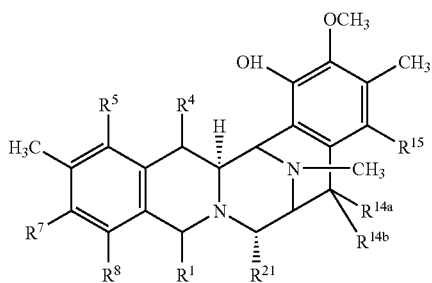

wherein
R$^1$ and R$^4$ together form a group of formula (VIa) or (VIb):

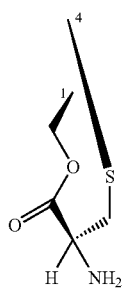

VIa

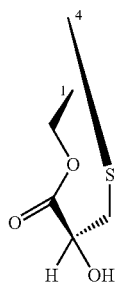

VIb wherein the —NH$_2$ group in formula (VIa) is derivatised to give derivative compounds in which the —CHNH$_2$ group of formula VIa is replaced by a group —CHNHX$_1$ or —CHN(X$_1$)$_2$, in which NHX$_1$ and N(X$_1$)$_2$ are not NH$_2$; wherein each X$_1$ is independently:

C(=O)R' where each of the R' groups is independently selected from the group consisting of H; OH; NO$_2$; NH$_2$; SH; CN; halogen; =O; C(=O)H; C(=O)CH$_3$; CO$_2$H; or C$_1$-C$_{18}$ alkyl, C$_2$-C$_{18}$ alkenyl, or C$_2$-C$_{18}$ alkynyl, each of which, independently, may be substituted with one or more substituents selected from the group consisting of halogen, cyano, hydroxy, nitro, azido; alkanoyl, carboxamido, alkyl, alkenyl, alkynyl, aryloxy, alkoxy, alkylthio, alkylsulfinyl, alkylsulfonyl, carbocylic aryl having 6 or more carbons, and aralkyl; or unsubstituted aryl; or unsubstituted C$_1$-C$_{18}$ alkyl, C$_2$-C$_{18}$ alkenyl, C$_2$-C$_{18}$ alkynyl, aryl, alkoxy, heterocyclyl, or two X$_1$ groups together form a cyclic substituent on the nitrogen atom, or N(X$_1$)$_2$ is NHCOalkylCOOH, NHbiotin, NH(aa)$_y$ where aa is amino acid acyl and y is 1, 2 or 3 optionally with a amide terminal group, protected NHCOCH(NH$_2$)CH$_2$SH, NHCOalkenylaryl substituted with CF$_3$, or m-methoxycarbonylbenzoylNH;

R$^5$ is —H; —OH; or O-acyl, wherein the acyl group is of formula —CO—R$^a$, wherein R$^a$ is alkyl, alkoxy, alkylene, alkenyl, arylalkyl, aryl, arylalkylene, amino acid, aromatic heterocyclyl, or partially or completely saturated heterocycyl, each optionally substituted with halo, cyano, nitro, carboxyalkyl, alkoxy, aryl, aryloxy, heterocyclyl, heterocycyloxy, alkyl, amino or substituted amino;

R$^7$ is —OCH$_3$ and R$^8$ is —OH or R$^7$ and R$^8$ together form a group —O—CH$_2$—O—;

R$^{14a}$ and R$^{14b}$ are both —H or one is —H and the other is —OH, —OCH$_3$ or —OCH$_2$CH$_3$, or R$^{14a}$ and R$^{14b}$ together form a keto group; and R$^{15}$ is —H or —OH;

R$^{21}$ is —H, —OH or —CN;

and derivatives where the group —NCH$_3$— at the 12-position is replaced by —NH— or —NCH$_2$CH$_3$—; and derivatives where the —OH group in the compound of formula (VIb) is derivatised to give derivative compounds where the —CHOH group of VIb is replaced by CHOX$_1$ where X$_1$ is:

C(=O)R' where each of the R' groups is independently selected from the group consisting of H; OH; NO$_2$; NH$_2$; SH; CN; halogen; =O; C(=O)H; C(=O)CH$_3$; CO$_2$H; or C$_1$-C$_{18}$ alkyl, C$_2$-C$_{18}$ alkenyl, C$_2$-C$_{18}$ alkynyl, or aryl, each of which, independently, may be substituted with one or more substituents selected from the group consisting of halogen, cyano, hydroxy, nitro, azido; alkanoyl, carboxamido, alkyl, alkenyl, alkynyl, aryloxy, alkoxy, alkylthio, alkylsulfinyl, alkylsulfonyl, aminoalkyl, carbocylic aryl having 6 or more carbons, and aralkyl; or C$_1$-C$_{18}$ alkyl, C$_2$-C$_{18}$ alkenyl, C$_2$-C$_{18}$ alkynyl, aryl, alkoxy, heterocyclyl, or X$_1$ is SO$_2$CH$_3$ when X$_2$ is OX$_1$;

with the exception of N-acetylecteinascidin 597. The compound can be a salt (e.g., a pharmaceutically acceptable salt) thereof.

In one aspect, this invention features a pharmaceutical composition which includes one (or more) of the compounds described herein, together with a pharmaceutically acceptable carrier or diluent.

In one aspect, this invention features a method of treating a tumor resulting from lung cancer, colon cancer or melanoma, the method includes administering to a mammal an effective amount of one (or more) compounds described herein (e.g., described generically, sub-generically, or specifically herein).

In one aspect, this invention features a method of treating leukemia, lung cancer, colon cancer or melanoma, the method includes administering to a mammal an effective amount of one (or more) compounds described herein (e.g., described generically, sub-generically, or specifically herein).

In embodiments, the compound can be administered in combination with another drug selected from the group consisting of taxol, paclitaxel, taxotere, docetaxel, vincristine, vinblastine, 5-fluorouracil, cytarabine, gemcitabine, pentostatin, methotrexate, cyclophosphamide, ifosphamide, adriamycin, doxorubicin, pharmorubicin, epirubicin, etoposide, tamoxifen, flutamide, leuprorelin, goserelin, cyprotrone, octreotide, herceptin, cis-platin, carbonplatin, oxaliplatin, paraplatin, aplidine, or dexamethasone.

Embodiments can include one or more of the following features.

$R_1$ can be C(=O)R', where R' is H, unsubstituted alkyl, or alkyl substituted with one or more substituents selected from the group consisting of halogen, cyano, hydroxy, nitro, azido; alkanoyl, carboxamido, alkyl, alkenyl, alkynyl, aryloxy, alkoxy, alkylthio, alkylsulfinyl, alkylsulfonyl, aminoalkyl, carbocylic aryl having 6 or more carbons, and aralkyl. For example, $R_1$ can be acetyl.

$R_2$ can be H or methyl. In certain embodiments, $R_2$ can be methyl.

$X_3$ can be OH or CN.

$X_4$ can be H or Me.

$X_5$ can be H or $C_1$-$C_{18}$ alkyl. In certain embodiments, $X_5$ can be H.

The compound can have the following formula:

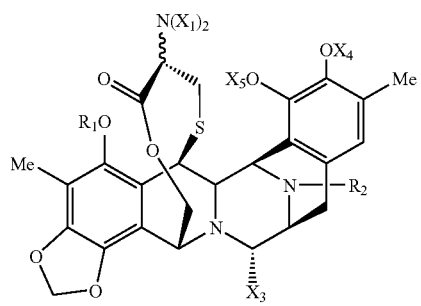

wherein the substituent groups $R_1$, $R_2$, $X_1$, $X_3$, $X_4$ and $X_5$ can be as defined anywhere herein.

In embodiments, one $X_1$ can be hydrogen.

$N(X_1)_2$ can be —NHCOalkyl and may be halosubstituted on the alkyl group; —NHCOalkylCOOH; protected —NHCOCH($NH_2$)$CH_2$SH where the $NH_2$ is protected with an alloc group and the SH is protected with an Fm group; —NH-biotin; —NHaryl; —NH(aa)y where aa is an amino acid acyl and y is 1, 2 or 3 and wherein any $NH_2$ is optionally protected with an alloc group; phthalimido formed from two X1 groups with the adjacent nitrogen; —NH(unsubstituted alkyl); —NHCOalkenylaryl, which is optionally substituted with 3-trifluoromethyl.

$N(X_1)_2$ can be NHAc, NHCO($CH_2$)$_2$COOH, NHCOCH(NHAlloc)$CH_2$SFm, NHCO($CH_2$)$_{14}$$CH_3$, NHTFA, NHCO($CH_2$)$_2$$CH_3$, NHCOCH$_2$CH($CH_3$)$_2$, NHCO($CH_2$)$_6$$CH_3$, NHBiotin, NHCOCinn, NHCO—(p-$F_3$C)-Cinn, NHVal-$NH_2$, NHVal-N—Ac, NHVal-N—COCinn, NHVal-Ala-$NH_2$, NHVal-Ala-N—Ac, NHAla-$NH_2$, NHCOCH($NH_2$)$CH_2$SFm, NPhth, NH—(m-$CO_2$Me)-Bz, $NMe_2$, NHVal-Ala-N—COCinn, NHAla-N—Ac, or NHAla-N—COCinn.

The compound according can have the following formula:

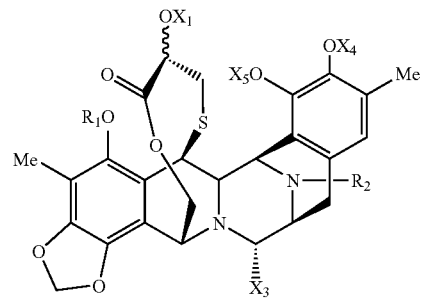

wherein the substituent groups $R_1$, $R_2$, $X_1$, $X_3$, $X_4$ and $X_5$ can be as defined anywhere herein.

In embodiments, $OX_1$ can be OH, OAc, $OCOCF_3$, $OCOCH_2CH_2CH_3$, $OCO(CH_2)_6CH_3$, $OCO(CH_2)_{14}CH_3$, OCOCH=CHPh, $OSO_2CH_3$.

$R^5$ can be acyloxy of up to 4 carbon atoms. For example, $R^5$ can be acetyloxy.

$R^7$ and $R^8$ together can form a group —O—$CH_2$—O—.

$R^5$ can be O-acyl, in which the acyl group can be alkanoyl, haloalkanoyl, arylalkanoyl, alkenoyl, heterocyclylacyl, or aroyl, arylaroyl, haloaroyl, or nitroaroyl.

$R^a$ can be alkyl, haloalkyl, alkoxyalkyl, haloalkoxyalkyl, arylalkylene, haloalkylarylalkylene, arylalkyl, alkenyl or amino acid.

$R^a$—CO— can be acetyl, trifluoroacetyl, 2,2,2-trichloroethoxycarbonyl, isovalerylcarbonyl, trans-3-(trifluoromethyl)cinnamoylcarbonyl, heptafluorobutyrylcarbonyl, decanoylcarbonyl, trans-cinnamoylcarbonyl, butyrylcarbonyl, 3-chloropropyonylcarbonyl, cinnamoylcarbonyl, 4-methylcinnamoylcarbonyl, hydrocinnamoylcarbonyl, trans-hexenoylcarbonyl, alanyl, arginyl, aspartyl, asparagyl, cystyl, glutamyl, glutaminyl, glycyl, histidyl, hydroxyprolyl., isoleucyl, leucyl, lysyl, methionyl, phenylalanyl, prolyl, seryl, threonyl, thyronyl, tryptophyl, tyrosyl, valyl, phthalimido or other cyclic amide.

—CO—$R^a$ can be derived from an amino acid and includes an amino group which itself forms an acyl derivative.

The N-acyl compound can be a dipeptide which in turn can form N-acyl derivatives.

$R^5$ can be O-acyl, in which the acyl group is an aliphatic acyl group.

$R^{14a}$ and $R^{14b}$ can be hydrogen.

$R^{15}$ can be hydrogen.

The compound can have formula (XVIII):

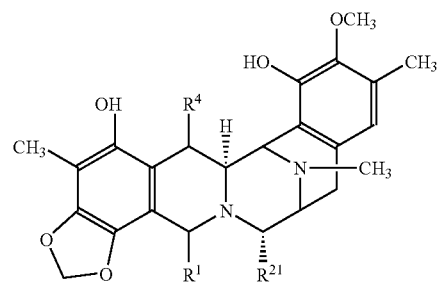

wherein $R^1$, $R^4$, and $R^{21}$ can be as defined anywhere herein.

The compound can be in accordance with the following definitions:

| X₂ | X₃ | X₄ | R₁ |
|---|---|---|---|
| AcNH— | OH | Me | Ac |
| F₃CCONH— | OH | Me | Ac |
| CH₃(CH₂)₂CONH— | OH | Me | Ac |
| (CH₃)₂CHCH₂CONH— | OH | Me | Ac |
| CH₃(CH₂)₆CONH— | OH | Me | Ac |
| CH₃(CH₂)₁₄CONH— | OH | Me | Ac |
| PhCONH— | OH | Me | Ac |
| CinnCONH— | OH | Me | Ac |
| p-F₃C-CinnCONH— | OH | Me | Ac |
| BiotinCONH— | OH | Me | Ac |
| HO₂CCH₂CH₂CONH— | OH | Me | Ac |
| PrNH— | OH | Me | Ac |
| NH₂-ValNH— | OH | Me | Ac |
| Ac—N-ValNH— | OH | Me | Ac |
| CinnCO—N-ValNH— | OH | Me | Ac |
| NH₂-Ala-ValNH— | OH | Me | Ac |
| Ac—N-Ala-ValNH— | OH | Me | Ac |
| CinnCO—N-Ala-ValNH— | OH | Me | Ac |
| NH₂-AlaNH— | OH | Me | Ac |
| CinnCO—N-AlaNH— | OH | Me | Ac |
| FmSCH₂CH(NHAlloc)CONH— | OH | Me | Ac |
| HO— | OH | Me | Ac |
| AcO— | OH | Me | Ac |
| CH₃(CH₂)₂COO— | OH | Me | Ac |
| CH₃(CH₂)₆COO— | OH | Me | Ac |
| CH₃(CH₂)₁₄COO— | OH | Me | Ac |
| CinnCOO— | OH | Me | Ac |
| MeSO₃— | OH | Me | Ac |
| AcNH— | CN | Me | Ac |
| AcNH— | CN | Me | H |
| AcNH— | CN | H | Ac |
| F₃CCONH— | CN | Me | Ac |
| CH₃(CH₂)₂CONH— | CN | Me | Ac |
| (CH₃)₂CHCH₂CONH— | CN | Me | Ac |
| CH₃(CH₂)₆CONH— | CN | Me | Ac |
| CH₃(CH₂)₁₄CONH— | CN | Me | Ac |
| PhCONH— | CN | Me | Ac |
| CinnCONH— | CN | Me | Ac |
| p-F₃C-CinnCONH— | CN | Me | Ac |
| PhtN— | CN | Me | Ac |
| —MeO₂C—C₆H₄—CONH— | CN | Me | Ac |
| BiotinNH— | CN | Me | Ac |
| HO₂C(CH₂)₂CONH— | CN | Me | Ac |
| (CH₃)₂N— | CN | Me | Ac |
| PrNH— | CN | Me | Ac |
| NH₂-ValNH— | CN | Me | Ac |
| Ac—N-ValNH— | CN | Me | Ac |
| CinnCO—N-ValNH— | CN | Me | Ac |
| NH₂-Ala-ValNH— | CN | Me | Ac |
| Ac—N-Ala-ValNH— | CN | Me | Ac |
| CinnCO—N-Ala-ValNH— | CN | Me | Ac |
| NH₂-AlaNH— | CN | Me | Ac |
| Ac—N-AlaNH— | CN | Me | Ac |
| CinnCO—N-AlaNH— | CN | Me | Ac |
| FmSCH₂CH(NHAlloc)CONH— | CN | Me | Ac |
| FmSCH₂CH(NH₂)CONH— | CN | Me | Ac |
| Cl₃CCH₂OCONH— | CN | Me | Ac |
| HO— | CN | Me | Ac |
| AcO— | CN | Me | Ac |
| F₃CCOO— | CN | Me | Ac |
| CH₃(CH₂)₂COO— | CN | Me | Ac |
| CH₃(CH₂)₆COO— | CN | Me | Ac |
| CH₃(CH₂)₁₄COO— | CN | Me | Ac |
| CinnCOO— | CN | Me | Ac |
| MeSO₃— | CN | Me | Ac |

$X_5$ is H and $R_2$ is Me.

The compound can be a compound (4b) of formula:

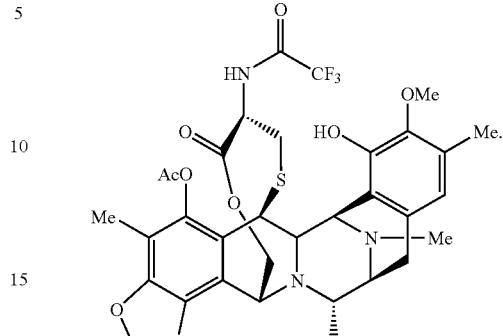

The compound can be a compound (4h) of formula:

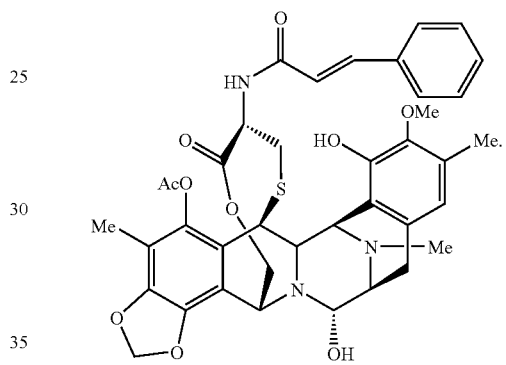

The compound can be a compound (4p) of formula:

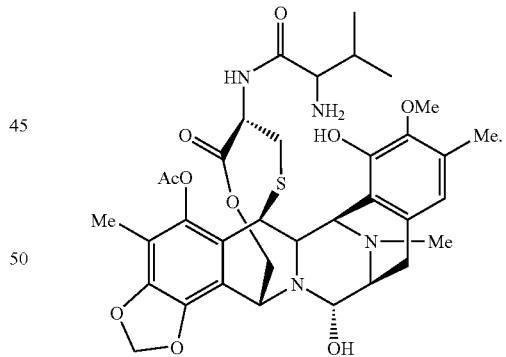

The composition can further include one or more other drugs selected from the group consisting of taxol, paclitaxel, taxotere, docetaxel, vincristine, vinblastine, 5-fluorouracil, cytarabine, gemcitabine, pentostatin, methotrexate, cyclophosphamide, ifosphamide, adriamycin, doxorubicin, pharmorubicin, epirubicin, etoposide, tamoxifen, flutamide, leuprorelin, goserelin, cyprotrone, octreotide, herceptin, cisplatin, carbonplatin, oxaliplatin, paraplatin, aplidine, or dexamethasone.

The substituent groups defined by $R_1$, $R_2$ can each be independently selected of H, C(=O)R', or unsubstituted $C_1$-$C_{18}$ alkyl.

The substituent groups defined by $R_1$, $R_2$ can each be independently selected of C(=O)R' or unsubstituted $C_1$-$C_{18}$ alkyl.

The substituent groups defined by $R_1$, $R_2$ can each be independently selected of H, C(=O)R', unsubstituted $C_2$-$C_{18}$ alkenyl, unsubstituted $C_2$-$C_{18}$ alkynyl, or unsubstituted aryl.

The substituent groups defined by $R_1$, $R_2$ can each be independently selected of:
H;
C(=O)R'; or
$C_1$-$C_{18}$ alkyl substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic.

The substituent groups defined by $R_1$, $R_2$ can each be independently selected of:
H;
C(=O)R';
$C_2$-$C_{18}$ alkenyl substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic; or
$C_2$-$C_{18}$ alkynyl substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic.

The substituent groups defined by $R_1$, $R_2$ can each be independently selected of:
H;
C(=O)R'; or
aryl substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic.

Each $X_1$ can be independently H or unsubstituted $C_1$-$C_{18}$ alkyl.

Each $X_1$ can be independently H or unsubstituted $C_2$-$C_{18}$ alkenyl, unsubstituted $C_2$-$C_{18}$ alkynyl, unsubstituted aryl, unsubstituted alkoxy, or unsubstituted heterocyclyl.

Each $X_1$ can be independently H or $C_2$-$C_{18}$ alkenyl substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic.

Each $X_1$ can be independently H or $C_2$-$C_{18}$ alkynyl substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic.

Each $X_1$ can be independently H or aryl substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic.

Each $X_1$ can be independently H or alkoxy substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic.

Each $X_1$ can be independently H or heterocyclyl substituted with one or more substituents selected from the group consisting of OH, OR', SH, SR', SOR', $SO_2R'$, $NO_2$, $NH_2$, NHR', $N(R')_2$, NHC(O)R', CN, halogen, =O, unsubstituted $C_1$-$C_{18}$ alkyl, unsubstituted $C_2$-$C_{18}$ alkenyl, unsubstituted $C_2$-$C_{18}$ alkynyl, unsubstituted aryl, and unsubstituted heteroaromatic.

The compound can be administered in combination with another drug selected from the group consisting of taxol, paclitaxel, taxotere, docetaxel, vincristine, vinblastine, 5-fluorouracil, cytarabine, gemcitabine, pentostatin, methotrexate, cyclophosphamide, ifosphamide, adriamycin, doxorubicin, pharmorubicin, epirubicin, etoposide, tamoxifen, flutamide, leuprorelin, goserelin, cyprotrone, octreotide, herceptin, cis-platin, carbonplatin, oxaliplatin, paraplatin, aplidine, or dexamethasone.

The compound can be administered in combination with another drug selected from the group consisting of taxane drugs, podophylotoxins, vinca alkaloids, purine analogues, nitrogen mustards, antracycline drugs, estrogens, antiestrogens, androgens, antibody derivatives, platinum drugs, nitrosoureas, matrix metalloproteinase inhibitors, or didemnins.

The compound can be administered in combination with another drug selected from the group consisting of microtubule modulators, antimetabolite drugs, alkylating agents, drugs which target DNA, drugs which target topoisomerases, hormones and hormone agonists or antagonists, drugs which target signal transduction in tumour cells, alkylating drugs, drugs potentially affecting metastasis of tumours, gene therapy and antisense agents, antibody therapeutics, bioactive compounds of marine origin, steroid analogues, anti-inflammatory drugs, or anti-emetic drugs.

In one aspect, this invention features a compound of formula (XVIIb):

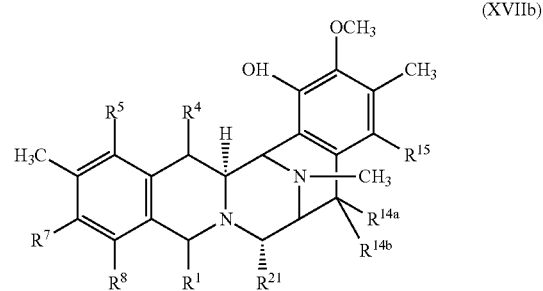

(XVIIb)

wherein
R$^1$ and R$^4$ together form a group of formula (VIa) or (VIb):

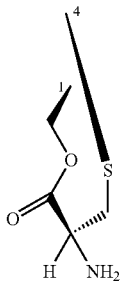

VIa

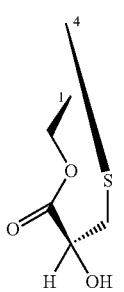

VIb wherein the group R$^1$ with R$^4$ can be acylated on the —CHNH$_2$— or —CHOH— group present in formula (VIa) or (VIb);

wherein the acyl derivatives can be N-acyl or N-thioacyl derivatives thereof, as well as cyclic amides including alkanoyl, haloalkanoyl, arylalkanoyl, alkenyl, heterocyclylacyl, aroyl, arylaroyl, haloaroyl, nitroaroyl; or the acyl group can be of formula —CO—R$^a$, where R$^a$ is selected from alkyl, alkoxy, alkylene, arylalkyl, arylalkylene, amino acid acyl, or heterocyclyl, each optionally substituted with halo, cyano, nitro, carboxyalkyl, alkoxy, aryl, aryloxy heterocyclyl, heterocyclyloxy, alkyl, amino or substituted amino;

R$^5$ is H, —OH, acetyloxy or acyloxy, wherein the acyl groups can be of formula —CO—R$^a$, where R$^a$ is selected from alkyl, alkoxy, alkylene, arylalkyl, arylalkylene, amino acid acyl, or heterocyclyl, each optionally substituted with halo, cyano, nitro, carboxyalkyl, alkoxy, aryl, aryloxy heterocyclyl, heterocyclyloxy, alkyl, amino or substituted amino;

R$^7$ is —OCH$_3$ and R$^8$ is —OH or R$^7$ and R$^8$ together form a group —O—CH$_2$—O—;

R$^{14a}$ and R$^{14b}$ are both —H or one is —H and the other is —OH, —OCH3 or —OCH$_2$CH$_3$, or R$^{14a}$ and R$^{14b}$ together form a keto group;

R$^{15}$ is —H or —OH;

R$^{21}$ is —H, —OH or —CN;

and derivatives where the group —NCH$_3$ at the 12-position is replaced by —NH or —NCH$_2$CH$_3$. The compound can be a salt (e.g., a pharmaceutically acceptable salt) thereof.

In one aspect, this invention features a compound of formula (XVIIb):

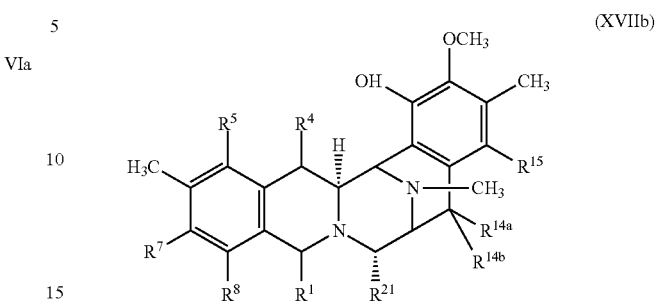

(XVIIb)

wherein
R$^1$ and R$^4$ together form a group of formula (VIa) or (VIb):

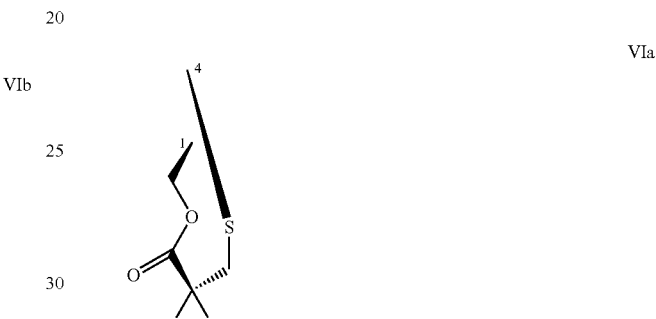

VIa

VIb wherein the —CHNH$_2$ in formula (VIa) is replaced by a group —CHN(—CO—R$^a$)(R$^b$), or the —CHOH group in formula (VIb) is replaced by a group —CHO—CO—R$^a$, wherein R$^a$ is:

(i) aromatic heterocyclyl (also referred to herein as "heteroaromatic"); or (ii) partially saturated heterocyclyl; or (iii) completely saturated heterocyclyl (also referred to herein as "heteroalicyclyl"); or (iv) carbocyclic aryl (e.g., phenyl);

each of which is optionally substituted with one or more substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyl, alkyl, haloalkyl, amino, and substituted amino; and R$^b$ can be H; or a substituent, e.g., C(=O)H; C(=O)CH$_3$; C$_1$-C$_{18}$ alkyl, C$_2$-C$_{18}$ alkenyl, C$_2$-C$_{18}$ alkynyl, aryl, alkoxy, each of which is optionally substituted with one or more substituents; or —CO—R$^a$;

R$^5$ is H, —OH or O-acyl, wherein the acyl group is of formula —CO—R$^{aa}$, wherein R$^{aa}$ is alkyl, alkoxy, alkenyl, arylalkyl, aryl, arylalkylene, amino acid, aromatic heterocyclyl, partially saturated heterocyclyl, or completely saturated heterocyclyl, each of which is optionally substituted with one or more substituents selected from the group consisting of halo, cyano, nitro, carboxyalkyl, alkoxy, haloalkoxy, aryl, aryloxy, heterocyclyl, heterocyclyloxy, alkyl, amino and substituted amino;

$R^7$ is —OCH$_3$ and $R^8$ is —OH or $R^7$ and $R^8$ together form a group —O—CH$_2$—O;

$R^{14a}$ and $R^{14b}$ are both —H or one is —H and the other is —OH, —OCH$_3$ or —OCH$_2$CH$_3$, or $R^{14a}$ and $R^{14b}$ together form a keto group;

$R^{15}$ is —H or —OH;

$R^{21}$ is —H, —OH or —CN;

and derivatives where the group —NCH$_3$ at the 12-position is replaced by —NH or —NCH$_2$CH$_3$; or a pharmaceutically acceptable salt thereof.

In another aspect, this invention features a compound of formula (XVIIb), in which $R^1$ and $R^4$ together form a group of formula (VIa) or (VIb) wherein the —CHNH$_2$ in formula (VIa) is replaced by a group —CHN(—CO—$R^a$)($R^b$), or the —CHOH group in formula (VIb) is replaced by a group —CHO—CO—$R^a$, wherein $R^a$ is:

(i) aromatic heterocyclyl; or
(ii) partially saturated heterocyclyl; or
(iii) completely saturated heterocyclyl;

each of which is optionally substituted with one or more substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyl, alkyl, haloalkyl, amino, and substituted amino; and $R^b$ is H; C(═O)H; C(═O)CH$_3$; C$_1$-C$_{18}$ alkyl, C$_2$-C$_{18}$ alkenyl, C$_2$-C$_{18}$ alkynyl, aryl, alkoxy, each of which is optionally substituted with one or more substituents; or —CO—$R^a$;

$R^5$ is H, —OH or O-acyl, wherein the acyl group is of formula —CO—$R^{aa}$, wherein $R^{aa}$ is alkyl, alkoxy, alkenyl, arylalkyl, aryl, arylalkylene, amino acid, aromatic heterocyclyl, partially saturated heterocyclyl, or completely saturated heterocyclyl, each of which is optionally substituted with one or more substituents selected from the group consisting of halo, cyano, nitro, carboxyalkyl, alkoxy, haloalkoxy, aryl, aryloxy, heterocyclyl, heterocyclyloxy, alkyl, amino and substituted amino;

$R^7$ is —OCH$_3$ and $R^8$ is —OH or $R^7$ and $R^8$ together form a group —O—CH$_2$—O;

$R^{14a}$ and $R^{14b}$ are both —H or one is —H and the other is —OH, —OCH$_3$ or —OCH$_2$CH$_3$, or $R^{14a}$ and $R^{14b}$ together form a keto group;

$R^{15}$ is —H or —OH;

$R^{21}$ is —H, —OH or —CN;

and derivatives where the group —NCH$_3$ at the 12-position is replaced by —NH or —NCH$_2$CH$_3$; or a pharmaceutically acceptable salt thereof.

In another aspect, this invention features a compound of formula (XVIIb), in which $R^1$ and $R^4$ together form a group of formula (VIa) or (VIb) wherein the —CHNH$_2$ in formula (VIa) is replaced by a group —CHN(—CO—$R^a$)($R^b$), or the —CHOH group in formula (VIb) is replaced by a group —CHO—CO—$R^a$, wherein $R^a$ is:

(iv) carbocyclic aryl, which is optionally substituted with one or more substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyl, alkyl, haloalkyl, amino, and substituted amino; and $R^b$ is H; C(═O)H; C(═O)CH$_3$; C$_1$-C$_{18}$ alkyl, C$_2$-C$_{18}$ alkenyl, C$_2$-C$_{18}$ alkynyl, aryl, alkoxy, each of which is optionally substituted with one or more substituents; or —CO—$R^a$;

$R^5$ is H, —OH or O-acyl, wherein the acyl group is of formula —CO—$R^{aa}$, wherein $R^{aa}$ is alkyl, alkoxy, alkenyl, arylalkyl, aryl, arylalkylene, amino acid, aromatic heterocyclyl, partially saturated heterocyclyl, or completely saturated heterocyclyl, each of which is optionally substituted with one or more substituents selected from the group consisting of halo, cyano, nitro, carboxyalkyl, alkoxy, haloalkoxy, aryl, aryloxy, heterocyclyl, heterocyclyloxy, alkyl, amino and substituted amino;

$R^7$ is —OCH$_3$ and $R^8$ is —OH or $R^7$ and $R^8$ together form a group —O—CH$_2$—O;

$R^{14a}$ and $R^{14b}$ are both —H or one is —H and the other is —OH, —OCH$_3$ or —OCH$_2$CH$_3$, or $R^{14a}$ and $R^{14b}$ together form a keto group;

$R^{15}$ is —H or —OH;

$R^{21}$ is —H, —OH or —CN;

and derivatives where the group —NCH$_3$ at the 12-position is replaced by —NH or —NCH$_2$CH$_3$; or a pharmaceutically acceptable salt thereof.

In embodiments, $R^b$ can be H (hydrogen).

In another aspect, this invention features a compound of formula (XVIIb), in which $R^1$ and $R^4$ together form a group of formula (VIa) or (VIb) wherein the —CHNH$_2$ in formula (VIa) is replaced by a group —CHNH—CO—$R^a$, or the —CHOH group in formula (VIb) is replaced by a group —CHO—CO—$R^a$, wherein $R^a$ is:

(i) aromatic heterocyclyl; or
(ii) partially saturated heterocyclyl; or
(iii) completely saturated heterocyclyl; or
(iv) carbocyclic aryl, each of which is optionally substituted with one or more substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocycyloxy, partially saturated heterocycyloxy, completely saturated heterocyclyl, alkyl, haloalkyl, amino, and substituted amino;

$R^5$ is H, —OH or O-acyl, wherein the acyl group is of formula —CO—$R^{aa}$, wherein $R^{aa}$ is alkyl, alkoxy, alkenyl, arylalkyl, aryl, arylalkylene, amino acid, aromatic heterocyclyl, partially saturated heterocyclyl, or completely saturated heterocyclyl, each of which is optionally substituted with one or more substituents selected from the group consisting of halo, cyano, nitro, carboxyalkyl, alkoxy, haloalkoxy, aryl, aryloxy, heterocyclyl, heterocyclyloxy, alkyl, amino and substituted amino;

$R^7$ is —OCH$_3$ and $R^8$ is —OH or $R^7$ and $R^8$ together form a group —O—CH$_2$—O;

$R^{14a}$ and $R^{14b}$ are both —H or one is —H and the other is —OH, —OCH$_3$ or —OCH$_2$CH$_3$, or $R^{14a}$ and $R^{14b}$ together form a keto group;

$R^{15}$ is —H or —OH;

$R^{21}$ is —H, —OH or —CN;

and derivatives where the group —NCH$_3$ at the 12-position is replaced by —NH or —NCH$_2$CH$_3$; or a pharmaceutically acceptable salt thereof.

In another aspect, this invention features a compound of formula (XVIIb), in which $R^1$ and $R^4$ together form a group of formula (VIa) or (VIb) wherein the —CHNH$_2$ in formula (VIa) is replaced by a group —CHNH—CO—$R^a$, or the —CHOH group in formula (VIb) is replaced by a group —CHO—CO—$R^a$, wherein $R^a$ is:

(i) aromatic heterocyclyl; or
(ii) partially saturated heterocyclyl; or
(iii) completely saturated heterocyclyl;

each of which is optionally substituted with one or more substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocycyloxy, partially saturated heterocycyloxy, completely saturated heterocyclyl, alkyl, haloalkyl, amino, and substituted amino;

$R^5$ is H, —OH or O-acyl, wherein the acyl group is of formula —CO—$R^{aa}$, wherein $R^{aa}$ is alkyl, alkoxy, alkenyl, arylalkyl, aryl, arylalkylene, amino acid, aromatic heterocyclyl, partially saturated heterocyclyl, or completely saturated heterocyclyl, each of which is optionally substituted with one or more substituents selected from the group consisting of halo, cyano, nitro, carboxyalkyl, alkoxy, haloalkoxy, aryl, aryloxy, heterocyclyl, heterocyclyloxy, alkyl, amino and substituted amino;

$R^7$ is —OCH$_3$ and $R^8$ is —OH or $R^7$ and $R^8$ together form a group —O—CH$_2$—O;

$R^{14a}$ and $R^{14b}$ are both —H or one is —H and the other is —OH, —OCH$_3$ or —OCH$_2$CH$_3$, or $R^{14a}$ and $R^{14b}$ together form a keto group;

$R^{15}$ is —H or —OH;

$R^{21}$ is —H, —OH or —CN;

and derivatives where the group —NCH$_3$ at the 12-position is replaced by —NH or —NCH$_2$CH$_3$; or a pharmaceutically acceptable salt thereof.

In one aspect, this invention features a pharmaceutical composition that includes one or more compounds described herein (generically, subgenerically, or specifically) or a pharmaceutically acceptable salt thereof, together with a pharmaceutically acceptable carrier or diluent.

In one aspect, this invention features a method of treating a tumour that includes administering to a mammal in need thereof an effective amount of one or more compounds described herein (generically, subgenerically, or specifically) or a pharmaceutically acceptable salt thereof.

Embodiments can include one or more of the following features.

$R^b$ can be hydrogen.

$R^a$ can be:
(i) aromatic heterocyclyl, which is optionally substituted with one or more substituents; or
(ii) partially saturated heterocyclyl, which is optionally substituted with one or more substituents; or
(iii) completely saturated heterocyclyl, which is optionally substituted with one or more substituents.

$R^a$ can be aromatic heterocyclyl, which is optionally substituted with one or more (e.g., 1-5, 1-3, 1-2, 1) substituents.

For example, $R^a$ can be coumarinyl (and optionally substituted with one or more (e.g., 1-5, 1-3, 1-2, 1) substituents).

As another example, $R^a$ can be pyridinyl, which is optionally substituted with one or more (e.g., 1-5, 1-3, 1-2, 1) substituents.

As a further example, $R^a$ can be pyrazolyl or isoxazolyl, each of which is optionally substituted with one or more (e.g., 1-5, 1-3, 1-2, 1) substituents.

$R^a$ can be completely saturated heterocyclyl, which is optionally substituted with one or more (e.g., 1-5, 1-3, 1-2, 1) substituents. For example, $R^a$ can be pyrrolidinyl, which is optionally substituted with one or more (e.g., 1-5, 1-3, 1-2, 1) substituents.

$R^a$ can be carbocyclic aryl, which is optionally substituted with one or more (e.g., 1-5, 1-3, 1-2, 1) substituents. For example, $R^a$ can be phenyl, which is optionally substituted with one or more (e.g., 1-5, 1-3, 1-2, 1) substituents.

$R^1$ and $R^4$ together can form a group of formula (VIa), wherein the —CHNH$_2$ in formula (VIa) is replaced by a group —CHN(—CO—$R^a$)($R^b$). $R^b$ can be H.

$R^5$ can be —O—CO—$R^{aa}$.

$R^{aa}$ can be alkyl, haloalkyl, alkoxyalkyl, haloalkoxyalkyl, arylalkylene, haloalkylarylalkylene, arylalkyl, aryl, aryl-aryl, haloaryl, nitroaryl, alkenyl, aromatic heterocyclyl, partially saturated heterocyclyl, completely saturated heterocyclyl, or amino acid. In certain embodiments, $R^{aa}$ can be alkyl (e.g., CH$_3$).

$R^7$ and $R^8$ together can form a group —O—CH$_2$—O—.

$R^{14a}$ and $R^{14b}$ can be hydrogen.

$R^{15}$ can be hydrogen.

$R^{21}$ can be —OH. $R^{21}$ can be —CN.

$R^1$ and $R^4$ together can form a group of formula (VIa), wherein the —CHNH$_2$ in formula (VIa) is replaced by a group —CHNH—CO—$R^a$, wherein $R^a$ can be aromatic heterocyclyl, which is optionally substituted with one or more substituents; $R^5$ can be —O—CO—$R^{aa}$, wherein $R^{aa}$ can be alkyl; $R^7$ and $R^8$ together can form a group —O—CH$_2$—O—; each of $R^{14a}$, $R^{14b}$ and $R^{15}$ can be hydrogen; and $R^{21}$ can be —OH or —CN.

$R^1$ and $R^4$ together can form a group of formula (VIa), wherein the —CHNH$_2$ in formula (VIa) is replaced by a group —CHNH—CO—$R^a$ wherein $R^a$ is completely saturated heterocyclyl, which is optionally substituted with one or more substituents; $R^5$ can be —O—CO—$R^{aa}$, wherein $R^{aa}$ is alkyl; $R^7$ and $R^8$ together can form a group —O—CH$_2$—O—; each of $R^{14a}$, $R^{14b}$, and $R^{15}$ can be hydrogen; and $R^{21}$ can be —OH or —CN.

The compound can have the formula:

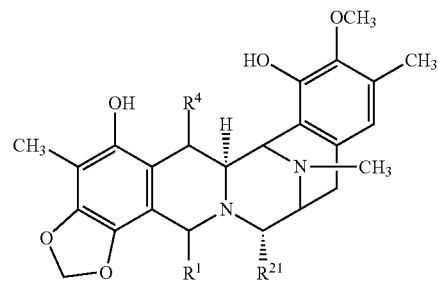

wherein $R^1$, $R^4$, and $R^{21}$ can be as defined anywhere herein.

The compound can be any of the compounds delineated in Examples 37-48 or compounds 2g, 3g, 4g, or 6 described herein.

PREFERRED EMBODIMENTS

The fused system of five rings (A) to (E) of formula (XIV) is preferably as in the ecteinascidins, and preferably substituted in positions other than 1,4 with naturally occurring substituents.

In one aspect, the present invention provides new compounds of the formula:

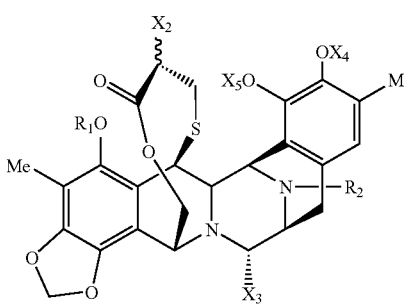

wherein:
the substituent groups defined by $R_1$, $R_2$ are each independently selected of H, C(=O)R', substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl; each of the R' groups is independently selected from the group consisting of H, OH, $NO_2$, $NH_2$, SH, CN, halogen, =O, C(=O)H, C(=O)$CH_3$, $CO_2H$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl;

$X_2$ is $OX_1$ or $N(X_1)_2$ wherein the or each $X_1$ is H, C(=O)R', substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted alkoxy, or substituted or unsubstituted heterocyclyl, or two $X_1$ groups may together form a cyclic substituent on the nitrogen atom;

$X_3$ is selected of $OR_1$, CN, (=O), or H;

$X_4$ is —H or $C_1$-$C_{18}$ alkyl; and $X_5$ is selected of H, OH, or —$OR_1$ (wherein $OR_1$ is as defined above).

In a related aspect, the invention provides compounds of formula:

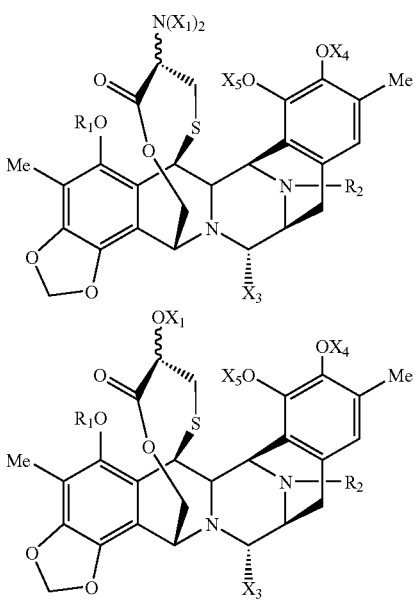

wherein the substituent groups defined by $R_1$, $R_2$, $X_3$, $X_4$ and $X_5$ are as defined; and $X_1$ is independently selected of H, C(=O)R', substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, or two $X_1$ groups may together form a cyclic substituent on the nitrogen atom.

Alkyl groups preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members. The alkyl groups may be straight chain or branched chain.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2 3 or 4 carbon atoms are particularly preferred.

Preferred alkylsulfonyl groups in the compounds of the present invention include those groups having one or more sulfonyl (SO2) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazolyl. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolidinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl such as 2-substituted phenyl, 3-substituted phenyl, 2,3-substituted phenyl, 2,5-substituted phenyl, 2,3,5-substituted phenyl and 2,4,5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

Substituent groups defined by $R_1$, $R_2$, $X_1$, $X_4$ and $X_5$ are each independently selected from the group consisting of H, OH, OR', SH, SR', SOR', $SO_2R'$, $NO_2$, $NH_2$, NHR', $N(R')_2$, NHC(O)R', CN, halogen, =O, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted heteroaromatic.

References herein to substituted R' groups in the compounds of the present invention refer to the specified moiety that may be substituted at one or more available positions by one or more suitable groups, e. g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl (e. g., R being a substituted or unsubstituted biphenyl moiety); and aralkyl such as benzyl.

$R_1$ is preferably C(=O)R', where R' is suitably H or substituted or unsubstituted alkyl, more preferably acetyl.

$R_2$ is preferably H or methyl, more preferably methyl.

Typically one of $X_1$ is often hydrogen. $X_2$, or where permitted $X_1$ is preferably H; —NHCOalkyl, particularly where the alkyl has up to 16 carbon atoms, such as 1, 4, 7, 15 carbon atoms and may be halosubstituted optionally perhalosubstituted; —NHalkylCOOH particularly where the alkyl has up to 4 carbon atoms; protected —$NHCOCH(NH_2)CH_2SH$ where the $NH_2$ and/or the SH are protected; —NHbiotin; —NHaryl; —NH(aa)$_y$ where aa is an amino acid acyl and y is suitably 1, 2 or 3 and wherein any $NH_2$ is optionally derivatised or protected, as with an amide terminal group or a Boc group; phthalimido formed —$NX_2$—; alkyl preferably having 1 to 4 carbon atoms; arylalkenyl, especially cinnamoyl which may be substituted as with 3-trifluoromethyl;

Preferred examples of the group $X_2$ include NHAc, NHCO$(CH_2)_2$COOH, NHCOCH(NHAlloc)$CH_2$SFm, NHCO$(CH_2)_{14}CH_3$, NHTFA, NHCO$(CH_2)_2CH_3$, NHCOCH$_2$CH$(CH_3)_2$, NHCO$(CH_2)_6CH_3$, NHBiotin, NHBz, NHCOCinn, NHCO—(p-$F_3$C)-Cinn, NHCOVal-$NH_2$, NHCOVal-N—Ac, NHCOVal-N—COCinn, NHCOVal-Ala-$NH_2$, NHCOVal-Ala-N—Ac, NHCOAla-$NH_2$, OH, OAc, NHAc, NHCO$(CH_2)_2$COOH, NHCOCH(NHAlloc)$CH_2$SFm, NHCOCH$(NH_2)CH_2$SFm, NPht, NH—(m-$CO_2$Me)-Bz, NHCO$(CH_2)_{14}CH_3$, NMe$_2$ NHTFA, NHCO$(CH_2)_2CH_3$, NHCOCH$_2$CH$(CH_3)_2$, NHCO$(CH_2)_6CH_3$, 'NHAlloc, NHTroc, NHBiotin, NHBz, NHCOCinn, NHCO—(p-$F_3$C)-Cinn, NHCOVal-$NH_2$, NHCOVal-N—Ac, NHCOVal-N—COCinn, NHCOVal-Ala-$NH_2$, NHCOVal-Ala-N—Ac, NHCOVal-Ala-N—COCinn, NHCOAla-$NH_2$, NHCOAla-N—Ac, NHCOAla-N—COCinn, OH, OAc, NHAc, NHCO$(CH_2)_2$COOH, NHCOCH(NHAlloc)$CH_2$SFm, Npht, along with similar groups where the number of carbon atoms is varied or the amino acid is changed or another change of this kind is made to give a similar group.

Other preferred examples of the group $X_2$ include OH, OAc, OCOCF$_3$, OCOCH$_2$CH$_2$CH$_3$, OCO$(CH_2)_6CH_3$, OCO$(CH_2)_{14}CH_3$, OCOCH=CHPh, OSO$_2$CH$_3$ along with similar groups where the number of carbon atoms is varied or different substituent groups are introduced or another change of this kind is made to give a similar group.

$X_3$ is preferably OH or CN.

$X_4$ is H or Me, preferably Me.

$X_5$ is H or $C_{1-18}$ alkyl, preferably H.

In a further, more general aspect of this invention, the compounds are typically of the formula (XVIIa):

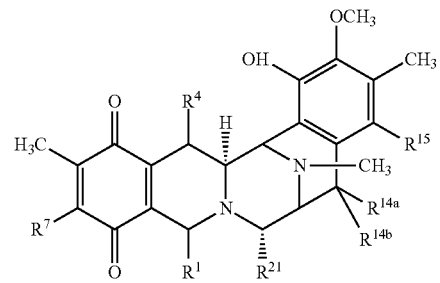

or formula (XVIIb):

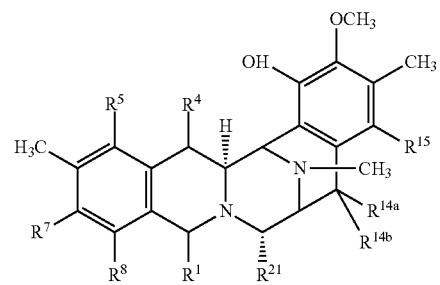

where
R¹ and R⁴ together form a group of formula (VIa) or (VIb):

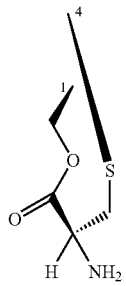

VIa

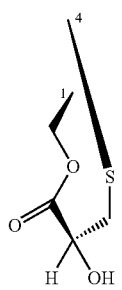

VIb

R⁵ is —H or —OH;
R⁷ is —OCH₃ and R⁸ is —OH or R⁷ and R⁸ together form a group —O—CH₂—O—;
R¹⁴ᵃ and R¹⁴ᵇ are both —H or one is —H and the other is —OH, —OCH₃ or —OCH₂CH₃, or R¹⁴ᵃ and R¹⁴ᵇ together form a keto group; and
R¹⁵ is —H or —OH;
R²¹ is —H, —OH or —CN;
and derivatives including acyl derivatives thereof especially where R⁵ is acetyloxy or other acyloxy group of up to 4 carbon atoms, and including derivatives where the group —NCH₃— at the 12-position is replaced by —NH— or —NCH₂CH₃—, and derivatives where the —NH₂ group in the compound of formula (VIa) and the —OH group in the compound of formula (VIb) are optionally derivatised.

The group R₁ with R₄ can be acylated on the —CHNH₂— or —CHOH— group present in the formulae (VIa and VIb). Other derivative compounds of this invention comprise those where the —CHNH₂ group of VIa is replaced by a group —CHNHX₁ or —C(X₂)₂— or where the —CHOH group of VIb is replaced by CHOX₁ or —C(X₂)₂— where X₁ or X₂ are as defined.

Preferred compounds are of the formula (XVIIb).
Furthermore, in preferred compounds of this invention, R⁷ and R⁸ together form a group —O—CH₂—O—.
The acyl derivatives can be N-acyl or N-thioacyl derivatives thereof, as well as cyclic amides. The acyl groups can illustratively be alkanoyl, haloalkanoyl, arylalkanoyl, alkenyl, heterocyclylacyl, aroyl, arylaroyl, haloaroyl, nitroaroyl, or other acyl groups. The acyl groups can be of formula —CO—Rᵃ, where Rᵃ can be various groups such as alkyl, alkoxy, alkylene, arylalkyl, arylalkylene, amino acid acyl, or heterocyclyl, each optionally substituted with halo, cyano, nitro, carboxyalkyl, alkoxy, aryl, aryloxy, heterocyclyl, heterocycyloxy, alkyl, amino or substituted amino. Other acylating agents include isothiocyanates, such as aryl isothiocyanates, notably phenyl isocyanate. The alkyl, alkoxy or alkylene groups of Rᵃ suitably have 1 to 6 or 12 carbon atoms, and can be linear, branched or cyclic. Aryl groups are typically phenyl, biphenyl or naphthyl. Heterocyclyl groups can be aromatic or partially or completely unsaturated and suitably have 4 to 8 ring atoms, more preferably 5 or 6 ring atoms, with one or more heteroatoms selected from nitrogen, sulphur and oxygen.

Without being exhaustive, typical Rᵃ groups include alkyl, haloalkyl, alkoxyalkyl, haloalkoxyalkyl, arylalkylene, haloalkylarylalkylene, acyl, haloacyl, arylalkyl, alkenyl and amino acid. For example, Rᵃ—CO— can be acetyl, trifluoroacetyl, 2,2,2-trichloroethoxycarbonyl, isovalerylcarbonyl, trans-3-(trifluoromethyl)cinnamoylcarbonyl, heptafluorobutyrylcarbonyl, decanoylcarbonyl, trans-cinnamoylcarbonyl, butyrylcarbonyl, 3-chloropropyonylcarbonyl, cinnamoylcarbonyl, 4-methylcinnamoylcarbonyl, hydrocinnamoylcarbonyl, or trans-hexenoylcarbonyl, or alanyl, arginyl, aspartyl, asparagyl, cystyl, glutamyl glutaminyl, glycyl, histidyl, hydroxyprolyl, isoleucyl, leucyl, lysyl, methionyl, phenylalanyl, prolyl, seryl, threonyl, thyronyl, tryptophyl, tyrosyl, valyl, as well as other less common amino acid acyl groups, as well as phthalimido and other cyclic amides. Other examples may be found among the listed protecting groups.

Compounds wherein —CO—Rᵃ is derived from an amino acid and include an amino group can themselves form acyl derivatives. Suitable N-acyl commands include dipeptides which in turn can form N-acyl derivatives.

Preferably R¹⁴ᵃ and R¹⁴ᵇ are hydrogen. Preferably R¹⁵ is hydrogen. The O-acyl derivatives are suitably aliphatic O-acyl derivatives, especially acyl derivatives of 1 to 4 carbon atoms, and typically an O-acetyl group, notably at the 5-position.

Suitable protecting groups for phenols and hydroxy groups include ethers and esters, such as alkyl, alkoxyalkyl, aryloxyalkyl, alkoxyalkoxyalkyl, alkylsilylalkoxyalkyl, alkylthioalkyl, arylthioalkyl, azidoalkyl, cyanoalkyl, chloroalkyl, heterocyclic, arylacyl, haloarylacyl, cycloalkylalkyl, alkenyl, cycloalkyl, alkylarylalkyl, alkoxyarylalkyl, nitroarylalkyl, haloarylalkyl, alkylaminocarbonylarylalkyl, alkylsulfinylarylalkyl, alkylsilyl and other ethers, and arylacyl, aryl alkyl carbonate, aliphatic carbonate, alkylsulfinylarylalkyl carbonate, alkyl carbonate, aryl haloalkyl carbonate, aryl alkenyl carbonate, aryl carbamate, alkyl phosphinyl, alkylphosphinothioyl, aryl phosphinothioyl, aryl alkyl sulphonate and other esters. Such groups may optionally be substituted with the previously mentioned groups in R¹.

Suitable protecting groups for amines include carbamates, amides, and other protecting groups, such as alkyl, arylalkyl, sulpho- or halo- arylalkyl, haloalkyl, alkylsilylalkyl, arylalkyl, cycloalkylalkyl, alkylarylalkyl, heterocyclylalkyl, nitroarylalkyl, acylaminoalkyl, nitroaryldithioarylalkyl, dicycloalkylcarboxamidoalkyl, cycloalkyl, alkenyl, arylalkenyl, nitroarylalkenyl, heterocyclylalkenyl, heterocyclyl, hydroxyheterocyclyl, alkyldithio, alkoxy- or halo- or alkylsulphinyl arylalkyl, heterocyclylacyl, and other carbamates, and alkanoyl, haloalkanoyl, arylalkanoyl, alkenoyl, heterocyclylacyl, aroyl, arylaroyl, haloaroyl, nitroaroyl, and other amides, as well as alkyl, alkenyl, alkylsilylalkoxyalkyl, alkoxyalkyl, cyanoalkyl, heterocyclyl, alkoxyarylalkyl, cycloalkyl, nitroaryl, arylalkyl, alkoxy- or hydroxy-arylalkyl, and many other groups. Such groups may optionally be substituted with the previously mentioned groups in R¹.

Examples of such protecting groups are given in the following tables.

| protection for —OH group | abbreviation |
|---|---|
| ethers | |
| methyl | |
| methoxymethyl | MOM |
| benzyloxymethyl | BOM |
| methoxyethoxymethyl | MEM |
| 2-(trimethylsilyl)ethoxymethyl | SEM |
| methylthiomethyl | MTM |
| phenylthiomethyl | PTM |
| azidomethyl | |
| cyanomethyl | |
| 2,2-dichloro-1,1-difluoroethyl | |
| 2-chloroethyl | |
| 2-bromoethyl | |
| tetrahydropyranyl | THP |
| 1-ethoxyethyl | EE |
| phenacyl | |
| 4-bromophenacyl | |
| cyclopropylmethyl | |
| allyl | |
| propargyl | |
| isopropyl | |
| cyclohexyl | |
| t-butyl | |
| benzyl | |
| 2,6-dimethylbenzyl | |
| 4-methoxybenzyl | MPM or PMB |
| o-nitrobenzyl | |
| 2,6-dichlorobenzyl | |
| 3,4-dichlorobenzyl | |
| 4-(dimethylamino)carbonylbenzyl | |
| 4-methylsufinylbenzyl | Msib |
| 9-anthrylmethyl | |
| 4-picolyl | |
| heptafluoro-p-tolyl | |
| tetrafluoro-4-pyridyl | |
| trimethylsilyl | TMS |
| t-butyldimethylsilyl | TBDMS |
| t-butyldiphenylsilyl | TBDPS |
| triisopropylsilyl | TIPS |
| esters | |
| aryl formate | |
| aryl acetate | |
| aryl levulinate | |
| aryl pivaloate | ArOPv |
| aryl benzoate | |
| aryl 9-fluorocarboxylate | |
| aryl methyl carbonate | |
| 1-adamantyl carbonate | |
| t-butyl carbonate | BOC-OAr |
| 4-methylsulfinylbenzyl carbonate | Msz-Oar |
| 2,4-dimethylpent-3-yl carbonate | Doc-Oar |
| aryl 2,2,2-trichloroethyl carbonate | |
| aryl vinyl carbonate | |
| aryl benzyl carbonate | |
| aryl carbamate | |
| dimethylphosphinyl | Dmp-OAr |
| dimethylphosphinothioyl | Mpt-OAr |
| diphenylphosphinothioyl | Dpt-Oar |
| aryl methanesulfonate | |
| aryl toluenesulfonate | |
| aryl 2-formylbenzenesulfonate | |

| protection for the —NH$_2$ group | abbreviation |
|---|---|
| carbamates | |
| methyl | |
| ethyl | |
| 9-fluorenylmethyl | Fmoc |
| 9-(2-sulfo)fluorenylmethyl | |
| 9-(2,7-dibromo)fluorenylmethyl | |
| 17-tetrabenzo[a,c,g,i]fluorenylmethyl | Tbfmoc |
| 2-chloro-3-indenylmethyl | Climoc |
| benz[f]inden-3-ylmethyl | Bimoc |
| 2,7-di-t-butyl[9-(10,10-dioxo-10,10,10-tetrahydrothioxanthyl)]methyl | DBD-Tmoc |
| 2,2,2-trichloroethyl | Troc |
| 2-trimethylsilylethyl | Teoc |
| 2-phenylethyl | hZ |
| 1-(1-adamantyl)-1-methylethyl | Adpoc |
| 2-chlooethyl | |
| 1,1-dimethyl-2-chloroethyl | |
| 1,1-dimethyl-2-bromoethyl | |
| 1,1-dimethyl-2,2-dibromoethyl | DB-t-BOC |
| 1,1-dimethyl-2,2,2-trichloroethyl | TCBOC |
| 1-methyl-1-(4-biphenyl)ethyl | Bpoc |
| 1-(3,5-di-t-butylphenyl)-1-1-methylethyl | t-Burmeoc |
| 2-(2'-and 4'-pyridyl)ethyl | Pyoc |
| 2,2-bis(4'-nitrophenyl)ethyl | Bnpeoc |
| n-(2-pivaloylamino)-1,1-dimethylethyl | |
| 2-[(2-nitrophenyl)dithio]-1-phenylethyl | NpSSPeoc |
| 2-(n,n-dicyclohexylcarboxamido)ethyl | |
| t-butyl | BOC |
| 1-adamantyl | 1-Adoc |
| 2-adamantyl | 2-Adoc |
| vinyl | Voc |
| allyl | Aloc or Alloc |
| 1-isopropylallyl | Ipaoc |
| cinnamyl | Coc |
| 4-nitrocinnamyl | Noc |
| 3-(3'-pyridyl)prop-2-enyl | Paloc |
| 8-quinolyl | |
| n-hydroxypiperidinyl | |
| alkyldithio | |
| benzyl | Cbz or Z |
| p-methoxybenzyl | Moz |
| p-nitrobenzyl | PNZ |
| p-bromobenzyl | |
| p-chlorobenzyl | |
| 2,4-dichlorobenzyl | |
| 4-methylsulfinylbenzyl | Msz |
| 9-anthrylmethyl | |
| diphenylmethyl | |
| phenothiazinyl-(10)-carbonyl | |
| n'-p-toluenesulfonylaminocarbonyl | |
| n'-phenylaminothiocarbonyl | |
| amides | |
| formamide | |
| acetamide | |
| chloroacetamide | |
| trifluoroacetamide | TFA |
| phenylacetamide | |
| 3-phenylpropanarnide | |
| pent-4-enamide | |
| picolinamide | |
| 3-pyridylcarboxamide | |
| benzamide | |
| p-phenylbenzamide | |
| n-phthalimide | |
| n-tetrachlorophthalimide | TCP |
| 4-nitro-n-phthalimide | |
| n-dithiasuccinimide | Dts |
| n-2,3-diphenylmaleimide | |
| n-2,5-dimethylpyrrole | |
| n-2,5-bis(triisopropylsiloxy)pyrrole | BIPSOP |
| n-1,1,4,4-tetramethyldisiliazacyclopentante adduct | STABASE |
| 1,1,3,3-tetramethyl-1,3-disilaisoindoline | BSB |

-continued

| protection for the —NH₂ group | |
|---|---|
| | abbreviation |
| special —NH protective groups | |
| n-methylamine | |
| n-t-butylamine | |
| n-allylamine | |
| n-[2-trimethylsilyl)ethoxy]methylamine | SEM |
| n-3-acetoxypropylamine | |
| n-cyanomethylamine | |
| n-(1-isopropyl-4-nitro-2-oxo-3-pyrrolin-3-yl)amine | |
| n-2,4-dimethoxybenzylamine | Dmb |
| 2-azanorbornenes | |
| n-2,4-dinitrophenylamine | |
| n-benzylamine | Bn |
| n-4-methoxybenzylamine | MPM |
| n-2,4-dimethoxybenzylamine | DMPM |
| n-2-hydroxybenzylamine | Hbn |
| n-(diphenylmethyl)amino | DPM |
| n-bis(4-methoxyphenyl)methylamine | |
| n-5-dibenzosuberylamine | DBS |
| n-triphenylmethylamine | Tr |
| n-[(4-methoxyphenyl)diphenylmethyl]amino | MMTr |
| n-9-phenylflurenylamine | Pf |
| n-ferrocenylmethylamine | Fcm |
| n-2-picolylamine n'-oxide | |
| n-1,1-dimethylthiomethyleneamine | |
| n-benzylideneamine | |
| n-p-methoxybenzylideneamine | |
| n-diphenylmethyleneamine | |
| n-(5,5-dimelhyl-3-oxo-1-cyclohexenyl)amine | |
| n-nitroamine | |
| n-nitrosoamine | |
| diphenylphosphinamide | Dpp |
| dimethylthiophosphinamide | Mpt |
| diphenylthiophosphinamide | Ppt |
| dibenzyl phosphoramidate | |
| 2-nitrobenzenesulfenamide | Nps |
| n-1-(2,2,2-trifluoro-1,1-diphenyl)ethylsufenamide | TDE |
| 3-nitro-2-pyridinesulfenamide | Npys |
| p-toluenesulfonamide | Ts |
| benzenesulfonamide | |

A preferred class of compounds of this invention include compounds of formula (XVIIb), where one or more, preferably all of the following conditions are met:

the amino group in the group of formula (VIa) is derivatised;
the hydroxy group in the group of formula (VIb) is derivatised;
$R^5$ is $OR_1$;
$R^7$ and $R^8$ together form a group —O—CH$_2$—O—;
$R^{14a}$ and $R^{14b}$ are both —H;
$R^{15}$ is H; and/or
$R^{21}$ is —OH or —CN.

Particular ecteinascidin products of this invention include compounds of the formula (XVIII);

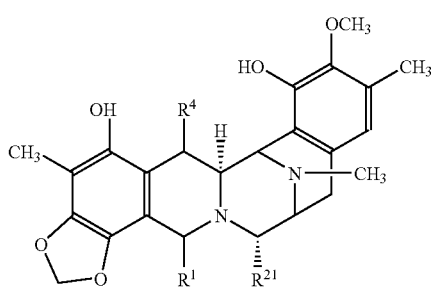

where R1 and R4 form a group of formula (VIa or VIb):

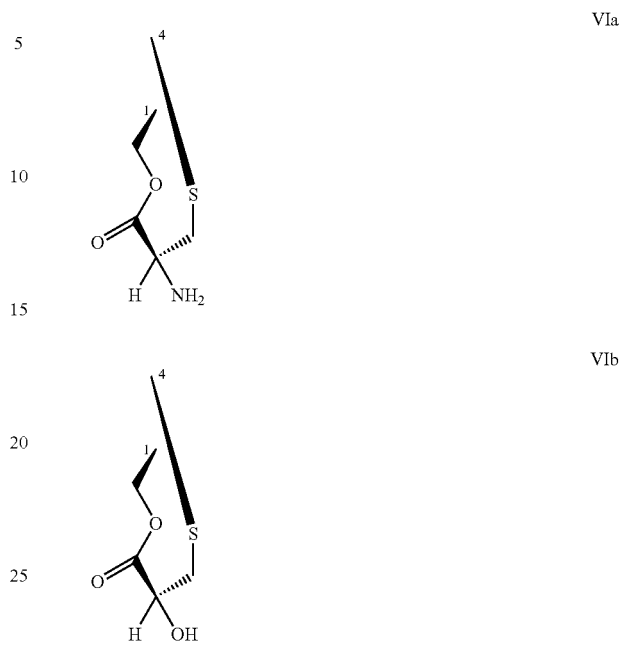

$R^{21}$ is —H, —OH or —CN, more particularly —OH or —CN;

and acyl derivatives thereof, more particularly 5-acyl derivatives including the 5-acetyl derivative, and where the —NH$_2$ group in the structure of formula (VIa) and the —OH group in the structure of formula (VIb) are optionally derivatised.

Compounds of the present invention notably with one of two group $X_1$ can be prepared synthetically from the intermediate compound (47) described in the U.S. Pat. No. 5,721,362, or a similar compound. Thus the present invention provides a process which involves derivatisation of the 1,4 bridge amino group, according to the following reaction scheme:

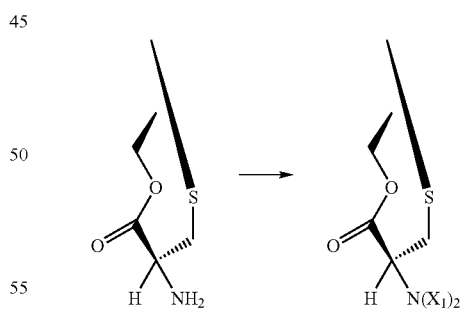

where $X_1$ is as defined, and other substituent groups on the molecule can be protected or derivatised as desired or appropriate.

Compounds of this invention notably with the groups $X_2$ being —OX$_2$ can be prepared from the intermediate compound (15) described in the U.S. Pat. No. 5,721,362 or a similar compound. Thus, the present invention provides a process which involves derivatisation of the 1,4 bridge amino group, according to the following reaction scheme:

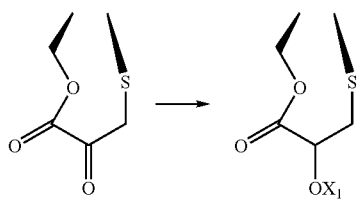

where $X_1$ is as defined, and other substituent groups on the molecule can be protected or derivatised as desired or appropriate. The reaction may proceed with formation of a substituent $—OX_1$ where $X_1$ is hydrogen, and then conversion to a compound where $X_1$ is another group.

It will be apparent that compounds of this invention may also be prepared by modification of the synthetic steps employed in the U.S. Pat. No. 5,721,362. Thus, for instance, different reactive groups may be introduced at functional positions, for example at the 5- or 18-positions.

A more general route to compounds of this invention is provided, and was first disclosed in WO 00/69862, incorporated herein in full by reference and from which priority is claimed.

A typical process of that WO application concerns method for preparing a compound with a fused ring structure of formula (XIV):

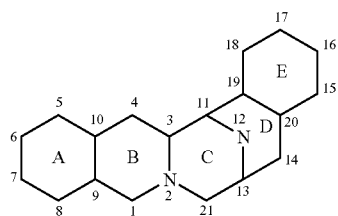

which comprises one or more reactions starting from a 21-cyano compound of formula (XVI):

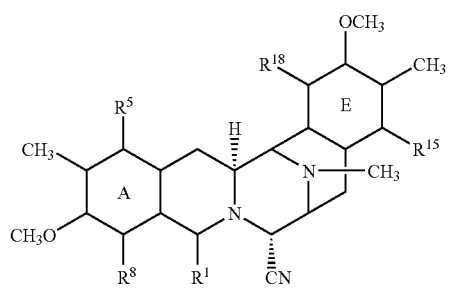

where:
$R^1$ is an amidomethylene group or an acyloxymethylene group;

$R^5$ and $R^8$ are independently chosen from —H, —OH or —OCOCH$_2$OH, or $R^5$ and $R^8$ are both keto and the ring A is a p-benzoquinone ring;

$R^{14a}$ and $R^{14b}$ are both —H or one is —H and the other is —OH, —OCH$_3$ or —OCH$_2$CH$_3$ or $R^{14a}$ and $R^{14b}$ together form a keto group; and $R^{15}$ and $R^{18}$ are independently chosen from —H or —OH, or $R^5$ and $R^8$ are both keto and the ring A is a p-benzoquinone ring.

In particular, such a method can provide a route to the starting materials for the reactions of Schemes I and II, along with related compounds.

Antitumoral activities of these compounds include leukaemias, lung cancer, colon cancer, kidney cancer, prostate cancer, ovarian cancer, breast cancer, sarcomas and melanomas.

Another especially preferred embodiment of the present invention is pharmaceutical compositions useful as antitumour agents which contain as active ingredient a compound or compounds of the invention, as well as the processes for their preparation.

Examples of pharmaceutical compositions include any solid (tablets, pills, capsules, granules etc.) or liquid (solutions, suspensions or emulsions) with suitable composition or oral, topical or parenteral administration.

Administration of the compounds or compositions of the present invention may be any suitable method, such as intravenous infusion, oral preparation, intraperitoneal and intravenous preparation.

For the avoidance of doubt, the stereochemistries indicated in this patent specification are based on our understanding of the correct stereochemistry of the natural products. To the extent that an error is discovered in the assigned stereochemistry, then the appropriate correction needs to be made in the formulae given throughout in this patent specification. Furthermore, to the extent that the syntheses are capable of modification, this invention extends to stereoisomers.

DETAILED DESCRIPTION OF PREFERRED PROCESSES

The compounds of the present invention can be synthetically prepared from the intermediate compounds 47 and 15 described in the U.S. Pat. No. 5,721,362, the compound 36 described in WO 00/69862 and from the secondary products (numbered here as 23 and 24) obtained in some deprotection steps using AlCl$_3$ of the compound 33 of WO 00/69862.

47(1)

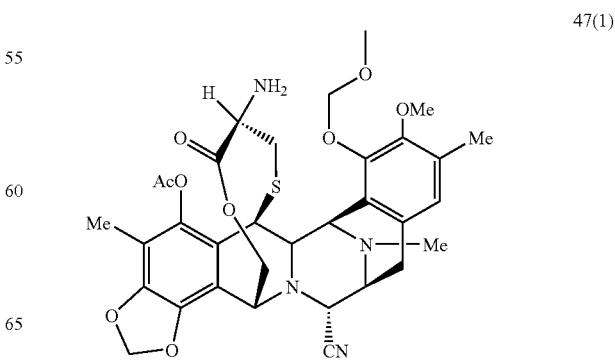

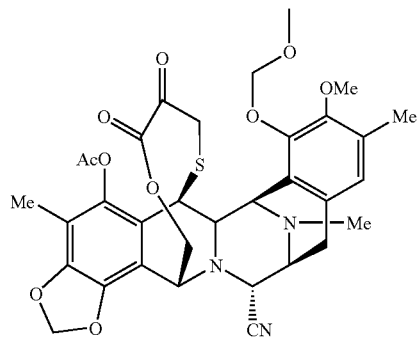

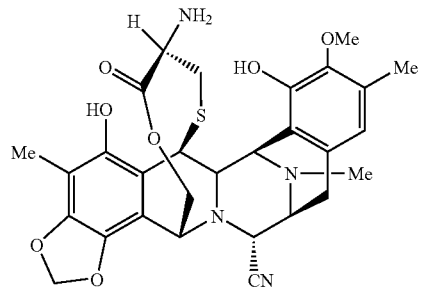

Compound (1) corresponds to the synthetic intermediate (47) described in the U.S. Pat. No. 5,721,362. Compounds 27 and 28 included in Table IV are described as 35 and 34 in WO 00/69862.

Some of the preferred methods of producing the compound of formula I are described below in the following reaction schemes with examples of typical substituent groups. These typical substituents are not limiting of the invention, and the process is to be understood in the more general sense, without special regard to the identities indicated by the code letters.

Numerous active antitumoral compounds have been prepared from this compounds and it is believed that many more compounds can be formed in accordance with the teachings of the present disclosure.

SCHEME I

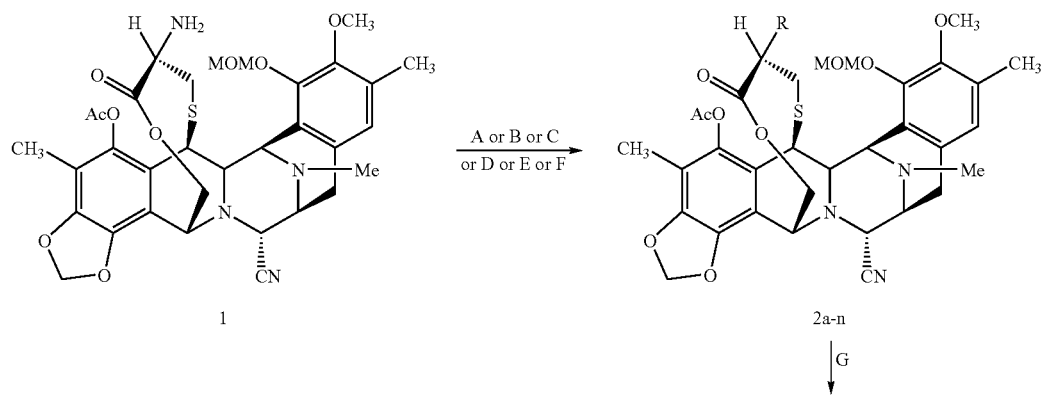

-continued
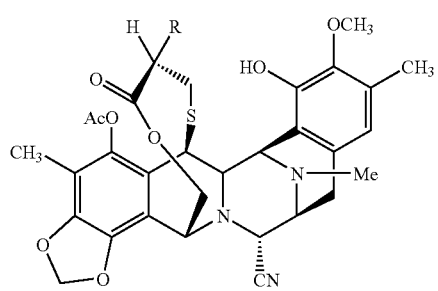
4a-i, 4k-l, 4n, 4o
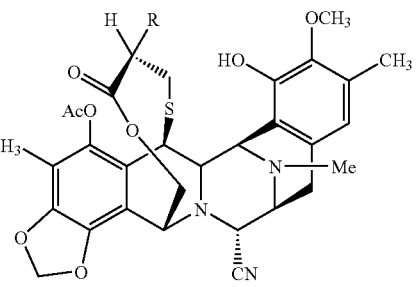
3a-n, 3o
I or J
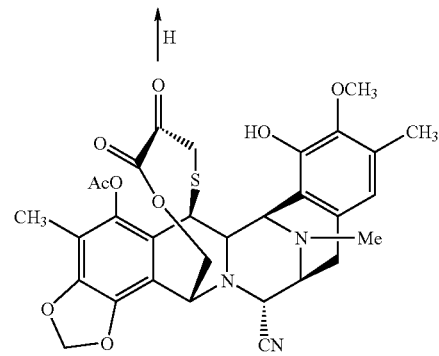
5
R: a: AcNH-
b: F$_3$CCONH-
c: CH$_3$(CH$_2$)$_2$CONH-
d: (CH$_3$)$_2$CHCH$_2$CONH-
e: CH$_3$(CH$_2$)$_6$CONH-
f: CH$_3$(CH$_2$)$_{14}$CONH-
g: BzNH-
h: CinnCONH-
i: p-F$_3$C-CinnCONH-
j: PhtN-
k: BiotinCONH-
l: HO$_2$CCH$_2$CH$_2$CONH-
m: (CH$_3$)$_2$N-
n: BnNH-
o: PrNH-
Cinn:
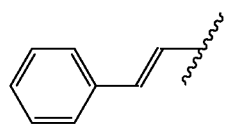
SCHEME II
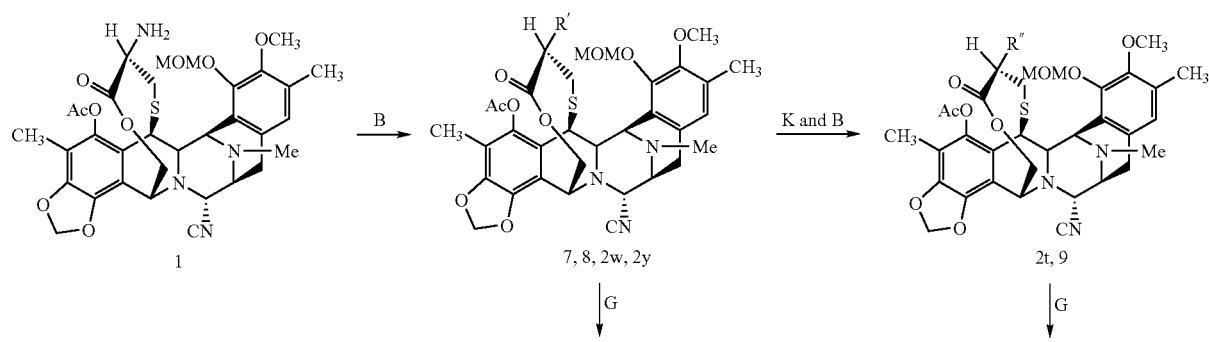

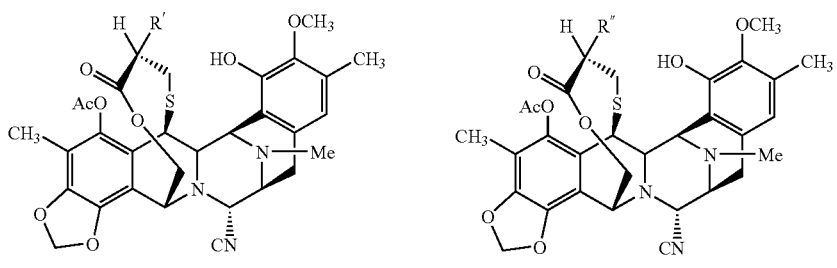
3p, 3v-w, 3y-z → 3s-t
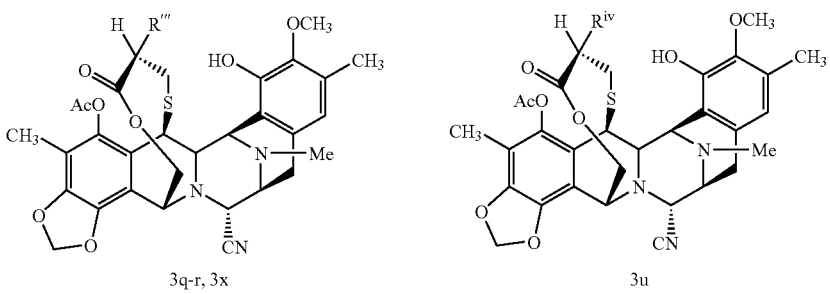
3q-r, 3x → 3u
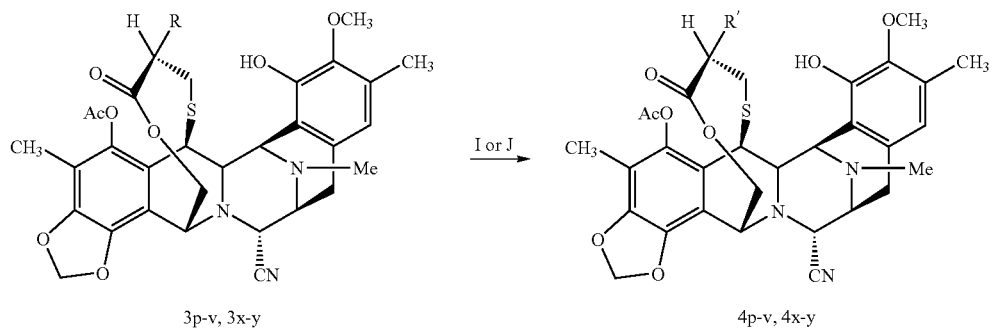
3p-v, 3x-y → I or J → 4p-v, 4x-y
R = R′, R″, R‴, R$^{iv}$
R: p: NH$_2$-ValCONH-
q: Ac-N-Val CONH-
r: CinnCO-N-ValCONH-
s: NH$_2$-Ala-ValCONH-
t: Ac-N-Ala-ValCONH-
u: CinnCO-N-Ala-ValCONH-
v: NH$_2$-AlaCONH-
w: Ac-N-AlaCONH-
x: CinnCO-N-AlaCONH-
y: FmSCH$_2$CH(NHAlloc)CONH-
z: FmSCH$_2$CH(NH$_2$)CONH-
7: Boc-N-ValCONH-
8: Boc-N-AlaCONH-
9: Boc-N-Ala-ValCONH
SCHEME III
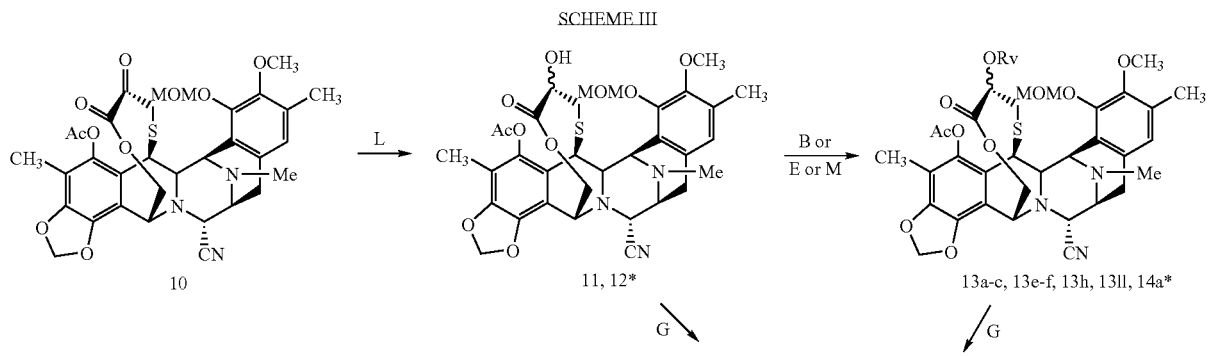
10 → L → 11, 12* → B or E or M → 13a-c, 13e-f, 13h, 13ll, 14a*
            ↓ G                                    ↓ G

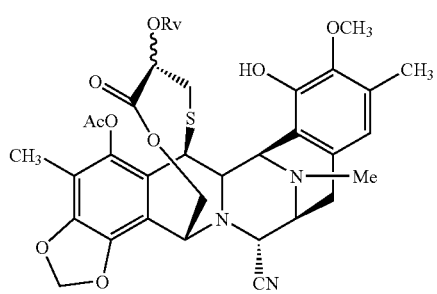

19, 21a, 21c, 21e-f, 21b, 21ll, 22a*

R$^v$:  a: Ac-
b: F$_3$CCO-
c: CH$_3$(CH$_2$)$_2$CO-
e: CH$_3$(CH$_2$)$_6$CO-
f: CH$_3$(CH$_2$)$_{14}$CO-

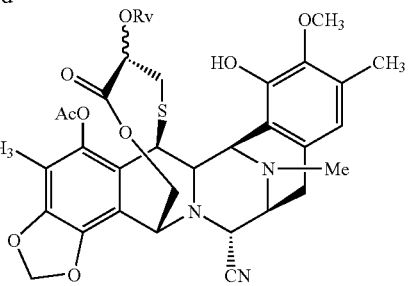

15, 16*, 17a-c, 17e-f, 17b, 17ll, 18a* h: CinnCO-
ll: MeSO$_2$-
15: H-
16: H-
19: H-

Cinn:

SCHEME IV

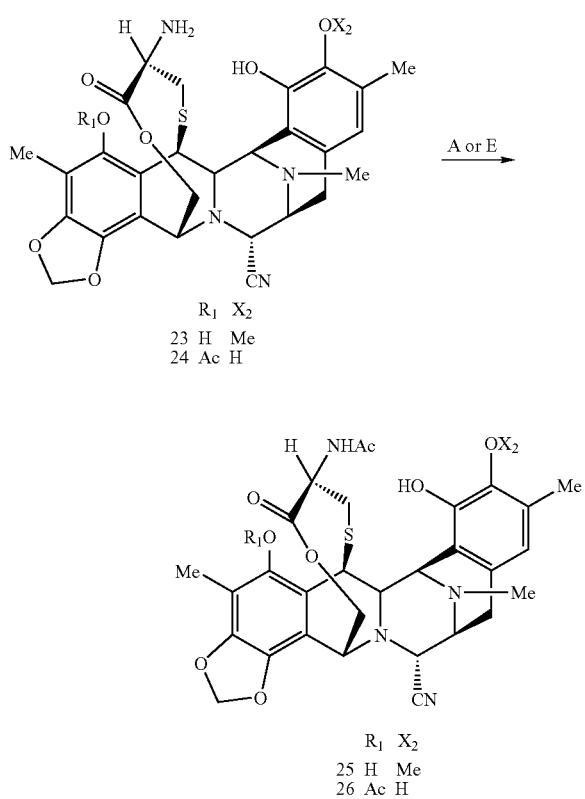

| | R$_1$ | X$_2$ |
|---|---|---|
| 23 | H | Me |
| 24 | Ac | H |

| | R$_1$ | X$_2$ |
|---|---|---|
| 25 | H | Me |
| 26 | Ac | H |

The type of reactions are the following:

Methods A, B, C, E and M include different acylation methods with acid chlorides, anhydrides, acids or sulfonyl chlorides, to obtain amide or ester bonds.

Methods D and H involve reductive alkylation reactions between an aldehyde and 1 or an amine and 5 to give 2m or 3o.

Method F transforms compound 1 to 2n by reaction with BnBr and Cs$_2$CO$_3$.

Method G involves the deprotection of methoxymethyl group (MOM) or MOM/tert-butyloxy carbonyl groups or MOM/allyloxy carbonyl groups using trimethylchlorosilane (TMSCl) and sodium iodide.

Methods I (AgNO$_3$) and J (CuBr) convert CN into OH in position C-21.

Method K involves the hydrolysis of a carbamate bond using aqueous trifluoroacetic acid.

Method L converts a cabonyl group to an alcohol by reduction with NaCNBH$_3$ in the presence of acetic acid. With this reaction a new chiral center is generated. Taking into account steric effects and spectroscopic data, it seem that the main compound (11) has R configuration at this center and the secondary product (12*) has S configuration. On this basis 13, 15, 17, 19, 21 will have R configuration and 14*, 18* and 22* will have S configuration. These assignments have been made based on the available spectral data and as such, in the absence of specific studies to confirm the assignments, should be considered as only tentative.

Modified processes can be used to prepare other compounds of this invention. In particular the starting material and/or reagents and reactions can be varied to suit other combinations of the substituent groups.

In another aspect, the present invention is directed at the use of a known compound, safracin B, also referred to as quinonamine, in hemisynthetic synthesis.

More generally, the invention relates to a hemisynthetic process for the formation of intermediates, derivatives and related structures of ecteinascidin or other tetrahydroisoquinolinephenol compounds starting from natural bis(tetrahydroisoquinoline) alkaloids.

Suitable preferred starting materials for the hemi-synthetic process include the classes of saframycin and safracin antibiotics available from different culture broths, and also the classes of reineramicin and xestomycin compounds available from marine sponges.

A general formula (XV) for the starting compounds is as follows:

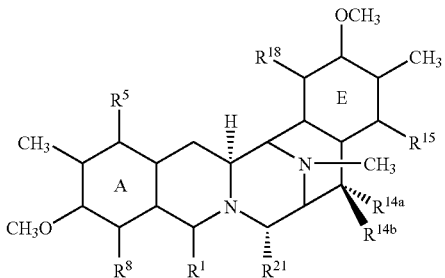

where:
- $R^1$ is an amidomethylene group such as —$CH_2$—NH—CO—$CR^{25a}R^{25b}R^{25c}$ where $R^{25a}$ and $R^{25b}$ form a keto group or one is —OH, —$NH_2$ or —$OCOCH_3$ and the other is —$CH_2COCH_3$, —H, —OH or —$OCOCH_3$, provided that when $R^{25a}$ is —OH or —$NH_2$ then $R^{25b}$ is not —OH, and $R^{25c}$ is —H, —$CH_3$ or —$CH_2CH_3$, or $R^1$ is an acyloxymethylene group such as —$CH_2$—O—CO—R, where R is —$C(CH_3)$=CH—$CH_3$ or —$CH_3$;
- $R^5$ and $R^8$ are independently chosen from —H, —OH or —$OCOCH_2OH$, or $R^5$ and $R^8$ are both keto and the ring A is a p-benzoquinone ring;
- $R^{14a}$ and $R^{14b}$ are both —H or one is —H and the other is —OH, —$OCH_3$ or —$OCH_2CH_3$, or $R^{14a}$ and $R^{14b}$ together form a keto group;
- $R^{15}$ and $R^{18}$ are independently chosen from —H or —OH, or $R^5$ and $R^8$ are both keto and the ring A is a p-benzoquinone ring; and
- $R^{21}$ is —OH or —CN.

A more general formula for these class of compounds is provided below:

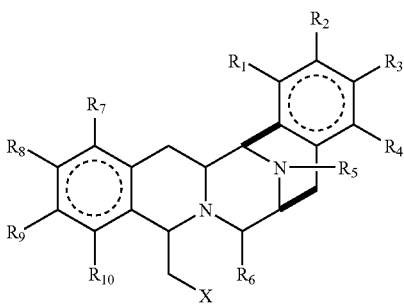

wherein the substituent groups defined by $R_1$, $R_2$, $R_3$, $R_4$, $R_5$, $R_6$, $R_7$, $R_8$, $R_9$, $R_{10}$ are each independently selected from the group consisting of H, OH, $OCH_3$, CN, =O, $CH_3$; wherein X are the different amide or ester functionalities contained in the mentioned natural products; wherein each dotted circle represents one, two or three optional double bonds.

Thus, according to the present invention, we now provide hemisynthetic routes for the production of new and known compounds. The hemisynthetic routes of the invention each comprise a number of transformation steps to arrive at the desired product. Each step in itself is a process in accordance with this invention. The invention is not limited to the routes that are exemplified, and alternative routes may be provided by, for example, changing the order of the transformation steps, as appropriate.

In particular, this invention involves the provision of a 21-cyano starting material of general formula (XVI):

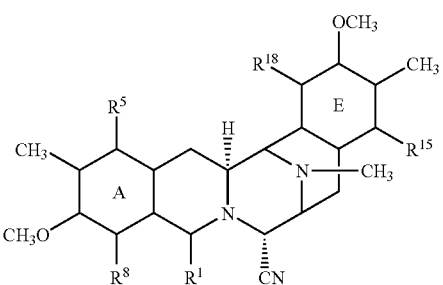

where $R^1$, $R^5$, $R^8$, $R^{14a}$, $R^{14b}$, $R^{15}$ and $R^{18}$ are as defined.

Other compounds of formula (XVI) with different substituents at the 21-position may also represent possible starting materials. In general, any derivative capable of production by nucleophilic displacement of the 21-hydroxy group of compounds of formula (XV) wherein $R^{21}$ is a hydroxy group is a candidate. Examples of suitable 21-substituents include but are not limited to:
- a mercapto group;
- an alkylthio group (the alkyl group having from 1 to 6 carbon atoms);
- an arylthio group (the aryl group having from 6 to 10 carbon atoms and being unsubstituted or substituted by from 1 to 5 substituents selected from, for example, alkyl group having from 1 to 6 carbon atoms, alkoxy groups having from 1 to 6 carbon atoms, halogen atoms, mercapto groups and nitro groups);
- an amino group;
- a mono-or dialkylamino (the or each alkyl group having from 1 to 6 carbon atoms);
- a mono-or diarylamino group (the or each aryl group being as defined above in relation to arylthio groups);
- an α-carbonylalkyl group of formula —$C(R^a)(R^b)$—C(=O)$R^c$, where $R^a$ and $R^b$ are selected from hydrogen atoms, alkyl groups having from 1 to 20 carbon atoms, aryl groups (as defined above in relation to arylthio groups) and aralkyl groups (in which an alkyl group having from 1 to 4 carbon atoms is substituted by an aryl group a defined above in relation to arylthio groups), with the proviso that one of $R^a$ and $R^b$ is a hydrogen atom;

$R^c$ is selected from a hydrogen atom, an alkyl group having from 1 to 20 carbon atoms, aryl groups (as defined above in relation to arylthio groups), an aralkyl group (in which an alkyl group having from 1 to 4 carbon atoms is substituted by an aryl group a defined above in relation to arylthio groups), an alkoxy group having from 1 to 6 carbon atoms, an amino group or a mono- or dialkylamino group as defined above.

Thus, in a more general aspect, the present invention relates to processes where the first step is to form a 21-derivative using a nucleophilic reagent. We refer to such compounds as 21-Nuc compounds. Preferred starting material 21-Nuc compounds have the structure of formula (XIV):

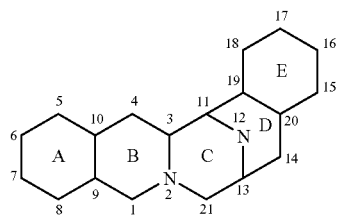

where at least one ring A or E is quinolic.

Thus, in addition to the use of 21-cyano compounds, processes using other nucleophile-containing compounds, to produce similar compounds of formula (XVI) wherein the 21-position is protected by another nuclephilic group, a 21-Nuc group, are also envisaged. For example, a 21-Nuc compound of formula (XVI) with an alkylamino substituent at the 21-position can be produced by reacting the compound of formula (XV) wherein $R^{21}$ is a hydroxy group with a suitable alkylamine. A 21-Nuc compound of formula (XVI) with an alkylthio substituent at the 21-position can also be produced by reacting the compound of formula (XV) wherein $R^{21}$ is a hydroxy group with a suitable alkanethiol. Alternatively, a 21-Nuc compound of formula (XVI) with an α-carbonylalkyl substituent at the 21-position can be produced by reacting the compound of formula (XV) wherein $R^{21}$ is a hydroxy group with a suitable carbonyl compound, typically in the presence of a base. Other routes are available for other 21-Nuc compounds.

The presence of the 21-cyano group is required for some of the end-products, notably ecteinascidin 770 and phthalascidin, while for other end-products it acts as a protecting group which can readily be converted to another substituent, such as the 21-hydroxy group. The adoption of the 21-cyano compound as the starting material effectively stabilises the molecule during the ensuing synthetic steps, until it is optionally removed. Other 21-Nuc compounds can offer this and other advantages.

Preferred starting materials include those compounds of formula (XV) or (XVI) where $R^{14a}$ and $R^{14b}$ are both hydrogen. Preferred starting materials also include compounds of formula (XV) or (XVI) where $R^{15}$ is hydrogen. Furthermore, the preferred starting materials include compounds of formula (XV) or (XVI) where ring E is a phenolic ring. Preferred starting materials further include compounds of formula (XV) or (XVI) where at least one, better at least two or three of $R^5$, $R^8$, $R^{15}$ and $R^{18}$ is not hydrogen.

Examples of suitable starting materials for this invention include saframycin A, saframycin B, saframycin C, saframycin G, saframycin H, saframycin S, saframycin $Y_3$, saframycin $Yd_1$, saframycin $Ad_1$, saframycin $Yd_2$, saframycin $AH_2$, saframycin $AH_2Ac$, saframycin $AH_1$, saframycin $AH_1Ac$, saframycin $AR_3$, renieramycin A, renieramycin B, renieramycin C, renieramycin D, renieramycin E, renieramycin F, xestomycin, saframycin D, saframycin F, saframycin Mx-1, saframycin Mx-2, safracin A, safracin B and saframycin R. Preferred starting materials have a cyano group in position 21, for the group $R^{21}$.

In a particularly preferred aspect, the invention involves a hemisynthetic process wherein the transformation steps are applied to safracin B:

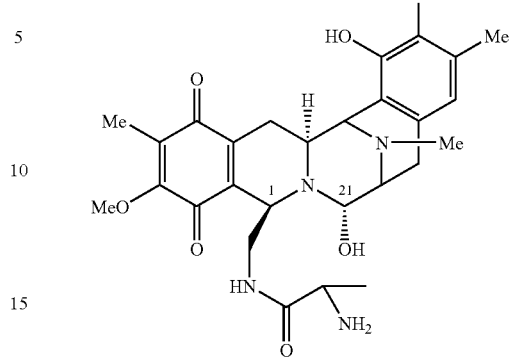

SAFRACIN B

Safracin B presents a ring system closely related to the ecteinascidins. This compound has the same pentacycle structure and the same substitution pattern in the right-hand aromatic ring, ring E.

The more preferred starting materials of this invention have a 21-cyano group. The currently most preferred compound of the present invention is the compound of Formula 2. This compound is obtained directly from safracin B and is considered a key intermediate in the hemisynthetic process.

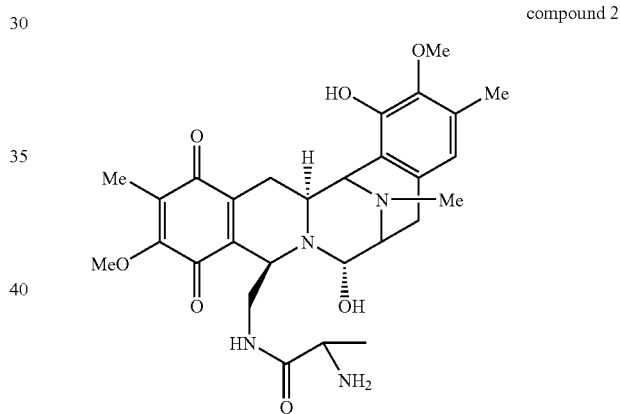

compound 2

Cyanosafracin B by fermentation of a safracin B-producing strain of *Pseudomonas fluorescens*, and working up the cultured broth using cyanide ion. The preferred strain of *Pseudomonas fluorescens* is strain A2-2, FERM BP-14, which is employed in the procedure of EP-A-055 299. A suitable source of cyanide ion is potassium cyanide. In a typical work-up, the broth is filtered and excess cyanide ion is added. After an appropriate interval of agitation, such as 1 hour, the pH is rendered alkaline, say pH 9.5, and an organic extraction gives a crude extract which can be further purified to give the cyanosafracin B.

In general, the conversion of the 21-cyano starting compound to a product of this invention involves:
a) conversion if necessary of a quinone system for the ring E into the phenol system
b) conversion if necessary of a quinone system for the ring A into the phenol system;
c) conversion of the phenol system for the ring A into the methylenedioxyphenol ring;
d) formation of the bridged spiro ring system of formula (IV), (VI) or (VII) across the 1-position and 4-position in ring B; and e) derivatisation as appropriate, such as acylation.

Step (a), conversion if necessary of a quinone system for the ring E into the phenol system, can be effected by conventional reduction procedures. A suitable reagent system is hydrogen with a palladium-carbon catalyst, though other reducing systems can be employed.

Step (b), conversion if necessary of a quinone system for the ring A into the phenol system is analogous to step (a), and more detail is not needed.

Step (c), conversion of the phenol system for the ring A into the methylenedioxyphenol ring, can be effected in several ways, possibly along with step (b). For example, a quinone ring A can be demethylated in the methoxy substituent at the 7-position and reduced to a dihydroquinone and trapped with a suitable electrophilic reagent such as $CH_2Br_2$, $BrCH_2Cl$, or a similar divalent reagent directly yielding the methylenedioxy ring system, or with a divalent reagent such as thiocarbonyldiimidazol which yields a substituted methylenedioxy ring system which can be converted to the desired ring.

Step (d) is typically effected by appropriate substitution at the 1-position with a bridging reagent that can assist formation of the desired bridge, forming an exendo quinone methide at the 4-position and allowing the methide to react with the 1-substituent to bring about the bridged structure. Preferred bridging reagents are of formula (XIX)

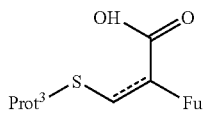

where Fu indicates a protected functional group, such as a group —NHProt$^{4a}$ or OProt$^{4b}$, Prot$^3$ is a protecting group, and the dotted line shows an optional double bond.

Suitably the methide is formed by first introducing a hydroxy group at the 10-position at the junction of rings A and B to give a partial structure of formula (XX):

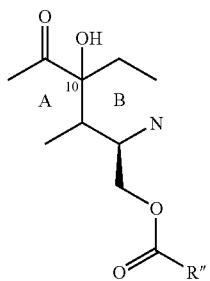

or more preferably a partial structure of formula (XXI):

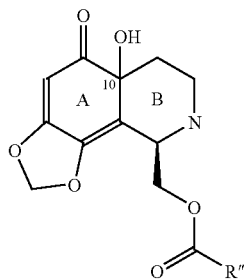

where the group R" is chosen for the desired group of formula (IV), (V), (VI) or (VII). For the first two such groups, the group R" typically takes the form —CHFu-CH$_2$—SProt$^3$. The protecting groups can then be removed and modified as appropriate to give the desired compound.

A typical procedure for step (d) is provided in U.S. Pat. No. 5,721,362 incorporated by reference. Particular reference is made to the passage at column 8, step (l) and Example 33 of the US patent, and related passages.

Derivatisation in step (e) can include acylation, for instance with a group R$^a$—CO— as well as conversion of the 12-NCH$_3$ group to 12-NH or 12-NCH$_2$CH$_3$. Such conversion can be effected before or after the other steps, using available methods.

By way of illustration, can be transformed into Intermediate 25;

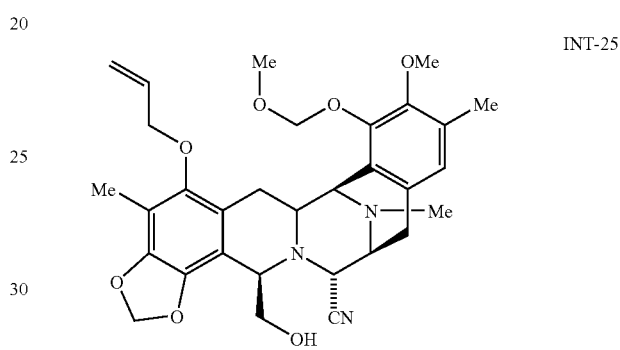

and from this derivative it is possible to introduce a number of cysteine derivatives that can be transformed into compounds of this invention. Preferred cysteine derivatives are exemplified by the following two compounds:

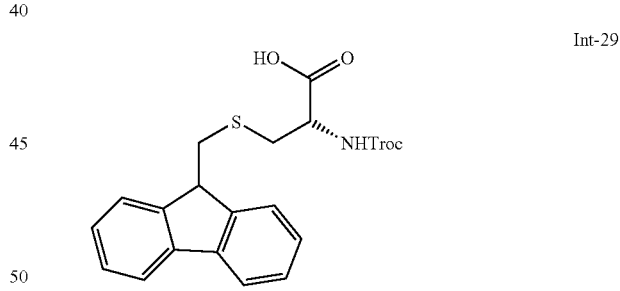

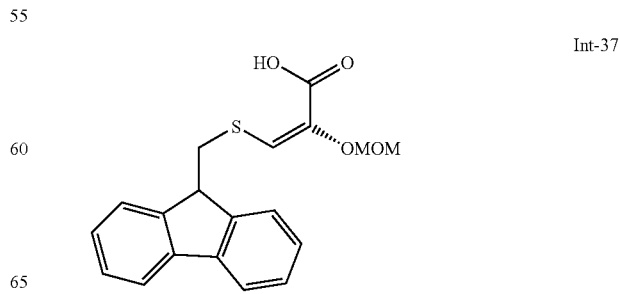

One method of this invention transforms cyanosafracin B into intermediate Int-25 through a sequence of reactions that involves essentially (1) removal of methoxy group placed in ring A, (2) reduction of ring A and formation of methylenedioxy group in one pot, (3) hydrolysis of amide function placed over carbon 1, (4) transformation of the resulting amine group into hydroxyl group, see scheme V.

Scheme V

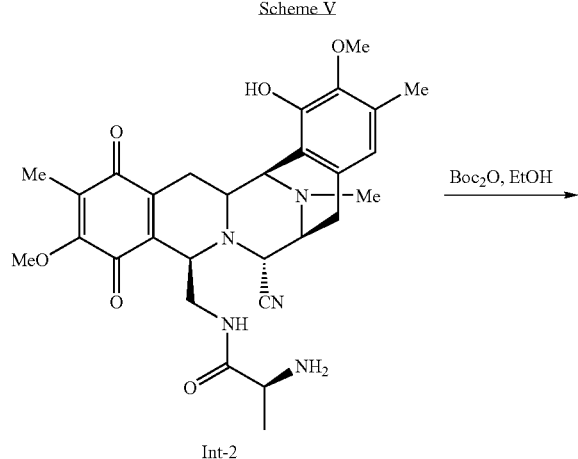

Int-2

Boc₂O, EtOH →

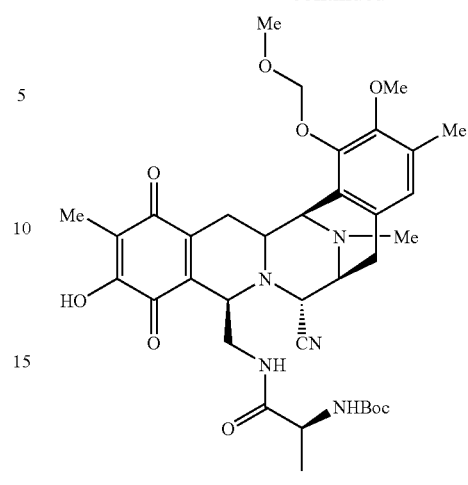

Int-16

1) H₂, Pd/c
2) ClBrCH₂, Cs₂CO₃
→

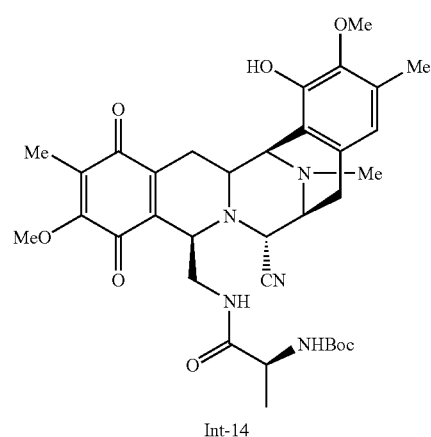

Int-14

MOMBr, DIPEA / CH₂CN →

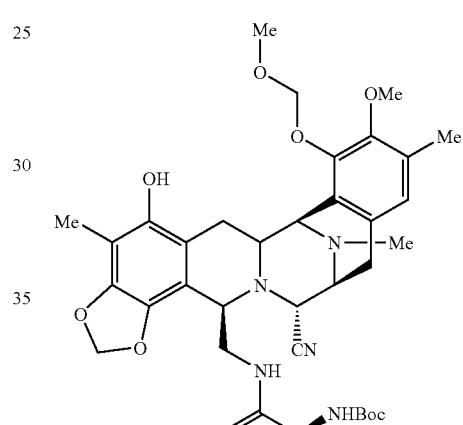

Int-17

Allyl bromide / Cs₂CO₃ →

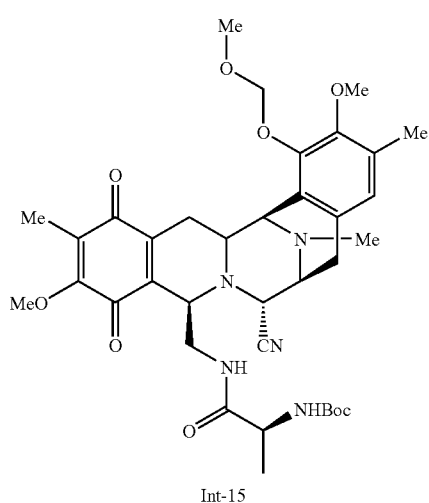

Int-15

NaOH 1M / MeOH →

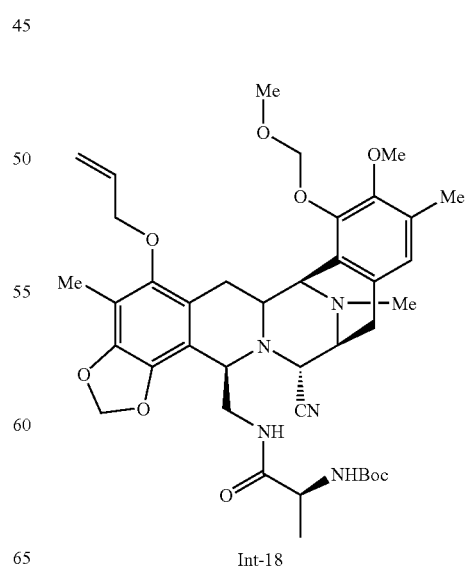

Int-18

HCl/Dioxane 4.3M →

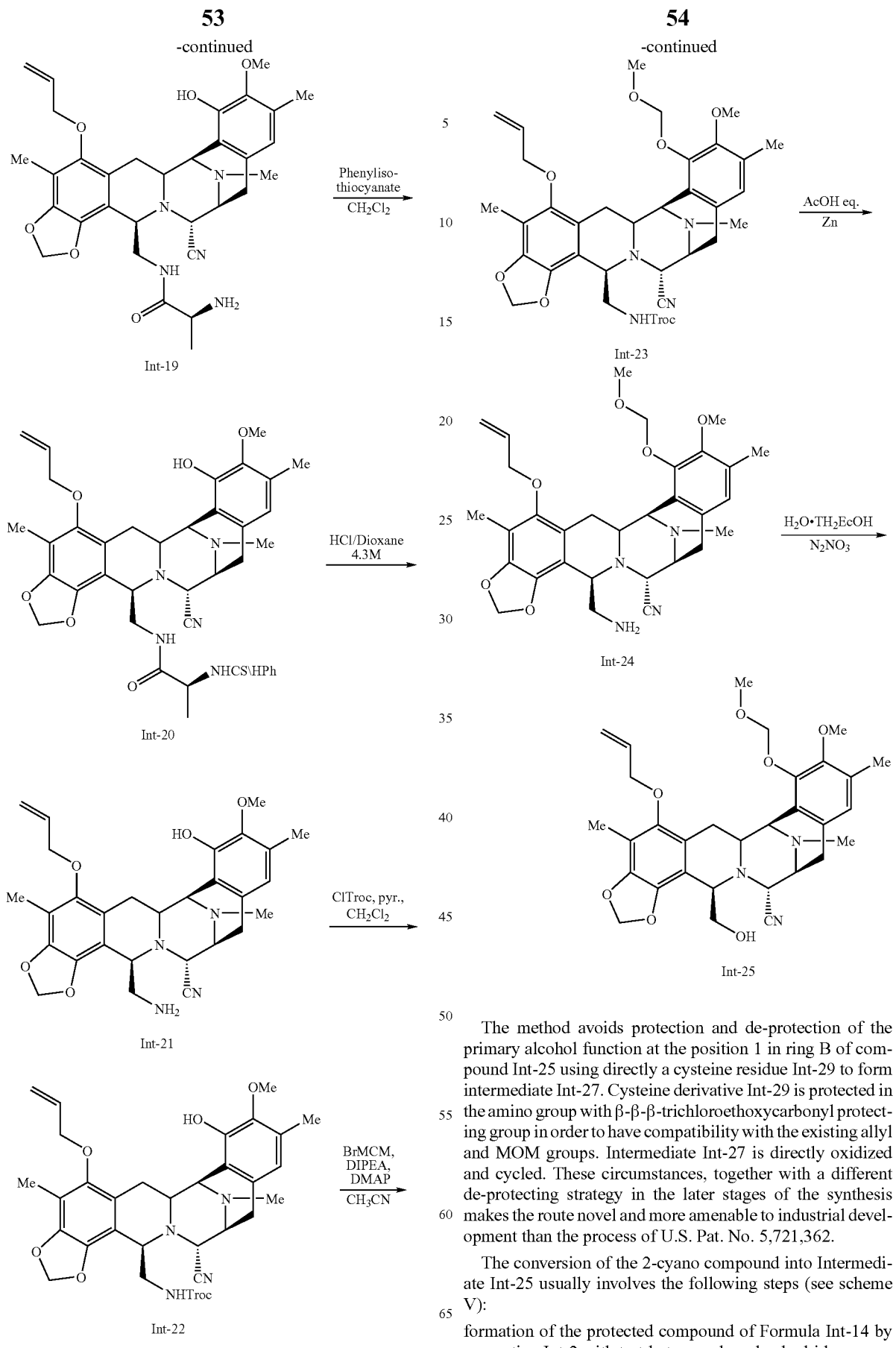

The method avoids protection and de-protection of the primary alcohol function at the position 1 in ring B of compound Int-25 using directly a cysteine residue Int-29 to form intermediate Int-27. Cysteine derivative Int-29 is protected in the amino group with β-β-β-trichloroethoxycarbonyl protecting group in order to have compatibility with the existing allyl and MOM groups. Intermediate Int-27 is directly oxidized and cycled. These circumstances, together with a different de-protecting strategy in the later stages of the synthesis makes the route novel and more amenable to industrial development than the process of U.S. Pat. No. 5,721,362.

The conversion of the 2-cyano compound into Intermediate Int-25 usually involves the following steps (see scheme V):

formation of the protected compound of Formula Int-14 by reacting Int-2 with tert-butoxycarbonyl anhydride;

converting of Int-14 into the di-protected compound of Formula Int-15 by reacting with bromomethylmethyl ether and diisopropylethylamine in acetonitrile;

selective elimination of the methoxy group of the quinone system in Int-15 to obtain the compound of Formula Int-16 by reacting with a methanolic solution of sodium hydroxide;

transforming of Int-16 into the methylene-dioxy compound of Formula Int-18 by employing the next preferred sequence: (1) quinone group of compound Int-16 is reduced with 10% Pd/C under hydrogen atmosphere; (2) the hydroquinone intermediate is converted into the methylenedioxy compound of Formula Int-17 by reacting with bromochloromethane and caesium carbonate under hydrogen atmosphere; (3) Int-17 is transformed into the compound of Formula lot-18 by protecting the free hydroxyl group as a OCH$_2$R group. This reaction is carried out with BrCH$_2$R and caesium carbonate, where R can be aryl, CH=CH$_2$, OR' etc.

elimination of the tert-butoxycarbonyl and the methyloxymethyl protecting groups of Int-18 to afford the compound of Formula Int-19 by reacting with a solution of HCl in dioxane. Also this reaction is achieved by mixing Int-18 with a solution of trifluoroacetic acid in dichloromethane;

formation of the thiourea compound of Formula Int-20 by reacting Int-19 with phenylisothiocyanate;

converting compound of Formula Int-20 into the amine compound of Formula Int-21 by reacting with a solution of hydrogen chloride in dioxane;

transforming compound of Formula Int-21 into the N-Troc derivative Int-22 by reacting with trichloroethyl chloroformate and pyridine;

formation of the protected hydroxy compound of Formula Int-23 by reacting Int-22 with bromomethylmethyl ether and diisopropylethylamine;

transforming compound of Formula Int-23 into the N—H derivative Int-24 by reacting with acetic acid and zinc;

conversion of compound of Formula Int-24 into the hydroxy compound of Formula Int-25 by reaction with sodium nitrite in acetic acid. Alternatively, it can be used nitrogen tetroxide in a mixture of acetic acid and acetonitrile followed by treatment with sodium hydroxide. Also, it can be used sodium nitrite in a mixture of acetic anhydride-acetic acid, followed by treatment with sodium hydroxide.

From intermediate Int-25 the conversion into final intermediate compounds Int-35 or Int-36 of this invention can then proceed as shown in Scheme VI:

Scheme VI

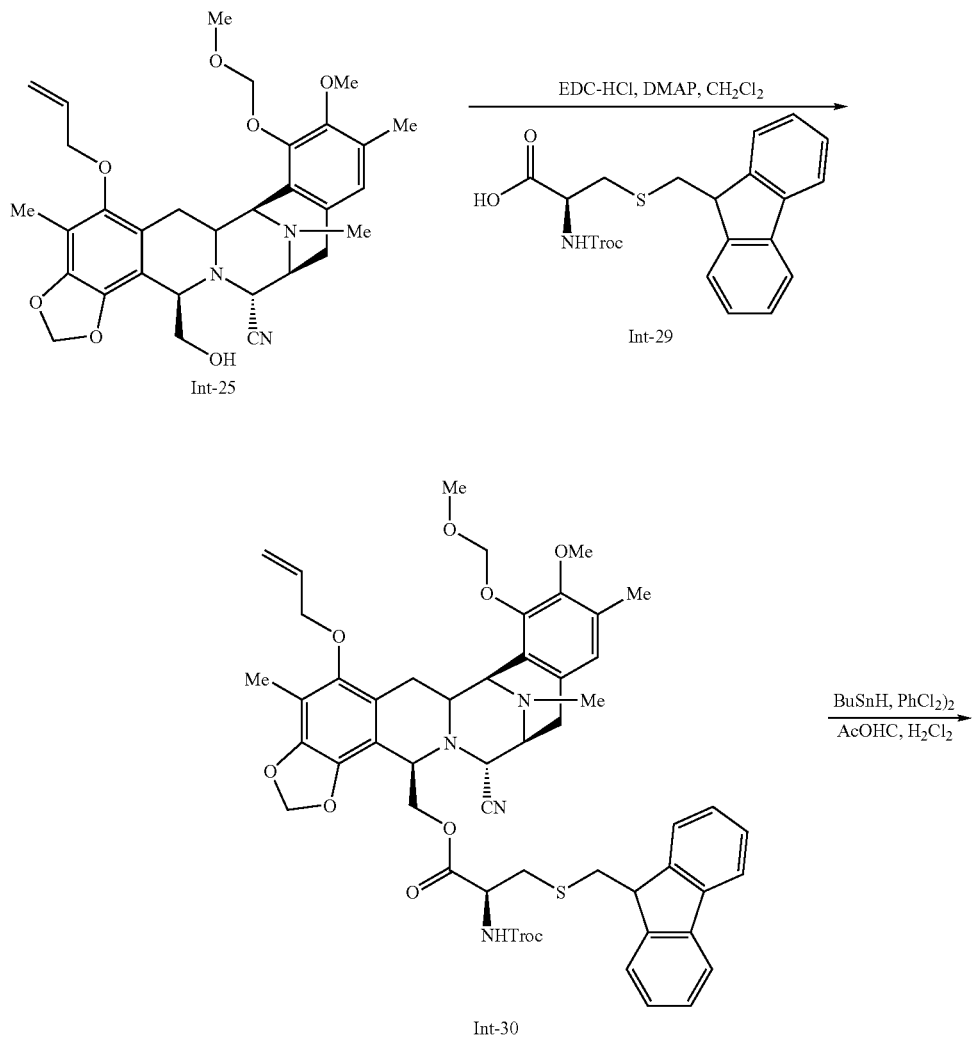

-continued
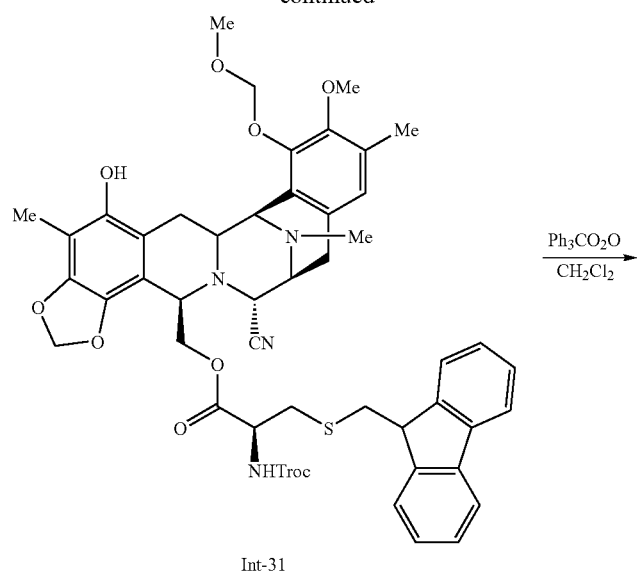
Int-31
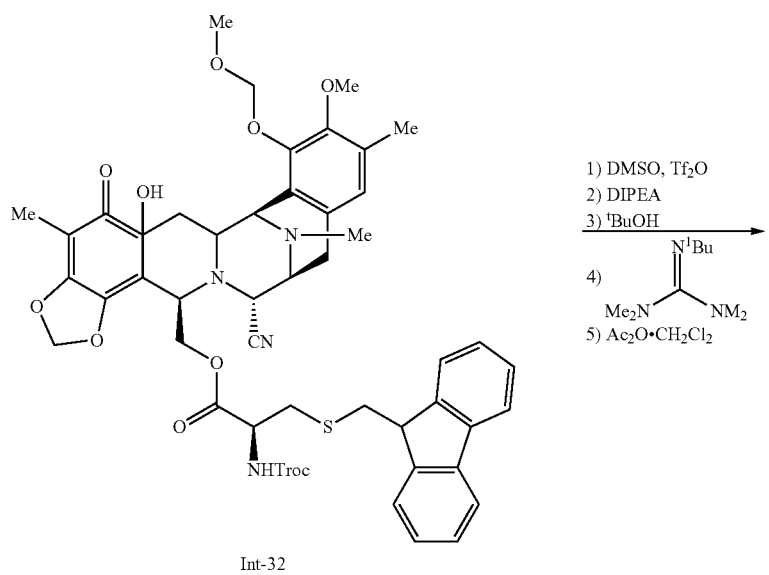
Int-32
1) DMSO, Tf₂O
2) DIPEA
3) ᵗBuOH
4) 
   Me₂N—C(=N^tBu)—NM₂
5) Ac₂O•CH₂Cl₂
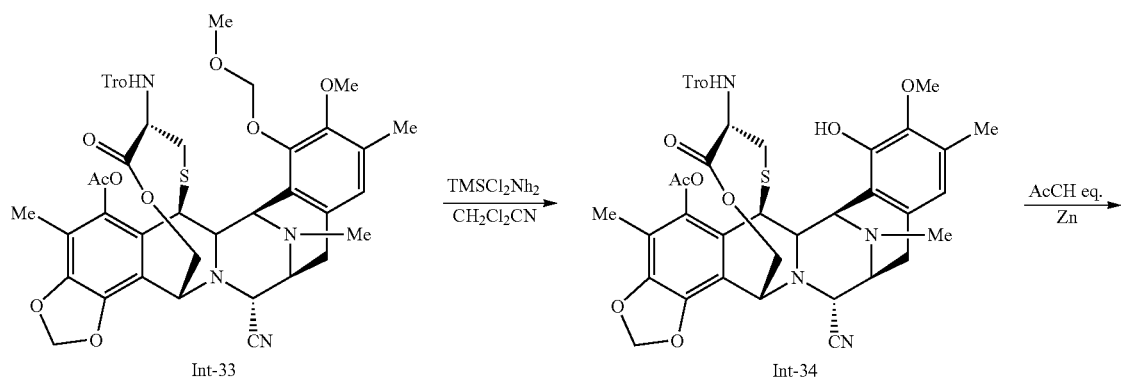
Int-33    Int-34

-continued

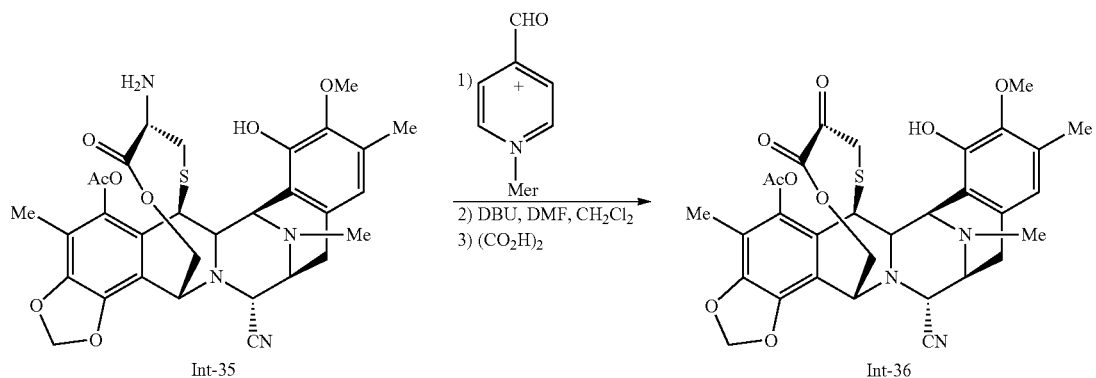

Int-35 → Int-36

1) [pyridinium CHO reagent]
2) DBU, DMF, CH$_2$Cl$_2$
3) (CO$_2$H)$_2$ transforming compound of formula Int-24 into the derivative Int-30 by protecting the primary hydroxyl function with (S)—N-2,2,2-tricloroethoxycarbonyl-S-(9H-fluoren-9-ylmethyl)cysteine Int-29;

converting the protected compound of formula Int-30 into the phenol derivative Int-31 by cleavage of the allyl group with tributyltin hydride and dichloropalladium-bis (triphenylphosphine);

transforming the phenol compound of Formula Int-31 into compound of formula Int-32 by oxidation with benzeneseleninic anhydride at low temperature;

transforming the hydroxy compound of formula Int-32 into the lactone Int-33 by the following sequence: (1) Reacting compound of formula Int-32 with 2 eq. of triflic anhydride and 5 eq. of DMSO. (2) followed by reaction with 8 eq. of diisopropylethylamine. (3) followed by reaction with 4 eq of t-butyl alcohol (4) followed by reaction with 7 eq of 2-tert-Butyl-1,1,3,3, tetramethylguanidine (5) followed by reaction with 10 eq of acetic anhydride;

transforming the lactone compound Int-33 into hydroxyl compound Int-34 by removal of MOM protecting group with TMSI;

cleaving the N-trichloroethoxycarbonyl group of the compound of formula Int-34 into compound Int-35 by reaction with Zn/AcOH;

transforming the amino compound Int-35 into the corresponding α-keto lactone compound Int-36 by reaction with N-methylpyridinium carboxaldehyde chloride followed by DBU;

The conversion of the Intermediate compound Int-25 into ET-743 using cysteine derivative Int-37 can be made in a similar manner and with the same reagents than with cysteine derivative Int-29 with the exception of transformations (f) and (g). The reaction sequence is exemplified in the following Scheme VII:

Scheme VII

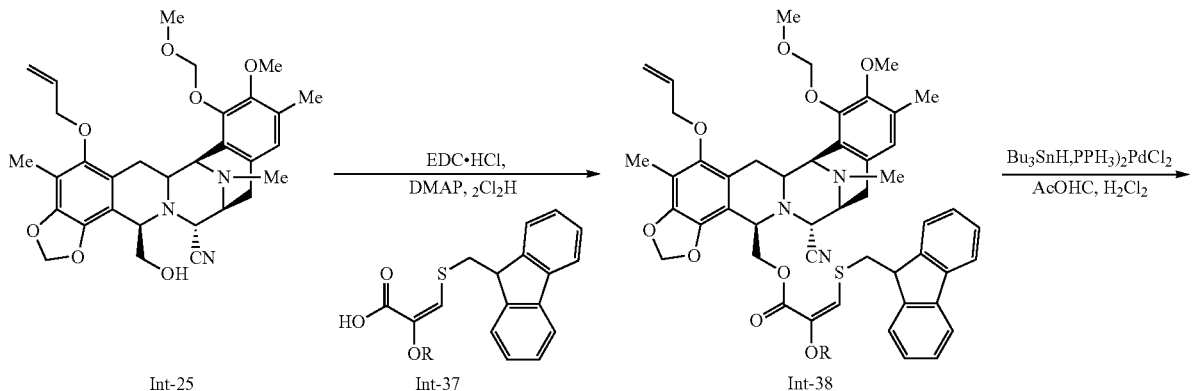

Int-25 + Int-37 → (EDC·HCl, DMAP, $_2$Cl$_2$H) → Int-38 → (Bu$_3$SnH, PPH$_3$)$_2$PdCl$_2$, AcOHC, H$_2$Cl$_2$)

-continued

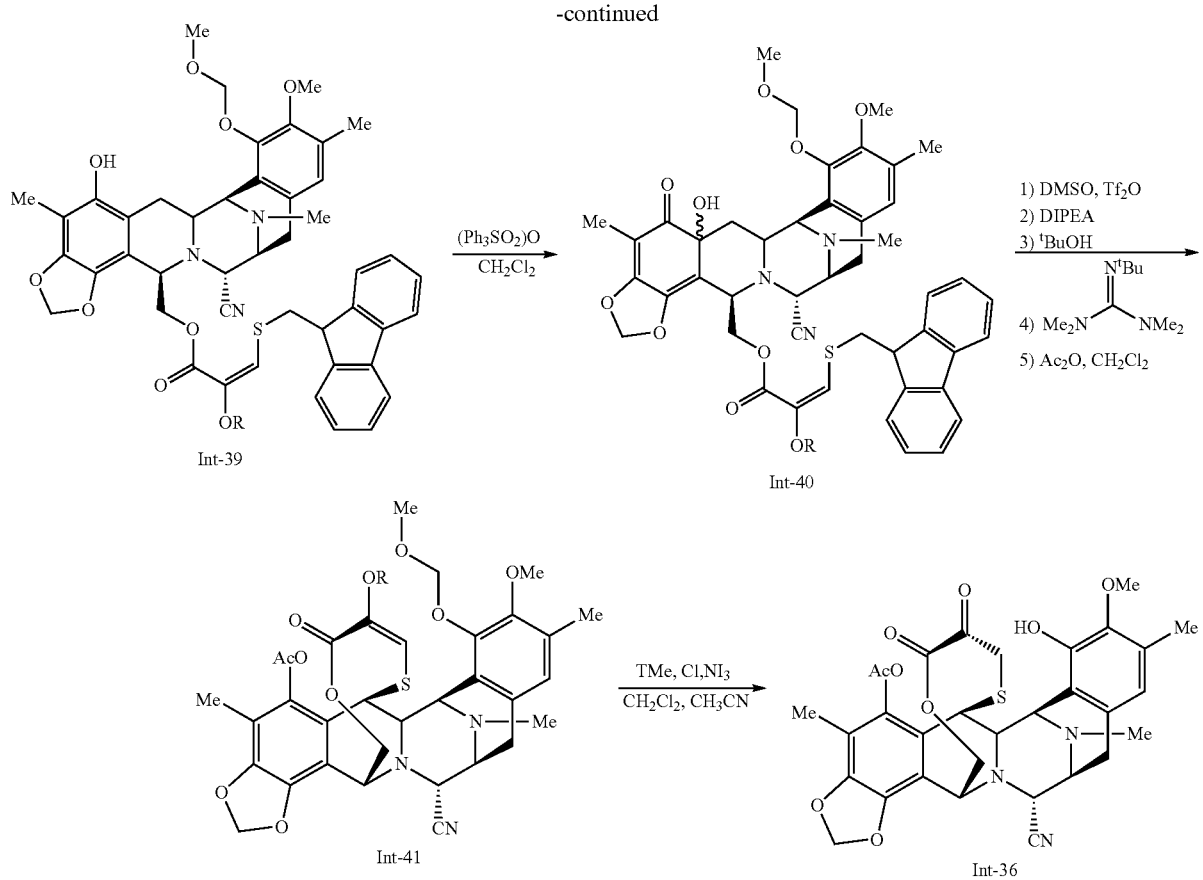

It will readily be appreciated that these synthetic routes can readily be modified, particularly by appropriate change of the starting material and reagents, so as to provide compounds of this invention with different fused ring systems or different substituents.

Novel Active Compounds

We have found that compounds of the invention have activity in the treatment of cancers, such as leukaemias, lung cancer, colon cancer, kidney cancer and melanoma.

Thus, the present invention provides a method of treating any mammal, notably a human, affected by cancer which comprises administering to the affected individual a therapeutically effective amount of a compound of the invention, or a pharmaceutical composition thereof.

The present invention also relates to pharmaceutical preparations, which contain as active ingredient a compound or compounds of the invention, as well as the processes for their preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);
d) drugs which target DNA such as the antracycline drugs adriamycin, doxorubicin, pharmorubicin or epirubicin;
e) drugs which target topoisomerases such as etoposide;
f) hormones and hormone agonists or antagonists such as estrogens, antiestrogens (tamoxifen and related compounds) and androgens, flutamide, leuprorelin, goserelin, cyprotrone or octreotide;
g) drugs which target signal transduction in tumour cells including antibody derivatives such as herceptin;
h) alkylating drugs such as platinum drugs (cis-platin, carbonplatin, oxaliplatin, paraplatin) or nitrosoureas;
i) drugs potentially affecting metastasis of tumours such as matrix metalloproteinase inhibitors;
j) gene therapy and antisense agents;
k) antibody therapeutics;
l) other bioactive compounds of marine origin, notably the didemnins such as aplidine;
m) steroid analogues, in particular dexamethasone;
n) anti-inflammatory drugs, in particular dexamethasone; and
o) anti-emetic drugs, in particular dexamethasone.

The present invention also extends to the compounds of the invention for use in a method of treatment, and to the use of the compounds in the preparation of a composition for treatment of cancer.

Cytotoxic Activity

Cell Cultures. Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serum (FCS), $10^{-2}$ M sodium bicarbonate and 0.1 g/l penicillin-G+streptomycin sulfate.

A simple screening procedure has been carried out to determine and compare the antitumour activity of these compounds, using an adapted form of the method described by Bergeron et al (1984). The tumour cell line employed have been P-388 (suspension culture of a lymphoid neoplasm from DBA/2 mouse), A-549 (monolayer culture of a human lung carcinoma), HT-29 (monolayer culture of a human colon carcinoma) and MEL-28 (monolayer culture of a human melanoma).

P-388 cell were seeded into 16 mm wells at $1\times10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, an approximately $IC_{50}$ was determined by comparing the growth in wells with drug to the growth in wells control.

A-549, HT-29 and MEL-28 were seeded into 16 mm wells at $2\times10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximately $IC_{50}$ was determined by comparing the growth in wells with drug to the growth in wells control.

1. Raymond J. Bergeron, Paul F. Cavanaugh, Jr., Steven J. Kline. Robert G. Hughes, Jr., Gary T. Elliot and Carl W. Porter. Antineoplastic and antiherpetic activity of spermidine catecholamide iron chelators. *Biochem. Bioph. Res. Comm.* 1984, 121(3), 848-854.

2. Alan C. Schroeder, Robert G. Hughes, Jr. and Alexander Bloch. Effects of Acyclic Pyrimidine Nucleoside Analoges. *J. Med. Chem.* 1981, 24 1078-1083.

Examples of biological activities of the compounds described in the present application are in Table IV ($IC_{50}$ (ng/mL)) on the following pages.

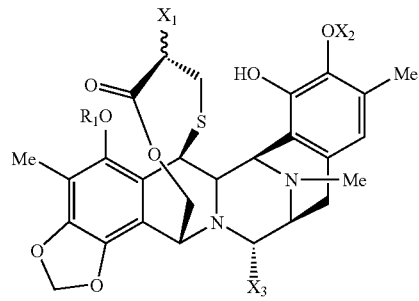

| Compound | $X_1$ | $X_2$ | $X_3$ | $R_1$ | P-388 | A-549 | HT-29 | MEL-28 | DU-145 |
|---|---|---|---|---|---|---|---|---|---|
| 4a | AcNH— | Me | OH | Ac | 0.1 | 0.5 | 0.1 | 0.5 | 0.1 |
| 4b | $F_3$CCONH— | Me | OH | Ac | 0.5 | 0.5 | 0.5 | 0.5 | 0.5 |
| 4c | $CH_3(CH_2)_2$CONH— | Me | OH | Ac | 0.1 | 0.1 | 0.1 | 0.1 | 0.1 |
| 4d | $(CH_3)_2CHCH_2$CONH— | Me | OH | Ac | 0.5 | 0.5 | 0.5 | 0.5 | 0.5 |
| 4e | $CH_3(CH_2)_6$CONH— | Me | OH | Ac | 1.0 | 1.0 | 1.0 | 1.0 | 1.0 |
| 4f | $CH_3(CH_2)_{14}$CONH— | Me | OH | Ac | 100 | 100 | 100 | 100 | 100 |
| 4g | PhCONH— | Me | OH | Ac | 0.1 | 0.5 | 0.5 | 0.5 | 0.5 |
| 4h | CinnCONH— | Me | OH | Ac | 0.5 | 0.5 | 0.5 | 0.5 | 0.5 |
| 4i | p-$F_3$C-CinnCONH— | Me | OH | Ac | 1.0 | 1.0 | 1.0 | 1.0 | 1.0 |
| 4k | BiotinCONH— | Me | OH | Ac | 10 | 10 | 10 | 10 | 10 |
| 4l | $HO_2CCH_2CH_2$CONH— | Me | OH | Ac | 100 | 100 | 100 | 100 | 100 |
| 4n | BnNH— | Me | OH | Ac | 0.5 | 0.5 | 0.5 | 0.5 | 0.5 |
| 4o | PrNH— | Me | OH | Ac | | 1.0 | 1.0 | | |
| 4p | $NH_2$-ValCONH— | Me | OH | Ac | 0.5 | 0.5 | 0.5 | 0.5 | 0.5 |
| 4q | Ac—N-ValCONH— | Me | OH | Ac | 1.0 | 1.0 | 1.0 | 1.0 | 1.0 |

-continued

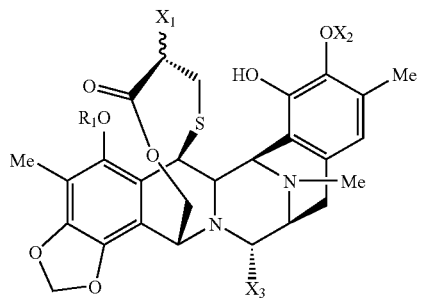

| Compound | X₁ | X₂ | X₃ | R₁ | P-388 | A-549 | HT-29 | MEL-28 | DU-145 |
|---|---|---|---|---|---|---|---|---|---|
| 4r | CinnCO—N-ValCONH— | Me | OH | Ac | 0.5 | 0.5 | 0.5 | 0.5 | 0.5 |
| 4s | NH₂-Ala-ValCONH— | Me | OH | Ac | 1.0 | 1.0 | 1.0 | 1.0 | 1.0 |
| 4t | Ac-N-Ala-ValCONH— | Me | OH | Ac | 100 | 100 | 10 | 10 | 10 |
| 4u | CinnCO-N-Ala-ValCONH— | Me | OH | Ac | 5.0 | 5.0 | 5.0 | 5.0 | 5.0 |
| 4v | NH₂-AlaCONH— | Me | OH | Ac | 1.0 | 1.0 | 1.0 | 1.0 | 1.0 |
| 4x | CinnCO-N-AlaCONH— | Me | OH | Ac | 1.0 | 1.0 | 1.0 | 1.0 | 1.0 |
| 4y | FmSCH₂CH(NHAlloc)CONH— | Me | OH | Ac | 50 | 50 | 50 | 50 | 50 |
| 19 | HO— | Me | OH | Ac | 1.0 | 1.0 | 1.0 | 1.0 | 1.0 |
| 21a | AcO— | Me | OH | Ac | 0.5 | 1.0 | 1.0 | 1.0 | 1.0 |
| 21c | CH₃(CH₂)₂COO— | Me | OH | Ac | 1.0 | 1.0 | 1.0 | 1.0 | 1.0 |
| 21e | CH₃(CH₂)₆COO— | Me | OH | Ac | 1.0 | 1.0 | 1.0 | 1.0 | 1.0 |
| 21f | CH₃(CH₂)₁₄COO— | Me | OH | Ac | | >1000 | >1000 | | |
| 21h | CinnCOO— | Me | OH | Ac | 1.0 | 1.0 | 1.0 | 1.0 | 1.0 |
| 21ll | MeSO₃— | Me | OH | Ac | 1.0 | 1.0 | 1.0 | 1.0 | 1.0 |
| 22a* | *AcO— | Me | OH | Ac | | 1.0 | 1.0 | | |
| 27 | NH₂ | Me | CN | Ac | 5.0 | 5.0 | 5.0 | 5.0 | — |
| 23 | NH₂ | Me | CN | H | | 10 | 10 | | |
| 24 | NH₂ | H | CN | Ac | | 100 | 100 | | |
| 3a | AcNH— | Me | CN | Ac | 0.5 | 0.5 | 0.5 | 0.5 | 0.5 |
| 25 | AcNH— | Me | CN | H | | 10 | 10 | | |
| 26 | AcNH— | H | CN | Ac | | 100 | 100 | | |
| 3b | F₃CCONH— | Me | CN | Ac | 1.0 | 1.0 | 1.0 | 1.0 | 1.0 |
| 3c | CH₃(CH₂)₂CONH— | Me | CN | Ac | 0.1 | 0.1 | 0.1 | 0.1 | 0.1 |
| 3d | (CH₃)₂CHCH₂CONH— | Me | CN | Ac | 0.1 | 0.1 | 0.1 | 0.1 | 0.1 |
| 3e | CH₃(CH₂)₆CONH— | Me | CN | Ac | 1.0 | 1.0 | 1.0 | 1.0 | 1.0 |
| 3f | CH₃(CH₂)₁₄CONH— | Me | CN | Ac | >1-10³ | >1-10³ | >1-10³ | >1-10³ | >1-10³ |
| 3g | PhCONH— | Me | CN | Ac | 0.1 | 0.1 | 0.1 | 0.1 | 0.1 |
| 3h | CinnCONH— | Me | CN | Ac | 0.5 | 0.5 | 0.5 | 0.5 | 0.5 |
| 3i | p-F₃C-CinnCONH— | Me | CN | Ac | 5.0 | 5.0 | 5.0 | 5.0 | 5.0 |
| 3j | PhtN— | Me | CN | Ac | 5 | 5 | 5 | 5 | 5 |
| 6 | 2-MeO₂C—C₆H₄—CONH— | Me | CN | Ac | 1 | 1 | 1 | 1 | 1 |
| 3k | BiotinNH— | Me | CN | Ac | 10 | 10 | 5 | 5 | 5 |
| 3l | HO₂C(CH₂)₂CONH— | Me | CN | Ac | 100 | 100 | 100 | 100 | 100 |
| 3m | (CH₃)₂N— | Me | CN | Ac | 10 | 10 | 10 | 10 | 10 |
| 3n | BnNH— | Me | CN | Ac | 0.5 | 0.5 | 0.5 | 0.5 | 0.5 |
| 3o | PrNH— | Me | CN | Ac | | 5 | 5 | | |
| 3p | NH₂-ValCONH— | Me | CN | Ac | 1 | 1 | 1 | 1 | 1 |
| 3q | Ac-N-ValCONH— | Me | CN | Ac | 1 | 1 | 1 | 1 | 1 |
| 3r | CinnCO-N-ValCONH— | Me | CN | Ac | 1 | 1 | 1 | 1 | 1 |
| 3s | NH₂-Ala-ValCONH— | Me | CN | Ac | 1 | 1 | 1 | 1 | 1 |
| 3t | Ac-N-Ala-ValCONH— | Me | CN | Ac | 10 | 10 | 10 | 10 | 10 |
| 3u | CinnCO-N-Ala-ValCONH— | Me | CN | Ac | 5 | 5 | 1 | 1 | 1 |
| 3v | NH₂-AlaCONH— | Me | CN | Ac | 1 | 1 | 1 | 1 | 1 |
| 3w | Ac-N-AlaCONH— | Me | CN | Ac | 1 | 1 | 1 | 1 | 1 |
| 3x | CinnCO-N-AlaCONH— | Me | CN | Ac | 0.1 | 0.1 | 0.1 | 0.1 | 0.1 |
| 3y | FmSCH₂CH(NHAlloc)CONH— | Me | CN | Ac | 10 | 10 | 10 | 50 | 50 |
| 3z | FmSCH₂CH(NH₂)CONH— | Me | CN | Ac | 50 | 50 | 50 | 50 | 50 |
| 28 | Cl₃CCH₂OCONH— | Me | CN | Ac | 1.0 | 1.0 | 1.0 | 1.0 | 1.0 |
| 15 | HO— | Me | CN | Ac | 5 | 5 | 5 | 5 | 5 |
| 16* | *HO— | Me | CN | Ac | | 10 | 10 | | |
| 17a | AcO— | Me | CN | Ac | 0.1 | 0.1 | 0.1 | 0.1 | 0.1 |
| 17b | F₃CCOO— | Me | CN | Ac | 5.0 | 5.0 | 5.0 | 5.0 | 5.0 |
| 17c | CH₃(CH2)₂COO— | Me | CN | Ac | 1.0 | 1.0 | 1.0 | 1.0 | 1.0 |
| 17e | CH₃(CH2)₆COO— | Me | CN | Ac | 1.0 | 1.0 | 1.0 | 1.0 | 1.0 |
| 17f | CH₃(CH2)₁₄COO— | Me | CN | Ac | >1000 | >1000 | >1000 | >1000 | >1000 |
| 17h | CinnCOO— | Me | CN | Ac | 0.1 | 0.1 | 0.1 | 0.1 | 0.1 |
| 17ll | MeSO₃— | Me | CN | Ac | 1 | 1 | 1 | 1 | — |
| 18a* | *AcO— | Me | CN | Ac | 1.0 | 1.0 | 1.0 | 1.0 | 1.0 |

EXAMPLES

Example 1

Method A: To a solution of 1 equiv. of 1 (23 for 25) coevaporated with anhydrous toluene in CH$_2$Cl$_2$ (0.08M) under Argon were added 1.2 equiv. of the anhydride. The reaction was followed by TLC and quenched with acid or base, extracted with CH$_2$Cl$_2$ and the organic layers dried with Na$_2$SO$_4$. Flash chromatography gives pure compounds.

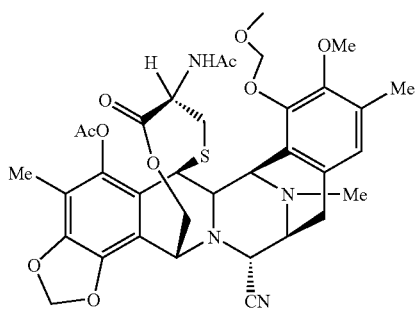

Compound 2a (using Ac$_2$O as the anhydride): $^1$H NMR (300 MHz, CDCl$_3$): δ 6.77 (s, 1H), 6.04 (dd, 2H), 5.53 (bd, 1H), 5.18 (dd, 2H), 5.02 (d, 1H), 4.58 (ddd, 1H), 4.52 (bs, 1H), 4.35 (d, 1H), 4.27 (s, 1H), 4.19-4.15 (m, 2H), 3.75 (s, 3H), 3.55 (s, 3H), 3.54-3.43 (m, 2H), 2.93 (bd, 2H), 2.35-2.02 (m, 2H), 2.28 (s, 3H), 2.27 (s, 3H), 2.18 (s, 3H), 2.02 (s, 3H), 1.89 (s, 3H); $^{13}$C NMR (75 MHz, CDCl$_3$): δ 170.5, 168.7, 168.4, 149.7, 148.5, 145.8, 141.0, 140.4, 131.0, 130.5, 125.7, 124.5, 120.3, 117.9, 113.5, 113.4, 102.0, 99.1, 61.4, 60.3, 59.6, 58.8, 55.0, 54.5, 52.1, 41.8, 41.3, 32.6, 23.7, 20.9, 20.2, 16.1, 9.5; ESI-MS m/z: Calcd. for C$_{35}$H$_{40}$N$_4$O$_{10}$S: 708.2. Found (M+H$^+$): 709.2.

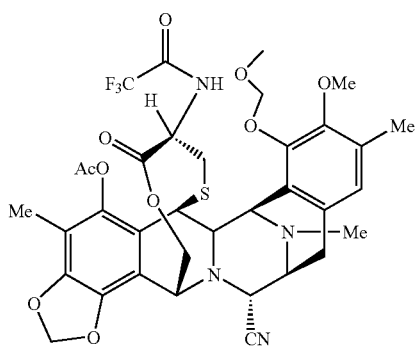

Compound 2b (using (F$_3$CCO)$_2$O as the anhydride): $^1$H NMR (300 MHz, CDCl$_3$): δ 6.74 (s, 1H), 6.41 (bd, 1H), 6.05 (dd, 2H), 5.17 (dd, 2H), 5.05 (d, 1H), 4.60 (bp, 1H), 4.54-4.51 (m, 1H), 4.36-4.32 (m, 2H), 4.25-4.19 (m, 2H), 3.72 (s, 3H), 3.56 (s, 3H), 3.48-3.43 (m, 2H), 2.99-2.82 (m, 2H), 2.46-2.41 (m, 1H), 2.30-2.03 (m, 1H), 2.29 (s, 3H), 2.24 (s, 3H), 2.17 (s, 3H), 2.04 (s, 3H); $^{13}$C NMR (75 MHz, CDCl$_3$): δ 168.9, 168.5, 156.3, 155.8, 155.3, 149.3, 148.5, 146.0, 141.2, 140.6, 132.0, 130.2, 124.8, 120.2, 117.9, 113.2, 102.1, 99.2, 61.5, 60.6, 59.7, 59.1, 58.7, 57.5, 54.9, 54.6, 52.9, 42.0, 41.4, 31.6, 23.8, 20.2, 14.1, 9.6; ESI-MS m/z: Calcd. for C$_{35}$H$_{37}$F$_3$N$_4$O$_{10}$S: 762.2. Found (M+H$^+$): 763.2.

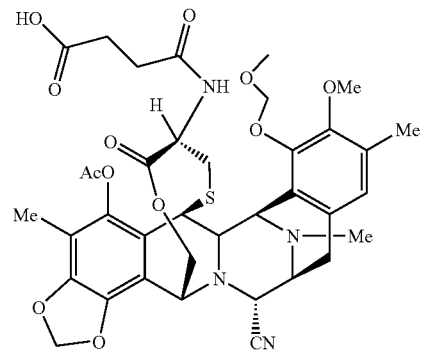

Compound 2l (using succinic anhydride): $^1$H NMR (300 MHz, CDCl$_3$): δ 6.79 (s, 1H), 6.04 (dd, 2H), 5.63 (bd, 1H), 5.18 (dd, 2H), 5.02 (d, 1H), 4.59-4.53 (m, 2H), 4.35 (d, 1H), 4.28 (s, 1H), 4.21-4.17 (m, 2H), 3.76 (s, 3H), 3.57 (s, 3H), 3.54-3.44 (m, 2H), 2.92 (bd, 2H), 2.69-2.63 (m, 2H), 2.53-2.48 (m, 2H), 2.38-2.07 (m, 2H), 2.28 (s, 6H), 2.18 (s, 3H), 2.02 (s, 3H); ESI-MS m/z: Calcd. for C$_{37}$H$_{42}$N$_4$O$_{12}$S: 766.2. Found (M+H$^+$): 767.3.

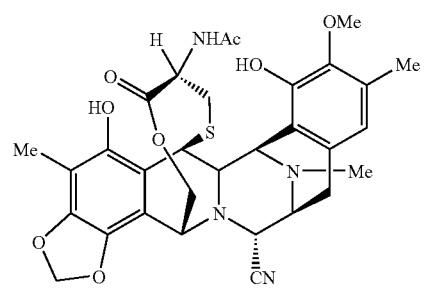

Compound 25 (from Compound 23 using 1 equiv of Ac$_2$O as the anhydride): $^1$H NMR (300 MHz, CDCl$_3$): δ 6.59 (s, 1H), 5.97 (dd, 2H), 5.87 (s, 1H), 5.53 (s, 1H), 5.51 (d, 1H), 5.00 (d, 1H), 4.62-4.58 (m, 1H), 4.44 (s 1H), 4.31 (s, 1H), 4.29 (d, 1H), 4.16 (d, 1H), 4.09 (dd, 1H), 3.79 (s, 3H), 3.54-3.52 (m, 1H), 3.44-3.42 (m, 1H), 2.93-2.91 (m, 2H), 2.46 (dd, 1H), 2.33 (s, 3H), 2.23 (dd, 1H), 2.15 (s, 3H), 2.14 (s, 3H), 1.90 (s, 1H); $^{13}$C NMR (75 MHz, CDCl$_3$): δ 170.1, 169.0, 148.3, 146.4, 146.0, 143.0, 136.4, 130.7, 129.2, 120.4, 119.0, 118.1, 112.4, 112.3, 107.8, 101.4, 61.1, 60.5, 59.2, 58.8, 54.7, 54.5, 51.6, 43.3, 41.4, 31.4, 23.8, 22.9, 16.2, 8.7; ESI-MS m/z: Calcd. for C$_{31}$H$_{34}$N$_4$O$_8$S: 580.2. Found (M+H$^+$): 581.3.

Example 2

Method B: To a solution of 1 equiv. of 1 (2p for 2t and 9, and 11 for 13e-f) and 1.5 equiv. of acid coevaporated twice with anhydrous toluene in CH$_2$Cl$_2$ (0.05M) under Argon, were added 2 equiv. of DMAP and 2 equiv. of EDC.HCl. The reaction was stirred for 3 h 30 min. After this time was diluted with CH$_2$Cl$_2$, washed with brine and the organic layer dried with Na$_2$SO$_4$. Flash chromatography gives pure compounds.

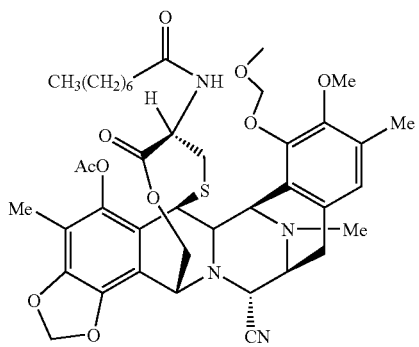

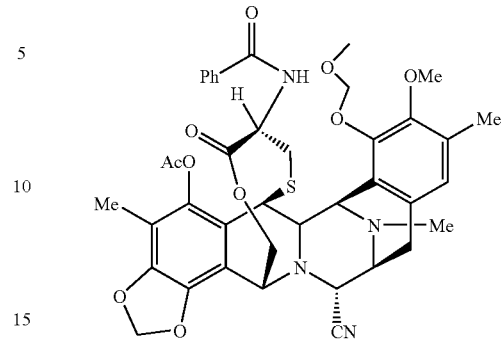

Compound 2e (using CH₃(CH₂)₆CO₂H as the acid): ¹H NMR (300 MHz, CDCl₃): δ 6.76 (s, 1H), 6.04 (dd, 2H), 5.50 (bd, 1H), 5.18 (dd, 2H), 5.02 (d, 1H), 4.60 (ddd, 1H), 4.53 (bp, 1H), 4.35 (d, 1H), 4.28 (s, 1H), 4.19 (d, 1H), 4.18 (dd, 1H), 3.76 (s, 3H), 3.58 (s, 3H), 3.48-3.43 (m, 2H), 2.93 (bd, 2H), 2.29-1.99 (m, 4H), 2.29 (s, 3H), 2.28 (s, 3H), 2.17 (s, 3H), 2.03 (s, 3H), 1.31-1.23 (m, 10H), 0.89 (t, 3H); ¹³C NMR (75 MHz, CDCl₃): δ 171.9, 170.6, 168.4, 149.6, 148.5, 145.8, 141.0, 140.4, 130.9, 130.5, 125.7, 124.5, 120.4, 117.9, 113.4, 102.0, 99.2, 61.5, 60.2, 59.6, 59.3, 58.7, 57.5, 55.0, 54.5, 51.9, 41.8, 41.4, 36.4, 32.7, 31.7, 29.3, 29.1, 25.4, 23.7, 22.6, 20.3, 16.1, 14.0, 9.6; ESI-MS m/z: Calcd. for C₄₁H₅₂N₄O₁₀S: 792.3. Found (M+H⁺): 793.3.

Compound 2g (using PhCO₂H as the acid): ¹H NMR (300 MHz, CDCl₃): δ 7.69-7.66 (m, 2H), 7.57-7.46 (m, 3H), 6.69 (s, 1H), 6.35 (d, 1H), 6.06 (dd, 2H), 5.14 (dd, 2H), 5.07 (d, 1H), 4.76 (dt, 1H), 4.58 (bp, 1H), 4.36-4.33 (m, 2H), 4.24-4.18 (m, 2H), 3.62 (s, 3H), 3.55 (s, 3H), 3.49-3.46 (m, 2H), 2.94 (bd, 2H), 2.62-2.55 (m, 1H), 2.28-1.93 (m, 1H), 2.28 (s, 3H), 2.16 (s, 3H), 2.04 (s, 3H), 1.93 (s, 3H); ¹³C NMR (75 MHz, CDCl₃): δ 170.5, 168.4, 166.4, 149.3, 148.4, 145.9, 141.1, 140.6, 134.5, 134.2, 131.6, 131.4, 130.5, 128.6, 126.9, 125.2, 124.5, 120.7, 118.0, 113.4, 102.0, 99.2, 61.6, 60.2, 59.8, 59.2, 58.6, 57.4, 55.0, 54.6, 53.2, 41.9, 41.4, 32.9, 23.9, 20.2, 15.7, 9.6; ESI-MS m/z: Calcd. for C₄₀H₄₂N₄O₁₀S: 770.3. Found (M+H⁺): 771.3.

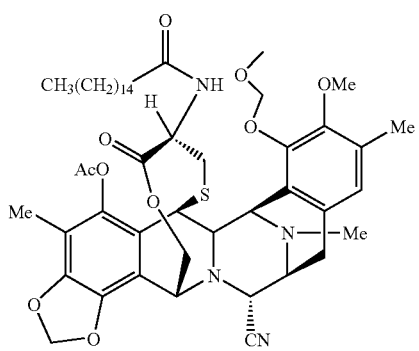

Found (M + H⁺):905.5.

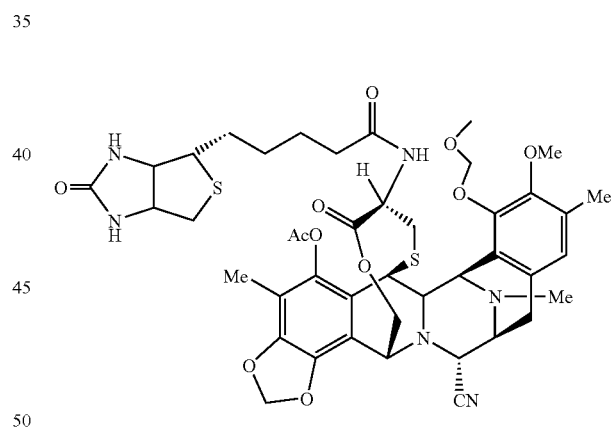

Compound 2f (using CH₃(CH₂)₁₄CO₂H as the acid): ¹H NMR (300 MHz, CDCl₃): δ 6.76 (s, 1H), 6.05 (dd, 2H), 5.50 (bd, 1H), 5.18 (dd, 2H), 5.02 (d, 1H), 4.60 (ddd, 1H), 4.56-4.50 (bp, 1H), 4.35 (d, 1H), 4.28 (bs, 1H), 4.20 (d, 1H), 4.18 (dd, 1H), 3.76 (s, 3H), 3.57 (s, 3H), 3.54-3.44 (m, 2H), 2.93-2.92 (bd, 2H), 2.37-2.01 (m, 4H), 2.29 (s, 3H), 2.28 (s, 3H), 2.18 (s, 3H), 2.03 (s, 3H), 1.60-1.56 (m, 2H), 1.40-1.20 (m, 24H), 0.88 (t, 3H); ESI-MS m/z: Calcd. for C₄₉H₆₈N₄O₁₀S: 904.5.

Compound 2k (using (+)-biotin as the acid): ¹H NMR (300 MHz, CDCl₃): δ 6.78 (s, 1H), 6.04 (dd, 2H), 6.00 (s, 1H), 5.80 (s, 1H), 5.39 (bd, 1H), 5.18 (dd, 3H), 4.78 (d, 1H), 4.64-4.51 (m, 3H), 4.34-4.28 (m, 3H), 4.19 (dd, 1H), 3.77 (s, 3H), 3.57 (s, 3H), 3.47-3.39 (m, 2H), 3.19-3.13 (m, 1H), 3.02-2.74 (m, 4H), 2.28-1.47 (m, 10H), 2.28 (s, 6H), 2.14 (s, 3H), 2.02 (s, 3H); ¹³C NMR (75 MHz, CDCl₃): δ 172.3, 171.3, 165.6, 163.7, 149.6, 148.4, 145.9, 141.0, 140.5, 131.1, 130.7, 125.8, 124.8, 120.2, 118.4, 113.7, 113.3, 102.0, 99.1, 61.5, 61.4, 61.3, 60.0, 59.6, 59.3, 58.4, 57.4, 56.1, 55.2, 54.6, 51.8, 42.2, 41.3, 41.1, 35.2, 32.1, 28.2, 28.1, 25.4, 24.0, 20.3, 16.1, 9.5; ESI-MS m/z: Calcd. for C₄₃H₅₂N₆O₁₁S₂: 892.3. Found (M+H⁺): 894.1.

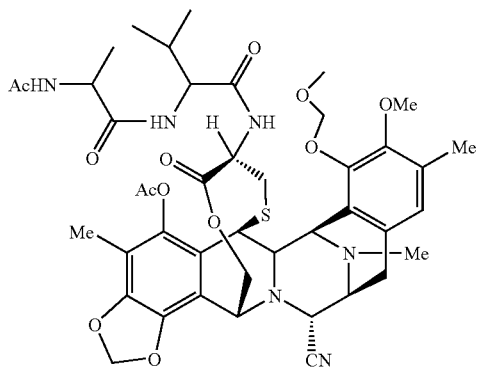

Compound 2t (from Compound 2p using Ac-L-alanine as the acid): $^1$H NMR (300 MHz, CDCl$_3$): δ 6.74 (s, 1H), 6.60-6.56 (m, 1H), 6.26 (bt, 1H), 6.04 (dd, 2H), 5.58 (bt, 1H), 5.17 (dd, 2H), 5.00 (d, 1H), 4.64-4.60 (m, 1H), 4.56 (bp, 1H), 4.48 (dt, 1H), 4.35 (d, 1H), 4.29 (s, 1H), 4.20-4.14 (m, 2H), 4.12-4.05 (m, 1H), 3.75, 3.76 (2s, 3H), 3.56 (s, 3H), 3.47-3.42 (m, 2H), 2.98-2.89 (m, 2H), 2.42-1.98 (m, 3H), 2.42 (s, 3H), 2.28 (s, 3H), 2.16 (s, 3H), 2.02 (s, 3H), 1.98 (s, 3H), 1.36, 1.33 (2d, 3H), 1.06, 1.03 (2d, 3H), 0.94, 0.93 (2d, 3H); $^{13}$C NMR (75 MHz, CDCl$_3$): δ 171.9, 170.2, 169.6, 169.7, 168.5, 149.6, 148.6, 145.9, 141.1, 140.5, 131.8, 130.3, 125.4, 124.4, 120.3, 117.9, 113.4, 102.0, 99.2, 61.5, 60.2, 59.6, 59.4, 59.3, 58.5, 57.8, 57.7, 57.4, 54.9, 54.5, 52.0, 51.9, 48.9, 48.8, 42.0, 41.3, 32.7, 32.2, 32.1, 23.8, 23.1, 23.1, 20.3, 19.2, 19.2, 19.1, 18.4, 17.7, 17.7, 16.2, 9.5. ESI-MS m/z: Calcd. for C$_{43}$H$_{54}$N$_6$O$_{12}$S: 878.3. Found (M+H$^+$): 879.2.

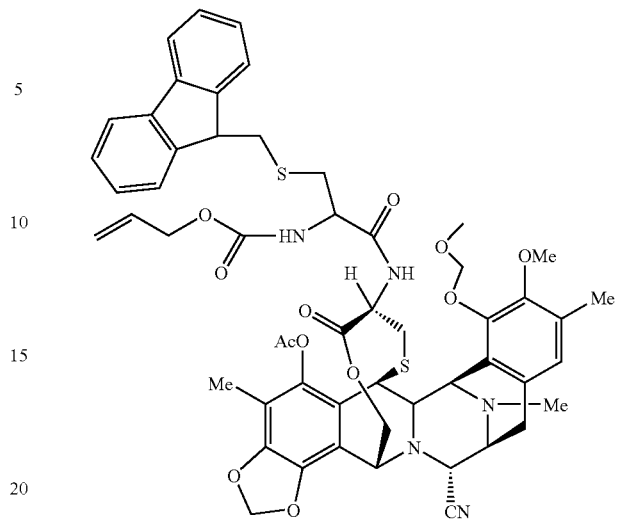

Compound 2y (using FmSCH$_2$CH(NHAlloc)CO$_2$H as the acid): $^1$H NMR (300 MHz, CDCl$_3$): δ 7.77-7.67 (m, 4H), 7.42-7.26 (m, 4H), 6.75 (s, 1H), 6.12 (bd, 1H), 6.04 (dd, 2H), 5.97-5.88 (m, 1H), 5.53 (bd, 1H), 5.35-5.21 (m, 2H), 5.15 (dd, 2H), 4.99 (d, 1H), 4.61-4.55 (m, 4H), 4.34 (d, 1H), 4.30 (s, 1H), 4.20-4.17 (m, 4H), 3.70 (s, 3H), 3.54 (s, 3H), 3.46 (d, 1H), 3.45-3.40 (m, 1H), 3.21-3.14 (m, 1H), 3.04-2.83 (m, 5H), 2.41-2.03 (m, 2H), 2.33 (s, 3H), 2.23 (s, 3H), 2.15 (s, 3H), 2.03 (s, 3H); ESI-MS m/z: Calcd. for C$_{54}$H$_{57}$N$_5$O$_{12}$S$_2$: 1031.3. Found (M$^+$): 1032.2.

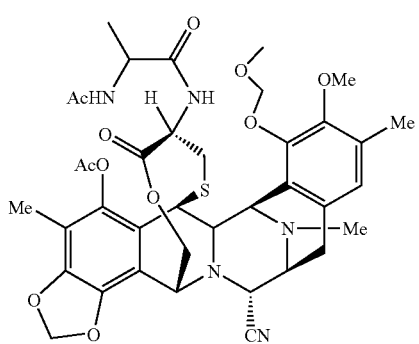

Compound 2w (using Ac-L-alanine as the acid): $^1$H NMR (300 MHz, CDCl$_3$): δ 6.89, 6.77 (2s, 1H), 6.25 (dd, 1H), 6.05 (dd, 2), 5.72, 5.55 (2bd, 1H), 5.22-5.13 (2dd, 2H), 5.02, 5.01 (2d, 1H), 4.60-4.18 (m, 7H), 3.77, 3.74 (2s, 3H), 3.56 (s, 3H), 3.48-3.43 (m, 2H), 2.93-2.91 (bd, 2H), 2.42-1.98 (m, 2H), 2.42, 2.37 (2s, 3H), 2.29, 2.28 (2s, 3H), 2.17, 2.15 (2s, 3H), 2.03 (s, 3H), 1.99, 1.97 (2s, 3H), 1.46, 1.22 (2d, 3H); $^{13}$C NMR (75 MHz, CDCl$_3$): δ 171.5, 170.1, 169.9, 169.3, 169.2, 168.6, 149.8, 149.4, 148.7, 148.5, 145.9, 141.1, 140.5, 140.4, 132.0, 131.6, 130.6, 130.2, 125.5, 124.9, 124.4, 120.4, 120.2, 117.9, 113.6, 113.4, 102.0, 99.2, 61.6, 61.5, 60.4, 60.3, 59.6, 59.5, 59.4, 59.2, 58.8, 58.3, 57.5, 55.0, 55.0, 54.6, 52.2, 51.8, 48.6, 48.5, 42.1, 42.0, 41.4, 32.5, 32.4, 23.8, 23.7, 23.2, 23.2, 20.3, 19.9, 19.8, 16.0, 15.9, 9.6. ESI-MS m/z: Calcd. for C$_{38}$H$_{45}$N$_5$O$_{11}$S: 779.3. Found (M+H$^+$): 780.2.

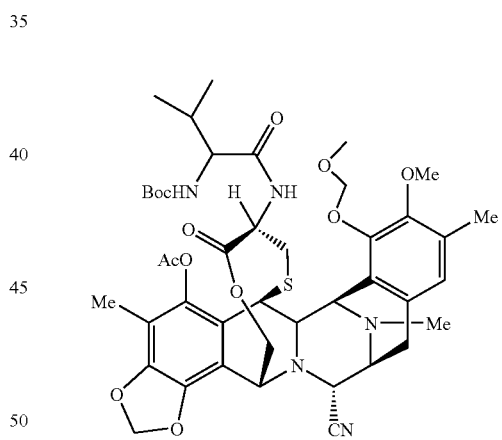

Compound 7 (using Boc-L-valine as the acid): $^1$H NMR (300 MHz, CDCl$_3$): δ 6.80 (s, 1H), 6.04 (dd, 2H), 5.86 (bd, 1H), 5.15 (dd, 2H), 5.02 (d, 1H), 4.98 (bd, 1H), 4.63-4.60 (m, 1H), 4.55 (bp, 1H), 4.35 (d, 1H), 4.30 (s, 1H), 4.22-4.16 (m, 2H), 3.83 (dd, 1H), 3.76 (s, 3H), 3.56 (s, 3H), 3.48-3.42 (m, 2H), 2.93-2.90 (m, 2H), 2.41-2.03 (m, 3H), 2.41 (s, 3H), 2.28 (s, 3H), 2.15 (s, 3H), 2.03 (s, 3H), 1.46 (s, 9H), 1.01 (d, 3H), 0.87 (d, 3H); $^{13}$C NMR (75 MHz, CDCl$_3$): δ 170.4, 170.2, 168.5, 165.2, 155.3, 148.6, 145.9, 141.1, 140.5, 131.6, 130.4, 125.5, 124.5, 120.5, 118.0, 113.5, 113.4, 102.0, 99.2, 61.6, 60.0, 59.6, 59.3, 58.4, 57.5, 55.0, 54.6, 52.1, 42.0, 41.4, 32.7, 31.6, 28.3, 23.8, 20.2, 19.1, 17.5, 16.3, 9.6. ESI-MS m/z: Calcd. for C$_{43}$H$_{55}$N$_5$O$_{12}$S: 865.4. Found (M+H$^+$): 866.3.

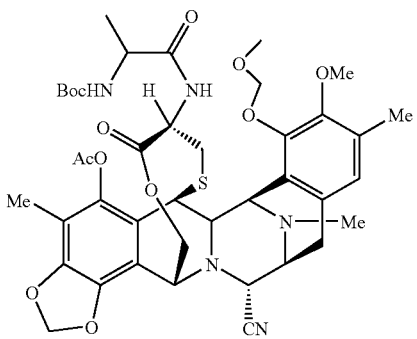
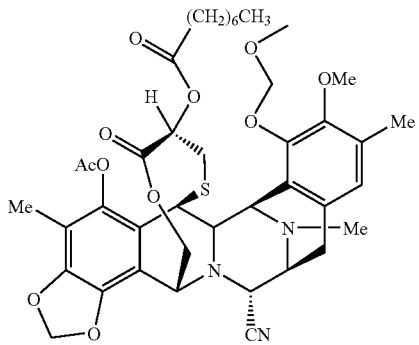

Compound 8 (using Boc-L-alanine as the acid): $^1$H NMR (300 MHz, CDCl$_3$): δ 6.81 (s, 1H), 6.04 (dd, 2H), 5.86 (bp, 1H), 5.16 (dd, 2H), 5.03 (bp, 1H), 5.02 (d, 1H), 4.56-4.50 (m, 2H), 4.34 (d, 1H), 4.29 (s, 1H), 4.20-4.15 (m, 2H), 3.98-3.78 (m, 1H), 3.75 (s, 3H), 3.55 (s, 3H), 3.47-3.43 (m, 2H), 2.91 (bd, 2H), 2.37-2.02 (m, 2H), 2.37 (s, 3H), 2.27 (s, 3H), 2.15 (s, 3H), 2.02 (s, 3H), 1.46 (s, 9H), 1.37 (d, 3H); $^{13}$C NMR (75 MHz, CDCl$_3$): δ 171.5, 170.1, 168.4, 154.6, 149.5, 148.5, 145.8, 141.0, 140.4, 131.3, 130.4, 125.6, 124.4, 120.3, 117.9, 113.3, 101.9, 99.1, 61.4, 60.1, 59.6, 59.2, 58.5, 57.4, 54.9, 54.5, 52.1, 49.9, 41.8, 41.3, 32.4, 28.3, 23.8, 20.2, 19.5, 16.1, 9.5. ESI-MS m/z: Calcd. for C$_{41}$H$_{51}$N$_5$O$_{12}$S: 837.3. Found (M+H$^+$): 838.4.

Compound 13e (using 5 equiv. of CH$_3$(CH$_2$)$_6$CO$_2$H as the acid, 7 equiv. of DMAP and 7 equiv. of EDC.HCl): $^1$H NMR (300 MHz, CDCl$_3$): δ 6.68 (s, 1H), 6.04 (dd, 2H), 5.17 (dd, 2H), 5.02-4.98 (m, 2H), 4.56 (bp, 1H), 4.34 (d, 1H), 4.28 (s, 1H), 4.19 (d, 1H), 4.11 (dd, 1H), 3.78 (s, 3H), 3.56 (s, 3H), 3.46 (d, 1H), 3.42-3.39 (m, 1H), 2.89-2.87 (m, 2H), 2.32-1.96 (m, 4H), 2.30 (s, 3H), 2.26 (s, 3H), 2.17 (s, 3H), 2.03 (s, 3H), 1.60-1.55 (m, 2H), 1.32-1.23 (m, 8H), 0.90 (t, 3H); $^{13}$C NMR (75 MHz, CDCl$_3$): δ 172.5, 168.6, 167.1, 148.9, 148.2, 145.8, 141.1, 140.6, 130.7, 125.3, 125.1, 124.7, 120.9, 118.1, 113.6, 113.1, 102.0, 99.2, 71.4, 61.5, 60.0, 59.8, 59.2, 58.6, 57.4, 55.0, 54.6, 41.6, 41.5, 33.8, 31.7, 29.1, 28.9, 24.7, 23.9, 22.6, 20.2, 15.9, 14.0, 9.6. ESI-MS m/z: Calcd. for C$_{41}$H$_{51}$N$_3$O$_{11}$S: 793.3. Found (M+H$^+$): 794.9.

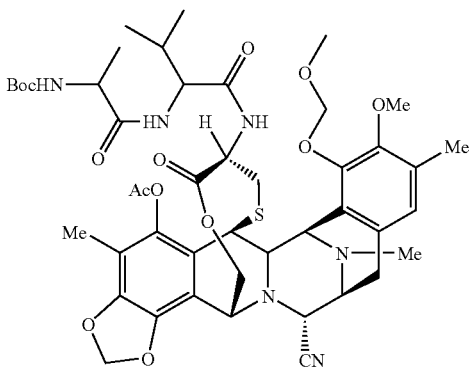
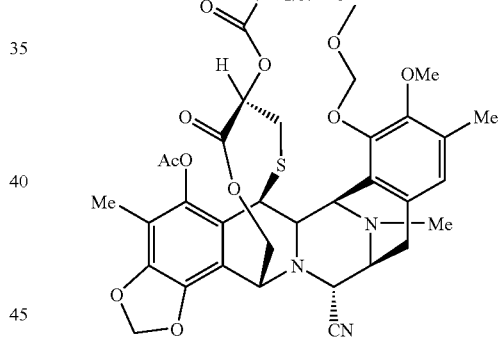

Compound 9 (using Boc-L-alanine as the acid): $^1$H NMR (300 MHz, CDCl$_3$): δ 6.76 (s, 1H), 6.66 (bd, 1H), 6.04 (dd, 2H), 5.58 (bd, 1H), 5.17 (dd, 2H), 5.01 (d, 1H), 4.99 (bp, 1H), 4.66-4.63 (m, 1H), 4.56 (bp, 1H), 4.35 (d, 1H), 4.29 (s, 1H), 4.19-4.05 (m, 4H), 3.76 (s, 3H), 3.56 (s, 3H), 3.47-3.42 (m, 2H), 2.92-2.89 (m, 2H), 2.44-2.02 (m, 3H), 2.44 (s, 3H), 2.28 (s, 3H), 2.16 (s, 3H), 2.02 (s, 3H), 1.41 (s, 9H), 1.32 (d, 3H), 1.03 (d, 3H), 0.93 (d, 3H); $^{13}$C NMR (75 MHz, CDCl$_3$): δ 172.1, 170.2, 169.7, 168.5, 149.7, 148.7, 145.9, 141.0, 140.5, 132.0, 130.2, 125.3, 124.4, 120.3, 117.9, 113.5, 102.0, 99.2, 61.5, 60.2, 59.6, 59.4, 58.5, 57.7, 57.4, 55.0, 54.6, 51.9, 50.2, 42.0, 41.4, 32.7, 32.2, 28.2, 23.8, 20.3, 19.1, 18.1, 17.8, 16.3, 9.6. ESI-MS m/z: Calcd. for C$_{46}$H$_{60}$N$_6$O$_{13}$S: 936.4. Found (M$^+$): 937.2.

Compound 13f (using 4 equiv. of CH$_3$(CH$_2$)$_{14}$CO$_2$H as the acid, 6 equiv. of DMAP and 6 equiv. of EDC.HCl): $^1$H NMR (300 MHz, CDCl$_3$): δ 6.68 (s, 1H), 6.04 (dd, 2H), 5.17 (dd, 2H), 5.02-4.98 (m, 2H), 4.56 (bp, 1H), 4.34 (d, 1H), 4.28 (s, 1H), 4.19 (d, 1H), 4.12 (dd, 1H), 3.78 (s, 3H), 3.57 (s, 3H), 3.46 (d, 1H), 3.45-3.41 (m, 1H), 2.89-2.87 (m, 2H), 2.37-1.96 (m, 4H), 2.30 (s, 3H), 2.26 (s, 3H), 2.17 (s, 3H), 2.04 (s, 3H), 1.63-1.58 (m, 2H), 1.35-1.23 (m, 24H), 0.88 (t, 3H); 13C NMR (75 MHz, CDCl$_3$): δ 172.6, 168.6, 167.1, 148.9, 148.2, 145.8, 141.1, 140.6, 130.7, 125.3, 125.1, 124.7, 120.9, 118.1, 113.6, 113.1, 102.0, 99.2, 71.4, 61.5, 60.0, 59.8, 59.2, 58.6, 57.4, 55.0, 54.6, 41.6, 41.5, 33.9, 31.9, 31.7, 30.9, 29.7, 29.5, 29.3, 29.3, 29.2, 29.1, 24.7, 23.9, 22.7, 20.2, 15.9, 14.1, 9.6.

Example 3

Method C: To a solution of 1 equiv. of 1 coevaporated twice with anhydrous toluene in CH$_2$Cl$_2$ (0.05M) under Argon, were added 1.05 equiv. of phthalic anhydride. After 30 min the reaction was cold to 0° C. and 2.5 equiv. of Et$_3$N and 1.5 equiv. of ClCO₂Et were added. 5 min later the reaction was warmed to RT and stirred for 7 h. Then it was diluted with CH₂Cl₂, washed with a saturated solution of NaHCO₃ and the organic layer dried with Na₂SO₄. Flash chromatography (hex/EtOAc, 3:2) gives 2d in 85% yield.

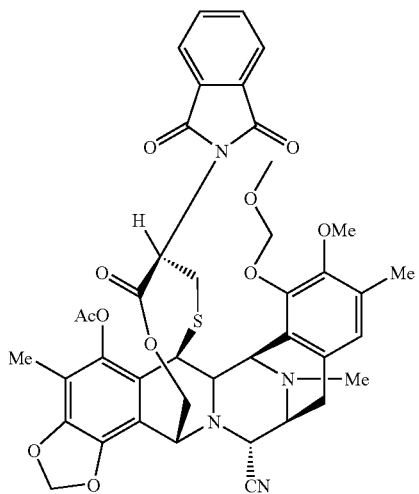

Compound 2j: $^1$H NMR (300 MHz, CDCl₃): δ 7.91-7.70 (m, 4H), 6.67 (s, 1H), 6.06 (dd, 2H), 5.19 (dd, 2H), 5.05 (d, 1H), 4.64-4.62 (m, 2H), 4.37 (d, 1H), 4.32 (s, 1H), 4.20 (d, 1H), 4.12 (dd, 1H), 3.79 (s, 3H), 3.58 (s, 3H), 3.50 (d, 1H), 3.41-3.40 (m, 1H), 2.85-2.83 (m, 2H), 2.36-2.11 (m, 2H), 2.33 (s, 3H), 2.31 (s, 3H), 2.14 (s, 3H), 2.05 (s, 3H); ESI– MS m/z: Calcd. for C₄₁H₄₀N₄O₁₁S: 796.2. Found (M+H⁺): 797.2.

Example 4

Method D: To a solution of 1 equiv. of 1 in CH₃CN/CH₂Cl₂ 3:1 (0.025M) under Argon, were added 1 equiv. of formaline solution (37%) and 1 equiv. of NaBH₃CN. The solution was stirred at room temperature for 30 min. Then, 2 equiv. of acetic acid were added the solution which turned to orange-yellow was stirred for 1 h 30 min. After this time the reaction mixture was diluted with CH₂Cl₂, neutralized with NaHCO₃ and extracted with CH₂Cl₂. The organic layer was dried with Na₂SO₄. Flash chromatography gives the pure compound.

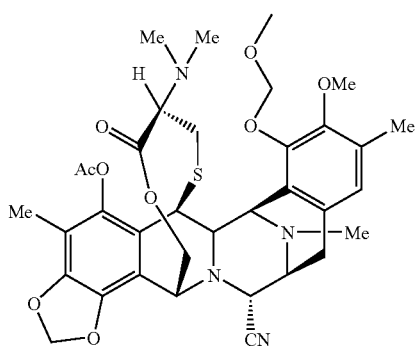

Compound 2m: $^1$H NMR (300 MHz, CDCl₃): δ 6.66 (s, 1H), 6.03 (dd, 2H), 5.17 (dd, 2H), 4.98 (d, 1H), 4.58 (bp, 1H), 4.32 (d, 1H), 4.25 (s, 1H), 4.15-4.13 (m, 1H), 3.95 (dd, 1H), 3.78 (s, 3H), 3.56 (s, 3H), 3.54-3.41 (m, 3H), 2.92-2.80 (m, 2H), 2.33 (s, 3H), 2.17 (s, 3H), 2.17-2.07 (bp, 6H), 2.16 (s, 3H), 2.04 (s, 3H), 1.86 (dd, 2H); ESI-MS m/z: Calcd. for C₃₅H₄₂N₄O₉S: 694.3. Found (M+H⁺): 695.3.

Example 5

Method E: To a solution of 1 equiv. of 1 (3p for 3q-r, 3s for 3u, 3v for 3x, 11 for 13c, 13h, 13ll and 24 for 26) in CH₂Cl₂ (0.08M) under Argon at RT were added 1.1 equiv. of pyridine. Then the reaction was cold to 0° C. and 1.1 equiv of the acid chloride were added. 5 min later the reaction was warmed to RT and stirred for 45 min. Then it was diluted with CH₂Cl₂, washed with a saturated solution of NaCl and the organic layer dried with Na₂SO₄. Flash chromatography gives pure compounds.

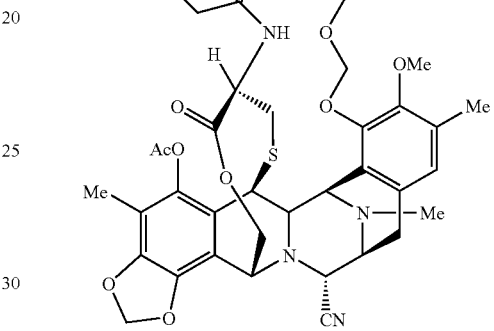

Compound 2c (using butyryl chloride): $^1$H NMR (300 MHz, CDCl₃): δ 6.76 (s, 1H), 6.04 (dd, 2H), 5.52 (bd, 1H), 5.17 (dd, 2H), 5.02 (d, 1H), 4.61 (ddd, 1H), 4.52 (bp, 1H), 4.34 (dd, 1H), 4.27 (s, 1H), 4.19 (d, 1H), 4.17 (dd, 1H), 3.75 (s, 3H), 3.56 (s, 3H), 3.47-3.43 (m, 2H), 2.92 (bd, 2H), 2.34-1.98 (m, 4H), 2.28 (s, 3H), 2.27 (s, 3H), 2.16 (s, 3H), 2.02 (s, 3H), 1.71-1.58 (m, 2H), 0.96 (t, 3H); $^{13}$C NMR (75 MHz, CDCl₃): δ 171.7, 170.6, 168.4, 149.6, 148.5, 145.8, 141.0, 140.4, 131.0, 130.5, 125.7, 124.6, 120.4, 117.9, 113.4, 102.0, 99.1, 61.5, 60.1, 59.6, 59.2, 58.6, 57.4, 55.0, 54.5, 51.9, 41.8, 41.3, 38.2, 32.7, 23.7, 20.2, 18.8, 16.1, 13.7, 9.5. ESI-MS m/z: Calcd. for C₃₇H₄₄N₄O₁₀S: 736.3. Found (M+H⁺): 737.2.

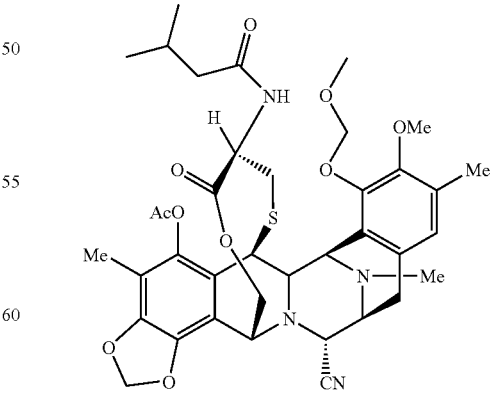

Compound 2d (using isovaleryl chloride): $^1$H NMR (300 MHz, CDCl₃): δ 6.76 (s, 1H), 6.05 (dd, 2H), 5.50 (bd, 1H), 5.17 (dd, 2H), 5.02 (d, 1H), 4.63 (ddd, 1H), 4.53 (bp, 1H), 4.35 (dd, 1H), 4.28 (s, 1H), 4.20 (d, 1H), 4.18 (dd, 1H), 3.76 (s, 3H), 3.56 (s, 3H), 3.47-3.43 (m, 2H), 2.92 (bd, 2H), 2.30-1.92 (m, 5H), 2.30 (s, 3H), 2.28 (s, 3H), 2.17 (s, 3H), 2.03 (s, 3H), 0.99 (d, 3H), 0.93 (d, 3H); $^{13}$C NMR (75 MHz, CDCl$_3$): δ 171.3, 170.6, 168.4, 149.6, 148.5, 141.0, 140.5, 130.9, 130.5, 125.7, 124.6, 120.4, 118.0, 113.5, 113.4, 102.0, 99.2, 61.5, 60.1, 59.6, 59.3, 58.6, 57.5, 55.0, 54.6, 51.8, 45.6, 41.9, 41.4, 31.8, 25.8, 23.8, 22.5, 22.4, 20.2, 16.3, 9.6. ESI-MS m/z: Calcd. for C$_{38}$H$_{46}$N$_4$O$_{10}$S: 750.3. Found (M+H$^+$): 751.3.

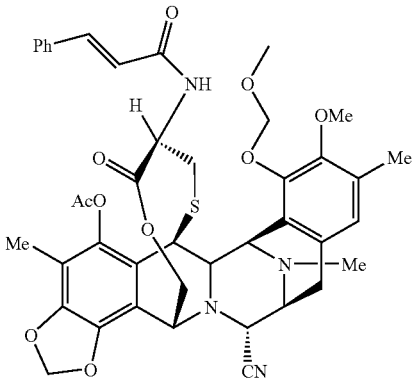

Compound 2h (using cinnamoyl chloride): $^1$H NMR (300 MHz, CDCl$_3$): δ 7.61 (d, 1H), 7.55-7.51 (m, 2H), 7.44-7.37 (m, 3H), 6.85 (s, 1H), 6.24 (d, 1H), 6.05 (dd, 2H), 5.72 (d, 1H), 5.16 (dd, 2H), 5.05 (d, 1H), 4.71 (ddd, 1H), 4.54 (bp, 1H), 4.35 (dd, 1H), 4.29 (s, 1H), 4.22-4.17 (m, 2H), 3.68 (s, 3H), 3.56 (s, 3H), 3.48-3.44 (m, 2H), 2.97-2.95 (m, 2H), 2.51-2.45 (m, 1H), 2.27-2.03 (m, 1H), 2.27 (s, 6H), 2.19 (s, 3H), 2.03 (s, 3H); $^{13}$C NMR (75 MHz, CDCl$_3$): δ 170.5, 168.4, 164.5, 149.7, 148.5, 145.8, 142.1, 141.0, 140.4, 134.7, 131.1, 130.5, 129.8, 128.8, 127.9, 125.5, 124.4, 120.4, 119.7, 118.0, 113.4, 113.3, 102.0, 99.1, 61.4, 60.3, 59.6, 59.2, 58.8, 57.4, 54.9, 54.5, 52.6, 41.7, 41.4, 32.7, 23.8, 20.2, 16.3, 9.6. ESI-MS m/z: Calcd. for C$_{42}$H$_{44}$N$_4$O$_{10}$S: 796.3. Found (M+H$^+$): 797.2.

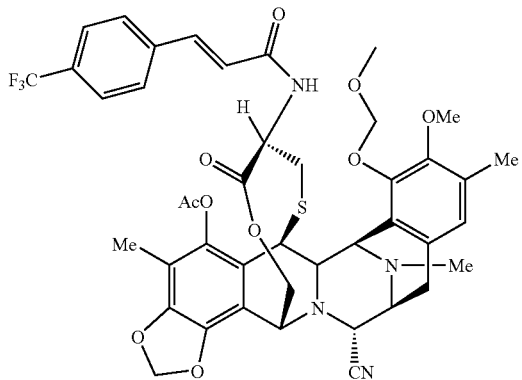

Compound 2i (using trans-3-(trifluoromethyl)-cinnamoyl chloride): $^1$H NMR (300 MHz, CDCl$_3$): δ 7.82-7.51 (m, 5H), 6.85 (s, 1H), 6.29 (d, 1H), 6.05 (dd, 2H), 5.75 (d, 1H), 5.17 (dd, 2H), 5.05 (d, 1H), 4.73-4.69 (m, 1H), 4.55 (bp, 1H), 4.36 (d, 1H), 4.39 (s, 1H), 4.23-4.18 (m, 2H), 3.69 (s, 3H), 3.57 (s, 3H), 3.48-3.44 (m, 2H), 2.96 (bd, 2H), 2.49-2.44 (m, 1H), 2.27-2.04 (m, 1H), 2.27 (s, 6H), 2.19 (s, 3H), 2.04 (s, 3H); $^{13}$C NMR (75 MHz, CDCl$_3$): δ 170.3, 168.4, 163.8, 149.7, 148.5, 145.9, 141.1, 140.5, 135.5, 134.6, 131.6, 131.0, 130.6, 129.5, 126.3, 126.2, 125.6, 124.4, 123.7, 123.6, 121.5, 120.3, 117.9, 113.5, 113.3, 102.0, 99.2, 61.4, 60.4, 59.6, 59.2, 58.9, 57.5, 54.9, 54.5, 52.6, 41.8, 41.4, 32.6, 23.8, 20.3, 16.2, 9.6. ESI-MS m/z: Calcd. for C$_{43}$H$_{43}$N$_4$F$_3$O$_{10}$S: 864.3. Found (M+H$^+$): 865.0.

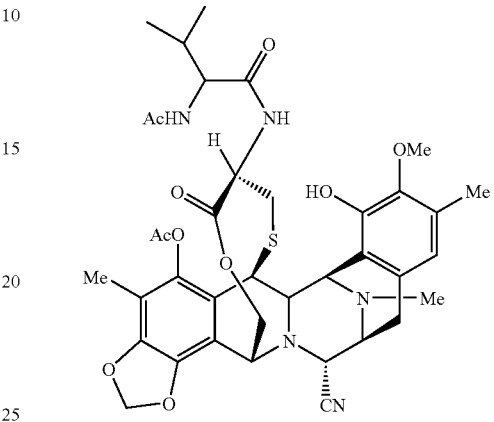

Compound 3q (from Compound 3p using acetyl chloride): $^1$H NMR (300 MHz, CDCl$_3$): δ 6.54 (s, 1H), 6.08 (d, 1H), 6.05 (dd, 2H), 5.81 (s, 1H), 5.59 (d, 1H), 5.02 (d, 1H), 4.67 (dt, 1H), 4.58 (bp, 1H), 4.29 (s, 1H), 4.26 (dd, 1H), 4.21-4.16 (m, 1H), 4.09 (dd, 1H), 3.80 (s, 3H), 3.45-3.42 (m, 2H), 2.91-2.88 (m, 2H), 2.49 (s, 3H), 2.29-1.98 (m, 3H), 2.29 (s, 3H), 2.16 (s, 3H), 2.03 (s, 3H), 1.98 (s, 3H), 1.06 (d, 3H), 0.96 (d, 3H); $^{13}$C NMR (75 MHz, CDCl$_3$): δ 170.2, 169.5, 168.6, 148.1, 145.9, 143.3, 141.1, 140.4, 130.4, 130.1, 120.4, 120.2, 118.5, 118.0, 113.5, 102.0, 61.4, 60.4, 59.3, 58.8, 57.7, 54.7, 54.6, 51.8, 42.0, 41.5, 32.7, 32.3, 23.8, 23.3, 20.5, 19.1, 18.0, 16.2, 9.6. ESI-MS m/z: Calcd. for C$_{38}$H$_{45}$N$_5$O$_{10}$S: 763.3. Found (M+H$^+$): 764.3

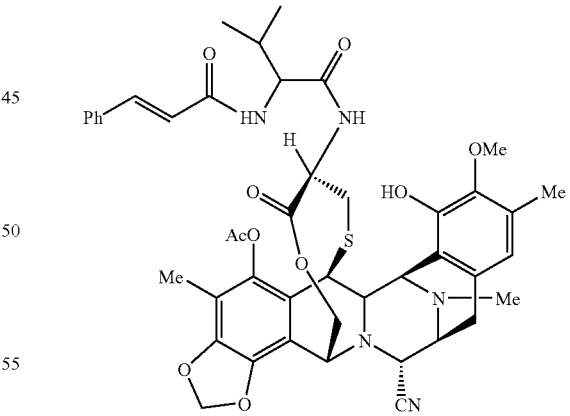

Compound 3r (from Compound 3p using cinnamoyl chloride): $^1$H NMR (300 MHz, CDCl$_3$): δ 7.59 (d, 1H), 7.50-7.46 (m, 2H), 7.37-7.34 (m, 3H), 6.57 (s, 1H), 6.42 (d, 1H), 6.30 (d, 1H), 6.05 (dd, 2H), 5.81 (s, 1H), 5.64 (d, 1H), 5.03 (d, 1H), 4.70-4.67 (m, 1H), 4.58 (bp, 1H), 4.30-4.24 (m, 3H), 4.21-4.17 (m, 2H), 3.82 (s, 3H), 3.45 (bd, 2H), 2.92-2.89 (m, 2H), 2.56 (s, 3H), 2.28-2.03 (m, 3H), 2.28 (s, 3H), 2.17 (s, 3H), 2.03 (s, 3H), 1.10 (d, 3H), 1.00 (d, 3H); $^{13}$C NMR (75 MHz, CDCl$_3$): δ 170.2, 170.1, 169.4, 168.5, 165.3, 148.1, 145.9, 143.4, 141.2, 140.4, 134.8, 130.5, 130.1, 129.7, 128.8, 127.8, 120.6, 120.4, 120.2, 118.5, 118.0, 113.5, 113.5, 102.0, 61.4, 60.4, 59.4, 58.9, 57.7, 54.7, 54.6, 51.9, 42.0, 41.5, 32.7, 23.8, 20.5, 19.2, 18.0, 16.4, 9.6. ESI-MS m/z: Calcd for $C_{45}H_{49}N_5O_{10}S$: 851.3. Found (M+H$^+$): 852.3

120.4, 120.0, 118.8, 118.0, 113.6, 113.4, 102.0, 61.4, 60.6, 60.4, 59.3, 59.1, 54.8, 54.6, 51.7, 48.7, 41.9, 41.5, 32.5, 23.8, 20.5, 20.0, 16.2, 9.6. ESI-MS m/z: Calcd. for $C_{43}H_{45}N_5O_{10}S$: 823.3. Found (M+H$^+$): 824.3.

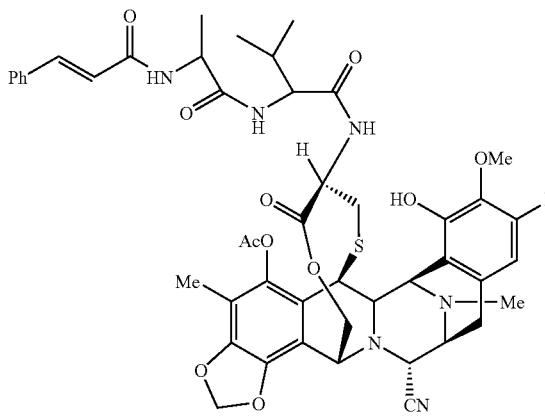

Compound 3u (from Compound 3s using cinnamoyl chloride): $^1$H NMR (300 MHz, CDCl$_3$): δ 7.63 (d, 1H), 7.50-7.47 (m, 2H), 7.38-7.35 (m, 3H), 6.62 (d, 1H), 6.55 (s, 1H), 6.41 (d, 1H), 6.35 (d, 1H), 6.05 (dd, 2H), 5.82 (s, 1H), 5.60 (d, 1H), 5.02 (d, 1H), 4.68-4.60 (m, 2H), 4.58 (bp, 1H), 4.29 (s, 1H), 4.26 (dd, 1H), 4.21-4.15 (m, 2H), 4.10 (dd, 1H), 3.79 (s, 3H), 3.45-3.43 (m, 2H), 2.91-2.88 (m, 2H), 2.48 (s, 3H), 2.30-2.03 (m, 3H), 2.28 (s, 3H), 2.16 (s, 3H), 2.03 (s, 3H), 1.41 (d, 3H), 1.04 (d, 3H), 0.94 (d, 3H); $^{13}$C NMR (75 MHz, CDCl$_3$): δ 171.8, 170.2, 169.6, 168.5, 165.4, 148.0, 145.9, 143.3, 141.6, 141.1, 140.5, 134.7, 130.6, 129.8, 129.8, 128.8, 127.8, 120.3, 120.1, 118.7, 118.0, 113.5, 102.0, 61.5, 60.3, 59.4, 58.8, 57.8, 54.7, 54.6, 51.9, 49.0, 42.1, 41.5, 32.6, 32.3, 23.8, 20.5, 19.2, 18.6, 17.7, 16.3, 9.6. ESI-MS m/z: Calcd. for $C_{48}H_{54}N_6O_{11}S$: 922.4. Found (M+H$^+$): 923.1.

Compound 13c (from Compound 11 using 20 equiv. of butyryl chloride and 30 equiv. of pyr): $^1$H NMR (300 MHz, CDCl$_3$): δ 6.68 (s, 1H), 6.04 (dd, 2H), 5.17 (dd, 2H), 5.02 (bt, 1H), 5.01 (d, 1H), 4.57 (bp, 1H), 4.34 (dd, 1H), 4.29 (s, 1H), 4.19 (d, 1H), 4.12 (dd, 1H), 3.78 (s, 3H), 3.56 (s, 3H), 3.46 (d, 1H), 3.45-3.42 (m, 1H), 2.88 (bd, 2H), 2.30-2.16 (m, 3H), 2.30 (s, 3H), 2.26 (s, 3H), 2.16 (s, 3H), 2.03 (s, 3H), 2.02-1.96 (m, 1H), 1.68-1.56 (m, 2H), 0.98 (t, 3H); $^{13}$C NMR (75 MHz, CDCl$_3$): δ 172.5, 168.8, 167.3, 149.1, 148.4, 146.0, 141.3, 140.9, 131.0, 125.6, 125.0, 121.2, 118.3, 113.8, 113.3, 102.2, 99.4, 71.7, 61.7, 60.3, 60.0, 59.4, 58.8, 57.6, 55.2, 54.9, 41.9, 41.7, 36.1, 32.0, 24.2, 20.5, 18.5, 16.1, 13.9, 9.8. ESI-MS m/z: Calcd. for $C_{37}H_{43}N_3O_{11}S$: 737.3. Found (M+Na$^+$): 760.2.

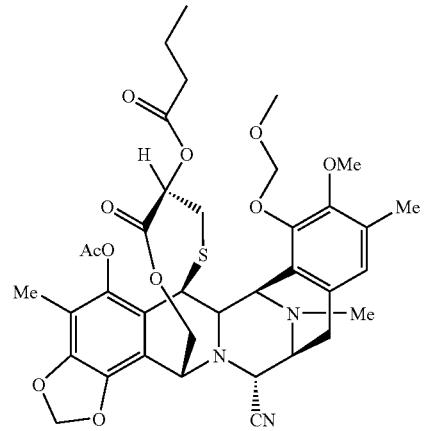

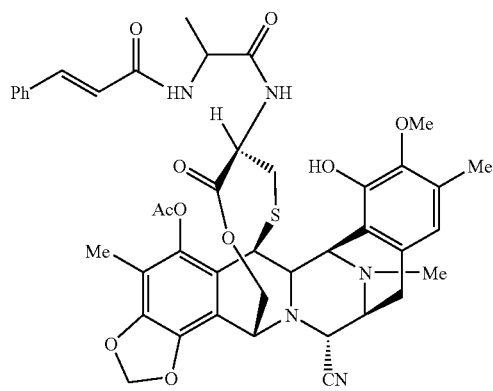

Compound 3x (from Compound 3v using cinnamoyl chloride): $^1$H NMR (300 MHz, CDCl$_3$): δ 7.60 (d, 1H), 7.49-7.46 (m, 2H), 7.37-7.34 (m, 3H), 6.59 (s, 1H), 6.48 (d, 1H), 6.39 (d, 1H), 6.05 (dd, 2H), 5.84 (s, 1H), 5.58 (d, 1H), 5.03 (d, 1H), 4.64-4.59 (m, 1H), 4.58 (bp, 1H), 4.36-4.8 (m, 1H), 4.28 (s, 1H), 4.26 (d, 1H), 4.22-4.17 (m, 2H), 3.81 (s, 3H), 3.45-3.43 (m, 2H), 2.92 (m, 2H), 2.53 (s, 3H), 2.28-2.03 (m, 2H), 2.28 (s, 3H), 2.16 (s, 3H), 2.03 (s, 3H), 1.54 (d, 3H); $^{13}$C NMR (75 MHz, CDCl$_3$): δ 171.4, 170.1, 168.6, 164.9, 148.2, 145.9, 143.2, 141.1, 134.8, 130.5, 130.0, 129.7, 128.8, 127.8, 120.4,

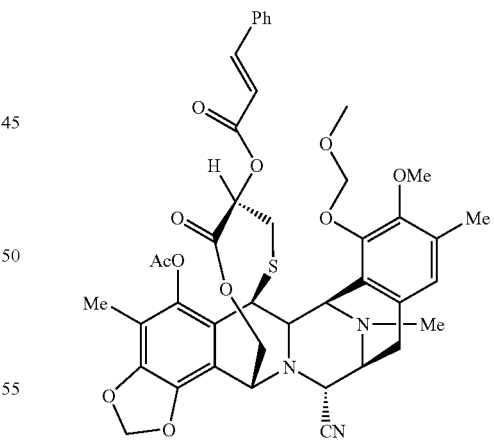

Compound 13h (from Compound 11 using 5 equiv. of cinnamoyl chloride, 7.5 equiv. of pyr and CH$_3$CN as cosolvent): $^1$H NMR (300 MHz, CDCl$_3$): δ 7.68 (d, 1H), 7.56-7.53 (m, 2H), 7.43-7.39 (m, 3H), 6.72 (s, 1H), 6.30 (d, 1H), 6.05 (dd, 2H), 5.22-5.13 (m, 3H), 5.04 (d, 1H), 4.58 (bp, 1H), 4.35 (d, 1H), 4.31 (s, 1H), 4.21 (d, 1H), 4.15 (dd, 1H), 3.79 (s, 3H), 3.57 (s, 3H), 3.48 (d, 1H), 3.43-3.39 (m, 1H), 2.90-2.88 (m, 2H), 2.47-2.41 (m, 1H), 2.31 (s, 3H), 2.24 (s, 3H), 2.17 (s, 3H), 2.07-2.03 (m, 1H), 2.04 (s, 3H); $^{13}$C NMR (75 MHz, CDCl$_3$): δ 168.6, 167.1, 165.6, 148.8, 148.2, 145.7, 141.1, 140.6, 134.4, 130.9, 130.7, 130.4, 128.9, 128.2, 128.1, 125.2, 124.7, 120.9, 118.1, 117.3, 113.7, 113.1, 102.0, 99.2, 71.9, 61.5, 60.0, 59.8, 59.3, 58.5, 57.4, 54.9, 54.6, 41.7, 41.5, 31.8, 23.9, 20.2, 16.0, 9.6. ESI-MS m/z: Calcd. for C$_{42}$H$_{43}$N$_3$O$_{11}$S: 797.3. Found (M+H$^+$): 798.8.

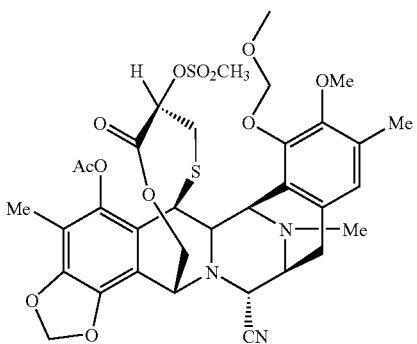

Compound 13ll (from Compound 11 using 5 equiv. of methanesulfonyl chloride and 5 equiv. of Et$_3$N as base): $^1$H NMR (300 MHz, CDCl$_3$): δ 6.65 (s, 1H), 6.04 (dd, 2H), 5.17 (dd, 2H), 5.00 (d, 1H), 4.93 (dd, 1H), 4.58 (bp, 1H), 4.34 (dd, 1H), 4.29 (s, 1H), 4.16-4.12 (m, 2H), 3.77 (s, 3H), 3.56 (s, 3H), 3.46 (d, 1H), 3.44-3.39 (m, 1H), 3.11 (s, 3H), 2.96-2.81 (m, 2H), 2.50-2.42 (m, 1H), 2.30 (s, 3H), 2.26 (s, 3H), 2.18 (s, 3H), 2.04-1.97 (m, 1H), 2.03 (s, 3H); ESI-MS m/z: Calcd. for C$_{34}$H$_{39}$N$_3$O$_{12}$S$_2$: 745.2. Found (M+H$^+$): 746.2.

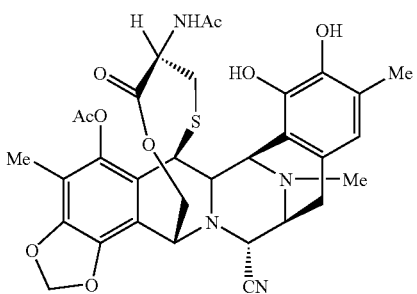

Compound 26 (from Compound 24 using 1.05 equiv. of acetyl chloride and without base): $^1$H NMR (300 MHz, CDCl$_3$): δ 6.51 (s, 1H), 6.05 (d, 2H), 5.95 (s, 1H), 5.60 (d, 1H), 5.59 (bp, 1H), 5.03 (d, 1H), 4.58-4.53 (m, 2H), 4.27 (s, 1H), 4.26 (d, 1H), 4.20-4.16 (m, 2H), 3.43-3.42 (m, 2H), 2.90-2.88 (m, 2H), 2.27-2.11 (m, 2H), 2.27 (s, 3H), 2.24 (s, 3H), 2.14 (s, 3H), 2.03 (s, 3H), 1.85 (s, 3H); $^{13}$C NMR (75 MHz, CDCl$_3$): δ 170.4, 169.5, 168.9, 145.8, 144.5, 140.9, 140.4, 139.9, 127.1, 123.6, 120.1, 119.8, 119.2, 118.1, 113.5, 113.4, 102.0, 61.3, 60.4, 59.2, 58.9, 54.7, 54.5, 52.0, 41.7, 41.4, 32.3, 23.5, 22.8, 20.6, 16.2, 9.6; ESI-MS m/z: Calcd. for C$_{32}$H$_{34}$N$_4$O$_9$S: 650.2. Found (M+H$^+$): 651.3.

Example 6

Method F: To a solution of 1 equiv. of 1 in DMF (0.03M) under Argon at room temperature, were added 0.9 equiv. of Cs$_2$CO$_3$ and 0.9 equiv on BnBr. After 2 h 30 min the reaction was quenched with 1 µL of AcOH, diluted with Hex/EtOAc (1:3), washed with H$_2$O and extracted with Hex/EtOAc (1:3). The organic layer was dried with Na$_2$SO$_4$. Flash chromatography give pure compound 2n.

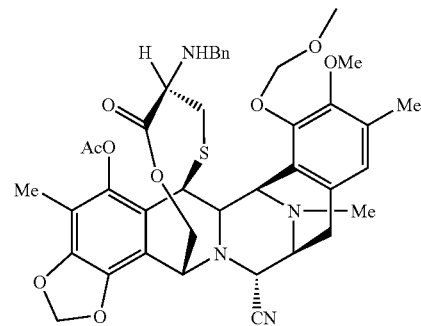

Compound 2n: $^1$H NMR (300 MHz, CDCl$_3$): δ 7.32-7.20 (m, 5H), 6.56 (s, 1H), 6.02 (dd, 2H), 5.15 (dd, 2H), 5.04 (d, 1H), 4.51 (bp, 1H), 4.32 (d, 1H), 4.25-4.23 (m, 2H), 4.12 (dd, 1H), 3.74 (s, 3H), 3.62 (dd, 2H), 3.56 (s, 3H), 3.44-3.40 (m, 2H), 3.38-3.20 (m, 1H), 3.19-2.84 (m, 2H), 2.36-1.91 (m, 2H), 2.29 (s, 3H), 2.19 (s, 3H), 2.03 (s, 3H), 1.91 (s, 3H); $^{13}$C NMR (75 MHz, CDCl$_3$): δ 172.7, 168.6, 149.3, 148.2, 145.6, 140.9, 140.4, 139.9, 131.5, 130.3, 128.3, 128.1, 126.9, 124.9, 124.7, 120.9, 118.1, 113.8, 113.2, 101.9, 99.1, 61.5, 59.7, 59.6, 59.5, 59.2, 58.9, 57.4, 54.9, 54.7, 51.3, 41.5, 41.4, 33.3, 23.8, 20.3, 15.3, 9.6. ESI-MS m/z: Calcd. for C$_{40}$H$_{44}$N$_4$O$_9$S: 756.3. Found (M+Na$^+$): 779.2.

Example 7

Method G: To a solution of 1 equiv. of 2a-n, 2t, 2w, 2y, 11, 12*, 13a-c, 13e-f, 13h, 13ll, 14a* or 7-9 in CH$_3$CN/CH$_2$Cl$_2$ 5:4 (0.026M) under Argon were added 6 equiv. of NaI and 6 equiv. of fresh distilled TMSCl. After 20 min the reaction was quenched with a saturated solution of Na$_2$S$_2$O$_4$, diluted with CH$_2$Cl$_2$, washed with Na$_2$S$_2$O$_4$ (x3), or with NaCl. The aqueous layer extracted with CH$_2$Cl$_2$. The organic layer was dried with Na$_2$SO$_4$. Flash chromatography gives pure compounds 3s-n, 3p, 3s-t, 3v-w, 3y-z, 15, 16*, 17a-c, 17e-f, 17h, 17ll, 18a*.

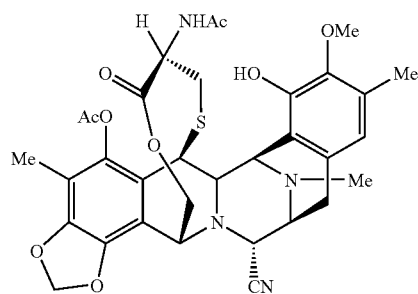

Compound 3a (from 2a): $^1$H NMR (300 MHz, CDCl$_3$): δ 6.56 (s, 1H), 6.04 (dd, 2H), 5.78 (s, 1H), 5.52 (bd, 1H), 5.02 (d, 1H), 4.58 (ddd, 1H), 4.53 (bs, 1H), 4.27-4.25 (m, 2H), 4.19-4.15 (m, 2H), 3.77 (s, 3H), 3.44-3.43 (m, 2H), 2.92-2.90 (m, 2H), 2.36-2.02 (m, 2H), 2.36 (s, 3H), 2.30 (s, 3H), 2.16 (s, 3H), 2.02 (s, 3H), 1.88 (s, 3H); $^{13}$C NMR (75 MHz, CDCl$_3$): δ 170.5, 168.8, 168.4, 148.1, 145.8, 143.1, 141.0, 140.3, 130.7, 129.9, 129.0, 120.3, 119.0, 117.9, 113.5, 102.0, 61.3, 60.3, 60.2, 59.3, 58.9, 54.7, 54.5, 51.9, 41.8, 41.4, 32.4, 23.7, 22.8, 20.4, 16.0, 9.5; ESI-MS m/z: Calcd. for C$_{33}$H$_{36}$N$_4$O$_9$S: 664.2. Found (M+H$^+$): 665.2.

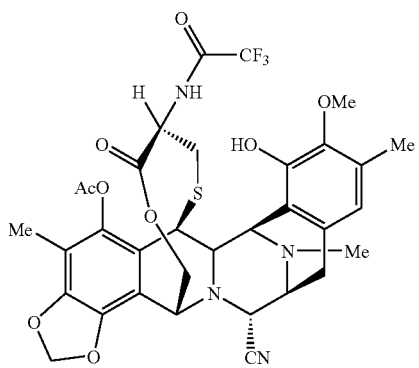

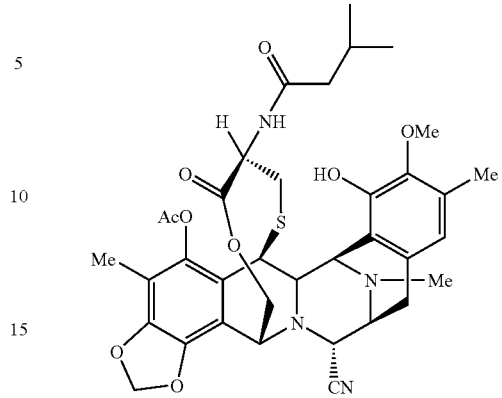

Compound 3b (from 2b): ¹H NMR (300 MHz, CDCl₃): δ 6.52 (s, 1H), 6.41 (bd, 1H), 6.05 (dd, 2H), 5.72 (s, 1H), 5.05 (d, 1H), 4.60 (bp, 1H), 4.54-4.51 (m, 1H), 4.32 (s, 1H), 4.26-4.18 (m, 3H), 3.74 (s, 3H), 3.46-3.42 (m, 2H), 2.97-2.80 (m, 2H), 2.44-2.38 (m, 1H), 2.30-2.03 (m, 1H), 2.30 (s, 3H), 2.27 (s, 3H), 2.15 (s, 3H), 2.03 (s, 3H); ¹³C NMR (75 MHz, CDCl₃): δ 168.8, 168.5, 156.3, 155.8, 155.3, 147.6, 146.0, 143.1, 141.2, 140.5, 130.5, 129.9, 120.7, 120.6, 120.1, 118.0, 117.9, 113.2, 101.1, 61.4, 60.7, 60.1, 59.5, 58.9, 54.6, 54.5, 52.8, 42.0, 41.5, 31.9, 23.8, 20.4, 15.6, 9.6; ESI-MS m/z: Calcd. for $C_{33}H_{33}F_3N_4O_9S$: 718.2. Found (M+H⁺): 719.2.

Compound 3d (from 2d): ¹H NMR (300 MHz, CDCl₃): δ 6.54 (s, 1H), 6.04 (dd, 2H), 5.76 (s, 1H), 5.48 (bd, 1H), 5.02 (d, 1H), 4.66-4.60 (m, 1H), 4.53 (bp, 1H), 4.27-4.23 (m, 2H), 4.19-4.15 (m, 2H), 3.76 (s, 3H), 3.44-3.42 (m, 2H), 2.90 (bd, 2H), 2.33-1.90 (m, 5H), 2.33 (s, 3H), 2.28 (s, 3H), 2.15 (s, 3H), 2.02 (s, 3H), 0.98 (d, 3H), 0.92 (d, 3H); ¹³C NMR (75 MHz, CDCl₃): δ 171.3, 170.6, 168.5, 148.0, 145.8, 143.1, 141.1, 140.4, 130.8, 129.0, 127.6, 120.5, 120.3, 119.1, 118.0, 113.5, 102.0, 74.2, 61.4, 60.3, 59.4, 58.8, 54.7, 54.6, 51.7, 45.5, 41.9, 41.5, 32.7, 25.8, 23.8, 22.5, 22.4, 20.5, 16.2, 9.6. ESI-MS m/z: Calcd. for $C_{36}H_{42}N_4O_9S$: 706.3. Found (M+Na⁺): 729.2.

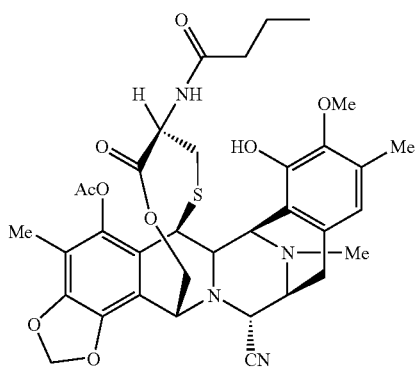

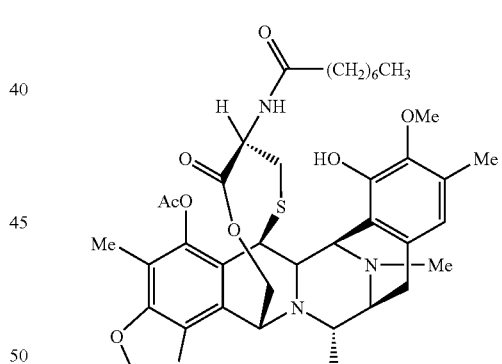

Compound 3c (from 2c): ¹H NMR (300 MHz, CDCl₃): δ 6.54 (s, 1H), 6.03 (dd, 2H), 5.82 (s, 1H), 5.49 (bd, 1H), 5.02 (d, 1H), 4.61 (ddd, 1H), 4.53 (bp, 1H), 4.27-4.24 (m, 2H), 4.19-4.15 (m, 2H), 3.76 (s, 3H), 3.44-3.41 (m, 2H), 2.90 (bd, 2H), 2.31-1.94 (m, 4H), 2.31 (s, 3H), 2.28 (s, 3H), 2.15 (s, 3H), 2.02 (s, 3H), 1.67-1.57 (m, 2H), 0.95 (t, 3H); ¹³C NMR (75 MHz, CDCl₃): δ 171.8, 170.5, 148.0, 145.8, 143.1, 141.0, 140.4, 130.8, 129.0, 120.4, 120.2, 119.0, 118.0, 113.4, 102.0, 61.4, 60.2, 59.4, 58.9, 54.7, 54.5, 51.7, 41.8, 41.4, 38.2, 32.6, 23.8, 20.5, 18.8, 16.0, 13.7, 9.6. ESI-MS m/z: Calcd. for $C_{35}H_{40}N_4O_9S$: 692.2. Found (M+H⁺): 693.9.

Compound 3e (from 2e): ¹H NMR (300 MHz, CDCl₃): δ 6.54 (s, 1H), 6.04 (dd, 2H), 5.75 (s, 1H), 5.48 (bd, 1H), 5.02 (d, 1H), 4.60 (ddd, 1H), 4.53 (bp, 1H), 4.27-4.24 (m, 2H), 4.19-4.15 (m, 2H), 3.77 (s, 3H), 3.48-3.42 (m, 2H), 2.91 (bd, 2H), 2.32-1.97 (m, 4H), 2.32 (s, 3H), 2.28 (s, 3H), 2.16 (s, 3H), 2.02 (s, 3H), 1.62-1.41 (m, 2H), 1.390-1.25 (m, 8H), 0.89 (t, 3H); ¹³C NMR (75 MHz, CDCl₃): δ 172.0, 170.6, 168.4, 148.0, 145.8, 143.1, 141.0, 140.4, 130.8, 129.0, 120.4, 120.2, 119.0, 118.0, 113.7, 113.5, 102.0, 61.4, 60.3, 59.4, 58.9, 54.7, 54.6, 51.8, 41.8, 41.5, 36.3, 32.6, 31.7, 29.3, 29.1, 25.4, 23.8, 22.6, 20.5, 16.1, 14.0, 9.6; ESI-MS m/z: Calcd. for $C_{39}H_{48}N_4O_9S$: 748.3. Found (M+H⁺): 749.3.

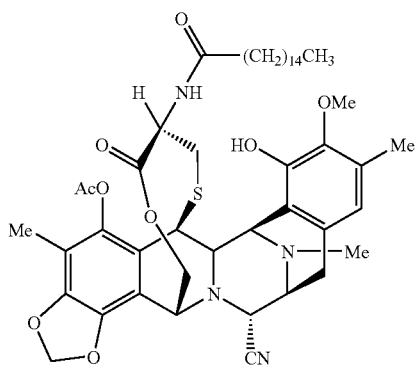

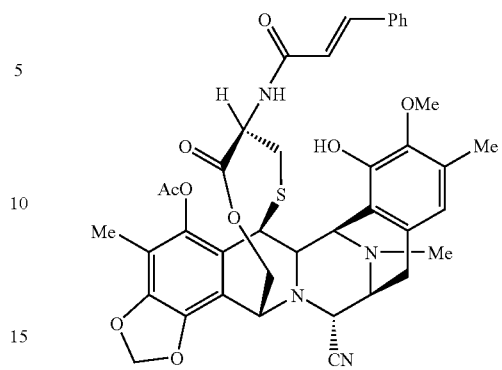

Compound 3f (from 2f): ¹H NMR (300 MHz, CDCl₃): δ 6.55 (s, 1H), 6.04 (dd, 2H), 5.73 (s, 1H), 5.48 (bd, 1H), 5.02 (d, 1H), 4.60 (ddd, 1H), 4.56-4.50 (bp, 1H), 4.28-4.24 (m, 2H), 4.20-4.14 (m, 2H), 3.77 (s, 3H), 3.44-3.40 (m, 2H), 2.92-2.90 (bd, 2H), 2.35-1.95 (m, 4H), 2.32 (s, 3H), 2.29 (s, 3H), 2.16 (s, 3H), 2.03 (s, 3H), 1.62-1.58 (m, 2H), 1.38-1.20 (m, 24H), 0.88 (t, 3H); ESI-MS m/z: Calcd. for $C_{47}H_{64}N_4O_9S$: 860.4. Found (M+H⁺): 861.5.

Compound 3h (from 2h): ¹H NMR (300 MHz, CDCl₃): δ 7.60 (d, 1H), 7.54-7.51 (m, 2H), 7.44-7.38 (m, 3H), 6.63 (s, 1H), 6.22 (d, 1H), 6.05 (dd, 2H), 5.79 (s, 1H), 5.73 (d, 1H), 5.05 (d, 1H), 4.71 (ddd, 1H), 4.55 (bp, 1H), 4.29 (s, 1H), 4.26 (s, 1H), 4.21-4.17 (m, 2H), 3.68 (s, 3H), 3.48-3.42 (m, 2H), 2.95-2.93 (m, 2H), 2.49-2.44 (m, 1H), 2.29-2.03 (m, 1H), 2.29 (s, 3H), 2.27 (s, 3H), 2.17 (s, 3H), 2.03 (s, 3H); ¹³C NMR (75 MHz, CDCl₃): δ 170.4, 168.4, 164.5, 148.1, 145.8, 143.1, 142.0, 141.0, 140.4, 134.7, 130.8, 129.8, 129.2, 128.8, 127.9, 120.2, 119.8, 118.9, 118.0, 113.6, 113.3, 102.0, 61.4, 60.4, 60.2, 59.4, 59.0, 54.6, 54.6, 52.5, 41.8, 41.5, 32.6, 23.8, 20.5, 16.2, 9.6. ESI-MS m/z: Calcd. for $C_{40}H_{40}N_4O_9S$: 752.2. Found (M+Na⁺): 775.8.

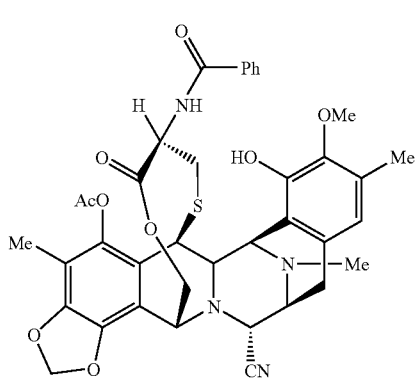

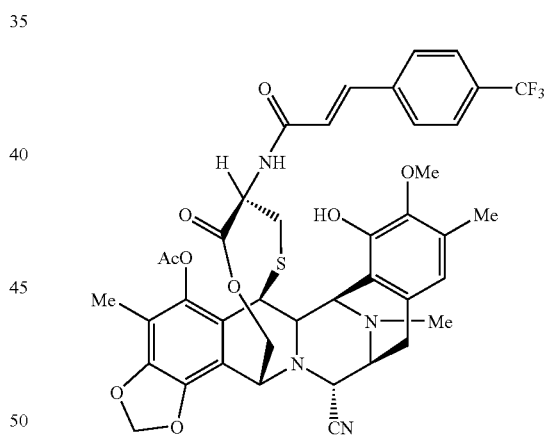

Compound 3g (from 2g): ¹H NMR (300 MHz, CDCl₃): δ 7.69-7.66 (m, 2H), 7.57-7.45 (m, 3H), 6.48 (s, 1H), 6.35 (d, 1H), 6.06 (dd, 2H), 5.70 (s, 1H), 5.07 (d, 1H), 4.78-4.74 (m, 1H), 4.58 (bp, 1H), 4.33 (s, 1H), 4.26-4.18 (m, 3H), 3.61 (s, 3H), 3.47-3.45 (m, 2H), 2.92 (bd, 2H), 2.60-2.53 (m, 1H), 2.28-1.93 (m, 1H), 2.28 (s, 3H), 2.14 (s, 3H), 2.04 (s, 3H), 1.93 (s, 3H); ¹³C NMR (75 MHz, CDCl₃): δ 171.7, 170.5, 166.4, 147.7, 145.9, 143.0, 141.1, 140.5, 134.2, 131.6, 130.8, 129.4, 128.6, 127.0, 120.4, 118.5, 118.0, 113.7, 113.4, 102.0, 61.5, 60.3, 60.1, 59.7, 58.8, 54.7, 53.1, 41.9, 41.5, 32.8, 23.9, 20.4, 15.6, 9.6; ESI-MS m/z: Calcd. for $C_{38}H_{38}N_4O_9S$: 726.2. Found (M+H⁺): 727.2.

Compound 3i (from 2i): ¹H NMR (300 MHz, CDCl₃): δ 7.82 (s, 1H), 7.66-7.51 (m, 4H), 6.64 (s, 1H), 6.26 (d, 1H), 6.05 (dd, 2H); 5.77 (s, 1H), 5.74 (d, 1H), 5.05 (d, 1H), 4.72 (ddd, 1H), 4.56 (bp, 1H), 4.29 (s, 1H), 4.26 (dd, 10H), 4.22-4.16 (m, 2H), 3.70 (s, 3H), 3.46-3.44 (m, 2H), 2.94 (d, 2H), 2.47-2.40 (m, 1H), 2.30-2.03 (m, 1H), 2.30 (s, 3H), 2.28 (s, 3H), 2.17 (s, 3H), 2.03 (s, 3H); ¹³C NMR (75 MHz, CDCl₃): δ 170.3, 163.9, 148.1, 143.1, 141.1, 140.4, 135.6, 131.7, 130.9, 129.5, 129.0, 126.2, 123.6, 121.7, 120.3, 118.0, 113.3, 102.0, 99.2, 61.4, 60.5, 60.2, 59.4, 59.1, 54.7, 54.6, 52.5, 41.8, 41.5, 32.6, 23.8, 20.5, 16.2, 9.6. ESI-MS m/z: Calcd. for $C_{41}H_{39}N_4F_3O_9S$: 820.2. Found (M+H⁺): 821.3.

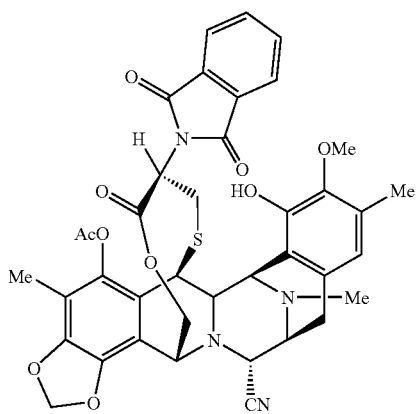
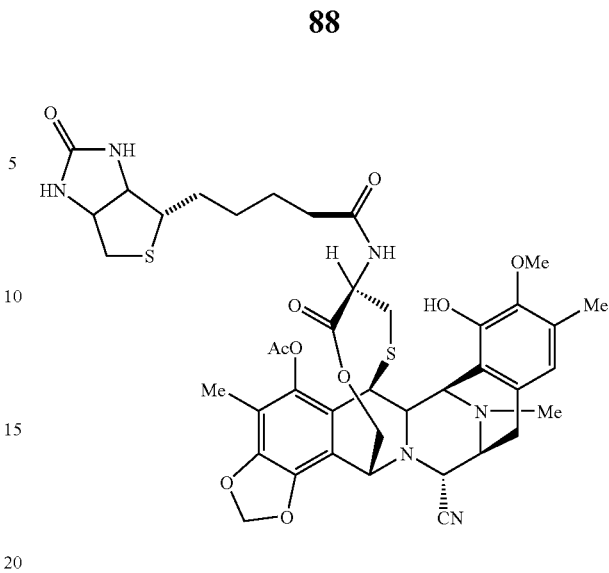

Compound 3j (from 2j): $^1$H NMR (300 MHz, CDCl$_3$): δ 7.77-7.68 (m, 4H), 6.26 (s, 1H), 6.06 (dd, 2H), 5.77 (s, 1H), 4.98 (d, 1H), 4.61-4.55 (m, 2H), 4.33-4.21 (m, 2H), 4.09 (d, 1H), 4.97 (dd, 1H), 3.97 (s, 3H), 3.47-3.31 (m, 2H), 2.93-2.77 (m, 2H), 2.36 (s, 3H), 2.33-2.14 (m, 2H), 2.23 (s, 3H), 2.17 (s, 3H), 2.05 (s, 3H); ESI-MS m/z: Calcd. for C$_{39}$H$_{36}$N$_4$O$_{10}$S: 752.2. Found (M+H$^+$): 753.2.

Compound 3k (from 2k): $^1$H NMR (300 MHz, CDCl$_3$): δ 7.78 (s, 1H), 6.55 (s, 1H), 6.45 (s, 1H), 6.04 (dd, 2H), 5.38 (bd, 1H), 5.29 (bs, 1H), 5.15 (d, 1H), 4.66 (m, 1H), 4.60 (bp, 1H), 4.55-4.51 (m, 1H), 4.40 (d, 1H), 4.34-4.29 (m, 2H), 4.25 (s, 1H), 4.14 (d, 1H), 3.79 (s, 3H), 3.43-3.39 (m, 2H), 3.09-3.05 (m, 1H), 2.96-2.90 (m, 3H), 2.70 (d, 1H), 2.34-1.94 (m, 4H), 2.34 (s, 3H), 2.30 (s, 3H), 2.11 (s, 3H), 2.02 (s, 3H), 1.81-1.25 (m, 6H); $^{13}$C NMR (75 MHz, CDCl$_3$): δ 171.5, 170.8, 168.7, 163.8, 148.8, 145.8, 142.8, 141.1, 140.3, 131.2, 128.9, 120.7, 120.3, 120.1, 118.3, 113.5, 102.0, 61.9, 61.2, 60.2, 59.8, 59.4, 59.4, 56.4, 55.1, 54.7, 51.3, 41.8, 41.4, 41.1, 34.5, 32.6, 27.8, 27.7, 25.0, 24.1, 20.7, 16.1, 9.6; ESI-MS m/z: Calcd. for C$_{41}$H$_{48}$N$_6$O$_{10}$S$_2$: 849.0. Found (M+H$^+$): 850.0.

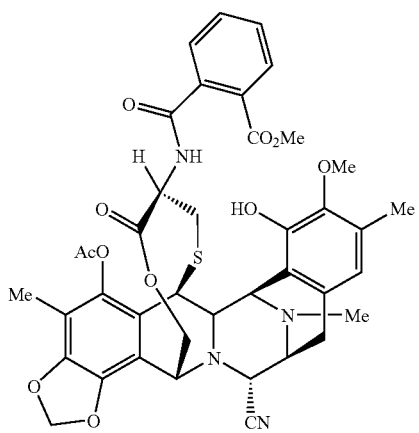
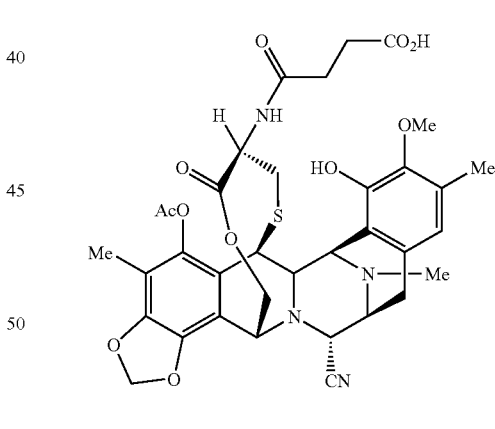

Compound 6: $^1$H NMR (300 MHz, CDCl$_3$): δ 7.95 (dd, 1H), 7.66-7.45 (m, 3H), 6.13 (s, 1H), 6.07 (dd, 2H), 5.88 (d, 1H), 5.64 (s, 1H), 5.06 (d, 1H), 4.83-4.81 (m, 1H), 4.53 (bp, 1H), 4.30-4.17 (m, 4H), 3.79 (s, 3H), 3.61 (s, 3H), 3.45-3.40 (m, 2H), 2.94-2.85 (m, 2H), 2.29-2.04 (m, 2H), 2.29 (s, 3H), 2.14 (s, 3H), 2.04 (s, 6H); ESI-MS m/z: Calcd. for C$_{40}$H$_{40}$N$_4$O$_{11}$S: 784.2. Found (M+H$^+$): 785.1.

Compound 3l (from 2l): $^1$H NMR (300 MHz, CDCl$_3$): δ 6.57 (s, 1H), 6.04 (dd, 2H), 5.90 (bp, 1H), 5.63 (bd, 1H), 5.02 (d, 1H), 4.60-4.55 (m, 2H), 4.27-4.17 (m, 4H), 3.76 (s, 3H), 3.47-3.39 (m, 2H), 2.90 (bd, 2H), 2.68-2.61 (m, 2H), 2.58-2.02 (m, 4H), 2.32 (s, 3H), 2.29 (s, 3H), 2.16 (s, 3H), 2.02 (s, 3H); $^{13}$C NMR (75 MHz, CDCl$_3$): δ 176.4, 170.5, 170.2, 168.6, 148.1, 145.8, 143.1, 141.0, 140.3, 130.7, 129.2, 120.3, 120.0, 119.0, 118.0, 113.5, 113.3, 102.0, 61.3, 60.4, 60.3, 59.2, 58.9, 54.6, 54.4, 51.9, 41.8, 41.4, 32.3, 30.2, 29.6, 29.1, 28.3, 23.7, 20.5, 16.0, 9.6. ESI-MS m/z: Calcd. for C$_{35}$H$_{38}$N$_4$O$_{11}$S: 722.2. Found (M+H$^+$): 723.2.

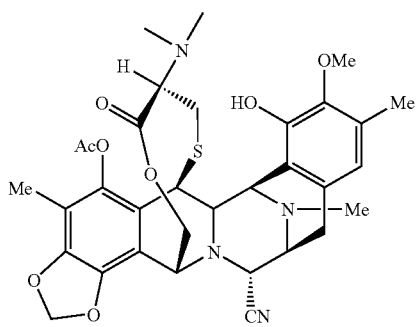

Compound 3m (from 2m): $^1$H NMR (300 MHz, CDCl$_3$): δ 6.45 (s, 1H), 6.02 (d, 2H), 5.67 (s, 1H), 4.98 (d, 1H), 4.55 (bp, 1H), 4.27-4.22 (m, 2H), 4.14 (d, 1H), 3.94 (dd, 1H), 3.78 (s, 3H), 3.65-3.38 (m, 3H), 2.96-2.79 (m, 2H), 2.44-2.02 (m, 7H), 2.34 (s, 3H), 2.20 (s, 3H), 2.16 (s, 3H), 2.03 (s, 3H), 1.88-1.82 (m, 1H); ESI-MS m/z: Calcd. for C$_{33}$H$_{38}$N$_4$O$_8$S: 650.2. Found (M+H$^+$): 651.3.

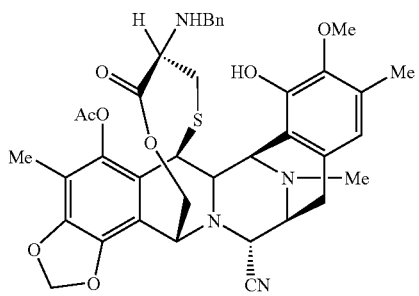

Compound 3n (from 2n): $^1$H NMR (300 MHz, CDCl$_3$): δ 7.31-7.21 (m, 5H), 6.37 (s, 1H), 6.02 (dd, 2H), 5.67 (s, 1H), 5.04 (d, 1H), 4.52 (bp, 1H), 4.24-4.22 (m, 3H), 4.11 (dd, 1H), 3.73 (s, 3H), 3.62 (dd, 2H), 3.42-3.41 (m, 2H), 3.19-3.18 (m, 1H), 3.03-2.83 (m, 2H), 2.34-2.30 (m, 1H), 2.30 (s, 3H), 2.18 (s, 3H), 2.05-2.02 (m, 1H), 2.02 (s, 3H), 1.93 (s, 3H); $^{13}$C NMR (75 MHz, CDCl$_3$): δ 172.7, 168.5, 147.7, 145.6, 142.9, 141.0, 140.4, 140.1, 130.6, 129.3, 128.2, 128.2, 126.8, 120.7, 118.2, 118.0, 113.8, 113.3, 101.9, 99.1, 61.5, 60.1, 59.6, 59.5, 59.2, 54.7, 51.3, 41.6, 41.5, 33.4, 23.8, 20.5, 15.3, 9.6. ESI-MS m/z: Calcd. for C$_{38}$H$_{40}$N$_4$O$_8$S: 712.3. Found (M+H$^+$): 713.3.

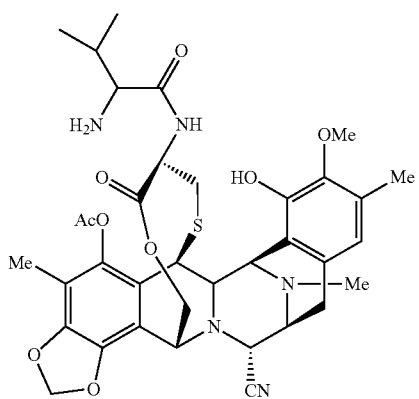

Compound 3p (from 7): $^1$H NMR (300 MHz, CDCl$_3$): δ 6.73 (bp, 1H), 6.51 (s, 1H), 6.05 (dd, 2H), 5.03 (d, 1H), 4.64 (dt, 1H), 4.55 (bp, 1H), 4.31 (s, 1H), 4.26 (dd, 1H), 4.21 (d, 1H), 4.17 (dd, 1H), 3.76 (s, 3H), 3.49-3.42 (m, 2H), 2.99 (d, 1H), 2.90-2.88 (m, 2H), 2.47-1.97 (m, 3H), 2.32 (s, 3H), 2.29 (s, 3H), 2.13 (s, 3H), 2.03 (s, 3H), 0.97 (d, 3H), 0.79 (d, 3H); $^{13}$C NMR (75 MHz, CDCl$_3$): δ 173.6, 170.4, 168.5, 147.6, 145.9, 143.1, 141.1, 140.5, 130.8, 129.0, 120.8, 120.6, 118.8, 118.0, 113.5, 113.3, 102.0, 61.5, 60.6, 60.2, 60.0, 59.6, 58.6, 54.7, 54.6, 51.9, 42.0, 41.5, 33.0, 31.6, 23.9, 20.4, 19.6, 16.8, 16.2, 9.6. ESI-MS m/z: Calcd. for C$_{36}$H$_{43}$N$_5$O$_9$S: 721.3. Found (M+H$^+$): 722.2

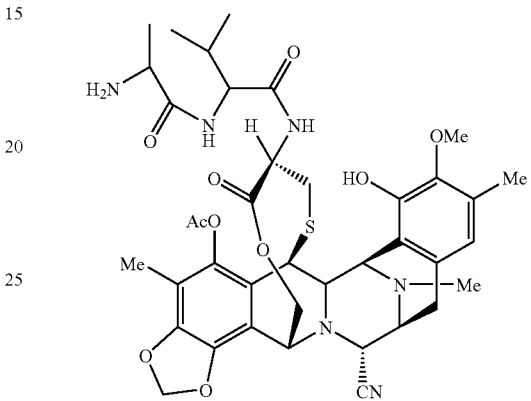

Compound 3s (from 9 using 9 equiv of TMSCl and NaI. The reaction was quenched with brine and Na$_2$CO$_3$): $^1$H NMR (300 MHz, CDCl$_3$): δ 7.74 (d, 1H), 6.55 (s, 1H), 6.05 (dd, 2H), 5.61 (d, 1H), 5.02 (d, 1H), 4.68-4.64 (m, 1H), 4.57 (bp, 1H), 4.29 (s, 1H), 4.27 (dd, 1H), 4.20-4.16 (m, 2H), 4.04 (dd, 1H), 3.79 (s, 3H), 3.52-3.43 (m, 3H), 2.91-2.89 (m, 2H), 2.49 (s, 3H), 2.29-2.02 (m, 3H), 2.29 (s, 3H), 2.16 (s, 3H), 2.02 (s, 3H), 1.33 (d, 3H), 1.07 (d, 3H), 0.97 (d, 3H); $^{13}$C NMR (75 MHz, CDCl$_3$): δ 175.2, 170.2, 170.2, 168.5, 148.0, 145.9, 143.3, 141.1, 140.4, 130.4, 130.1, 120.4, 120.2, 118.5, 118.0, 113.5, 102.0, 61.5, 60.4, 60.3, 59.4, 58.8, 57.4, 54.7, 54.6, 51.8, 50.9, 42.0, 41.5, 32.7, 32.2, 23.8, 21.8, 20.5, 19.3, 18.0, 16.3, 9.6. ESI-MS m/z: Calcd. for C$_{39}$H$_{48}$N$_6$O$_{10}$S: 792.3. Found (M+H$^+$): 793.3.

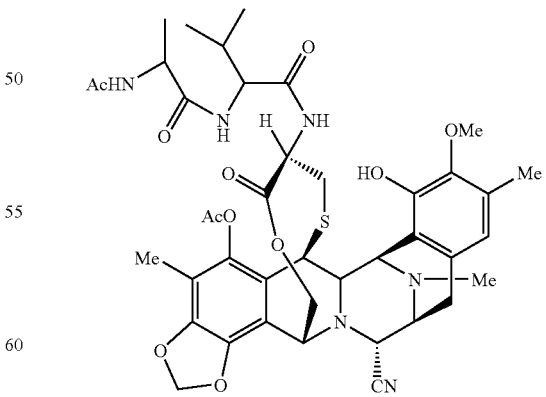

Compound 3t (from 2t): $^1$H NMR (300 MHz, CDCl$_3$): δ 6.59 (bd, 1H), 6.53 (s, 1H), 6.28-6.22 (m, 1H), 6.04 (dd, 2H), 5.89 (s, 1H), 5.60, 5.58 (2d, 1H), 5.01 (d, 1H), 4.66-4.62 (m, 1H), 4.57 (bp, 1H), 4.50-4.43 (m, 1H), 4.28 (s, 1H), 4.25 (d, 1H), 4.20-4.12 (m, 2H), 4.09-4.04 (m, 1H), 3.78, 3.77 (2s, 3H), 3.47-3.42 (m, 2H), 2.90-2.87 (m, 2H), 2.46 (s, 3H), 2.28-1.98 (m, 3H), 2.28 (s, 3H), 2.16, 2.15 (2s, 3H), 2.03, 2.02 (2s, 3H), 1.98 (s, 3H), 1.36, 1.32 (2d, 3H), 1.05, 1.03 (2d, 3H), 0.93 (d, 3H); $^{13}$C NMR (75 MHz, CDCl$_3$): δ 171.9, 170.1, 169.7, 169.6, 168.5, 148.0, 145.9, 143.2, 141.1, 140.4, 130.6, 129.8, 120.3, 120.2, 118.7, 118.0, 113.4, 102.0, 61.4, 60.3, 60.3, 59.4, 58.8, 57.7, 57.6, 54.6, 54.5, 51.9, 48.9, 48.9, 42.0, 41.5, 32.6, 32.3, 32.2, 23.8, 23.1, 20.5, 19.2, 19.1, 19.1, 18.5, 17.7, 17.7, 16.2, 9.6. ESI-MS m/z: Calcd. for C$_{41}$H$_{50}$N$_6$O$_{11}$S: 834.3. Found (M+H$^+$): 835.3.

(m, 2H), 2.46, 2.40 (2s, 3H), 2.29, 2.28 (2s, 3H), 2.17, 2.15 (2s, 3H), 2.02 (s, 3H), 1.98, 1.95 (2s, 3H), 1.45, 1.20 (2d, 3H); $^{13}$C NMR (75 MHz, CDCl$_3$): δ 171.5, 170.1, 169.9, 169.1, 168.6, 148.2, 147.7, 145.9, 143.2, 141.1, 140.4, 130.9, 130.4, 130.0, 129.8, 120.8, 120.3, 118.8, 118.0, 113.6, 113.4, 102.0, 61.5, 61.4, 60.5, 60.4, 59.3, 59.1, 58.7, 54.8, 54.6, 51.9, 51.7, 48.5, 42.1, 41.9, 41.5, 32.4, 32.3, 23.8, 23.2, 20.5, 19.9, 16.0, 15.8, 9.6. ESI-MS m/z: Calcd. for C$_{36}$H$_{41}$N$_5$O$_{10}$S: 735.3. Found (M+H$^+$): 736.2.

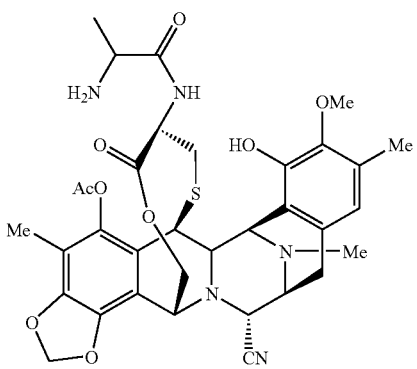

Compound 3v (from 8; the reaction was quenched with brine and Na$_2$CO$_3$): $^1$H NMR (300 MHz, CDCl$_3$): δ 6.70 (bp, 1H), 6.52 (s, 1H), 6.04 (dd, 2H), 5.03 (d, 1H), 4.58-4.53 (m, 2H), 4.30 (s, 1H), 4.25 (dd, 1H), 4.20-4.14 (m, 2H), 3.76 (s, 3H), 3.45-3.42 (m, 2H), 3.30 (dd, 1H), 2.90-2.88 (m, 2H), 2.38-2.00 (m, 2H), 2.30 (s, 3H), 2.29 (s, 3H), 2.14 (s, 3H), 2.03 (s, 3H), 1.25 (d, 3H); $^{13}$C NMR (75 MHz, CDCl$_3$): δ 175.0, 170.3, 168.4, 147.6, 145.9, 143.1, 141.1, 140.5, 130.8, 129.0, 120.9, 120.5, 118.7, 118.0, 113.5, 113.3, 102.0, 61.5, 60.2, 60.1, 59.6, 58.8, 54.8, 54.6, 52.1, 50.8, 41.9, 41.5, 32.7, 23.9, 21.6, 20.4, 16.1, 9.6. ESI-MS m/z: Calcd. for C$_{34}$H$_{39}$N$_5$O$_9$S: 693.2. Found (M+H$^+$): 694.3.

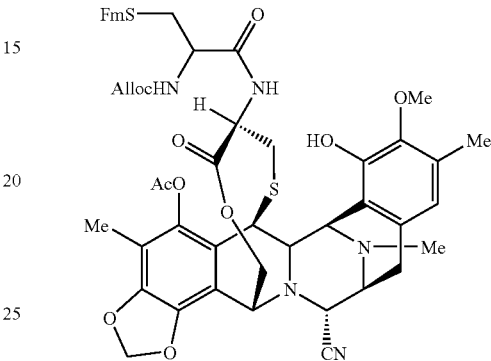

Compound 3y (from 2y): $^1$H NMR (300 MHz, CDCl$_3$): δ 7.77-7.68 (m, 4H), 7.42-7.26 (m, 4H), 6.53 (s, 1H), 6.05 (bd, 1H), 6.04 (dd, 2H), 5.96-5.87 (m, 1H), 5.74 (s, 1H), 5.58 (bd, 1H), 5.38-5.20 (m, 2H), 5.00 (d, 1H), 4.60-4.55 (m, 4H), 4.33-4.08 (m, 6H), 3.73 (s, 3H), 3.44-3.42 (m, 2H), 3.19-3.13 (m, 1H), 3.05-2.83 (m, 5H), 2.38-2.02 (m, 2H), 2.38 (s, 3H), 2.24 (s, 3H), 2.13 (s, 3H), 2.03 (s, 3H); ESI-MS m/z: Calcd. for C$_{52}$H$_{53}$N$_5$O$_{11}$S$_2$: 987.3. Found (M+H$^+$): 988.1.

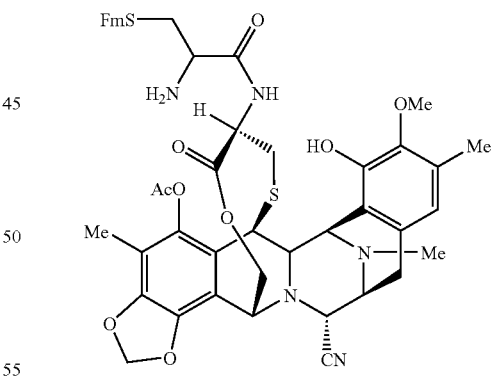

Compound 3z was also obtained in the reaction of 2y: $^1$H NMR (300 MHz, CDCl$_3$): δ 7.76 (d, 2H), 7.66 (dd, 2H), 7.42-7.30 (m, 4H), 6.49 (s, 1H), 6.05 (dd, 2H), 5.67 (bp, 1H), 5.02 (d, 1H), 4.59-4.54 (m, 2H), 4.30 (bs, 1H), 4.25-4.23 (dd, 1H), 4.19-4.09 (m, 3H), 3.71 (s, 3H), 3.68-3.43 (m, 2H), 3.33 (dd, 1H), 3.14-2.85 (m, 5H), 2.46 (dd, 1H), 2.35-2.24 (m, 2H), 2.25 (s, 3H), 2.24 (s, 3H), 2.12 (s, 3H), 2.03 (s, 3H); ESI-MS m/z: Calcd. for C$_{48}$H$_{49}$N$_5$O$_9$S$_2$: 903.3. Found (M+H$^+$): 904.2.

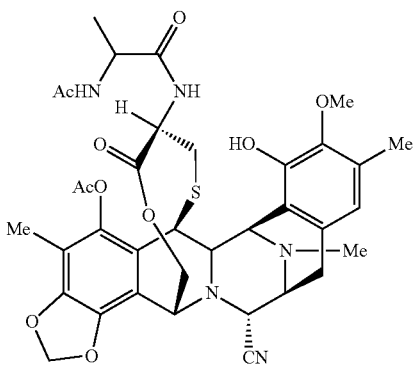

Compound 3w (from 2w; the reaction was quenched with brine): $^1$H NMR (300 MHz, CDCl$_3$): δ 6.67, 6.55 (2s, 1H), 6.30 (m, 1H), 6.05 (dd, 2H), 5.86, 5.79 (2s, 1H), 5.65, 5.54 (2bd, 1H), 5.03, 5.02 (2d, 1H), 4.60-4.17 (m, 7H), 3.79, 3.76 (2s, 3H), 3.45-3.40 (m, 2H), 2.92-2.85 (bd, 2H), 2.46-1.95

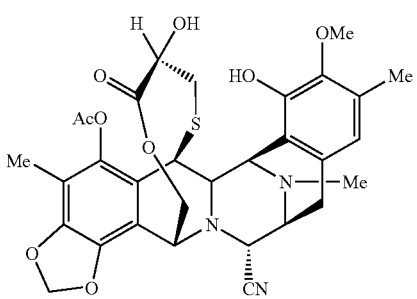

Compound 15 (from 11): $^1$H NMR (300 MHz, CDCl$_3$): δ 6.56 (s, 1H), 6.03 (dd, 2H), 5.74 (s, 1H), 5.04 (d, 2H), 4.54 (bp, 1H), 4.26-4.23 (m, 2H), 4.20-4.14 (m, 2H), 4.02-3.96 (m, 1H), 3.78 (s, 3H), 3.42-3.39 (m, 2H), 2.93-2.90 (m, 2H), 2.31-2.03 (m, 2H), 2.31 (s, 3H), 2.29 (s, 3H), 2.20 (s, 3H), 2.03 (s, 3H); ESI-MS m/z: Calcd. for C$_{31}$H$_{33}$N$_3$O$_9$S: 623.2. Found (M+H$^+$): 624.2.

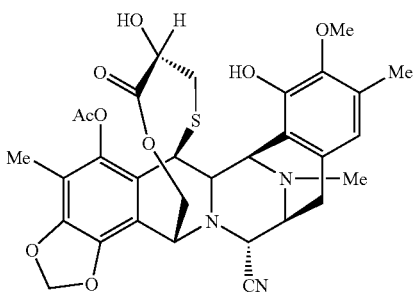

Compound 16* (from 12*): $^1$H NMR (300 MHz, 45° C., CDCl$_3$): δ 6.49 (s, 1H), 6.04 (dd, 2H), 5.67 (s, 1H), 4.94 (bd, 1H), 4.47 (s, 1H), 4.24-4.17 (m, 3H), 4.05 (d, 1H), 3.80 (s, 3H), 3.57-3.55 (m, 2H), 3.40-3.37 (m, 1H), 2.98-2.90 (m, 1H), 2.73 (d, 1H), 2.51-2.47 (bm, 1H), 2.33 (s, 3H), 2.30 (s, 3H), 2.15 (s, 3H), 2.02 (s, 3H), 1.66 (dd, 1H); ESI-MS m/z: Calcd. for C$_{31}$H$_{33}$N$_3$O$_9$S: 623.2. Found (M+H$^+$): 624.3.

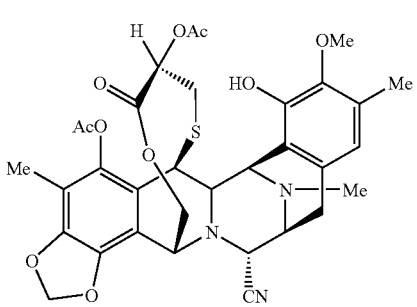

Compound 17a (from 13a): $^1$H NMR (300 MHz, CDCl$_3$): δ 6.50 (s, 1H), 6.04 (dd, 2H), 5.67 (s, 1H), 5.02-4.99 (m, 2H), 4.56 (bp, 1H), 4.27 (s, 1H), 4.25 (dd, 1H), 4.17 (d, 1H), 4.11 (dd, 1H), 3.79 (s, 3H), 3.44-3.41 (m, 2H), 2.88-2.86 (m, 2H), 2.31-1.97 (m, 2H), 2.31 (s, 3H), 2.28 (s, 3H), 2.16 (s, 3H), 2.03 (s, 3H), 1.97 (s, 3H); $^{13}$C NMR (75 MHz, CDCl$_3$): δ 169.7, 168.5, 167.0, 147.2, 145.7, 142.9, 141.1, 140.6, 130.9, 128.7, 121.2, 120.7, 118.1, 118.0, 113.5, 102.0, 71.6, 61.4, 60.2, 60.0, 59.9, 59.0, 54.7, 54.6, 41.6, 41.5, 31.5, 23.9, 20.5, 20.3, 15.8, 9.6. ESI-MS m/z: Calcd. for C$_{33}$H$_{35}$N$_3$O$_{10}$S: 665.2. Found (M+H$^+$): 666.1.

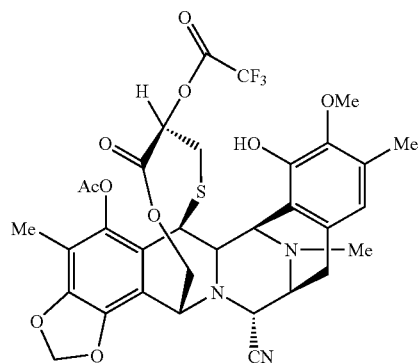

Compound 17b (from 13b): $^1$H NMR (300 MHz, CDCl$_3$): δ 6.46 (s, 1H), 6.05 (dd, 2H), 5.68 (s, 1H), 5.09 (bt, 1H), 5.02 (d, 1H), 4.62 (bp, 1H), 4.31 (s, 1H), 4.24 (dd, 1H), 4.19-4.14 (m, 2H), 3.77 (s, 3H), 3.46-3.40 (m, 2H), 2.93-2.75 (m, 2H), 2.44-2.37 (dd, 1H), 2.32 (s, 3H), 2.26 (s, 3H), 2.16 (s, 3H), 2.10-2.04 (m, 1H), 2.04 (s, 3H); $^{13}$C NMR (75 MHz, CDCl$_3$): δ 168.6, 164.9, 147.0, 145.9, 142.9, 141.2, 140.7, 132.2 (CF3?), 130.6, 129.5, 125.1 (CF3?), 121.6, 120.5 (CF3?), 118.0, 117.3, 113.7, 113.3, 113.3 (CF3?), 102.1, 74.8, 61.4, 60.6, 60.1, 59.9, 58.9, 54.6, 41.7, 41.6, 31.0, 23.9, 20.4, 15.5, 9.6. ESI-MS m/z: Calcd. for C$_{33}$H$_{32}$F$_3$N$_3$O$_{10}$S: 719.2. Found (M+H$^+$): 720.2.

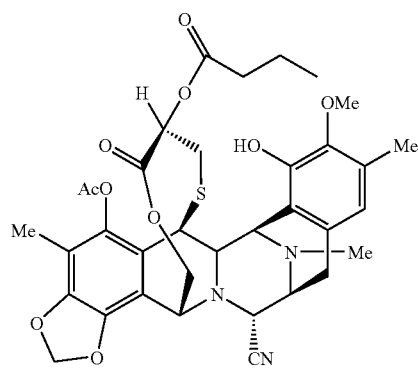

Compound 17c (from 13c): $^1$H NMR (300 MHz, CDCl$_3$): δ 6.47 (s, 1H), 6.04 (dd, 2H), 5.66 (s, 1H), 5.02-4.99 (m, 2H), 4.57 (bp, 1H), 4.28 (s, 1H), 4.24 (dd, 1H), 4.18 (d, 1H), 4.11 (dd, 1H), 3.79 (s, 3H), 3.45-3.41 (m, 2H), 2.87-2.85 (m, 2H), 2.31-1.99 (m, 4H), 2.31 (s, 3H), 2.29 (s, 3H), 2.15 (s, 3H), 2.03 (s, 3H), 1.67-1.55 (m, 2H), 0.97 (t, 3H); $^{13}$C NMR (75 MHz, CDCl$_3$): δ 172.3, 168.5, 167.0, 147.2, 145.8, 142.9, 141.1, 140.6, 131.0, 128.8, 121.2, 120.8, 118.1, 118.1, 113.6, 113.1, 102.0, 71.4, 61.4, 60.2, 59.9, 59.9, 58.8, 54.8, 54.7, 41.6, 35.9, 31.7, 24.0, 20.4, 18.2, 15.8, 13.7, 9.6. ESI-MS m/z: Calcd. for C$_{33}$H$_{39}$N$_3$O$_{10}$S: 693.2. Found (M+H$^+$): 694.2.

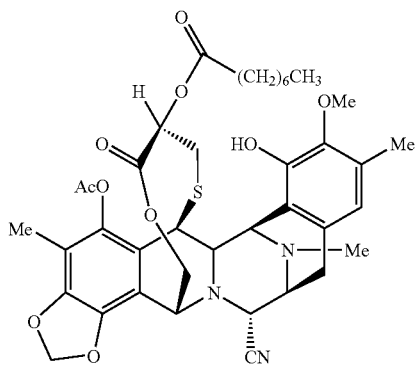

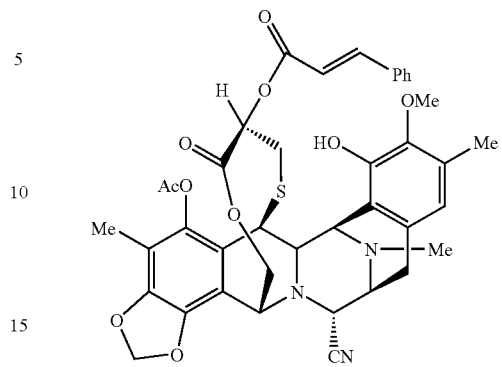

Compound 17e (from 13e): $^1$H NMR (300 MHz, CDCl$_3$): δ 6.47 (s, 1H), 6.03 (dd, 2H), 5.66 (s, 1H), 5.02-4.98 (m, 2H), 4.56 (bp, 1H), 4.27 (s, 1H), 4.24 (dd, 1H), 4.17 (d, 1H), 4.10 (dd, 1H), 3.79 (s, 3H), 3.44-3.42 (m, 2H), 2.87-2.85 (m, 2H), 2.30-1.98 (m, 4H), 2.30 (s, 3H), 2.29 (s, 3H), 2.15 (s, 3H), 2.03 (s, 3H), 1.61-1.57 (m, 2H), 1.31-1.23 (m, 8H), 0.89 (t, 3H); $^{13}$C NMR (75 MHz, CDCl$_3$): δ 172.6, 168.5, 167.0, 147.2, 145.8, 142.9, 141.1, 140.6, 130.0, 128.7, 121.2, 120.8, 118.1, 118.1, 113.6, 113.1, 102.0, 71.4, 61.4, 60.2, 59.9, 58.8, 54.8, 54.7, 41.6, 33.8, 31.7, 31.6, 29.1, 28.9, 24.7, 24.0, 22.6, 20.4, 15.8, 14.1, 9.6. ESI-MS m/z: Calcd. for C$_{39}$H$_{47}$N$_3$O$_{10}$S: 749.3. Found (M+H$^+$): 750.9.

Compound 17h (from 13h): $^1$H NMR (300 MHz, CDCl$_3$): δ 7.64 (d, 1H), 7.55-7.52 (m, 2H), 7.43-7.40 (m, 3H), 6.51 (s, 1H), 6.28 (d, 1H), 6.05 (dd, 2H), 5.70 (s, 1H), 5.17 (bt, 1H), 5.04 (d, 1 μl), 4.58 (bp, 1H), 4.30 (s, 1H), 4.26 (d, 1H), 4.20 (d, 1H), 4.14 (dd, 1H), 3.79 (s, 3H), 3.45 (d, 1H), 3.42-3.39 (m, 1H), 2.92-2.80 (m, 2H), 2.42 (dd, 1H), 2.31 (s, 3H), 2.26 (s, 3H), 2.15 (s, 3 μl), 2.09-2.04 (m, 1H), 2.04 (s, 3H); $^{13}$C NMR (75 MHz, CDCl$_3$): δ 168.5, 167.0, 165.6, 147.2, 145.8, 145.6, 142.9, 141.1, 140.6, 134.5, 131.1, 130.4, 128.9, 128.8, 128.1, 121.1, 120.8, 118.1, 118.0, 117.4, 113.6, 113.1, 102.0, 71.9, 61.5, 60.3, 59.9, 58.7, 54.7, 54.7, 41.7, 41.6, 31.8, 24.0, 20.4, 15.9, 9.6. ESI-MS m/z: Calcd. for C$_{40}$H$_{39}$N$_3$O$_{10}$S: 753.2. Found (M+H$^+$): 754.7.

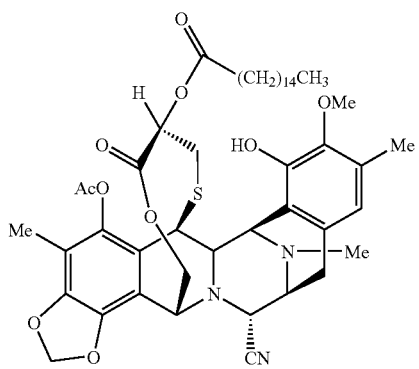

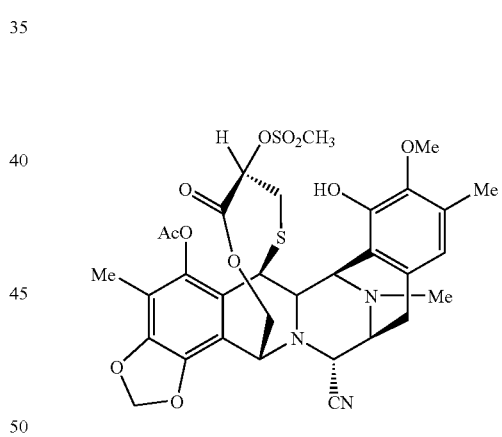

Compound 17f (from 13f): $^1$H NMR (300 MHz, CDCl$_3$): δ 6.48 (s, 1H), 6.04 (dd, 2H), 5.66 (s, 1H), 5.02-4.98 (m, 2H), 4.57 (bp, 1H), 4.28 (s, 1H), 4.25 (dd, 1H), 4.17 (d, 1H), 4.10 (dd, 1H), 3.79 (s, 3H), 3.44-3.40 (m, 2H), 2.87-2.85 (m, 2H), 2.37-1.98 (m, 4H), 2.31 (s, 3H), 2.29 (s, 3H), 2.15 (s, 3H), 2.03 (s, 3H), 1.62-1.55 (m, 2H), 1.35-1.26 (m, 24H), 0.88 (t, 3H); $^{13}$C NMR (75 MHz, CDCl$_3$): δ 172.6, 168.6, 167.1, 147.2, 145.7, 142.8, 141.0, 140.6, 130.9, 128.7, 121.2, 120.7, 118.1, 117.9, 113.5, 113.1, 102.0, 71.4, 61.4, 60.3, 59.8, 58.8, 54.7, 54.6, 41.6, 33.8, 31.9, 31.6, 29.7, 29.5, 29.4, 29.3, 29.2, 24.6, 23.9, 22.7, 20.5, 15.9, 14.1, 9.6. ESI-MS m/z: Calcd. for C$_{47}$H$_{63}$N$_3$O$_{10}$S: 861.4. Found (M+H$^+$): 862.3.

Compound 17ll (from 13ll): $^1$H NMR (300 MHz, CDCl$_3$): δ 6.43 (s, 1H), 6.04 (dd, 2H), 5.70 (s, 1H), 5.00 (d, 1H), 4.94-4.90 (m, 1H), 4.59 (bp, 1H), 4.28 (s, 1H), 4.24 (d, 1H), 4.17-4.11 (m, 2H), 3.78 (s, 3H), 3.46 (d, 1H), 3.45-3.39 (m, 2H), 3.10 (s, 3H), 2.94-2.78 (m, 2H), 2.50-2.42 (m, 1H), 2.31 (s, 3H), 2.29 (s, 3H), 2.17 (s, 3H), 2.08-2.03 (m, 1H), 2.03 (s, 3H); $^{13}$C NMR (75 MHz, CDCl$_3$): δ 168.8, 166.9, 147.8, 146.1, 143.2, 141.4, 140.8, 130.7, 129.4, 121.3, 120.5, 118.2, 118.0, 113.6, 113.3, 102.3, 77.4, 61.4, 61.0, 60.5, 60.1, 59.6, 55.0, 54.8, 41.8, 41.7, 39.6, 33.0, 24.3, 20.6, 16.0, 9.8. ESI-MS m/z: Calcd. for C$_{32}$H$_{35}$N$_3$O$_{11}$S$_2$: 701.2. Found (M+Na$^+$): 724.6.

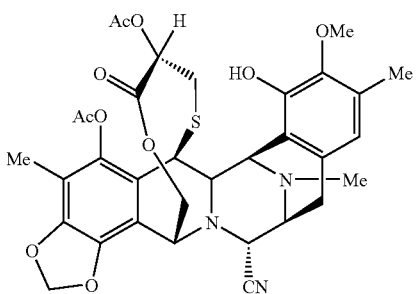

Compound 18a* (from 14a*): $^1$H NMR (300 MHz, CDCl$_3$): δ 6.49 (s, 1H), 6.04 (dd, 2H), 5.69 (s, 1H), 4.50-4.06 (m, 7H), 3.80 (s, 3H), 3.53 (d, 1H), 3.41-3.38 (m, 1H), 2.96-2.87 (m, 1H), 2.75 (d, 1H), 2.33-1.84 (m, 2H), 2.33 (s, 3H), 2.30 (s, 3H), 2.14 (s, 3H), 2.02 (s, 3H), 1.94 (s, 3H); ESI-MS m/z: Calcd. for C$_{33}$H$_{35}$N$_3$O$_{10}$S: 665.2. Found (M+H$^+$): 666.7.

Example 8

Method H: To a solution of 1 equiv. of 5 in CH$_3$CN (0.05M) under Argon at room temperature, were added the amine and 3 equiv. of AcOH. After 40 min. 1.5 equiv. of NaBH$_3$CN were added and the solution was stirred for 40 min. After this time the reaction mixture was diluted with CH$_2$Cl$_2$, neutralized with NaHCO$_3$ and extracted with CH$_2$Cl$_2$. The organic layer was dried with Na$_2$SO$_4$. Flash chromatography gives pure compounds.

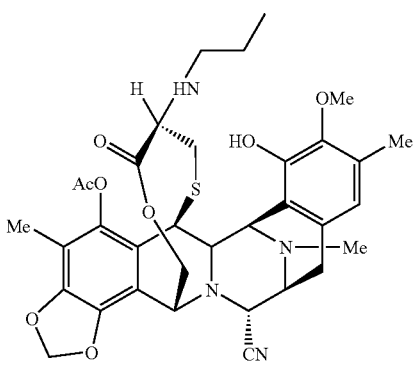

Compound 3o (using propyl amine): $^1$H NMR (300 MHz, CDCl$_3$): δ 6.51 (s, 1H), 6.02 (dd, 2H), 5.71 (s, 1H), 5.01 (d, 1H), 4.53 (bp, 1H), 4.24-4.19 (m, 3H), 4.10 (dd, 1H), 3.77 (s, 3H), 3.41-3.40 (m, 2H), 3.17-3.16 (m, 1H), 3.00-2.82 (m, 2H), 2.46-1.97 (m, 4H), 2.29 (s, 3H), 2.27 (s, 3H), 2.16 (s, 3H), 2.02 (s, 3H), 1.44-1.25 (m, 2H), 0.84 (t, 3H); $^{13}$C NMR (75 MHz, CDCl$_3$): δ 172.5, 168.6, 147.6, 145.5, 142.9, 140.8, 140.4, 130.6, 129.1, 120.8, 120.7, 118.2, 113.7, 113.2, 101.9, 61.4, 60.1, 60.0, 59.5, 59.0, 54.7, 54.6, 49.2, 41.5, 32.9, 23.8, 23.3, 20.6, 15.7, 11.7, 9.6. ESI-MS m/z: Calcd. for C$_{34}$H$_{40}$N$_4$O$_8$S: 664.3. Found (M+H$^+$): 665.3.

Example 9

Method I: To a solution of 1 equiv. of 3b-i, 3k-l, 3q, 3s, 3u-v, 3x-y or 15 in CH$_3$CN/H$_2$O 3:2 (0.009M) were added 30 equiv. of AgNO$_3$. After 24 h the reaction was quenched with a mixture 1:1 of saturated solutions of brine and NaHCO$_3$, stirred for 10 min and diluted and extracted with CH$_2$Cl$_2$. The organic layer was dried with Na$_2$SO$_4$. Chromatography gives pure compounds 4b-i, 4k-l, 4q, 4s, 4u-v, 4x-y or 19.

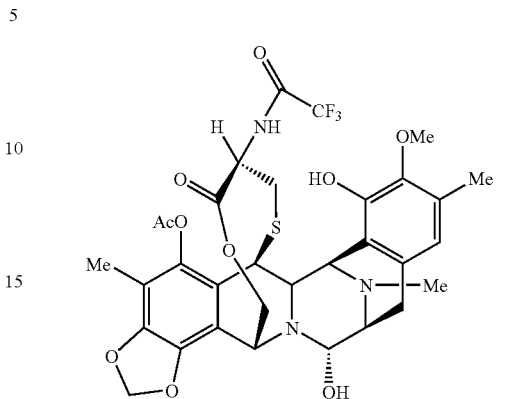

Compound 4b: t$_R$=48.2 min [HPLC, Symmetry 300 C18, 5 μm, 250×4.6 mm, λ=285 nm, flow=1.2 ml/min, temp=40° C., grad.: CH$_3$CNaq. —NH$_4$OAc (10 mM), 1% DEA, pH=3.0, 10%-60% (90')]; $^1$H NMR (300 MHz, CDCl$_3$): δ 6.53 (s, 1H), 6.49 (bd, 1H), 6.02 (dd, 2H), 5.69 (bp, 1H), 5.17 (d, 1H), 4.81 (s, 1H), 4.52-4.46 (m, 3H), 4.16-4.10 (m, 2H), 3.74 (s, 3H), 3.51-3.48 (m, 1H), 3.25-3.20 (m, 1H), 2.83-2.80 (m, 2H), 2.45-2.40 (m, 1H), 2.29-2.02 (m, 1H), 2.29 (s, 3H), 2.27 (s, 3H), 2.15 (s, 3H), 2.02 (s, 3H); $^{13}$C NMR (75 MHz, CDCl$_3$): δ 168.8, 168.6, 156.8, 156.3, 155.7, 147.4, 145.7, 142.9, 141.1, 140.9, 131.2, 129.7, 120.8, 120.7, 117.9, 114.9, 112.7, 101.9, 81.4, 62.0, 60.1, 57.7, 57.6, 56.0, 54.8, 52.9, 42.2, 41.3, 29.7, 23.6, 20.5, 15.6, 9.6. ESI-MS m/z: Calcd. for C$_{32}$H$_{34}$F$_3$N$_3$O$_{10}$S: 709.2. Found (M–H$_2$O+H$^+$): 692.2.

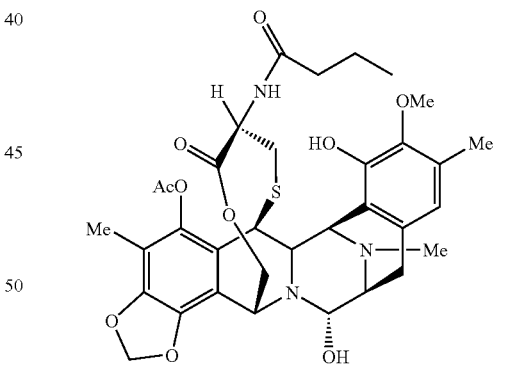

Compound 4c: $^1$H NMR (300 MHz, CDCl$_3$): δ 6.56 (s, 1H), 6.01 (dd, 2H), 5.70 (s, 1H), 5.57 (bd, 1H), 5.15 (d, 1H), 4.77 (s, 1H), 4.61-4.57 (m, 1H), 4.50-4.42 (m, 2H), 4.15-4.07 (m, 2H), 3.77 (s, 3H), 3.49-3.47 (m, 1H), 3.23-3.15 (m, 1H), 2.85-2.82 (m, 2H), 2.32-1.98 (m, 4H), 2.32 (s, 3H), 2.28 (s, 3H), 2.13 (s, 3H), 2.01 (s, 3H), 1.65-1.58 (m, 2H), 0.96 (t, 3H); $^{13}$C NMR (75 MHz, CDCl$_3$): δ 171.8, 170.5, 147.9, 145.6, 143.0, 141.0, 140.8, 131.6, 128.8, 121.0, 120.7, 118.9, 115.3, 101.8, 81.5, 61.6, 60.3, 57.8, 57.6, 56.0, 55.0, 51.9, 42.0, 41.3, 38.3, 32.6, 23.7, 20.5, 18.9, 16.1, 13.8, 9.6. ESI-MS m/z: Calcd. for C$_{34}$N$_3$O$_{10}$S: 683.2. Found (M–H$_2$O+H$^+$): 666.3.

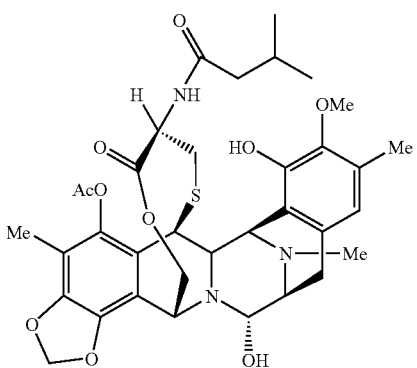

Compound 4d: ¹H NMR (300 MHz, CDCl₃): δ 6.56 (s, 1H), 6.02 (dd, 2H), 5.72 (bs, 1H), 5.55 (bd, 1H), 5.15 (d, 1H), 4.78 (s, 1H), 4.64-4.60 (m, 1H), 4.48-4.42 (m, 2H), 4.17-4.12 (m, 1H), 4.09 (dd, 1H), 3.77 (s, 3H), 3.53-3.48 (m, 1H), 3.27-3.20 (m, 1H), 2.90-2.75 (m, 2H), 2.34-1.91 (m, 5H), 2.34 (s, 3H), 2.28 (s, 3H), 2.14 (s, 3H), 2.01 (s, 3H), 0.98 (d, 3H), 0.93 (d, 3H); ESI-MS m/z: Calcd. for $C_{35}H_{43}N_3O_{10}S$: 697.3. Found (M−H₂O+H⁺): 680.0.

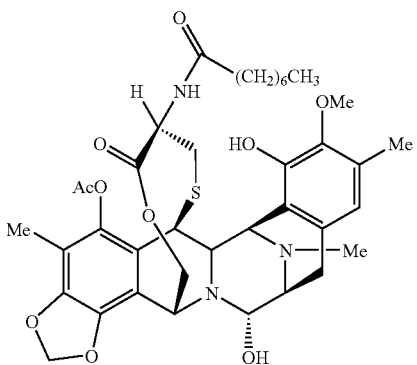

Compound 4e: ¹H NMR (300 MHz, CDCl₃): δ 6.56 (s, 1H), 6.02 (d, 2H), 5.70 (s, 1H), 5.55 (bd, 1H), 5.15 (d, 1H), 4.77 (s, 1H), 4.61-4.55 (m, 1H), 4.50-4.42 (m, 2H), 4.17-4.14 (m, 10H), 4.08 (dd, 1H), 3.77 (s, 3H), 3.51-3.48 (m, 1H), 3.26-3.19 (m, 1H), 2.86-2.79 (m, 2H), 2.32-1.98 (m, 4H), 2.32 (s, 3H), 2.28 (s, 3H), 2.15 (s, 3H), 2.01 (s, 3H), 1.65-1.58 (m, 2H), 1.37-1.22 (m, 8H), 0.89 (t, 3H); ESI-MS m/z: Calcd. for $C_{38}H_{49}N_3O_{10}S$: 739.3. Found (M−H₂O+H⁺): 722.3.

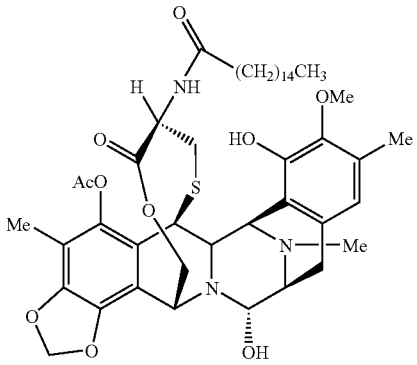

Compound 4f: ¹H NMR (300 MHz, CDCl₃): δ 6.56 (s, 1H), 6.02 (dd, 2H), 5.70 (s, 1H), 5.57-5.53 (bd, 1H), 5.14 (d, 1H), 4.77 (s, 1H), 4.58 (ddd, 1H), 4.47-4.43 (m, 2H), 4.18-4.13 (m, 1H), 4.08 (dd, 1H), 3.77 (s, 3H), 3.50-3.46 (m, 1H), 3.25-3.19 (m, 1H), 2.88-2.82 (m, 1H), 2.32-1.95 (m, 4H), 2.32 (s, 3H), 2.28 (s, 3H), 2.15 (s, 3H), 2.01 (s, 3H), 1.40-1.20 (m, 26H), 0.88 (t, 3H); ESI-MS m/z: Calcd. for $C_{46}H_{65}N_3O_{10}S$: 851.4. Found (M−H₂O+H⁺): 834.5.

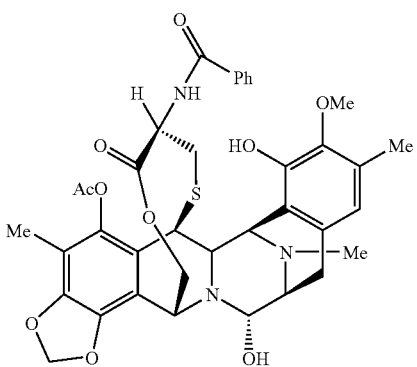

Compound 4g: ¹H NMR (300 MHz, CDCl₃): δ 7.70-7.67 (m, 2H), 7.56-7.45 (m, 3H), 6.49 (s, 1H), 6.42 (d, 1H), 6.03 (dd, 2H), 5.66 (s, 1H), 5.20 (d, 1H), 4.82 (s, 1H), 4.73 (dt, 1H), 4.52-4.45 (m, 2H), 4.16-4.10 (m, 2H), 3.61 (s, 3H), 3.52 (bd, 1H), 3.27-3.22 (m, 1H), 2.90-2.85 (m, 2H), 2.62-2.56 (m, 1H), 2.28-1.92 (m, 1H), 2.28 (s, 3H), 2.13 (s, 3H), 2.03 (s, 3H), 1.92 (s, 3H); ¹³C NMR (75 MHz, CDCl₃): δ 170.4, 168.5, 166.4, 147.6, 145.7, 142.9, 141.1, 140.9, 134.4, 131.5, 129.3, 128.6, 127.0, 125.1, 121.2, 120.5, 115.1, 112.6, 101.8, 81.5, 61.6, 60.1, 57.9, 56.0, 55.0, 53.3, 42.1, 41.3, 32.7, 23.9, 20.4, 15.6, 9.6; ESI-MS m/z: Calcd. for $C_{37}H_{39}N_3O_{10}S$: 717.2. Found (M−H₂O+H⁺): 699.9.

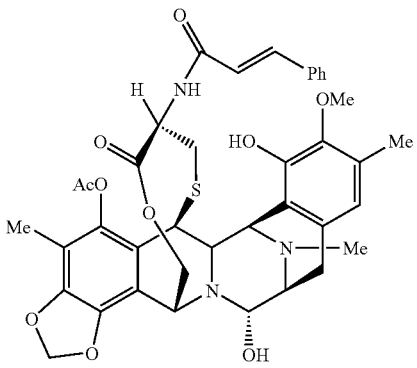

Compound 4h: ¹H NMR (300 MHz, CDCl₃): δ 7.60 (d, 1H), 7.55-7.51 (m, 2H), 7.44-7.38 (m, 3H), 6.65 (s, 1H), 6.25 (d, 1H), 6.02 (dd, 2H), 5.80 (d, 1H), 5.71 (s, 1H), 5.18 (d, 1H), 4.79 (s, 1H), 4.69 (ddd, 1H), 4.49-4.43 (m, 2H), 4.16-4.09 (m, 2H), 3.68 (s, 3H), 3.51-3.49 (m, 1H), 3.26-3.20 (m, 1H), 2.89-2.86 (m, 2H), 2.52-2.47 (m, 1H), 2.29-2.03 (m, 1H), 2.29 (s, 3H), 2.27 (s, 3H), 2.17 (s, 3H), 2.03 (s, 3H); ¹³C NMR (75 MHz, CDCl₃): δ 170.4, 168.5, 164.5, 147.9, 145.6, 143.0, 141.8, 141.5, 141.0, 140.8, 134.8, 131.6, 129.7, 129.0, 128.8, 127.9, 121.0, 120.5, 120.1, 118.7, 115.2, 112.7, 101.8, 81.6, 61.7, 60.2, 57.7, 57.6, 56.0, 54.9, 52.7, 42.0, 41.3, 32.5, 23.7, 20.5, 16.3, 9.6. ESI-MS m/z: Calcd. for $C_{39}H_{41}N_3O_{10}S$: 743.2. Found (M−H₂O+H⁺): 726.3.

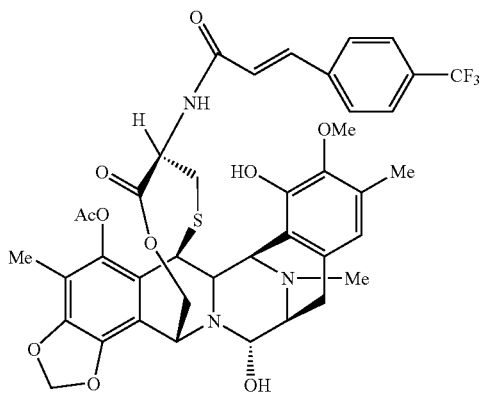

Compound 4i: $^1$H NMR (300 MHz, CDCl$_3$): δ 7.83 (s, 1H), 7.65-7.51 (m, 4H), 6.65 (s, 1H), 6.29 (d, 1H), 6.03 (dd, 2H), 5.81 (d, 1H), 5.71 (s, 1H), 5.18 (d, 1H), 4.79 (s, 1H), 4.71-4.67 (m, 1H), 4.49-4.47 (m, 2H), 4.16-4.09 (m, 2H), 3.70 (s, 3H), 3.51-3.49 (m, 1H), 3.23-3.20 (m, 1H), 2.88-2.86 (m, 2H), 2.47-2.33 (m, 1H), 2.30-2.02 (m, 1H), 2.30 (s, 3H), 2.28 (s, 3H), 2.16 (s, 3H), 2.02 (s, 3H); ESI-MS m/z: Calcd. for C$_{40}$H$_{40}$N$_3$F$_3$O$_{10}$S: 811.2. Found (M–H$_2$O+H$^+$): 794.2.

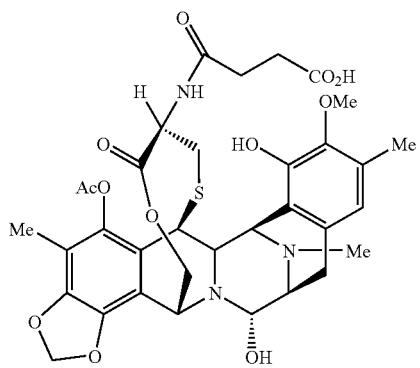

Compound 4l: $^1$H NMR (300 MHz, CDCl$_3$): δ 6.58 (s, 1H), 6.02 (dd, 2H), 5.82-5.72 (bm, 2H), 5.15 (d, 1H), 4.79 (bs, 1H), 4.57-4.45 (m, 3H), 4.22-4.15 (bp, 1H), 4.11 (dd, 1H), 3.78 (s, 3H), 3.59-3.49 (bp, 1H), 3.30-3.23 (bp, 1H), 2.91-2.83 (m, 2H), 2.68-2.45 (m, 4H), 2.35-2.02 (m, 2H), 2.32 (s, 3H), 2.29 (s, 3H), 2.17 (s, 3H), 2.01 (s, 3H); ESI-MS m/z: Calcd. for C$_{34}$H$_{39}$N$_3$O$_{12}$S: 713.2. Found (M–H$_2$O+H$^+$): 696.2.

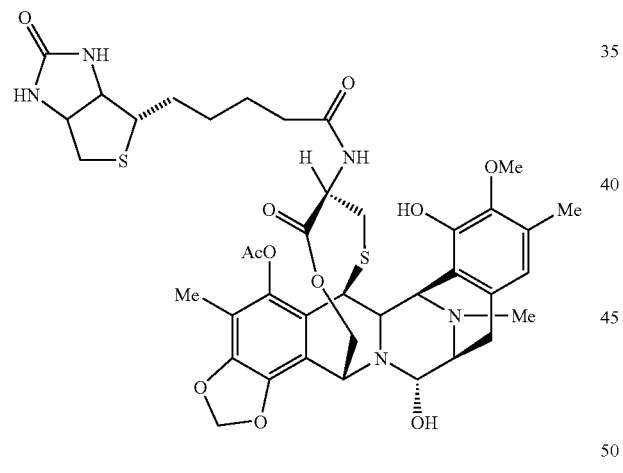

Compound 4k: $^1$H NMR (300 MHz, CDCl$_3$): δ 8.32 (bp, 1H), 6.56 (s, 1H), 6.54 (s, 1H), 6.01 (dd, 2H), 5.48 (bd, 1H), 5.14 (d, 1H), 4.75 (s, 1H), 4.68-4.63 (m, 1H), 4.55-4.45 (m, 3H), 4.33 (dd, 1H), 4.22 (bp, 1H), 4.05 (dd, 1H), 3.80 (s, 3H), 3.53-3.45 (m, 1H), 3.22-3.13 (m, 1H), 3.10-3.02 (m, 1H), 2.94-2.84 (m, 3H), 2.66 (d, 1H), 2.34-1.91 (m, 4H), 2.34 (s, 3H), 2.30 (s, 3H), 2.10 (bs, 3H), 2.01 (bs, 3H), 1.75-1.22 (m, 6H); $^{13}$C NMR (75 MHz, CDCl$_3$): δ 171.0, 170.4, 163.7, 148.9, 145.5, 142.7, 141.1, 140.5, 131.8, 128.8, 122.2, 120.3, 112.6, 101.7, 82.0, 62.1, 60.1, 59.7, 57.2, 56.4, 55.7, 55.3, 51.2, 41.9, 41.2, 41.1, 34.3, 32.9, 27.8, 27.5, 24.8, 23.9, 20.7, 16.2, 9.6; ESI-MS m/z: Calcd. for C$_{40}$H$_{49}$N$_5$O$_{11}$S$_2$: 840.0. Found (M–H$_2$O$^+$): 822.3.

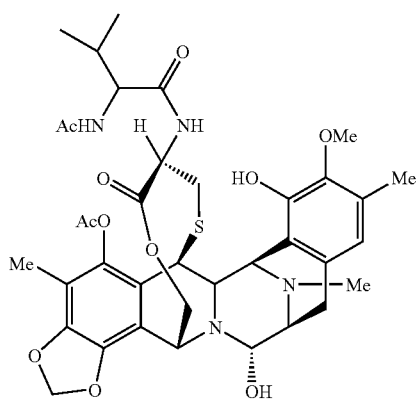

Compound 4q: $^1$H NMR (300 MHz, CDCl$_3$): δ 6.55 (s, 1H), 6.07 (d, 1H), 6.02 (d, 2H), 5.75 (s, 1H), 5.64 (d, 1H), 5.15 (d, 1H), 4.78 (s, 1H), 4.67-4.62 (m, 1H), 4.50-4.45 (m, 2H), 4.14-4.09 (m, 3H), 3.80 (s, 3H), 3.51-3.47 (m, 1H), 3.25-3.20 (m, 1H), 2.85-2.82 (m, 2H), 2.50 (s, 3H), 2.29-1.98 (m, 3H), 2.29 (s, 3H), 2.13 (s, 3H), 2.02 (s, 3H), 1.98 (s, 3H), 1.06 (d, 3H), 0.97 (d, 3H); ESI-MS m/z: Calcd. for C$_{37}$H$_{46}$N$_4$O$_{11}$S: 754.3. Found (M–H$_2$O+H$^+$): 737.3.

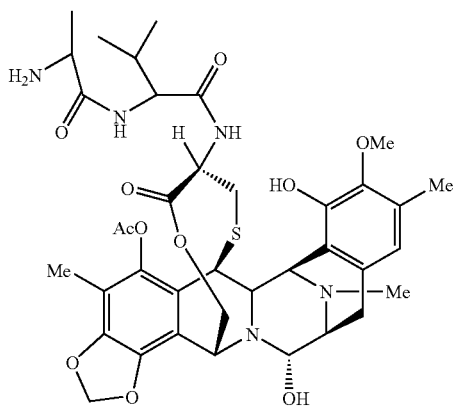

Compound 4s ESI-MS m/z: Calcd. for C₃₈H₄₉N₅O₁₁S: 783.3. Found (M⁺): 766.3.

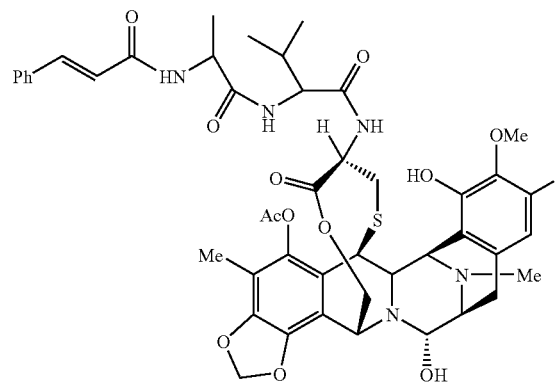

Compound 4u: ESI-MS m/z: Calcd. for C₄₇H₅₅N₅O₁₂S: 914.0. Found (M–H₂O+H⁺): 897.0.

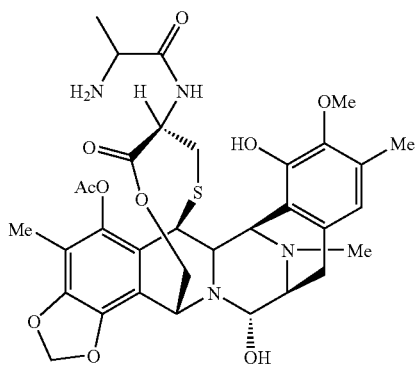

Compound 4v: ¹H NMR (300 MHz, CDCl₃): δ 6.70 (bp, 1H), 6.54 (s, 1H), 6.02 (d, 2H), 5.16 (d, 1H), 4.79 (s, 1H), 4.55-4.48 (m, 3H), 4.15-4.07 (m, 2H), 3.77 (s, 3H), 3.52-3.49 (m, 1H), 3.32-3.21 (m, 2H), 2.85-2.80 (m, 2H), 2.31-2.02 (m, 2H), 2.31 (s, 3H), 2.29 (s, 3H), 2.12 (s, 3H), 2.02 (s, 3H), 1.26 (d, 3H); ESI-MS m/z: Calcd. for C₃₃H₄₀N₄O₁₀S: 684.2. Found (M–H₂O+H⁺): 667.2.

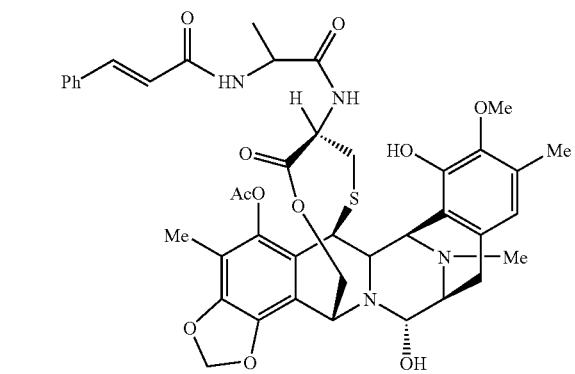

Compound 4x: ESI-MS m/z: Calcd. for C₄₂H₄₆N₄O₁₁S: 814.9. Found (M–H₂O+H⁺): 797.9.

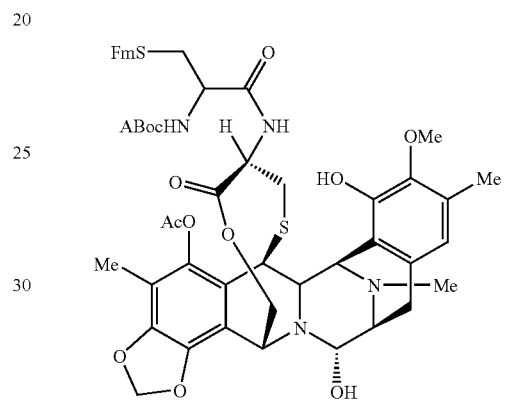

Compound 4y: ¹H NMR (300 MHz, CDCl₃): δ 7.77-7.67 (m, 4H), 7.42-7.28 (m, 4H), 6.55 (s, 1H), 6.18-6.06 (bp, 1H), 6.02 (dd, 2H), 6.03-5.86 (m, 1H), 5.70 (bs, 1H), 5.58 (bd, 1H), 5.35-5.20 (m, 2H), 5.15 (d, 1H), 4.79 (s, 1H), 4.60-4.55 (m, 3H), 4.46 (d, 1H), 4.20-4.11 (m, 4H), 3.73 (s, 3H), 3.49-3.47 (m, 1H), 3.21-3.15 (m, 2H), 3.06-2.70 (m, 6H), 2.38-2.11 (m, 2H), 2.38 (s, 3H), 2.24 (s, 3H), 2.11 (s, 3H), 2.02 (s, 3H); ¹³C NMR (75, CDCl₃): δ 169.8, 168.9, 147.8, 145.8, 145.7, 143.0, 141.0, 140.8, 132.5, 131.4, 127.5, 127.1, 127.0, 125.0, 125.0, 120.6, 119.8, 117.9, 115.1, 101.8, 81.4, 65.8, 61.6, 60.3, 57.8, 55.9, 55.0, 54.4, 52.4, 47.0, 42.1, 41.3, 37.2, 36.5, 33.3, 23.6, 20.4, 16.1, 9.6. ESI-MS m/z: Calcd. for C₅₁H₅₄N₄O₁₂S₂: 978.3. Found (M–H₂O+H⁺): 961.3.

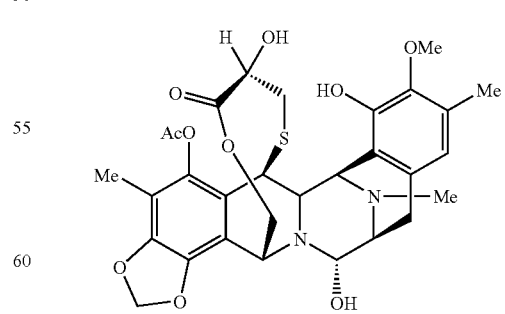

Compound 19: ¹H NMR (300 MHz, CDCl₃): δ 6.58 (s, 1H), 6.01 (dd, 2H), 5.71 (s, 1H), 5.16 (d, 1H), 4.76 (s, 1H), 4.47-4.43 (m, 2H), 4.15-4.11 (m, 1H), 4.08 (dd, 1H), 4.01-3.96 (m, 1H), 3.78 (s, 3H), 3.49-3.45 (m, 1H), 3.21-3.17 (m, 1H), 2.88-2.83 (m, 2H), 2.35-2.02 (m, 2H), 2.31 (s, 3H), 2.29 (s, 3H), 2.17 (s, 3H), 2.02 (s, 3H); ESI-MS m/z: Calcd. for $C_{30}H_{34}N_2O_{10}S$: 614.2. Found (M–$H_2O$+$H^+$): 597.1.

Example 10

Method J: To a solution of 1 equiv. of 3a, 3n-p, 3r, 3t, 17a, 17cc, 17e-f, 17h, 17ll or 18a* in THF/$H_2O$ 4:1 (0.03M) were added 5 equiv. of CUBr. After 24 h the reaction was diluted with $CH_2Cl_2$, washed with saturated solutions of $NaHCO_3$ and brine, and the organic layer dried with $Na_2SO_4$. Chromatography gives pure compounds 4a, 4n-p, 4r, 4t, 21a, 21c, 21e-f, 21h, 21ll or 22a*.

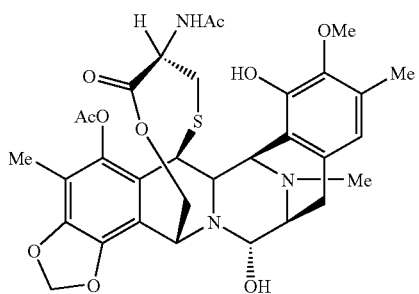

Compound 4a: $t_R$=24.6 min [HPLC, Symmetry 300 C18, 5 μm, 250×4.6 mm, λ=285 nm, flow=1.2 ml/min, temp=40° C., grad.: $CH_3CNaq$.—$NH_4OAc$ (10 mM), 1% DEA, pH=3.0, 10%-60% (90')]; $^1$H NMR (300 MHz, CDCl$_3$): δ 6.57 (s, 1H), 6.02 (dd, 2H), 5.79 (bs, 1H), 5.60 (bd, 1H), 5.15 (d, 1H), 4.77 (s, 1H), 4.56 (ddd, 1H), 4.46-4.43 (m, 2H), 4.15 (dd, 1H), 4.09 (dd, 1H), 3.77 (s, 3H), 3.49-3.47 (m, 1H), 3.23-3.20 (m, 1H), 2.91-2.76 (m, 2H), 2.31-2.11 (m, 2H), 2.31 (s, 3H), 2.28 (s, 3H), 2.14 (s, 3H), 2.01 (s, 3H), 1.89 (s, 3H); $^{13}$C NMR (75 MHz, CDCl$_3$): δ 170.4, 168.8, 168.5, 148.0, 145.6, 143.0, 141.0, 140.7, 131.5, 128.8, 120.9, 120.6, 118.9, 115.2, 112.7, 101.8, 81.5, 61.6, 60.2, 57.7, 57.4, 55.9, 55.0, 52.1, 52.0, 41.3, 32.4, 23.6, 22.9, 20.5, 16.1, 9.5. ESI-MS m/z: Calcd. for $C_{32}H_{37}N_3O_{10}S$: 655.2. Found (M–$H_2O$+$H^+$): 638.1.

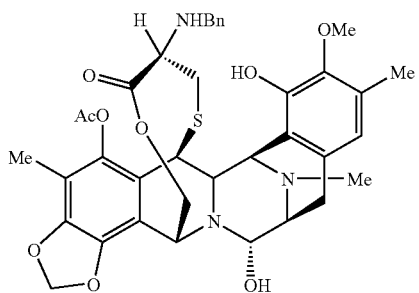

Compound 4n: $^1$H NMR (300 MHz, CDCl$_3$): δ 7.29-7.21 (m, 5H), 6.39 (s, 1H), 5.99 (dd, 2H), 5.66 (s, 1H), 5.16 (d, 1H), 4.74 (s, 1H), 4.52 (d, 1H), 4.44 (bp, 1H), 4.12 (d, 1H), 4.03 (dd, 1H), 3.73 (s, 3H), 3.64 (dd, 2H), 3.48-3.47 (m, 1H), 3.21-3.17 (m, 2H), 2.95 (d, 1H), 2.84-2.75 (m, 1H), 2.35-2.30 (m, 1H), 2.30 (s, 3H), 2.16 (s, 3H), 2.07-2.01 (m, 1H), 2.01 (s, 3H), 1.93 (s, 3H); $^{13}$C NMR (75 MHz, CDCl$_3$): δ 172.6, 168.6, 147.6, 145.4, 142.8, 140.9, 140.8, 140.2, 131.3, 130.8, 129.1, 128.8, 128.2, 126.8, 121.4, 120.9, 117.9, 115.6, 112.4, 101.7, 81.8, 60.9, 60.1, 59.5, 57.8, 57.6, 56.1, 54.9, 51.4, 41.8, 41.3, 33.3, 23.6, 20.6, 15.2, 9.6. ESI-MS m/z: Calcd. for $C_{37}H_{41}N_3O_9S$: 703.3. Found (M–$H_2O$+$H^+$): 686.7.

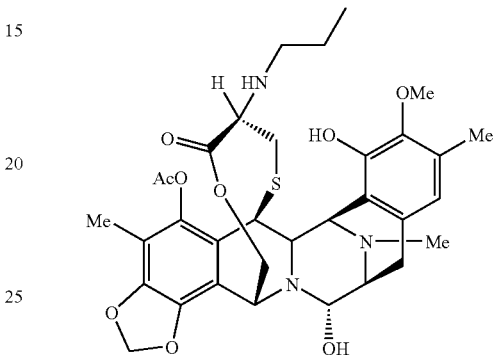

Compound 4o: $^1$H NMR (300 MHz, CDCl$_3$): δ 6.53 (s, 1H), 6.00 (dd, 2H), 5.69 (bp, 1H), 5.14 (d, 1H), 4.74 (s, 1H), 4.44-4.49 (m, 2H), 4.13 (bd, 1H), 4.04 (dd, 1H), 3.78 (s, 3H), 3.49-3.47 (m, 1H), 3.22-3.16 (m, 2H), 2.96-2.75 (m, 2H), 2.51-2.02 (m, 4H), 2.29 (s, 3H), 2.28 (s, 3H), 2.15 (s, 3H), 2.02 (s, 3H), 1.42-1.25 (m, 2H), 0.86 (t, 3H); ESI-MS m/z: Calcd. for $C_{33}H_{41}N_3O_9S$: 655.3. Found (M–$H_2O$+$H^+$): 638.3.

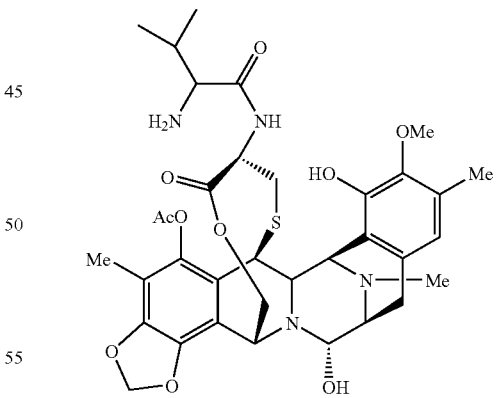

Compound 4p: $^1$H NMR (300 MHz, CDCl$_3$): δ 6.67 (bp. 1H), 6.52 (s, 1H), 6.02 (dd, 2H), 5.67 (bp, 1H), 5.16 (d, 1H), 4.80 (s, 1H), 4.63-4.60 (m, 1H), 4.49 (d, 1H), 4.45 (bp, 1H), 4.16 (d, 1H), 4.08 (dd, 1H), 3.77 (s, 3H), 3.52-3.9 (m, 1H), 3.25-3.20 (m, 1H), 3.00 (d, 1H), 2.85-2.82 (m, 2H), 2.32-2.02 (m, 3H), 2.32 (s, 3H), 2.29 (s, 3H), 2.11 (s, 3H), 2.02 (s, 3H), 0.99 (d, 3H), 0.81 (d, 3H); ESI-MS m/z: Calcd. for $C_{35}H_{44}N_4O_{10}S$: 712.3. Found (M–$H_2O$+$H^+$): 695.2

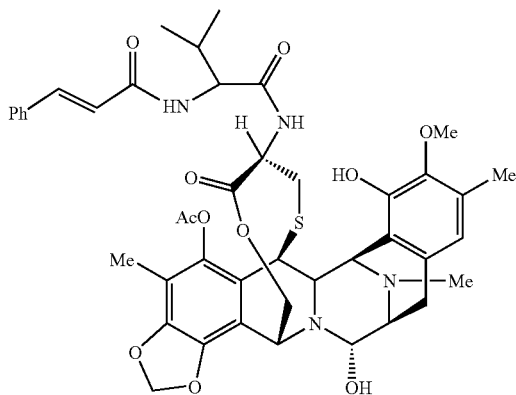

Compound 4r: $^1$H NMR (300 MHz, CDCl$_3$): δ 7.59 (d, 1H), 7.49-7.46 (m, 2H), 7.36-7.34 (m, 3H), 6.58 (s, 1H), 6.42 (d, 1H), 6.34 (d, 1H), 6.01 (dd, 2H), 5.79 (s, 1H), 5.69 (d, 1H), 5.15 (d, 1H), 4.78 (s, 1H), 4.70-4.65 (m, 1H), 4.50-4.47 (m, 2H), 4.28 (dd, 1H), 4.15 (d, 1H), 4.10 (dd, 1H), 3.81 (s, 3H), 3.49 (d, 1H), 3.25-3.22 (m; 1H), 2.85-2.83 (m, 2H), 2.57 (s, 3H), 2.28-2.14 (m, 3H), 2.28 (s, 3H), 2.14 (s, 3H), 2.01 (s, 3H), 1.10 (d, 3H), 1.01 (d, 3H); $^{13}$C NMR (75 MHz, CDCl$_3$): δ 170.1, 170.0, 168.6, 165.2, 148.0, 145.7, 143.2, 141.12, 140.84, 134.8, 131.2, 129.9, 129.6, 128.8, 127.8, 120.8, 120.7, 120.6, 118.4, 115.3, 112.7, 101.8, 81.5, 61.7, 60.4, 57.8, 57.7, 57.5, 56.0, 55.0, 52.0, 42.2, 41.3, 32.7, 32.6, 23.7, 20.5, 19.2, 18.0, 16.4, 9.6. ESI-MS m/z: Calcd. for C$_{44}$H$_{50}$N$_4$O$_{11}$S: 842.9. Found (M−H$_2$O+H$^+$): 825.3.

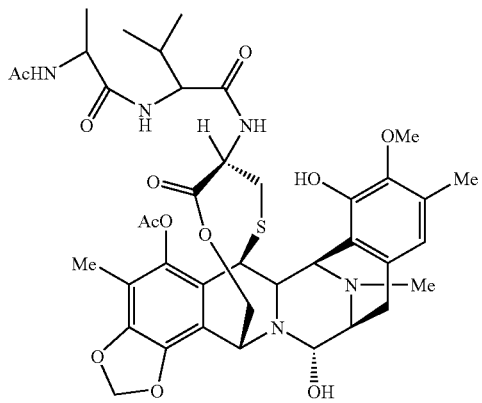

Compound 4t: $^1$H NMR (300 MHz, CDCl$_3$): δ 6.54 (s, 1H), 6.49 (d, 1H), 6.21-6.16 (m, 1H), 6.07-5.96 (m, 2H), 5.78 (s, 1H), 5.63 (bd, 1H), 5.14 (d, 1H), 4.81, 4.78 (2s, 1H), 4.64-4.60 (m, 1H), 4.53-4.08 (m, 6H), 3.78, 3.7s (2s, 3H), 3.65-3.45 (m, 1H), 3.33-3.22 (m, 1H), 2.90-2.66 (m, 2H), 2.48 (s, 3H), 2.28-1.99 (m, 3H), 2.28 (s, 3H), 2.16, 2.13 (2s, 3H), 2.01 (s, 3H), 1.99 (s, 3H), 1.37, 1.34 (2d, 3H), 1.08-1.03 (m, 3H), 0.96-0.93 (m, 3H); $^{13}$C NMR (75 MHz, CDCl$_3$): δ 171.8, 170.1, 169.6, 169.5, 169.5, 168.7, 147.9, 145.7, 143.1, 141.0, 140.8, 131.3, 129.6, 120.7, 120.4, 118.5, 115.2, 112.6, 101.8, 81.4, 61.6, 60.4, 60.3, 57.7, 57.6, 57.5, 55.9, 54.9, 51.9, 48.9, 48.9, 42.2, 41.3, 32.5, 32.3, 23.6, 23.2, 20.5, 19.2, 19.1, 18.6, 17.7, 17.6, 16.3, 9.6 ESI-MS m/z: Calcd. for C$_{40}$H$_{51}$N$_5$O$_{12}$S: 825.3. Found (M−H$_2$O+H$^+$): 808.3.

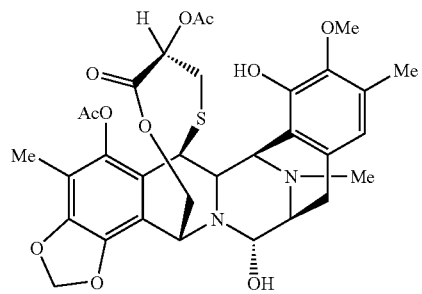

Compound 21a: $^1$H NMR (300 MHz, CDCl$_3$): δ 6.52 (s, 1H), 6.01 (dd, 2H), 5.64 (s, 1H), 5.13 (d, 1H), 5.00 (t, 1H), 4.76 (s, 1H), 4.48-4.45 (m, 2H), 4.15-4.12 (m, 1H), 4.02 (dd, 1H), 3.79 (s, 3H), 3.50-3.47 (m, 1H), 3.22-3.17 (m, 1H), 2.82-2.79 (m, 2H), 2.30-1.98 (m, 2H), 2.30 (s, 3H), 2.29 (s, 3H), 2.15 (s, 3H), 2.02 (s, 3H), 1.98 (s, 3H); ESI-MS m/z: Calcd. for C$_{32}$H$_{36}$N$_2$O$_{11}$S: 656.2. Found (M−H$_2$O+H$^+$): 639.2.

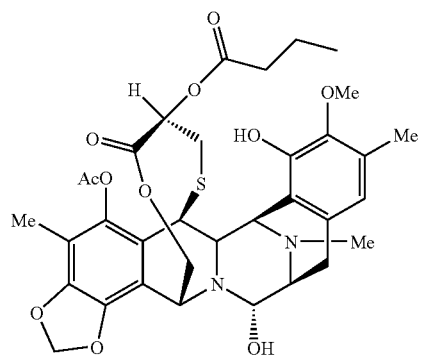

Compound 21c: $^1$H NMR (300 MHz, CDCl$_3$): δ 6.45 (s, 1H), 6.01 (dd, 2H), 5.63 (s, 1H), 5.13 (d, 1H), 5.03 (t, 1H), 4.77 (s, 1H), 4.50-4.48 (m, 2H), 4.14 (bd, 1H), 4.02 (dd, 1H), 3.79 (s, 3H), 3.51-3.49 (bd, 1H), 3.21-3.12 (m, 1H), 2.85-2.75 (m, 2H), 2.31-2.02 (m, 4H), 2.31 (s, 3H), 2.29 (s, 3H), 2.13 (s, 3H), 2.02 (s, 3H), 1.66-1.56 (m, 2H), 0.97 (t, 3H); $^{13}$C NMR (75 MHz, CDCl$_3$): δ 172.4, 168.6, 166.9, 147.1, 145.6, 142.8, 141.1, 131.8, 128.6, 125.1, 121.4, 115.4, 101.8, 81.5, 71.6, 61.2, 60.2, 58.2, 57.9, 56.1, 55.0, 41.8, 41.4, 36.0, 31.6, 23.9, 20.4, 18.3, 15.8, 13.7, 9.6. ESI-MS m/z: Calcd. for C$_{34}$H$_{40}$N$_2$O$_{11}$S: 684.2. Found (M−H$_2$O+H$^+$): 667.2.

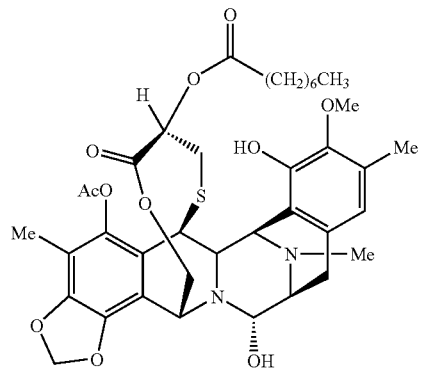

Compound 21e: $^1$H NMR (300 MHz, CDCl$_3$): δ 6.49 (s, 1H), 6.01 (dd, 2H), 5.63 (s, 1H), 5.13 (d, 1H), 5.02 (t, 1H), 4.76 (s, 1H), 4.47-4.46 (m, 2H), 4.13 (dd, 1H), 4.02 (dd, 1H), 3.79 (s, 3H), 3.50-3.49 (m, 1H), 3.21-3.19 (m, 1H), 2.81-2.78 (m, 2H), 2.30-2.02 (m, 4H), 2.30 (s, 3H), 2.29 (s, 3H), 2.13 (s, 3H), 2.02 (s, 3H), 1.62-1.54 (m, 2H), 1.32-1.25 (m, 8H), 0.90 (t, 3H); $^{13}$C NMR (75 MHz, CDCl$_3$): δ 172.6, 168.6, 166.9, 147.1, 145.5, 142.8, 141.1, 141.0, 131.7, 128.6, 121.4, 117.9, 115.4, 112.3, 101.8, 81.5, 71.5, 61.2, 60.2, 58.1, 57.9, 56.1, 55.0, 41.8, 41.4, 33.9, 31.7, 31.6, 29.1, 28.9, 24.7, 23.9, 22.6, 20.4, 15.8, 14.1, 9.6. ESI-MS m/z: Calcd. for C$_{38}$H$_{48}$N$_2$O$_{11}$S: 740.3. Found (M−H$_2$O+H$^+$): 723.2.

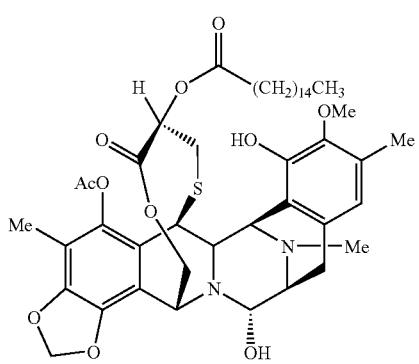

Compound 21f: $^1$H NMR (300 MHz, CDCl$_3$): δ 6.50 (s, 1H), 6.01 (dd, 2H), 5.63 (s, 1H), 5.13 (d, 1H), 5.02 (t, 1H), 4.77 (bs, 1H), 4.50-4.48 (m, 2H), 4.16-4.12 (m, 1H), 4.02 (dd, 1H), 3.79 (s, 3H), 3.51-3.49 (m, 1H), 3.22-3.19 (m, 1H), 2.82-2.77 (m, 2H), 2.37-2.02 (m, 7H), 2.30 (s, 3H), 2.29 (s, 3H), 2.02 (s, 3H), 1.65-1.59 (m, 2H), 1.40-1.16 (m, 24H), 0.88 (t, 3H); ESI-MS m/z: Calcd. for C$_{46}$H$_{64}$N$_2$O$_{10}$S: 852.4. Found (M−H$_2$O+H$^+$): 835.4.

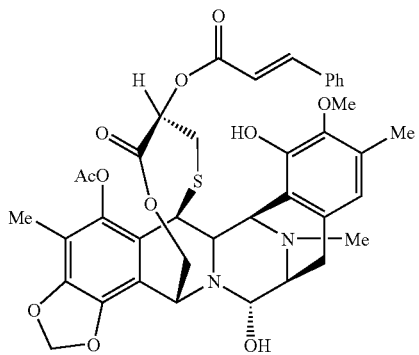

Compound 21h: $^1$H NMR (300 MHz, CDCl$_3$): δ 7.64 (d, 1H), 7.55-7.52 (m, 2H), 7.42-7.40 (m, 3H), 6.54 (s, 1H), 6.30 (d, 1H), 6.02 (dd, 2H), 5.65 (s, 1H), 5.19-5.16 (m, 2H), 4.79 (s, 1H), 4.50-4.49 (m, 2H), 4.15 (d, 1H), 4.05 (dd, 1H), 3.79 (s, 3H), 3.51 (d, 1H), 3.22-3.19 (m, 1H), 2.89-2.76 (m, 2H), 2.45-2.41 (m, 1H), 2.31 (s, 3H), 2.26 (s, 3H), 2.13 (s, 3H), 2.13-2.03 (m, 1H), 2.03 (s, 3H); $^{13}$C NMR (75 MHz, CDCl$_3$): δ 168.6, 166.9, 165.7, 147.1, 145.5, 145.4, 142.8, 141.1, 141.0, 134.6, 131.9, 130.3, 128.9, 128.1, 121.3, 117.6, 115.4, 112.3, 101.8, 81.5, 72.0, 61.2, 60.3, 58.2, 57.9, 56.1, 55.0, 41.9, 41.4, 31.8, 23.9, 20.4, 15.9, 9.6. ESI-MS m/z: Calcd. for C$_{39}$H$_{40}$N$_2$O$_{11}$S: 744.2. Found (M−H$_2$O+H$^+$): 727.2.

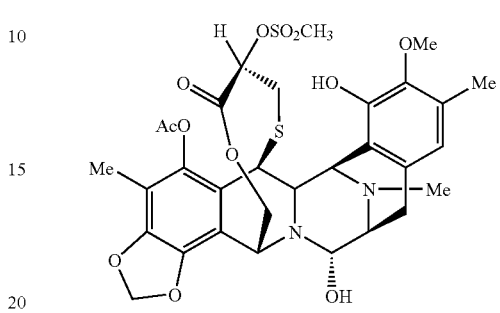

Compound 21ll: $^1$H NMR (300 MHz, CDCl$_3$): δ 6.45 (s, 1H), 6.01 (dd, 2H), 5.68 (s, 1H), 5.12 (d, 1H), 4.92 (t, 1H), 4.78 (s, 1H), 4.53-4.42 (m, 2H), 4.15-4.03 (m, 2H), 3.78 (s, 3H), 3.51-3.48 (m, 1H), 3.24-3.20 (m, 1H), 3.10 (s, 3H), 2.83-2.78 (m, 2H), 2.50-2.42 (m, 1H), 2.31 (s, 3H), 2.30 (s, 3H), 2.17 (s, 3H), 2.08-2.03 (m, 1H), 2.03 (s, 3H); ESI-MS m/z: Calcd. for C$_{31}$H$_{36}$N$_2$O$_{12}$S$_2$: 692.2. Found (M−H$_2$O+H$^+$): 675.2.

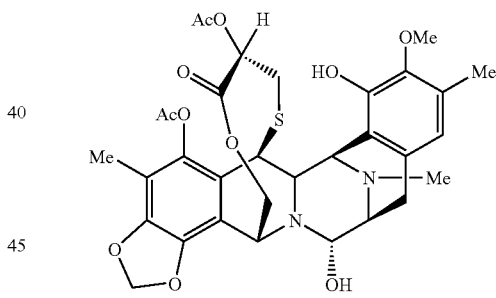

Compound 22a*: $^1$H NMR (300 MHz, CDCl$_3$): δ 6.50 (s, 1H), 6.02 (dd, 2H), 5.67 (s, 1H), 4.73 (bp, 1H), 4.71 (s, 1H), 4.48-4.38 (m, 4H), 4.12-4.10 (m, 1H), 3.80 (s, 3H), 3.61-3.59 (m, 1H), 3.22-3.18 (m, 1H), 2.89-2.80 (m, 1H), 2.70 (d, 1H), 2.33-1.86 (m, 2H), 2.33 (s, 3H), 2.30 (s, 3H), 2.12 (s, 3H), 2.01 (s, 3H), 1.94 (s, 3H); ESI-MS m/z: Calcd. for C$_{32}$H$_{36}$N$_2$O$_{11}$S: 656.2. Found (M−H$_2$O+H$^+$): 639.2.

Example 11

Method K: A solution of 7 in CH$_2$Cl$_2$/H$_2$O/TFA 2:1:4 (0.013M) was stirred for 15 min at RT. Then the reaction was diluted with CH$_2$Cl$_2$, neutralized with a saturated solution of NaHCO$_3$ and Na$_2$CO$_3$ and extracted with CH$_2$Cl$_2$. The organic layer was dried with Na$_2$SO$_4$. Flash chromatography (CH$_2$Cl$_2$/MeOH) gives pure 2p.

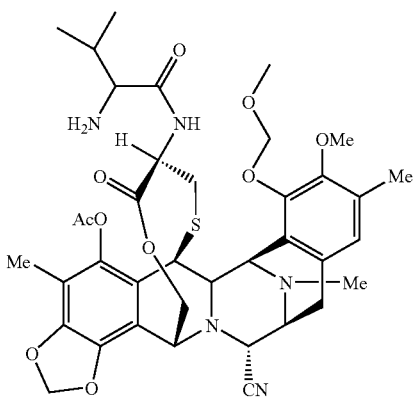

Compound 2p: $^1$H NMR (300 MHz, CDCl$_3$): δ 6.93 (bp. 1H), 6.72 (s, 1H), 6.05 (dd, 2H), 5.15 (dd, 2H), 5.03 (d, 1H), 4.66-4.63 (m, 1H), 4.54 (bp, 1H), 4.35 (d, 1H), 4.32 (s, 1H), 4.23 (d, 1H), 4.17 (dd, 1H), 3.75 (s, 3H), 3.56 (s, 3H), 3.49-3.42 (m, 2H), 3.04 (d, 1H), 2.93-2.90 (m, 2H), 2.28-2.03 (m, 3H), 2.28 (s, 6H), 2.14 (s, 3H), 2.03 (s, 3H), 0.97 (d, 3H), 0.77 (d, 3H); ESI-MS m/z: Calcd. for C$_{38}$H$_{47}$N$_5$O$_{10}$S: 765.3. Found (M+H$^+$): 766.3.

Example 12

Method L: To a solution of 10 in CH$_3$CN (0.03M) were added 2 equiv. of NaCNBH$_3$ and 4 equiv. of AcOH. After 4 h the reaction was diluted with CH$_2$Cl$_2$, neutralized with a saturated solution of NaHCO$_3$ and extracted with CH$_2$Cl$_2$. The organic layer was dried with Na$_2$SO$_4$. Flash chromatography (Hex/EtOAc 2:1) gives pure compounds.

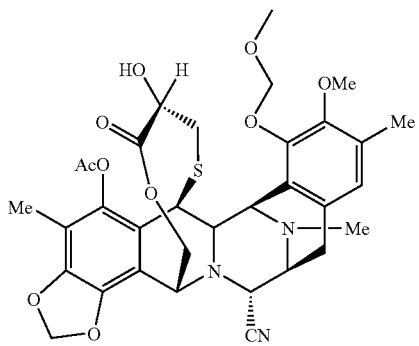

Compound 12*: $^1$H NMR (300 MHz, 45° C., CDCl$_3$): δ 6.70 (s, 1H), 6.04 (dd, 2H), 5.17 (dd, 2H), 4.88 (bd, 1H), 4.49 (bs, 1H), 4.33 (bd, 1H), 4.27-4.24 (m, 1H), 4.24 (s, 1H), 4.08 (d, 1H), 3.79 (s, 3H), 3.60-3.55 (m, 2H), 3.56 (s, 3H), 3.42-3.39 (m, 1H), 3.00-2.91 (m, 1H), 2.76 (d, 1H), 2.50-2.42 (m, 1H), 2.32 (s, 3H), 2.27 (s, 3H), 2.16 (s, 3H), 2.02 (s, 3H), 1.66 (dd, 1H); ESI-MS m/z: Calcd. for C$_{33}$H$_{37}$N$_3$O$_{10}$S: 667.3. Found (M+H$^+$): 668.2.

Example 13

Method M: To a solution of 1 equiv. of 11 for 13a-b or 12* for 14a* in CH$_2$Cl$_2$ (0.1M) under Argon were added 30 equiv of pyr. Then the reaction was cold to 0° C. and 20 equiv. of the anhydride and 5 equiv. of DMAP were added. After 5 min the reaction was warmed to room temperature and stirred for 24 h. After this time it was quenched with NaCl, extracted with CH$_2$Cl$_2$ and the organic layers dried with Na$_2$SO$_4$. Flash chromatography gives pure compounds.

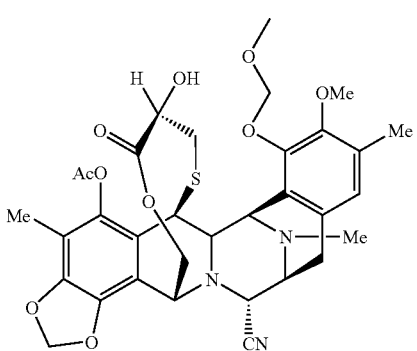

Compound 11: $^1$H NMR (300 MHz, CDCl$_3$): δ 6.77 (s, 1H), 6.03 (dd, 2H), 5.17 (dd, 2H), 5.04 (d, 1H), 4.53 (bp, 1H), 4.34 (d, 1H), 4.27 (s, 1H), 4.20 (d, 1H), 4.19 (dd, 1H), 4.01 (bdd, 1H), 3.77 (s, 3H), 3.57 (s, 3H), 3.55-3.39 (m, 2H), 2.94-2.91 (m, 2H), 2.30-1.98 (m, 2H), 2.30 (s, 3H), 2.25 (s, 3H), 2.20 (s, 3H), 2.03 (s, 3H); $^{13}$C NMR (75 MHz, CDCl$_3$): δ 172.6, 168.6, 149.6, 148.3, 145.7, 141.0, 140.4, 131.6, 130.3, 124.8, 124.7, 120.5, 118.0, 113.3, 102.0, 99.1, 69.8, 61.4, 60.4, 59.6, 59.1, 59.0, 57.4, 54.9, 54.6, 41.4, 41.4, 35.0, 23.8, 20.3, 15.7, 9.6. ESI-MS m/z: Calcd. for C$_{33}$H$_{37}$N$_3$O$_{10}$S: 667.3. Found (M+H$^+$): 668.2.

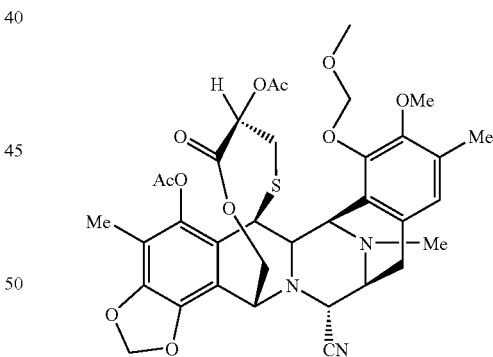

Compound 13a (using Ac$_2$O): $^1$H NMR (300 MHz, CDCl$_3$): δ 6.70 (s, 1H), 6.04 (dd, 2H), 5.17 (dd, 2H), 5.02-4.99 (m, 2H), 4.56 (bp, 1H), 4.34 (dd, 1H), 4.27 (s, 1H), 4.18 (d, 1H), 4.14 (dd, 1H), 3.78 (s, 3H), 3.57 (s, 3H), 3.46-3.39 (m, 2H), 2.90-2.87 (m, 2H), 2.30-1.96 (m, 2H), 2.30 (s, 3H), 2.25 (s, 3H), 2.17 (s, 3H), 2.03 (s, 3H), 1.99 (s, 3H); $^{13}$C NMR (75 MHz, CDCl$_3$): δ 169.7, 167.1, 148.9, 148.2, 145.9, 141.2, 140.6, 130.7, 130.7, 125.3, 124.6, 120.8, 118.1, 113.5, 113.1, 102.0, 99.2, 71.6, 61.4, 60.0, 59.9, 59.2, 58.7, 57.4, 55.0, 54.6, 41.5, 31.6, 23.9, 20.3, 20.2, 15.8, 9.6. ESI-MS m/z: Calcd. for C$_{35}$H$_{39}$N$_3$O$_{11}$S: 709.6. Found (M+H$^+$): 710.2.

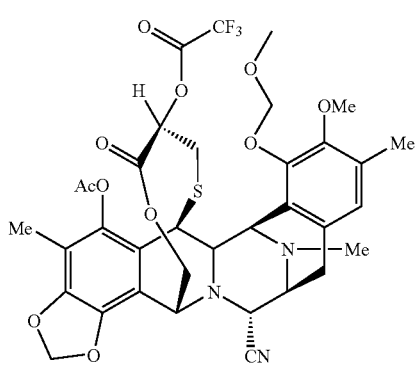

Compound 13b (using (F₃CCO)₂O): ¹H NMR (300 MHz, CDCl₃): δ 6.67 (s, 1H), 6.04 (dd, 2H), 5.17 (dd, 2H), 5.10 (bt, 1H), 5.02 (d, 1H), 4.62 (bp, 1H), 4.34-4.32 (m, 2H), 4.19-4.15 (m, 2H), 3.76 (s, 3H), 3.56 (s, 3H), 3.47 (d, 1H), 3.44-3.41 (m, 1H), 2.94-2.77 (m, 2H), 2.47-2.37 (m, 1H), 2.31 (s, 3H), 2.23 (s, 3H), 2.17 (s, 3H), 2.07-2.04 (m, 1H), 2.04 (s, 3H); ¹³C NMR (75 MHz, CDCl₃): δ 168.7, 164.9, 148.7, 148.2, 145.9, 141.2, 140.7, 131.6, 130.3, 125.7, 124.0, 120.6, 118.0, 113.3, 102.1, 99.2, 74.7, 61.4, 60.5, 60.0, 59.1, 59.2, 58.7, 57.4, 54.9, 54.6, 41.7, 41.5, 31.1, 23.9, 20.2, 15.5, 9.6. ESI-MS m/z: Calcd. for $C_{35}H_{36}F_3N_3O_{11}S$: 763.2. Found (M+H⁺): 764.2.

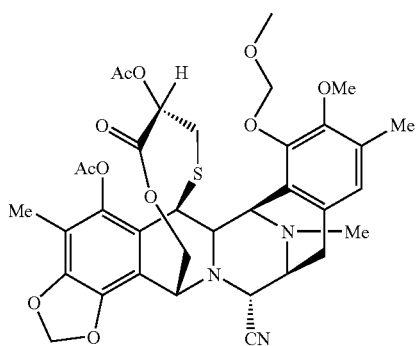

Compound 14a* (using Ac₂O): ¹H NMR (300 MHz, CDCl₃): δ 6.71 (s, 1H), 6.05 (dd, 2H), 5.16 (dd, 2H), 4.65-4.10 (m, 7H), 3.79 (s, 3H), 3.57-3.54 (m, 1H), 3.56 (s, 3H), 3.43-3.40 (m, 1H), 2.97-2.88 (m, 1H), 2.78 (d, 1H), 2.33-1.82 (m, 2H), 2.32 (s, 3H), 2.27 (s, 3H), 2.15 (s, 3H), 2.03 (s, 3H), 1.94 (s, 3H); ESI-MS m/z: Calcd. for $C_{35}H_{39}N_3O_{11}S$: 709.6. Found (M+H⁺): 710.7.

Compounds 23 and 24:

Compound 23: ¹H NMR (300 MHz, CDCl₃): δ 6.52 (s, 1H), 5.95 (dd, 2H), 4.97 (d, 1H), 4.42 (d, 1H), 4.28 (bs, 2H), 4.15 (d, 1H), 4.05 (dd, 1H), 3.78 (s, 3H), 3.51-3.50 (m, 1H), 3.40-3.39 (m, 1H), 3.27 (t, 1H), 2.91-2.89 (m, 2H), 2.38-2.36 (m, 2H), 2.28 (s, 3H), 2.17 (s, 3H), 2.14 (s, 3H); ¹³C NMR (75 MHz, CDCl₃): δ 173.9, 148.1, 146.2, 146.1, 142.8, 136.2, 130.4, 129.5, 120.8, 118.2, 112.7, 112.7, 107.7, 101.3, 61.1, 60.9, 60.4, 59.4, 58.8, 54.6, 54.6, 53.5, 43.3, 41.4, 33.0, 23.9, 15.7, 8.7; ESI-MS m/z: Calcd. for $C_{29}H_{32}N_4O_7S$: 580.2. Found (M+H⁺): 581.3.

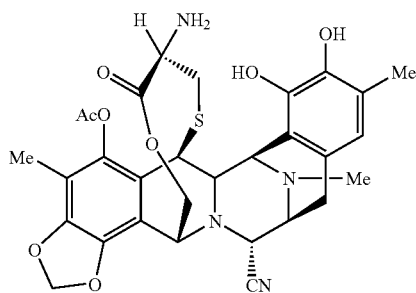

Compound 24: ¹H NMR (300 MHz, CDCl₃): δ 6.40 (s, 1H), 6.02 (d, 2H), 5.00 (d, 1H), 4.46 (bp, 1H), 4.24 (s, 1H), 4.21-4.14 (m, 3H), 3.39-3.37 (m, 2H), 3.29 (t, 1H), 2.93-2.78 (m, 2H), 2.31-2.03 (m, 2H), 2.31 (s, 3H), 2.25 (bs, 3H), 2.14 (s, 6H); ¹³C NMR (75 MHz, CDCl₃): δ 173.6, 168.9, 145.6, 145.3, 140.9, 140.2, 139.3, 126.1, 123.9, 120.2, 119.7, 118.1, 117.7, 113.6, 113.3, 101.9, 61.3, 60.3, 59.1, 59.1, 54.7, 54.6, 53.3, 41.9, 41.4, 33.0, 23.5, 20.5, 16.8, 9.6; ESI-MS m/z: Calcd. for $C_{30}H_{32}N_4O_8S$: 608.2. Found (M+H⁺): 609.3.

Example 14

Compound Int-14

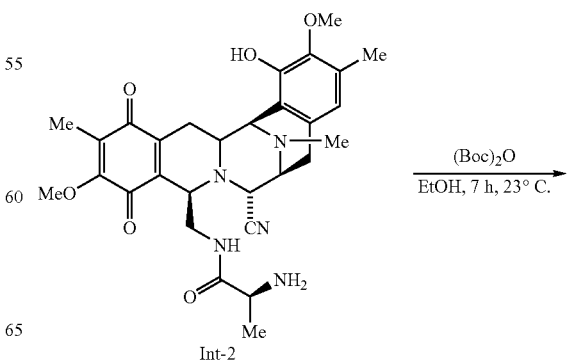

115

-continued

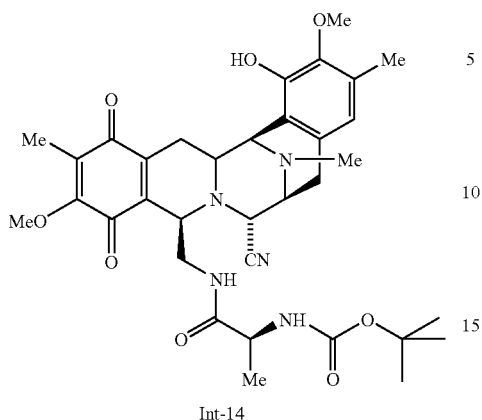
Int-14

To a solution of Int-2 (21.53 g, 39.17 ml) in ethanol (200 ml), tert-butoxycarbonyl anhydride (7.7 g, 35.25 ml) was added and the mixture was stirred for 7 h at 23° C. Then, the reaction was concentrated in vacuo and the residue was purified by flash column chromatography (SiO$_2$, hexane:ethyl acetate 6:4) to give Int-14 (20.6 g, 81%) as a yellow solid.

Rf: 0.52 (ethyl acetate:CHCl$_3$ 5:2).

$^1$H NMR (300 MHz, CDCl$_3$): δ 6.49 (s, 1H), 6.32 (bs, 1H), 5.26 (bs, 1H), 4.60 (bs, 1H), 4.14 (d, J=2.4 Hz, 1H), 4.05 (d, J=2.4 Hz, 1H), 3.94 (s, 3H), 3.81 (d, J=4.8 Hz, 1H), 3.7 (s, 3H), 3.34 (br d, J=7.2 Hz, 1H), 3.18-3.00 (m, 5H), 2.44 (d, J=18.3 Hz, 1H), 2.29 (s, 3H), 2.24 (s, 3H), 1.82 (s, 3H), 1.80-1.65 (m, 1H), 1.48 (s, 9H), 0.86 (d, J=5.7 Hz, 3H)

$^{13}$C NMR (75 MHz, CDCl$_3$): δ 185.5, 180.8, 172.7, 155.9, 154.5, 147.3, 143.3, 141.5, 135.3, 130.4, 129.2, 127.5, 120.2, 117.4, 116.9, 80.2, 60.7, 60.3, 58.5, 55.9, 55.8, 54.9, 54.4, 50.0, 41.6, 40.3, 28.0, 25.3, 24.0, 18.1, 15.6, 8.5.

ESI-MS m/z: Calcd. for C$_{34}$H$_{43}$N$_5$O$_8$: 649.7. Found (M+H)$^+$: 650.3.

Example 15

Compound Int-15

116

-continued

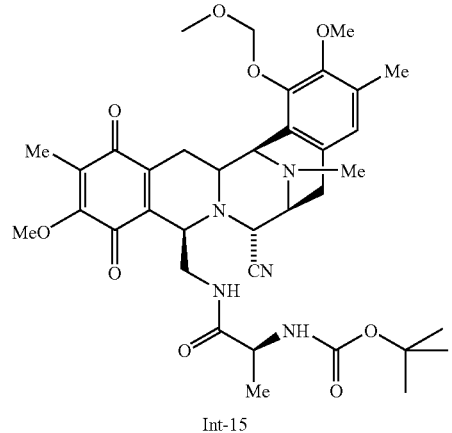
Int-15

To a stirred solution of Int-14 (20.6 g, 31.75 ml) in CH$_3$CN (159 ml), diisopropylethylamine (82.96 ml, 476.2 ml), methoxymethylene bromide (25.9 ml, 317.5 ml) and dimethylaminopyridine (155 mg, 1.27 ml) were added at 0° C. The mixture was stirred at 23° C. for 24 h. The reaction was quenched at 0° C. with aqueous 0.1N HCl (750 ml) (pH=5), and extracted with CH$_2$Cl$_2$ (2×400 ml). The organic phase was dried (sodium sulphate) and concentrated in vacuo. The residue was purified by flash column chromatography (SiO$_2$, gradient hexane:ethyl acetate 4:1 to hexane:ethyl acetate 3:2) to give Int-15 (17.6 g, 83%) as a yellow solid.

Rf: 0.38 (hexane:ethyl acetate 3:7).

$^1$H NMR (300 MHz, CDCl$_3$): δ 6.73 (s, 1H), 5.35 (bs, 1H), 5.13 (s, 2H), 4.50 (bs, 1H), 4.25 (d, J=2.7 Hz, 1H), 4.03 (d, J=2.7 Hz, 1H), 3.97 (s, 3H), 3.84 (bs, 1H), 3.82-3.65 (m, 1H), 3.69 (s, 3H), 3.56 (s, 3H), 3.39-3.37 (m, 1H), 3.20-3.00 (m, 5H), 2.46 (d, J=18 Hz, 1H), 2.33 (s, 3H), 2.23 (s, 3H), 1.85 (s, 3H), 1.73-1.63 (m, 1H), 1.29 (s, 9H), 0.93 (d, J=5.1 Hz, 3H)

$^{13}$C NMR (75 MHz, CDCl$_3$): δ 185.4, 180.9, 172.4, 155.9, 154.5, 149.0, 148.4, 141.6, 135.1, 131.0, 129.9, 127.6, 124.4, 123.7, 117.3, 99.1, 79.3, 60.7, 59.7, 58.4, 57.5, 56.2, 55.9, 55.0, 54.2, 50.0, 41.5, 39.9, 28.0, 25.2, 24.0, 18.1, 15.6, 8.5.

ESI-MS m/z: Calcd. for C$_{36}$H$_{47}$N$_5$O$_9$: 693.8. Found (M+H)$^+$: 694.3.

Example 16

Compound Int-16

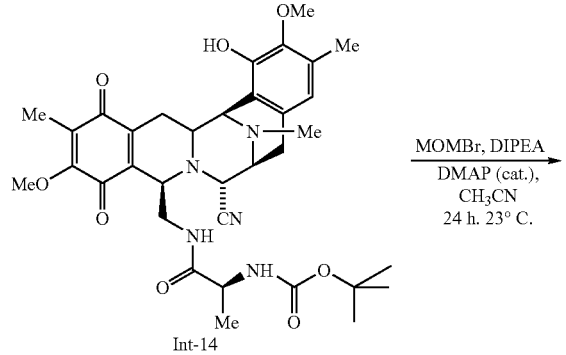
Int-14

MOMBr, DIPEA
DMAP (cat.),
CH$_3$CN
24 h. 23° C.

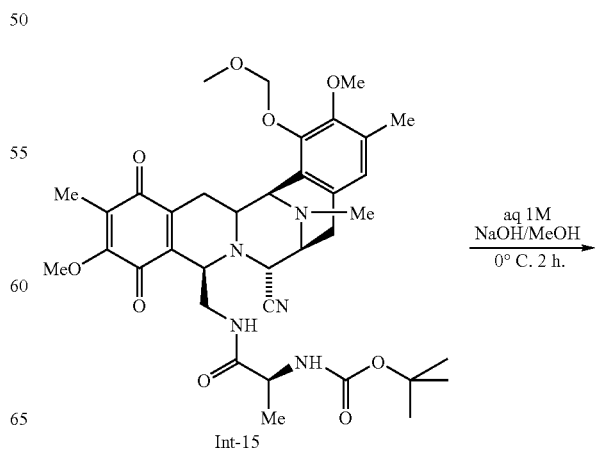
Int-15 aq 1M
NaOH/MeOH
0° C. 2 h.

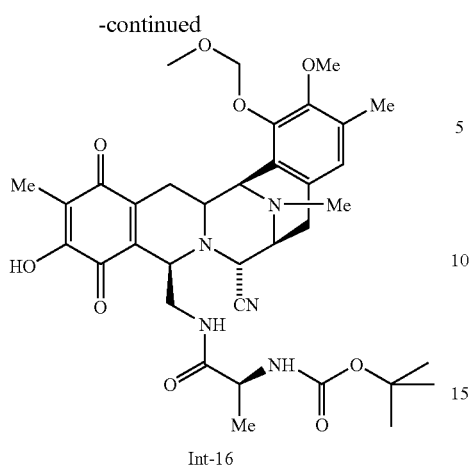

Int-16

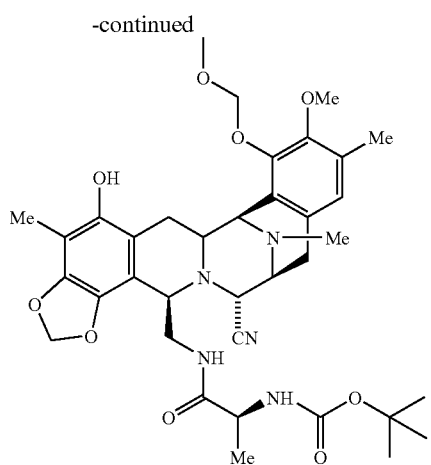

Int-17

To a flask containing Int-15 (8 g, 1.5 ml) in methanol (1.6 l) an aqueous solution of 1M sodium hydroxide (3.2 l) was added at 0° C. The reaction was stirred for 2 h at this temperature and then, quenched with 6M HCl to pH=5. The mixture was extracted with ethyl acetate (3×1 l) and the combined organic layers were dried over sodium sulphate and concentrated in vacuo. The residue was purified by flash column chromatography (SiO$_2$, gradient CHCl$_3$ to CHCl$_3$:ethyl acetate 2:1) to afford Int-16 (5.3 mg, 68%).

Rf: 0.48 (CH$_3$CN:H$_2$O 7:3, RP-C18)

$^1$H NMR (300 MHz, CDCl$_3$): δ 6.73 (s, 1H), 5.43 (bs, 1H), 5.16 (s, 2H), 4.54 (bs, 1H), 4.26 (d, J=1.8 Hz, 1H), 4.04 (d, J=2.7 Hz 1H), 3.84 (bs, 1H), 3.80-3.64 (m, 1H), 3.58 (s, 3H), 3.41-3.39 (m, 1H), 3.22-3.06 (m, 5H), 2.49 (d, J=18.6 Hz 1H), 2.35 (s, 3H), 2.30-2.25 (m, 1H), 2.24 (s, 3H), 1.87 (s, 3H), 1.45-1.33 (m, 1H), 1.19 (s, 9H), 1.00 (br d, J=6.6 Hz 3H)

$^{13}$C NMR (75 MHz, CDCl$_3$): δ 184.9, 180.9, 172.6, 154.7, 151.3, 149.1, 148.6, 144.7, 132.9, 131.3, 129.8, 124.5, 123.7, 117.3, 116.8, 99.1, 79.4, 59.8, 58.6, 57.7, 56.2, 55.6, 54.9, 54.5, 50.1, 41.6, 40.1, 28.0, 25.3, 24.4, 18.1, 15.7, 8.0.

ESI-MS m/z: Calcd. for C$_{35}$H$_{45}$N$_5$O$_9$: 679.7. Found (M+H)$^+$: 680.3.

Example 17

Compound Int-17

To a degassed solution of compound Int-16 (1.8 g, 2.64 ml) in DMF (221 ml) 10% Pd/C (360 mg) was added and stirred under H$_2$ (atmospheric pressure) for 45 min. The reaction was filtered through celite under argon, to a flask containing anhydrous Cs$_2$CO$_3$ (2.58 g, 7.92 ml). Then, bromochloromethane (3.40 ml 52.8 ml), was added and the tube was sealed and stirred at 100° C. for 2 h. The reaction was cooled, filtered through a pad of celite and washed with CH$_2$Cl$_2$. The organic layer was concentrated and dried (sodium sulphate) to afford Int-17 as a brown oil that was used in the next step with no further purification.

Rf: 0.36 (hexane:ethyl acetate 1:5, SiO$_2$).

$^1$H NMR (300 MHz, CDCl$_3$): δ 6.68 (s, 1H), 6.05 (bs, 1H), 5.90 (s, 1H), 5.79 (s, 1H), 5.40 (bs, 1H), 5.31-5.24 (m, 2H), 4.67 (d, J=8.1 Hz, 1H), 4.19 (d, J=2.7 Hz, 1H), 4.07 (bs, 1H), 4.01 (bs, 1H), 3.70 (s, 3H), 3.67 (s, 3H), 3.64-2.96 (m, 5H), 2.65 (d, J=18.3 Hz, 1H), 2.33 (s, 3H), 2.21 (s, 3H), 2.04 (s, 3H), 2.01-1.95 (m, 1H), 1.28 (s, 9H), 0.87 (d, J=6.3 Hz, 3H)

$^{13}$C NMR (75 MHz, CDCl$_3$): δ 172.1, 162.6, 154.9, 149.1, 145.7, 135.9, 130.8, 130.7, 125.1, 123.1, 117.8, 100.8, 99.8, 76.6, 59.8, 59.2, 57.7, 57.0, 56.7, 55.8, 55.2, 49.5, 41.6, 40.1, 36.5, 31.9, 31.6, 29.7, 28.2, 26.3, 25.0, 22.6, 18.2, 15.8, 14.1, 8.8.

ESI-MS m/z: Calcd. for C$_{36}$H$_{47}$N$_5$O$_9$: 693.34. Found (M+H)$^+$: 694.3.

Example 18

Compound Int-18

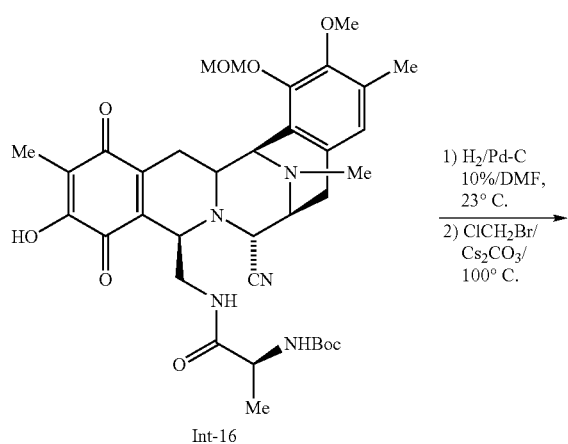

Int-16

1) H$_2$/Pd-C 10%/DMF, 23° C.
2) ClCH$_2$Br/ Cs$_2$CO$_3$/ 100° C.

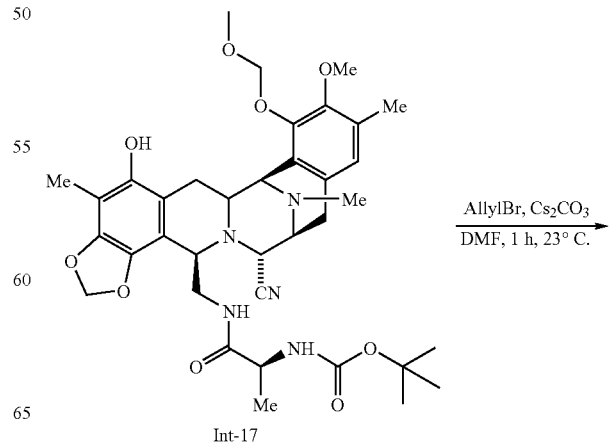

Int-17

AllylBr, Cs$_2$CO$_3$
DMF, 1 h, 23° C.

119

-continued

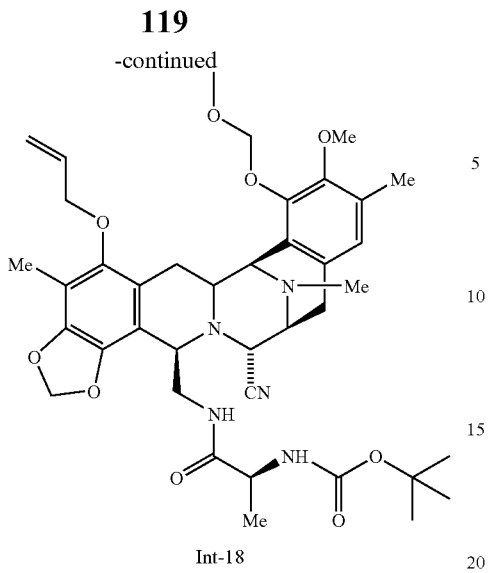

Int-18

To a flask containing a solution of Int-17 (1.83 g, 2.65 ml) in DMF (13 ml), Cs$_2$CO$_3$ (2.6 g, 7.97 ml), and allyl bromide (1.15 ml, 13.28 ml) were added at 0° C. The resulting mixture was stirred at 23° C. for 1 h. The reaction was filtered through a pad of celite and washed with CH$_2$Cl$_2$. The organic layer was dried and concentrated (sodium sulphate). The residue was purified by flash column chromatography (SiO$_2$, CHCl$_3$: ethyl acetate 1:4) to afford Int-18 (1.08 mg, 56%) as a white solid.

Rf: 0.36 (CHCl$_3$:ethyl acetate 1:3).

$^1$H NMR (300 MHz, CDCl$_3$): δ 6.70 (s, 1H), 6.27-6.02 (m, 1H), 5.94 (s, 1H), 5.83 (s, 1H), 5.37 (dd, J=1.01 Hz, J$_2$=16.8 Hz, 1H), 5.40 (bs, 1H), 5.25 (dd, J=1.0 Hz, J$_2$=10.5 Hz, 1H), 5.10 (s, 2H), 4.91 (bs, 1H), 4.25-4.22 (m, 1H), 4.21 (d, J=2.4 Hz, 1H), 4.14-4.10 (m, 1H), 4.08 (d, J=2.4 Hz, 1H), 4.00 (bs, 1H), 3.70 (s, 3H), 3.59 (s, 3H), 3.56-3.35 (m, 2H), 3.26-3.20 (m, 2H), 3.05-2.96 (dd, J$_1$=8.1 Hz, J$_2$=18 Hz, 1H), 2.63 (d, J=18 Hz, 1H), 2.30 (s, 3H), 2.21 (s, 3H), 2.09 (s, 3H), 1.91-1.80 (m, 1H), 1.24 (s, 9H), 0.94 (d, J=6.6 Hz, 3H)

$^{13}$C NMR (75 MHz, CDCl$_3$): δ 172.0, 154.8, 148.8, 148.6, 148.4, 144.4, 138.8, 133.7, 130.9, 130.3, 125.1, 124.0, 120.9, 117.8, 117.4, 112.8, 112.6, 101.1, 99.2, 73.9, 59.7, 59.3, 57.7, 56.9, 56.8, 56.2, 55.2, 40.1, 34.6, 31.5, 28.1, 26.4, 25.1, 22.6, 18.5, 15.7, 14.0, 9.2.

ESI-MS m/z: Calcd. for C$_{39}$H$_{51}$N$_5$O$_9$: 733.4. Found (M+H)$^+$: 734.4.

Example 19

Compound Int-19

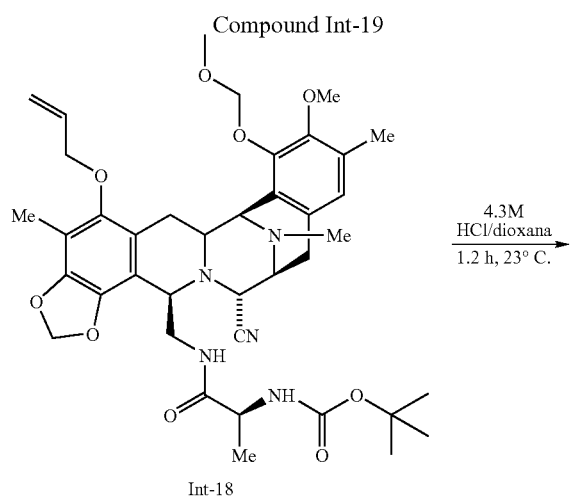

120

-continued

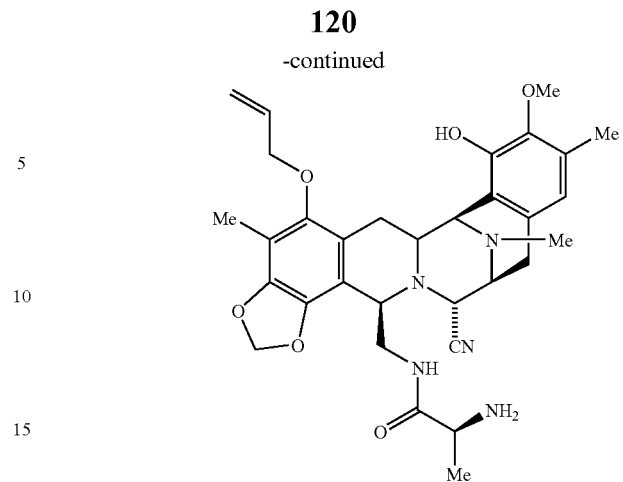

Int-19

To a solution of Int-18 (0.1 g, 0.137 ml) in dioxane (2 ml), 4.2M HCl/dioxane (1.46 ml) was added and the mixture was stirred for 1.2 h at 23° C. The reaction was quenched at 0° C. with sat. Aqueous sodium bicarbonate (60 ml) and extracted with ethyl acetate (2×70 ml). The organic layers were dried (sodium sulphate) and concentrated in vacuo to afford Int-19 (267 mg, 95%) as a white solid that was used in subsequent reactions with no further purification.

Rf: 0.17 (ethyl acetate:methanol 10:1, SiO$_2$)

$^1$H NMR (300 MHz, CDCl$_3$): δ 6.49 (s, 1H), 6.12-6.00 (m, 1H), 5.94 (s, 1H), 5.86 (s, 1H), 5.34 (dd, J=1.0 Hz, J=17.4 Hz, 1H), 5.25 (dd, J=1.0 Hz, J=10.2 Hz, 1H), 4.18-3.76 (m, 5H), 3.74 (s, 3H), 3.71-3.59 (m, 1H), 3.36-3.20 (m, 4H), 3.01-2.90 (m, 1H), 2.60 (d, J=18.0 Hz, 1H), 2.29 (s, 3H), 2.24 (s, 3H), 2.11 (s, 3H), 1.97-1.86 (m, 1H), 0.93 (d, J=8.7 Hz, 3H)

$^{13}$C NMR (75 MHz, CDCl$_3$): δ 175.5, 148.4, 146.7, 144.4, 142.4, 138.9, 133.7, 131.3, 128.3, 120.8, 117.9, 117.4, 113.8, 112.4, 101.1, 74.2, 60.5, 59.1, 56.5, 56.1, 56.3, 56.0, 55.0, 50.5, 41.6, 39.5, 29.5, 26.4, 24.9, 21.1, 15.5, 9.33.

ESI-MS m/z: Calcd. for C$_{32}$H$_{39}$N$_5$O$_6$: 589. Found (M+H)$^+$: 590.

Example 20

Compound Int-20

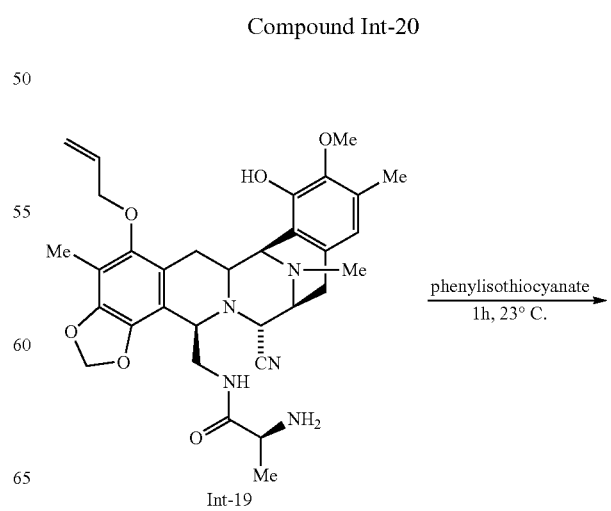

121
-continued

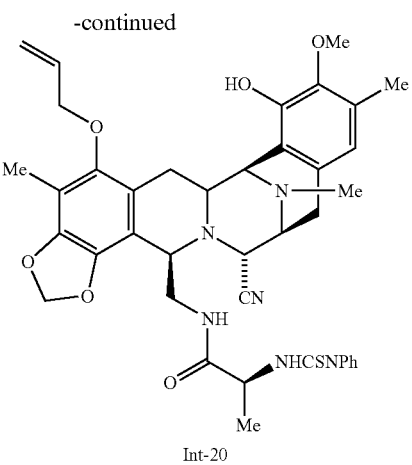
Int-20

To a solution of Int-19 (250 mg, 0.42 ml) in CH$_2$Cl$_2$ (1.5 ml), phenyl isothiocyanate (0.3 ml, 2.51 ml) was added and the mixture was stirred at 23° C. for 1 h. The reaction was concentrated in vacuo and the residue was purified by flash column chromatography (SiO$_2$, gradient Hexane to 5:1 hexane:ethyl acetate) to afford Int-20 (270 mg, 87%) as a white solid.

Rf: 0.56 (CHCl$_3$:ethyl acetate 1:4).

$^1$H NMR (300 MHz, CDCl$_3$): δ 8.00 (bs, 1H), 7.45-6.97 (m, 4H), 6.10 (s, 1H), 6.08-6.00 (m, 1H), 5.92 (s, 1H), 5.89 (s, 1H), 5.82 (s, 1H), 5.40 (dd, J=1.5 Hz, J=17.1 Hz, 1H), 3.38 (bs, 1H), 5.23 (dd, J=1.5 Hz, J=10.5 Hz, 1H), 4.42-4.36 (m, 1H), 4.19-4.03 (m, 5H), 3.71 (s, 3H), 3.68-3.17 (m, 4H), 2.90 (dd, J=7.8 Hz, J=18.3 Hz, 1H), 2.57 (d, J=18.3 Hz, 1H), 2.25 (s, 3H), 2.12 (s, 3H), 2.10 (s, 3H), 1.90 (dd, J=12.3 Hz, J=16.5 Hz, 1H), 0.81 (d, J=6.9 Hz, 3H).

$^{13}$C N (75 MHz, CDCl$_3$): δ 178.4, 171.6, 148.6, 146.8, 144.3, 142.7, 138.7, 136.2, 133.6, 130.7, 129.8, 126.6, 124.2, 124.1, 120.9, 120.5, 117.7, 117.4, 116.7, 112.6, 112.5, 101.0, 74.0, 60.6, 59.0, 57.0, 56.2, 56.1, 55.0, 53.3, 41.4, 39.7, 26.3, 24.8, 18.3, 15.5, 9.2.

ESI-MS m/z: Calcd. for C$_{39}$H$_{44}$N$_6$O$_6$S: 724.8 Found (M+H)$^+$: 725.3.

Example 21

Compound Int-21

122
-continued

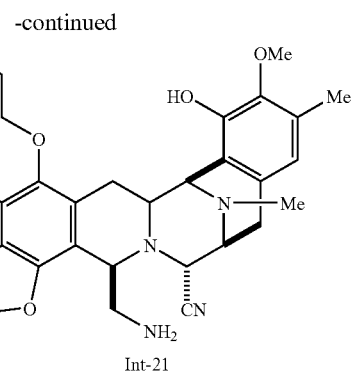
Int-21

To a solution of Int-20 (270 mg, 0.37 ml) in dioxane (1 ml), 4.2N HCl/dioxane (3.5 ml) was added and the reaction was stirred at 23° C. for 30 min. Then, ethyl acetate (20 ml) and H$_2$O (20 ml) were added and the organic layer was decanted. The aqueous phase was basified with saturated aqueous sodium bicarbonate (60 ml) (pH=8) at 0° C. and then, extracted with CH$_2$Cl$_2$ (2×50 ml). The combined organic extracts were dried (sodium sulphate), and concentrated in vacuo. The residue was purified by flash column chromatography (SiO$_2$, ethyl acetate:methanol 5:1) to afford compound Int-21 (158 mg, 82%) as a white solid.

Rf: 0.3 (ethyl acetate:methanol 1:1).

$^1$H NMR (300 MHz, CDCl$_3$): δ 6.45 (s, 1H), 6.12-6.03 (m, 1H), 5.91 (s, 1H), 5.85 (s, 1H), 5.38 (dd, J$_1$=1.2 Hz, J$_2$=17.1 Hz, 1H), 5.24 (dd, J$_1$=1.2 Hz, J$_2$=10.5 Hz, 1H), 4.23-4.09 (m, 4H), 3.98 (d, J=2.1 Hz, 1H), 3.90 (bs, 1H), 3.72 (s, 3H), 3.36-3.02 (m, 5H), 2.72-2.71 (m, 2H), 2.48 (d, J=18.0 Hz, 1H), 2.33 (s, 3H), 2.22 (s, 3H), 2.11 (s, 3H), 1.85 (dd, J$_1$=11.7 Hz, J$_2$=15.6 Hz, 1H)).

$^{13}$C NMR (75 MHz, CDCl$_3$): δ 148.4, 146.7, 144.4, 142.8, 138.8, 133.8, 130.5, 128.8, 121.5, 120.8, 118.0, 117.5, 116.9, 113.6, 112.2, 101.1, 74.3, 60.7, 59.9, 58.8, 56.6, 56.5, 55.3, 44.2, 41.8, 29.7, 26.5, 25.7, 15.7, 9.4.

ESI-MS m/z: Calcd for C$_{29}$H$_{34}$N$_4$O$_5$: 518.3. Found (M+H)$^+$: 519.2.

Example 22

Compound Int-22

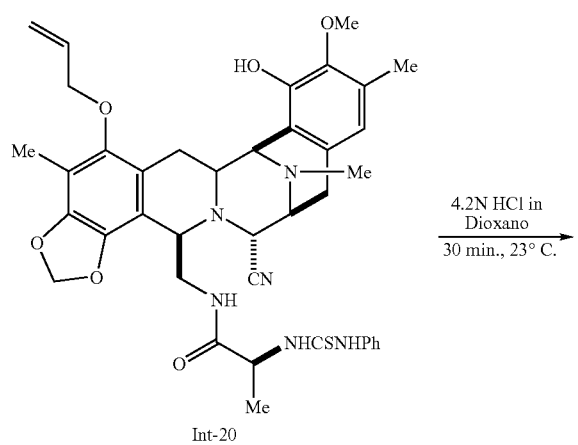
Int-20

4.2N HCl in Dioxano
30 min., 23° C.

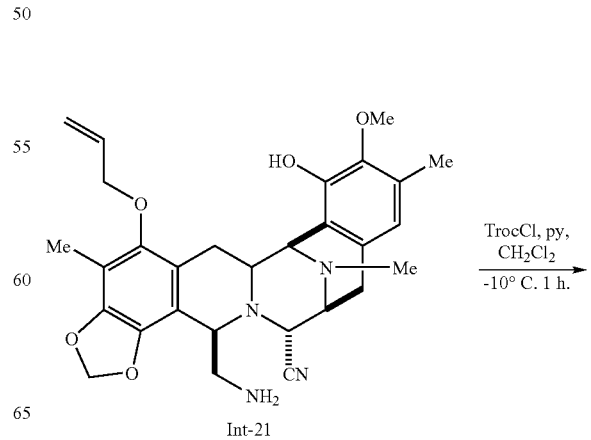
Int-21

TrocCl, py, CH$_2$Cl$_2$
-10° C. 1 h.

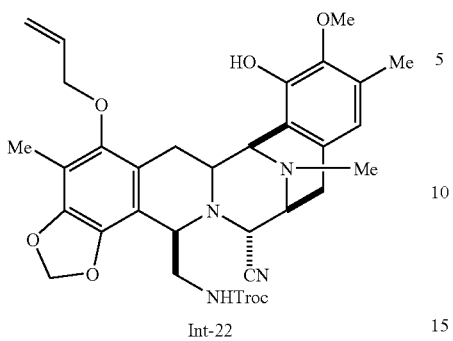

Int-22

To a solution of Int-21 (0.64 g, 1.22 ml) in CH$_2$Cl$_2$ (6.13 ml), pyridine (0.104 ml, 1.28 ml) and 2,2,2-trichloroethyl chloroformate (0.177 ml, 1.28 ml) were added at −10° C. The mixture was stirred at this temperature for 1 h and then, the reaction was quenched by addition of 0.1N HCl (10 ml) and extracted with CH$_2$Cl$_2$ (2×10 ml). The organic layer was dried over sodium sulphate and concentrated in vacuo. The residue was purified by flash column chromatography (SiO$_2$, (hexane:ethyl acetate 1:2) to afford Int-22 (0.84 g, 98%) as a white foam solid.

Rf: 0.57 (ethyl acetate:methanol 5:1).

$^1$H NMR (300 MHz, CDCl$_3$): δ 6.50 (s, 1H), 6.10-6.00 (m, 1H), 6.94 (d, J=1.5 Hz, 1H), 5.87 (d, J=1.5 Hz, 1H), 5.73 (bs, 1H), 5.37 (dq, J$_1$=1.5 Hz, J$_2$=17.1 Hz, 1H), 5.26 (dq, J$_1$=1.8 Hz, J$_2$=10.2 Hz, 1H), 4.60 (d, J=12 Hz, 1H), 4.22-4.10 (m, 4H), 4.19 (d, J=12 Hz, 1H), 4.02 (m, 2H), 3.75 (s, 3H), 3.37-3.18 (m, 5H), 3.04 (dd, J$_1$=8.1 Hz, J$_2$=18 Hz, 1H), 2.63 (d, J=18 Hz, 1H), 2.31 (s, 3H), 2.26 (s, 3H), 2.11 (s, 3H), 1.85 (dd, J$_1$=12.3 Hz, J$_2$=15.9 Hz, 1H).

$^{13}$C NMR (75 MHz, CDCl$_3$) δ 154.3, 148.5, 146.7, 144.5, 142.8, 139.0, 133.8, 130.7, 128.7, 121.3, 120.8, 117.8, 117.7, 116.8, 112.7, 101.2, 77.2, 74.3, 60.7, 59.9, 57.0, 56.4, 55.3, 43.3, 41.7, 31.6, 26.4, 25.3, 22.6, 15.9, 14.1, 9.4.

ESI-MS m/z: Calcd. for C$_{32}$H$_{35}$Cl$_3$N$_4$O$_7$: 694.17. Found (M+H)$^+$: 695.2.

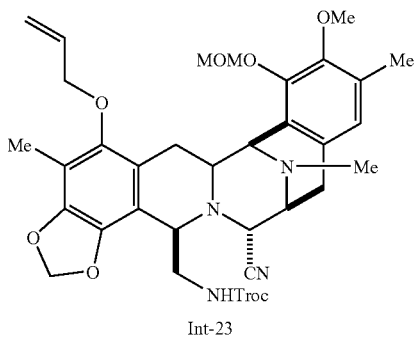

Int-23

To a solution of Int-22 (0.32 g, 0.46 ml) in CH$_3$CN (2.33 ml), diisopropylethylamine (1.62 ml, 9.34 ml), bromomethyl methyl ether (0.57 ml, 7.0 ml) and dimethylaminopyridine (6 mg, 0.046 ml) were added at 0° C. The mixture was heated at 30° C. for 10 h. Then, the reaction was diluted with dichloromethane (30 ml) and poured in an aqueous solution of HC at pH=5 (10 ml). The organic layer was dried over sodium sulphate and the solvent was eliminated under reduced pressure to give a residue which was purified by flash column chromatography (SiO$_2$, hexane:ethyl acetate 2:1) to afford Int-23 (0.304 g, 88%) as a white foam solid.

Rf: 0.62 (hexane:ethyl acetate 1:3).

$^1$H NMR (300 MHz, CDCl$_3$): δ 6.73 (s, 1H), 6.10 (m, 1H), 5.94 (d, J=1.5 Hz, 1H), 5.88 (d, J=1.5 Hz, 1H), 5.39 (dq, J$_1$=1.5 Hz, J$_2$=17.1 Hz, 1H), 5.26 (dq, J$_1$=1.8 Hz, J$_2$=10.2 Hz, 1H), 5.12 (s, 2H), 4.61 (d, J=12 Hz, 1H), 4.55 (t, J=6.6 Hz, 1H), 4.25 (d, J=12 Hz, 1H), 4.22-4.11 (m, 4H), 4.03 (m, 2H), 3.72 (s, 3H), 3.58 (s, 3H), 3.38-3.21 (m, 5H), 3.05 (dd, J$_1$=8.1 Hz, J$_2$=18 Hz, 1H), 2.65 (d, J=18 Hz, 1H), 2.32 (s, 3H), 2.23 (s, 3H), 2.12 (s, 3H), 1.79 (dd, J$_1$=12.3 Hz, J$_2$=15.9 Hz, 1H);

$^{13}$C NMR (75 MHz, CDCl$_3$) δ 154.3, 148.6, 148.4, 144.5, 139.0, 133.6, 130.6, 130.1, 125.07, 124.7, 124.0, 121.1, 117.7, 112.6, 101.2, 99.2, 77.2, 74.4, 74.1, 59.8, 59.8, 57.7, 57.0, 56.8, 56.68, 55.3, 43.2, 41.5, 26.4, 25.2, 15.9, 9.3.

ESI-MS m/z: Calcd. for C$_{34}$H$_{39}$Cl$_3$N$_4$O$_8$: 738.20. Found (M+H)$^+$: 739.0.

Example 23

Compound Int-23

Example 24

Compound Int-24

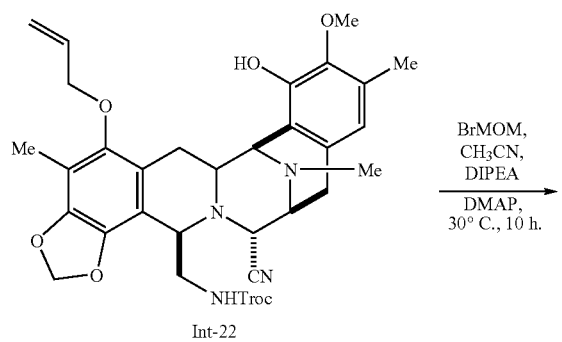

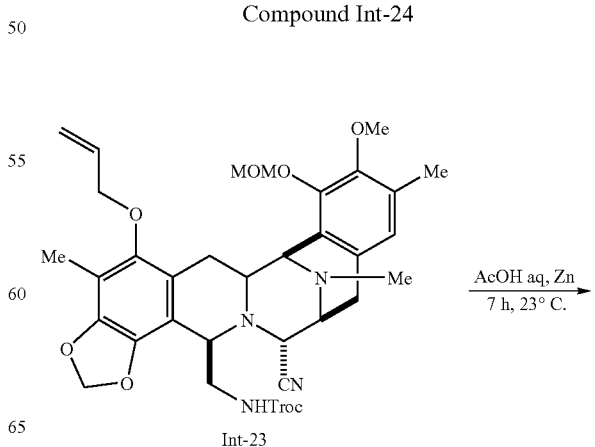

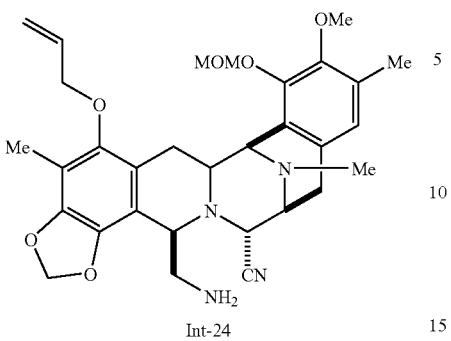

Int-24

To a suspension of Int-23 (0.304 g, 0.41 ml) in 90% aqueous acetic acid (4 ml), powder zinc (0.2 g, 6.17 ml) was added and the reaction was stirred for 7 hour at 23° C. The mixture was filtered through a pad of celite which was washed with $CH_2Cl_2$. The organic layer was washed with an aqueous sat. solution of sodium bicarbonate (pH=9) (15 ml) and dried over sodium sulphate. The solvent was eliminated under reduced pressure to give Int-24 (0.191 g, 83%) as a white solid.

Rf: 0.3 (ethyl acetate:methanol 5:1).

$^1$H NMR (300 MHz, $CDCl_3$): δ 6.68 (s, 1H), 6.09 (m, 1H), 5.90 (d, J=1.5 Hz, 1H), 5.83 (d, J=1.5 Hz, 1H), 5.39 (dq, $J_1$=1.5 Hz, $J_2$=17.1 Hz, 1H), 5.25 (dq, $J_1$=1.5 Hz, $J_2$=10.2 Hz, 1H), 5.10 (s, 2H), 4.22-4.09 (m, 3H), 3.98 (d, J=2.4 Hz, 1H), 3.89 (m, 1H), 3.69 (s, 3H), 3.57 (s, 3H), 3.37-3.17 (m, 3H), 3.07 (dd, $J_1$=8.1 Hz, $J_2$=18 Hz, 1H), 2.71 (m, 2H), 2.48 (d, J=18 Hz, 1H), 2.33 (s, 3H), 2.19 (s, 3H), 2.17 (s, 3H), 1.80 (dd, $J_1$=12.3 Hz, $J_2$=15.9 Hz, 1H)

$^{13}$C NMR (75 MHz, $CDCl_3$): δ 148.5, 148.2, 144.3, 138.7, 133.7, 130.7, 129.9, 125.0, 123.9, 121.3, 117.9, 117.5, 113.6, 112.0, 101.0, 99.2, 74.0, 59.8, 59.7, 58.8, 57.6, 57.0, 56.2, 55.2, 44.2, 41.5, 31.5, 26.4, 25.6, 22.5, 16.7, 14.0, 9.2.

ESI-MS m/z: Calcd. for $C_{31}H_{38}N_4O_6$: 562.66. Found $(M+H)^+$: 563.1.

Example 25

Compound Int-25

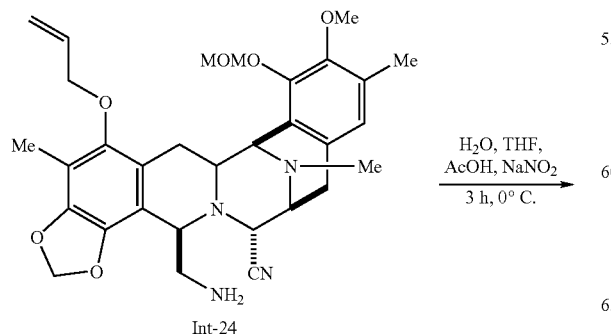

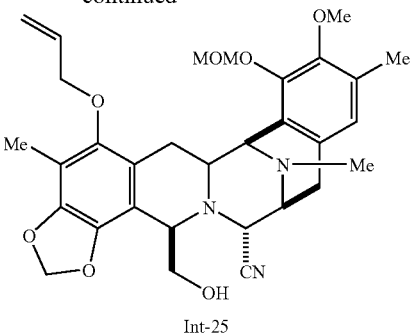

Int-25

To a solution of Int-24 (20 mg, 0.035 ml), in $H_2O$ (0.7 ml) and THF (0.7 ml), $NaNO_2$ (12 mg, 0.17 ml) and 90% aqueous AcOH (0.06 ml) were added at 0° C. and the mixture was stirred at 0° C. for 3 h. After dilution with $CH_2Cl_2$ (5 ml), the organic layer was washed with water (1 ml), dried over sodium sulphate and concentrated in vacuo. The residue was purified by flash column chromatography ($SiO_2$, hexane: ethyl acetate 2:1) to afford Int-25 (9.8 mg, 50%) as a white solid.

Rf: 0.34 (hexane:ethyl acetate 1:1).

$^1$H NMR (300 MHz, $CDCl_3$): δ 6.71 (s, 1H), 6.11 (m, 1H), 5.92 (d, J=1.5 Hz, 1H), 5.87 (d, J=1.5 Hz, 1H), 5.42 (dq, $J_1$=1.5 Hz, $J_2$=17.1 Hz, 1H), 5.28 (dq, $J_1$=1.5 Hz, $J_2$=10.2 Hz, 1H), 5.12 (s, 2H), 4.26-4.09 (m, 3H), 4.05 (d, J=2.4 Hz, 1H), 3.97 (t, J=3.0 Hz, 1H), 3.70 (s, 3H), 3.67-3.32 (m, 4H), 3.58 (s, 3H), 3.24 (dd, $J_1$=2.7 Hz, $J_2$=15.9 Hz, 1H), 3.12 (dd, $J_1$=8.1 Hz, $J_2$=18.0 Hz, 1H), 2.51 (d, J=18 Hz, 1H), 2.36 (s, 3H), 2.21 (s, 3H), 2.12 (s, 3H), 1.83 (dd, $J_1$=12.3 Hz, $J_2$=15.9 Hz, 1H)

$^{13}$C NMR (75 MHz, $CDCl_3$) δ 148.7, 148.4, 138.9, 133.7, 131.1, 129.4, 125.1, 123.9, 120.7, 117.6, 117.5, 113.2, 112.3, 101.1, 99.2, 74.0, 63.2, 59.8, 59.7, 57.9, 57.7, 57.0, 56.5, 55.2, 41.6, 29.6, 26.1, 25.6, 22.6, 15.7, 9.2.

ESI-MS m/z: Calcd. for $C_{31}H_{37}N_3O_7$: 563.64. Found $(M+H)^+$: 564.1.

Example 29

Compound Int-29

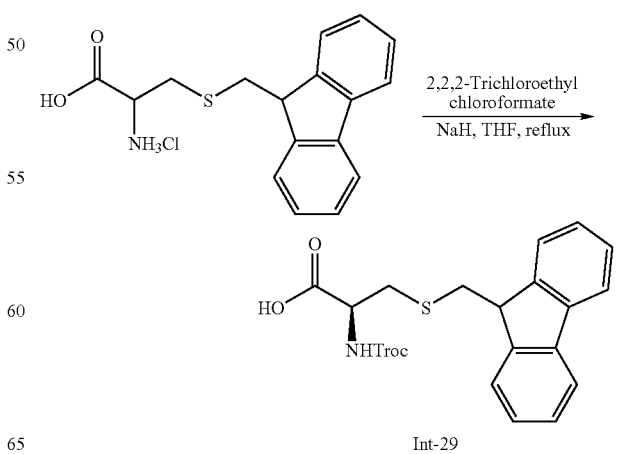

Int-29

The starting material (2.0 g, 5.90 ml) was added to a suspension of sodium hydride (354 mg, 8.86 ml) in THF (40 ml) at 23° C., following the suspension was treated with allyl chloroformate (1.135 ml, 8.25 ml) at 23° C. and then refluxed for 3 hours. The suspension was cooled, filtered off, the solid washed with ethyl acetate (100 ml), and the filtrate was concentrated. The oil crude was ground with hexane (100 ml) and kept at 4° C. overnight. After, the solvent was decanted and the light yellow slurry was treated with $CH_2Cl_2$ (20 ml), and precipitated with hexane (100 ml). After 10 minutes, the solvent was decanted again. The operation was repeated until appearing a white solid. The white solid was filtered off and dried to afford compound Int-29 (1.80 g, 65%) as a white solid.

$^1$H-NMR (300 MHz, $CDCl_3$): δ 7.74 (d, J=7.5 Hz, 2H), 7.62 (d, J=6.9 Hz, 2H), 7.33 (t, J=7.5 Hz, 2H), 7.30 (t, J=6.3 Hz, 2H), 5.71 (d, J=7.8 Hz, 1H), 4.73 (d, J=7.8 Hz, 2H), 4.59 (m, 1H), 4.11 (t, J=6.0 Hz, 1H), 3.17 (dd, J=6.0 Hz, J=2.7 Hz, 2H), 3.20 (dd, J=5.4 Hz, J=2.1 Hz, 2H).

$^{13}$C-NMR (75 MHz, $CDCl_3$): δ 173.6, 152.7, 144.0, 139.7, 137.8, 126.0, 125.6, 123.4, 118.3, 73.4, 52.4, 45.5, 35.8, 33.7.

ESI-MS m/z: Calcd. for $C_{20}H_{18}Cl_3NO_4S$: 474.8. Found $(M+Na)^+$: 497.8

Example 30

Compound Int-30

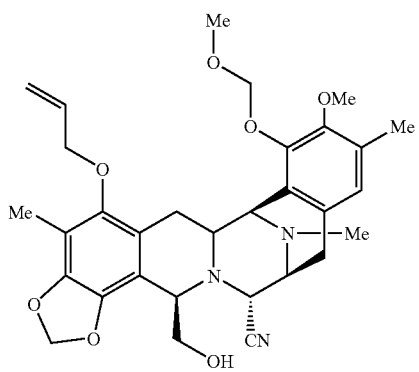

A mixture of compound Int-25 (585 mg, 1.03 ml) and compound Int-29 (1.47 mg, 3.11 ml) were azeotroped with anhydrous toluene (3×10 ml). To a solution of Int-25 and Int-29 in anhydrous $CH_2Cl_2$ (40 ml) was added DMAP (633 mg, 5.18 ml) and EDC.HCl (994 mg, 5.18 ml) at 23° C. The reaction mixture was stirred at 23° C. for 3 hours. The mixture was partitioned with saturated aqueous solution of sodium bicarbonate (50 ml) and the layers were separated. The aqueous layer was washed with $CH_2Cl_2$ (50 ml). The combined organic layers were dried over sodium sulphate, filtered and concentrated. The crude was purified by flash column chromatography (ethyl acetate/hexane 1:3) to obtain Int-30 (1.00 g, 95%) as a pale cream yellow solid.

$^1$H-NMR (300 MHz, $CDCl_3$): δ 7.72 (m, 2H), 7.52 (m, 2H), 7.38 (m, 2H), 7.28 (m, 2H), 6.65 (s, 1H), 6.03 (m, 1H), 5.92 (d, J=1.5 Hz, 1H), 5.79 (d, J=1.5 Hz, 1H), 5.39 (m, 1H), 5.29 (dq, J=10.3 Hz, J=1.5 Hz, 1H), 5.10 (s, 2H), 4.73 (d, J=11.9 Hz, 1H), 4.66 (d, J=11.9 Hz, 1H), 4.53 (m, 1H), 4.36-3.96 (m, 9H), 3.89 (t, J=6.4 Hz, 1H), 3.71 (s, 3H), 3.55 (s, 3H), 3.33 (m, 1H), 3.20 (m, 2H), 2.94 (m, 3H), 2.59 (m, 1H), 2.29 (s, 3H), 2.23 (s, 3H), 2.02 (s, 3H), 1.83 (dd, J=16.0 Hz, J=11.9 Hz, 1H).

$^{13}$C-NMR (75 MHz, $CDCl_3$): δ 169.7, 154.0, 148.8, 148.4, 145.7, 144.5, 140.9, 139.0, 133.7, 130.9, 130.6, 127.6, 127.0, 124.8, 124.6, 124.1, 120.8, 119.9, 118.2, 117.7, 117.3, 112.7, 112.1, 101.3, 99.2, 74.7, 73.9, 64.4, 59.8, 57.7, 57.0, 56.8, 55.4, 53.3, 46.7, 41.4, 36.5, 34.7, 31.5, 26.4, 24.9, 22.6, 15.7, 14.0, 9.1.

ESI-MS m/z: Calcd. for $C_{51}H_{53}Cl_3N_4O_{10}S$: 1020.4. Found $(M+H)^+$: 1021.2

Example 31

Compound Int-31

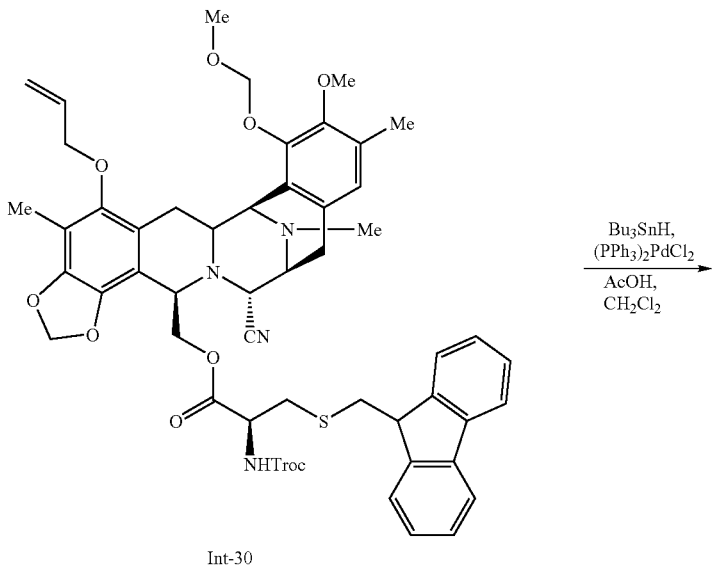

-continued

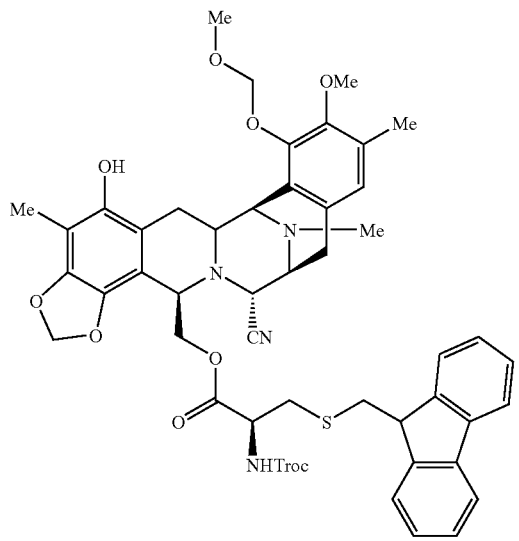

Int-31

To a solution of Int-30 (845 mg, 0.82 ml), acetic acid (500 mg, 8.28 ml) and (PPh$_3$)$_2$PdCl$_2$ (29 mg, 0.04 ml) in anhydrous CH$_2$Cl$_2$ 20 ml at 23° C. was added, dropwise, Bu$_3$SnH (650 mg, 2.23 ml). The reaction mixture was stirred at this temperature for 15 min., bubbling was. The crude was quenched with water (50 ml) and extracted with CH$_2$Cl$_2$ (3×50 ml). The organic layers were dried over sodium sulphate, filtered and concentrated. The crude was purified by flash column chromatography (ethyl acetate/hexane in gradient from 1:5 to 1:3) to obtain compound Int-31 (730 mg, 90%) as a pale cream yellow solid.

$^1$H-NMR (300 MHz, CDCl$_3$): δ 7.72 (m, 2H), 7.56 (m, 2H), 7.37 (m, 2H), 7.30 (m, 2H), 6.65 (s, 1H), 5.89 (s, 1H), 5.77 (s, 1H), 5.74 (s, 1H), 5.36 (d, J=5.9 Hz, 1H), 5.32 (d, J=5.9 Hz, 1H), 5.20 (d, J=9.0, 1H), 4.75 (d, J=12.0 Hz, 1H), 4.73 (m, 1H), 4.48 (d, J=11.9 Hz, 1H), 4.08 (m, 4H), 3.89 (m, 1H), 3.86, (t, J=6.2 Hz, 1H), 3.70 (s, 3H), 3.69 (s, 3H), 3.38 (m, 1H), 3.25 (m, 1H), 3.02-2.89 (m, 4H), 2.67 (s, 1H), 2.61 (s, 1H), 2.51 (dd, J=14.3 Hz, J=4.5 Hz, 1H), 2.29 (s, 3H), 2.23 (s, 3H), 1.95 (s, 3H), 1.83 (m, 1H).

$^{13}$C-NMR (75 MHz, CDCl$_3$): δ 168.2, 152.5, 148.1, 146.2, 144.4, 144.3, 143.3, 139.6, 134.6, 129.7, 129.6, 126.2, 125.6, 123.4, 123.3, 121.6, 118.5, 116.3, 110.7, 110.2, 105.1, 99.4, 98.5, 75.2, 73.3, 61.7, 58.4, 57.9, 56.3, 56.1, 55.1, 54.7, 53.9, 51.9, 45.2, 40.1, 35.6, 33.3, 24.8, 23.3, 14.5, 7.3.

ESI-MS m/z: Calcd. for C$_{48}$H$_{49}$Cl$_3$N$_4$O$_{10}$S: 980.3. Found (M+H)$^+$: 981.2

Example 32

Compound Int-32

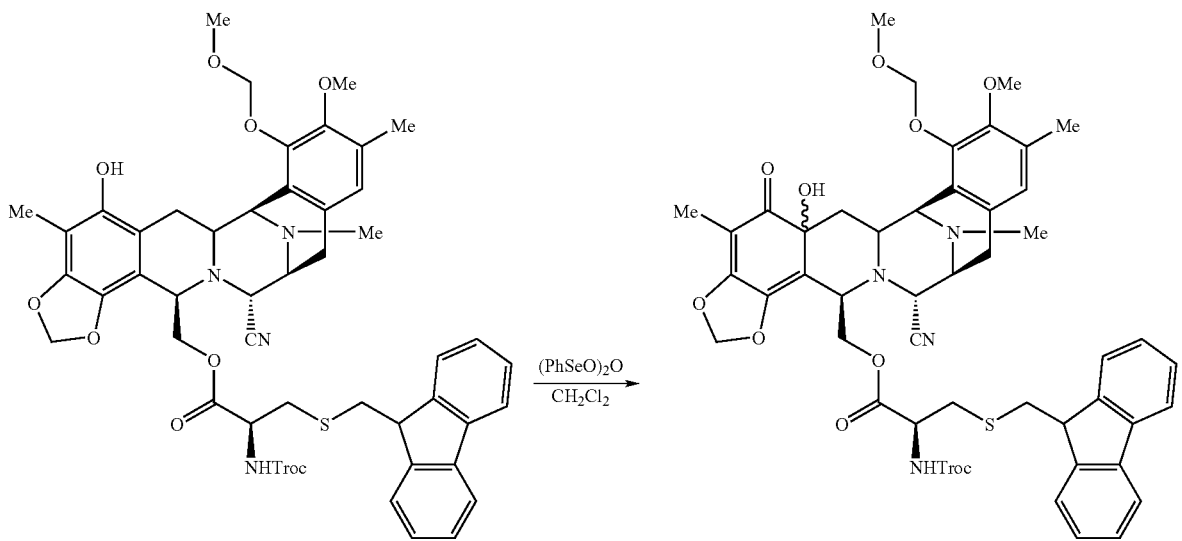

To a solution of Int-31 (310 mg, 0.32 ml), in anhydrous CH$_2$Cl$_2$ (15 ml) at −10° C. was added a solution of benzeneseleninic anhydride 70% (165 mg, 0.32 ml), in anhydrous CH$_2$Cl$_2$ (7 ml), via cannula, keeping the temperature at −10° C. The reaction mixture was stirred at −10° C. for 5 min. A saturated solution of sodium bicarbonate (30 ml) was added at this temperature. The aqueous layer was washed with more CH$_2$Cl$_2$ (40 ml). The organic layers were dried over sodium sulphate, filtered and concentrated. The crude was purified by flash column chromatography (ethyl acetate/hexane in gradient from 1:5 to 1:1) to obtain Int-32 (287 mg, 91%, HPLC: 91.3%) as a pale cream yellow solid and as a mixture of two isomers (65:35) which were used in the next step.

$^1$H-NMR (300 MHz, CDCl$_3$): δ (Mixture of isomers) 7.76 (m, 4H), 7.65 (m, 4H), 7.39 (m, 4H), 7.29 (m, 4H), 6.62 (s, 1H), 6.55 (s, 1H), 5.79-5.63 (m, 6H), 5.09 (s, 1H), 5.02 (d, J=6.0 Hz, 1H), 4.99 (d, J=6.0 Hz, 1H), 4.80-4.63 (m, 6H), 4.60 (m, 1H), 4.50 (m, 1H), 4.38 (d, J=12.8 Hz, J=7.5 Hz, 1H), 4.27 (dd, J=12.8 Hz, J=7.5 Hz, 1H), 4.16-3.90 (m, 10H), 3.84 (s, 3H), 3.62 (s, 3H), 3.50 (s, 3H), 3.49 (s, 3H), 3.33-2.83 (m, 14H), 2.45-2.18 (m, 2H), 2.21 (s, 6H), 2.17 (s, 6H), 1.77 (s, 6H), 1.67 (m, 2H).

$^{13}$C-NMR (75 MHz, CDCl$_3$): δ (Mixture of isomers) 168.6, 168.4, 158.6, 154.8, 152.8, 152.5, 147.3, 147.2, 146.8, 144.1, 144.0, 140.8, 139.7, 137.1, 129.8, 129.3, 128.4, 128.7, 126.5, 125.5, 123.7, 123.6, 123.5, 123.4, 122.2, 121.3, 118.3, 115.8, 115.5, 110.2, 106.9, 103.5, 103.2, 100.1, 99.6, 97.9, 97.7, 93.8, 73.4, 70.9, 69.2, 64.9, 62.5, 59.3, 58.9, 58.4, 56.7, 56.3, 56.2, 55.4, 55.2, 55.1, 54.9, 54.7, 54.3, 54.1, 53.8, 52.8, 45.5, 40.5, 40.0, 39.8, 35.8, 35.5, 33.9, 33.7, 30.1, 28.8, 24.2, 24.1, 21.2, 14.5, 14.4, 12.7, 6.0, 5.7.

ESI-MS m/z: Calcd. for C$_{48}$H$_{49}$Cl$_3$N$_4$O$_{11}$S: 996.3. Found (M+H)$^+$: 997.2

Example 33

Compound Int-33

The reaction flask was flamed twice, purged vacuum/Argon several times and kept under Argon atmosphere for the reaction. To a solution of DMSO (39.1 ml, 0.55 ml, 5 equivalents.) in anhydrous CH$_2$Cl$_2$ (4.5 ml) was dropwise added triflic anhydride (37.3 ml, 0.22 ml, 2 equivalents.) at −78° C. The reaction mixture was stirred at −78° C. for 20 minutes, then a solution of Int-32 (110 mg, 0.11 ml, HPLC: 91.3%) in anhydrous CH$_2$Cl$_2$ (1 ml, for the main addition and 0.5 ml for wash) at −78° C. was added, via cannula. During the addition the temperature was kept at −78° C. in both flasks and the colour changed from yellow to brown. The reaction mixture was stirred at 40° C. for 35 minutes. During this period of time the solution was turned from yellow to dark green. After this time, $^i$Pr$_2$NEt (153 ml, 0.88 ml, 8 equivalents.) was dropwise added and the reaction mixture was kept at 0° C. for 45 minutes, the colour of the solution turned to brown during this time. Then t-butanol (41.6 ml, 0.44 ml, 4 equivalents.) and 2-$^t$Butyl-1,1,3,3-tetramethylguanidine (132.8 ml, 0.77 ml, 7 equivalents.) were dropwise added and the reaction mixture was stirred at 23° C. for 40 minutes. After this time, acetic anhydride (104.3 ml, 1.10 ml, 10 equivalents.) was dropwise added and the reaction mixture was kept at 23° C. for 1 hour more. Then the reaction mixture was diluted with CH$_2$Cl$_2$ (20 ml) and washed with aqueous saturated solution of NH$_4$Cl (50 ml), sodium bicarbonate (50 ml), and sodium chloride (50 ml). The combined organic layers were dried over sodium sulphate, filtered and concentrated. The residue was purified by flash column chromatography (eluent: ethyl acetate/hexane gradient from 1:3 to 1:2) to afford compound Int-33 (54 mg, 58%) as a pale yellow solid.

$^1$H-NMR (300 MHz, CDCl$_3$): δ 6.85 (s, 1H), 6.09 (s, 1H), 5.99 (s, 1H), 5.20 (d, J=5.8 Hz, 1H), 5.14 (d, J=5.3 Hz, 1H), 5.03 (m, 1H), 4.82 (d, J=12.2 Hz, 1H), 4.63 (d, J=12.0 Hz, 1H), 4.52 (m, 1H), 4.35-4.17 (m, 4H), 3.76 (s, 3H), 3.56 (s, 3H), 3.45 (m, 2H), 2.91 (m, 2H), 2.32 (s, 3H), 2.28 (s, 3H), 2.21 (s, 3H), 2.12 (m, 2H), 2.03 (s, 3H).

$^{13}$C-NMR (75 MHz, CDCl$_3$): δ 168.5, 167.2, 152.7, 148.1, 147.1, 144.5, 139.6, 139.1, 130.5, 129.0, 123.7, 123.5, 123.3,

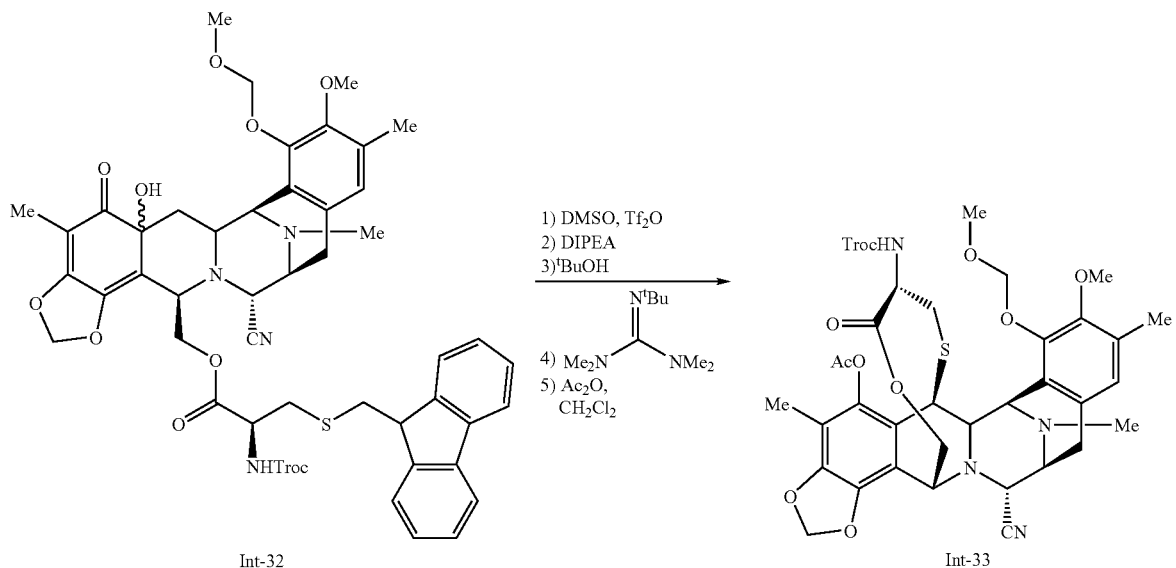

118.8, 116.5, 112.1, 100.6, 97.8, 73.3, 60.5, 59.4, 59.2, 58.3, 57.6, 57.4, 56.1, 53.3, 53.1, 40.6, 40.0, 31.0, 22.2, 18.9, 14.4, 8.1.

ESI-MS m/z: Calcd. for $C_{36}H_{39}Cl_3N_4O_{11}S$: 842.1. Found (M+H)+: 843.1

Example 34

Compound Int-34

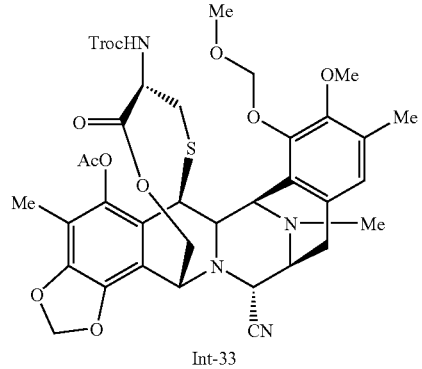

To a solution of Int-33 (12 mg, 0.014 ml) in dry dichloromethane (1.2 ml) and HPLC grade acetonitrile (1.2 ml) was added at 23° C. sodium iodide (21 mg, 0.14 ml) and freshly distilled (over calcium hydride at atmospheric pressure) trimethylsilyl chloride (15.4 mg, 0.14 ml). The reaction mixture turned to orange colour. After 15 min the solution was diluted with dichloromethane (10 ml) and was washed with a freshly aqueous saturated solution of $Na_2S_2O_4$ (3×10 ml). The organic layer was dried over sodium sulphate, filtered and concentrated. It was obtained compound Int-34 (13 mg, quantitative) as pale yellow solid which was used without further purification.

$^1$H-NMR (300 MHz, $CDCl_3$): δ 6.85 (s, 1H), 6.09 (s, 1H), 5.99 (s, 1H), 5.27 (d, J=5.8 Hz, 1H), 5.14 (d, J=5.3 Hz, 1H), 5.03 (d, J=11.9 Hz, 1H), 4.82 (d, J=12.2, 1H), 4.63 (d, J=13.0 Hz, 1H), 4.52 (m, 1H), 4.34 (m, 1H), 4.27 (bs, 1H), 4.18 (m, 2H), 3.76 (s, 3H), 3.56 (s, 3H), 3.44 (m, 1H), 3.42 (m, 1H), 2.91 (m, 2H), 2.32 (s, 3H), 2.28 (s, 3H), 2.21 (s, 3H), 2.03 (s, 3H).

ESI-MS m/z: Calcd. for $C_{34}H_{35}N_4O_{10}S$: 798.1. Found (M+H)+: 799.1

Example 35

Compound Int-35

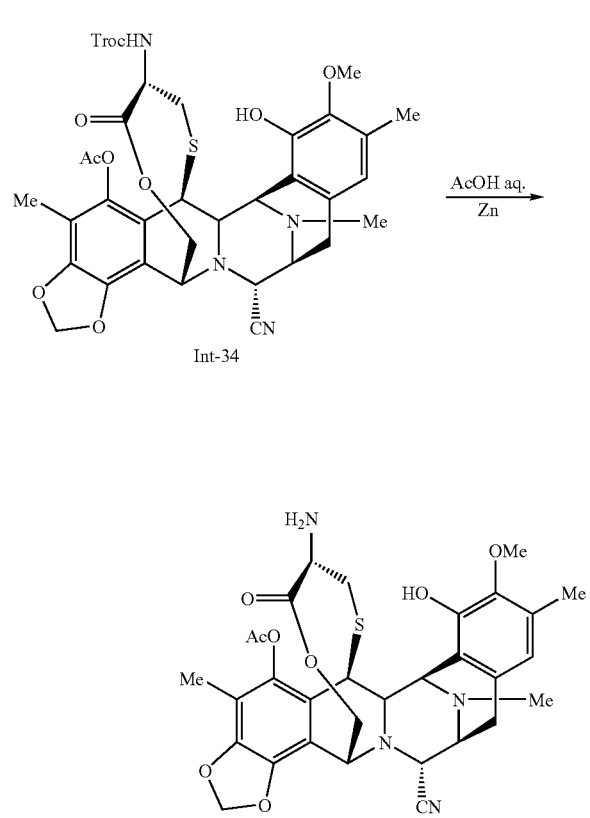

To a solution of Int-34 (13 mg, 0.016 ml) in a mixture of acetic acid/$H_2O$ (90:10, 1 ml) was added powder Zinc (5.3 mg, 0.081 ml) at 23° C. The reaction mixture was heated at 70° C. for 6 h. After this time, was cooled to 23° C., diluted with $CH_2Cl_2$ (20 ml) and washed with aqueous saturated solution of sodium bicarbonate (15 ml) and aqueous solution of $Et_3N$ (15 ml). The organic layer was dried over sodium sulphate, filtered and concentrated. The residue was purified by flash column chromatography with Silica-$NH_2$ (eluent: ethyl acetate/hexane gradient from 0:100 to 50:50) to afford compound Int-35 (6.8 mg, 77% for two steps) as a pale yellow solid.

$^1$H-NMR (300 MHz, $CDCl_3$): δ 6.51 (s, 1H), 6.03 (dd, J=1.3 Hz, J=26.5 Hz, 2H), 5.75 (bs, 1H), 5.02 (d, J=11.6 Hz, 1H), 4.52 (m, 1H), 4.25 (m, 2H), 4.18 (d, J=2.5 Hz, 1H), 4.12 (dd, J=1.9 Hz, J=11.5 Hz, 1H), 3.77 (s, 3H), 3.40 (m, 2H), 3.26 (t, J=6.4 Hz, 1H), 2.88 (m, 2H), 2.30-2.10 (m, 2H), 2.30 (s, 3H), 2.28 (s, 3H), 2.18 (s, 3H), 2.02 (s, 3H).

$^{13}$C-NMR (75 MHz, $CDCl_3$): δ 174.1, 168.4, 147.8, 145.4, 142.9, 140.8, 140.1, 131.7, 130.2, 129.1, 128.3, 120.4, 118.3, 117.9, 113.8, 111.7, 101.7, 61.2, 59.8, 59.2, 58.9, 54.4, 53.8, 54.4, 41.3, 41.5, 34.1, 23.6, 20.3, 15.5, 9.4.

ESI-MS m/z: Calcd. for $C_{31}H_{34}N_4O_8S$: 622.7. Found $(M+H)^+$: 623.2.

Example 36

Compound Int-36

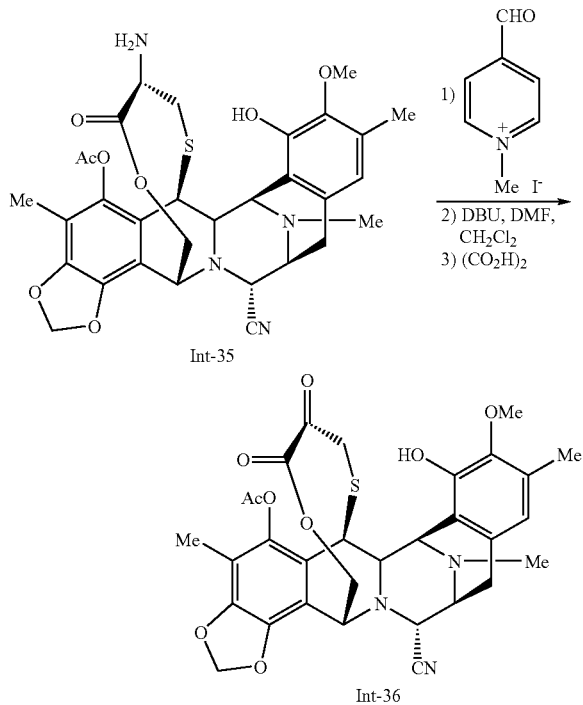

A solution of N-methylpyridine carboxaldehyde iodide (378 mg, 1.5 mmol) in anhydrous DMF (5.8 mL) was treated with anhydrous toluene (2×10 mL) to eliminate the amount of water by azeotropic removal of the toluene. A solution of 35 (134 mg, 0.21 mmol), previously treated with anhydrous toluene (2×10 mL), in anhydrous $CH_2Cl_2$ (distilled over $CaH_2$, 7.2 mL) was added, via cannula, at 23° C. to this orange solution. The reaction mixture was stirred at 23° C. for 4 hours. After this time DBU (32.2 L, 0.21 mmol) was dropwise added at 23° C. and it was stirred for 15 minutes at 23° C. A freshly aqueous saturated solution of oxalic acid (5.8 mL) was added to the reaction mixture and was stirred for 30 minutes at 23° C. Then the reaction mixture was cooled to 0° C. and $NaHCO_3$ was portionwise added followed by addition of aqueous saturated solution of $NaHCO_3$. The mixture was extracted with $Et_2O$. $K_2CO_3$ was added to the aqueous layer and it was extracted with $Et_2O$. The combined organic layers were dried over $MgSO_4$ and the solvent was removed under reduced pressure. The crude was purified by flash column chromatography (AcOEt/hexane from 1/3 to 1/1) to afford compound 36 (77 mg, 57%) as pale yellow solid. $^1$H-NMR (300 MHz, $CDCl_3$): 6.48 (s, 1H), 6.11 (d, J=1.3 Hz, 1H), 6.02 (d, J=1.3 Hz, 1H), 5.70 (bs, 1H), 5.09 (d, J=11.3 Hz, 1H), 4.66 (bs, 1H), 4.39 (m, 1H), 4.27 (d, J=5.6 Hz, 1H), 4.21 (d, J=10.5 Hz, 1H), 4.16 (d, J=2.6 Hz, 1H), 3.76 (s, 3H), 3.54 (d, J=5.1 Hz, 1H), 3.42 (d, J=8.5 Hz, 1H), 2.88-2.54 (m, 3H), 2.32 (s, 3H), 2.24 (s, 3H), 2.14 (s, 3H), 2.04 (s, 3H). $^{13}$C-NMR (75 MHz, $CDCl_3$): 186.7, 168.5, 160.5, 147.1, 146.4, 142.9, 141.6, 140.7, 130.4, 129.8, 121.7 (2C), 120.0, 117.8, 117.1, 113.5, 102.2, 61.7, 61.4, 60.3, 59.8, 58.9, 54.6, 41.6, 36.9, 29.7, 24.1, 20.3, 15.8, 14.1, 9.6. ESI-MS m/z: Calcd. for C31H31N3O9S: 621.7. Found (M+H)+: 622.2.

MAIN REFERENCES

European Patent 309,477.
U.S. Pat. No. 5,721,362.
Sakai, R., Jares-Erijman, E. A., Manzanares, I., Elipe, M. V. S., and Rinehart, K. L. J. Am. Chem. Soc. (1996) 118, 9017-9023
Martinez, E. J., Owa, T., Schreiber, S. L. and Corey, E. J. Proc. Natl. Acad. Sci. USA, 1999, 96, 3496-3501.
Japanese Kokai JP-A2 59/225189.
Japanese Kokai JP-A2 60/084288.
Arai, T.; Kubo, A. In The Alkaloids, Chemistry and Pharmacology; Brossi, A. Ed.; Academic: New York, 1983, Vol 21; pp 56-110.
Remers, W. A.: In The Chemistry of Antitumor Antibiotics; Vol. 2; Wiley; New York, 1988, pp 93-118.
Gulavita N. K; Scheuer, P. J.: Desilva, E. D. Abst. Indo-United States Symp. on Bioactive Compounds from Marine Organisms, Goa, India, Feb. 23-27, 1989, p 28.
Arai, T; Takahashi, K; Kubo, A. J. Antibiot, 1977, 30, 1015-1018.
Arai. T.; Takahashi, K.; Nakahara, S.; Kubo, A. Experientia 1980, 36, 1025-1028.
Mikami, Y.; Takahashi, K; Yazawa, K.; Hour-Young, C.; Arai, T.; Saito, N.; Kubo, A. J. Antibiot. 1988, 41, 734-740.
Arai, T.; Takahashi, K.; Ishiguro, K; Yazawa, K. J. Antibiot. 1980, 33, 951-960.
Yazawa, K; Takahashi, K.; Mikami, Y.; Arai, T.; Saito, N.; Kubo, A. J. Antibiot. 1986, 39, 1639-1650.
Arai, T.; Yazawa, K.; Takahashi, K.; Maeda, A.; Mikami, Y. Antimicrob. Agent Chemother. 1985, 28, 5-11.
Takahashi, K.; Yazawa, K.; Kishi, K.; Mikami, Y.; Arai, T.; Kubo, A. J. Antibiot. 1982, 35, 196-201.
Yazawa, K.; Asaoka, T.; Takahashi, K.; Mikami, Y.; Arai, T. J. Antibiot. 1982, 35, 915-917.
Frincke, J. M.; Faulkner, D. J. J. Am. Chem. Soc. 1982, 104, 265-269.
He, H.-Y.; Faulkner, D. J. J. Org. Chem. 1989, 54, 5822-5824.
Kubo, A.; Saito, N.; Kitahara, Y.; Takahashi, K.; Tazawa, K.; Arai, T. Chem Pharm. Bull. 1987, 35, 440-442.
Trowitzsch-Kienast, W.; Irschik, H.; Reichenback, H.; Wray, V.; Höfle, G. Liebigs Ann. Chem. 1988, 475-481.
Ikeda, Y.; Idemoto, H.; Hirayama, F.; Yamamoto, K.; Iwao, K.; Asano, T.; Munakata, T. J. Antibiot. 1983, 36, 1279-1283.
Asaoka, T.; Yazawa, K.; Mikami, Y. Arai, T.; Takahashi, K. J. Antibiot. 1982, 35, 1708-1710.
Lown, J. W.; Hanstock, C. C.; Joshua, A. V.; Arai, T; Takahashi, K. J. Antibiot. 1983, 36, 1184-1194.
Munakata et al. U.S. Pat. No. 4,400,752, 1984.
Y. Ikeda et al. The Journal of Antibiotics. VOL XXXVI, No. 10, 1284, 1983.
R. Cooper, S. Unger. The Journal of Antibiotics. VOL XXXVIII, No. 1, 1985.
Corey et al. U.S. Pat. No. 5,721,362. 1998.
Corey et al. J. Am. Chem. Soc. vol 118 pp 9202-92034, 1996.
Proc. Natl. Acad. Sci. USA. Vol. 96, pp 3496-3501, 1999.

Example 37

To a solution of 1 equiv. of Int-35 (30.6 mg) in $CH_2Cl_2$ (0.05 M) under Argon 1.0 equiv. of coumarine 3-carboxilic acid, 1.1 equiv. of DIPEA and 1.1 equiv. of EDC.HCl were added. The reaction mixture was stirred for 3 hours at 23° C.

After this time, 0.15 equiv. of coumarine 3-carboxilic acid, 0.15 equiv. of DIPEA and 0.15 equiv. of EDC.HCl were added. 2 hours later the reaction was diluted with CH₂Cl₂, washed with brine, extracted with CH₂Cl₂ and the combined organic layers dried over Na₂SO₄, filtered and concentrated under vacuum. Silica gel chromatography purification (Hex:EtOAc, 3:2, 5:2, 4:5) gave pure 15a (75% yield).

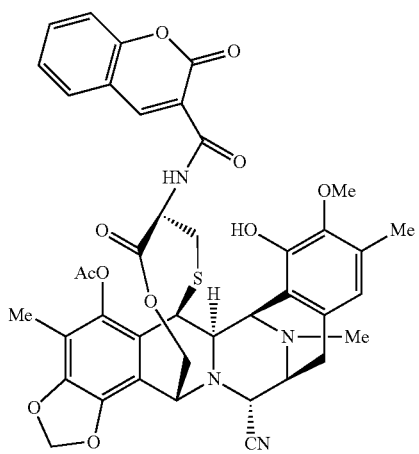

15a $R_f$: 0.55 (Hex:EtOAc, 1:2).

¹H-NMR (300 MHz, CDCl₃): δ 9.00 (d, 1H), 8.74 (s, 1H), 7.70-7.62 (m, 2H), 7.45-7.26 (m, 2H), 6.65 (s, 1H), 6.05 (dd, 2H), 5.62 (s, 1H), 5.09 (d, 1H), 4.71-4.68 (m, 1H), 4.59 (bd, 1H), 4.34 (s, 1H), 4.26-4.24 (m, 2H), 4.18 (dd, 1H), 3.67 (s, 3H), 3.47-3.45 (m, 2H), 2.95 (d, 2H), 2.66-2.62 (m, 1H), 2.28 (s, 3H), 2.16 (s, 3H), 2.12 (s, 3H), 2.04 (s, 3H), 2.04-2.01 (m, 1H).

¹³C NMR (75 MHz, CDCl₃): δ 169.5, 168.4, 160.7, 160.1, 154.6, 148.0, 146.8, 145.8, 142.8, 141.1, 140.6, 134.0, 130.5, 129.8, 129.3, 125.1, 122.0, 121.0, 118.4, 118.2, 118.1, 117.5, 116.6, 113.6, 113.1, 102.0, 61.5, 60.1, 59.9, 59.8, 58.6, 54.6, 54.6, 54.0, 41.9, 41.6, 32.1, 23.9, 20.4, 15.6, 9.7.

MS: 795.7 (M+1)⁺.

Example 38

To a solution of 1 equiv. of Int-35 (47.5 mg) in CH₂Cl₂ (0.05 M) under Argon 1.25 equiv. of Boc-L-Pro, 1.25 equiv. of DIPEA and 1.25 equiv. of EDC.HCl were added. The reaction mixture was stirred for 4 hours at 23° C. and then 0.30 equiv of Boc-L-Pro, 0.30 equiv. of DIPEA and 0.30 equiv. of EDC.HCl were added. After 2 hours the reaction was diluted with CH₂Cl₂, washed with brine, extracted with CH₂Cl₂ and the combined organic layers dried over Na₂SO₄, filtered and concentrated under vacuum. Silica gel chromatography purification (Hex:EtOAc, 1:2, CH₂Cl₂:CH₃OH 30:1, 15:1) gave pure 15b (81% yield).

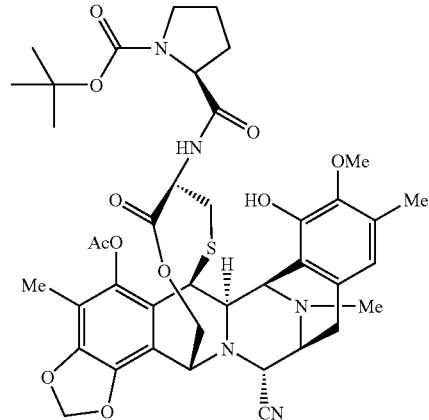

15b

Rf: 0.6 (CH₂Cl₂:CH₃OH, 40:1).

¹H-NMR (300 MHz, CDCl₃, 40° C.): δ 6.52 (bs, 1H), 6.03 (d, 2H), 5.80-5.78 (m, 1H), 5.74 (s, 1H), 5.01 (d, 1H), 4.60-4.57 (m, 1H), 4.54 (s, 1H), 4.30 (s, 1H), 4.25 (d, 1H), 4.20-4.14 (m, 2H), 4.00-3.94 (m, 1H), 3.78 (s, 3H), 3.46-3.40 (m, 4H), 2.88-2.86 (m, 2H), 2.31-2.02 (m, 4H), 2.31 (s, 3H), 2.27 (s, 3H), 2.11 (s, 3H), 2.02 (s, 3H), 1.81-1.79 (m, 2H), 1.50-1.35 (m, 9H).

¹³C-NMR (75 MHz, CDCl₃, 40° C.): δ 171.9, 168.3, 154.2, 147.8, 145.9, 143.2, 141.2, 140.5, 131.0, 129.2, 120.6, 119.1, 117.9, 113.6, 113.3, 102.0, 61.6, 60.3, 60.0, 59.5, 58.5, 54.8, 54.7, 51.9, 46.7, 42.2, 41.5, 28.3, 24.0, 20.3, 16.0, 9.5.

MS: 820.8 (M+1)⁺.

Example 39

To a solution of 1 equiv. of Int-35 (149.1 mg) in CH₂Cl₂ (0.025 M) under Argon 1.05 equiv. of pyridine and 1.05 equiv. of Nicotinoyl chloride were added. The reaction mixture was stirred for 2 hours at 23° C. and then diluted with CH₂Cl₂, washed with brine and dried over Na₂SO₄, filtered and concentrated under vacuum. Silica gel chromatography purification (hexane/EtOAc, 4:5, 2:3) gave pure 15c (85% yield).

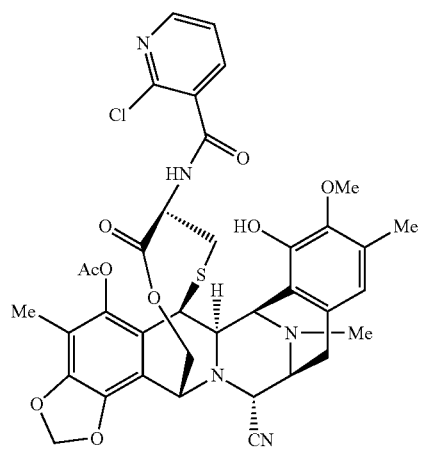

15c

Rf: 0.64 (Hex:EtOAc, 1:2).

¹H-NMR (300 MHz, CDCl₃): δ 8.52 (dd, 1H), 7.95 (dd, 1H), 7.38 (dd, 1H), 6.43 (d, 1H), 6.24 (s, 1H), 6.05 (dd, 2H), 5.73 (s, 1H), 5.06 (d, 1H), 4.81-4.78 (m, 1H), 4.56 (bd, 1H), 4.32-4.20 (m, 4H), 3.65 (s, 3H), 3.45-3.41 (m, 2H), 2.87-2.85 (m, 2H), 2.51-2.46 (m, 1H), 2.29 (s, 3H), 2.19-2.14 (m, 1H), 2.12 (s, 3H), 2.04 (s, 3H), 1.72 (s, 3H).

$^{13}$C-NMR (75 MHz, CDCl$_3$): δ 169.8, 168.5, 164.0, 151.0, 147.6, 147.5, 145.9, 142.9, 141.1, 140.5, 139.2, 131.2, 130.6, 129.3, 122.6, 120.4, 120.3, 118.4, 118.0, 113.4, 102.0, 61.4, 60.3, 60.1, 59.4, 58.7, 54.5, 53.1, 42.0, 41.4, 32.3, 23.7, 20.5, 15.2, 9.6.

MS: 735.2 (M−26)$^+$.

Example 40

To a solution of 1 equiv. of Int-35 (30 mg) in CH$_2$Cl$_2$ (0.05 M) under Argon 1.35 equiv. of pyridine and 1.35 equiv. of 1-phenyl-5-(trifluoromethyl)-1H-pyrazole-4-carbonyl chloride were added at 23° C. The reaction mixture was stirred for 4 h at 23° C. and then quenched with a saturated aqueous solution of NaCl. The aqueous layer was extracted with CH$_2$Cl$_2$ and the combined organic layers were dried over Na$_2$SO$_4$, filtered and concentrated under vacuum. Silica gel chromatography purification (Hexane:EtOAc, 5:4) gave pure 15d (75% yield).

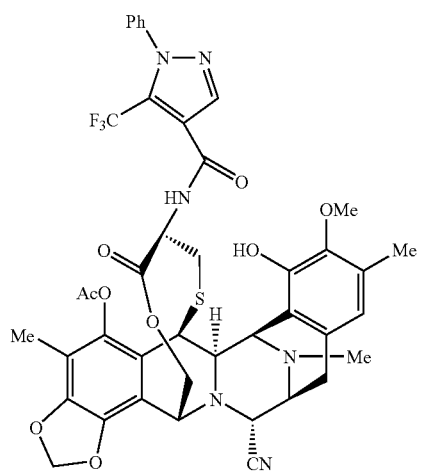

15d

Rf: 0.41 (Hex:EtOAc, 50:50).

$^1$H NMR (300 MHz, CDCl$_3$): δ 7.80 (s, 1H), 7.55-7.44 (m, 5H), 6.44 (s, 1H), 6.10 (d, 1H), 6.06 (dd, 2H), 5.76 (s, 1H), 5.07 (d, 1H), 4.76-4.73 (m, 1H), 4.58 (bd, 1H), 4.33 (s, 1H), 4.26-4.19 (m, 3H), 3.69 (s, 3H), 3.47-3.45 (m, 2H), 2.92-2.90 (bd, 2H), 2.54-2.49 (m, 1H), 2.30 (s, 3H), 2.14-2.03 (m, 1H), 2.14 (s, 3H), 2.04 (s, 3H), 2.03 (s, 3H).

MS: 861.0 (M+1)$^+$.

Example 41

To a solution of 1 equiv. of Int-35 (30.0 mg) in CH$_2$Cl$_2$ (0.05 M) under Argon 1.05 equiv. of pyridine, and 1.05 equiv of isoxazolyl chloride were added. The reaction was stirred for 1 hour at 23° C. and then diluted with CH$_2$Cl$_2$, washed with a saturated aqueous solution of NaCl and the combined organic layers were dried over Na$_2$SO$_4$, filtered and concentrated under vacuum. Silica gel chromatography purification (Hex/EtOAc, 50:50) gave pure 15e (83% yield).

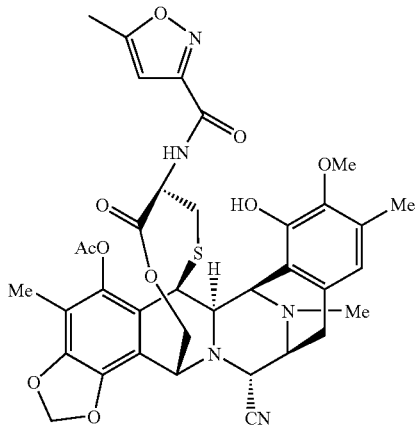

15e $^1$H NMR (300 MHz, CDCl$_3$): δ 6.88 (d. 1H), 6.62 (s, 1H), 6.32 (s, 1H), 6.05 (dd, 2H), 5.71 (s, 1H), 5.05 (d, 1H), 4.76-4.71 (m, 1H), 4.59 (bd, 1H), 4.30 (s, 1H), 4.25 (d, 1H), 4.21-4.15 (m, 2H), 3.70 (s, 3H), 3.45-3.40 (m, 2H), 2.97-2.86 (m, 2H), 2.48-2.42 (m, 1H), 2.48 (s, 3H), 2.28 (s, 3H), 2.24 (s, 3H), 2.17 (s, 3H), 2.12-2.06 (m, 1H), 2.03 (m, 3H).

MS: 732.5 (M+1)$^+$.

Example 42

A solution of 1 equiv. of 15b (18.2 mg) in CH$_2$Cl$_2$:H$_2$O:TFA (2:1:3, 0.015 M) was stirred for 25 min at 23° C. Then the reaction mixture was neutralized with aqueous saturated solution of NaHCO$_3$, extracted with CH$_2$Cl$_2$ and the combined organic layers dried over Na$_2$SO$_4$, filtered and concentrated under vacuum. Silica gel chromatography purification (CH$_2$Cl$_2$:CH$_3$OH, 40:1, 30:1, 20:1, 10:1) gave pure 15f (97% yield).

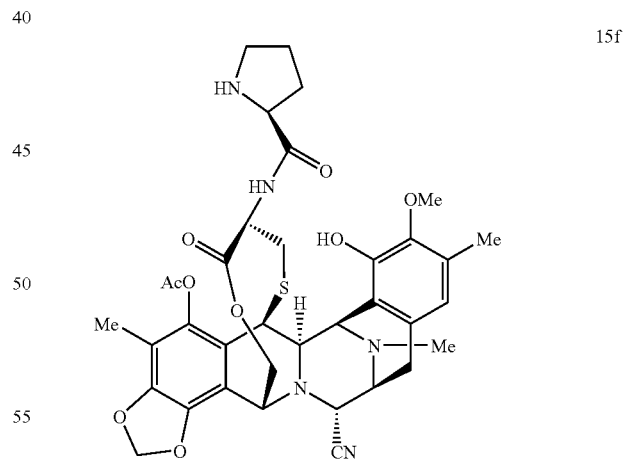

15f

Rf: 0.22 (CH$_2$Cl$_2$:CH$_3$OH, 15:1).

$^1$H-NMR (300 MHz, CDCl$_3$): δ 7.05 (bd, 1H), 6.51 (s, 1H), 6.04 (dd, 2H), 5.80 (bd, 1H), 5.02 (d, 1H), 4.58-4.55 (m, 2H), 4.31 (s, 1H), 4.25 (d, 1H), 4.20 (d, 1H), 4.14 (dd, 1H), 3.75 (s, 3H), 3.57-3.53 (m, 1H), 3.46-3.42 (m, 2H), 3.01-2.82 (m, 4H), 2.34-2.29 (m, 1H), 2.29 (s, 6H), 2.10-2.02 (m, 2H), 2.10 (s, 3H), 2.02 (s, 3H), 1.83-1.61 (m, 3H).

$^{13}$C-NMR (75 MHz, CDCl$_3$): δ 174.4, 170.1, 168.5, 147.4, 145.9, 143.0, 141.1, 140.6, 131.0, 129.1, 120.7, 120.6, 118.6, 118.1, 113.6, 113.1, 102.0, 61.5, 60.5, 60.3, 59.9, 59.6, 58.5, 54.8, 54.6, 52.2, 47.2, 42.1, 41.6, 33.0, 31.0, 25.9, 24.1, 20.4, 16.1, 9.6.

MS: 720.7 (M+1)⁺.

Example 43

To a solution of 1 equiv. of 15a (139.4 mg) in CH₃CN:H₂O (2.8:1, 0.021 M) 12 equiv. of CuCl were added. The reaction mixture was stirred for 24 h at 23° C. without light. After this time, the reaction was quenched with a saturated aqueous solution of NH₄Cl and diluted and extracted with CH₂Cl₂, the combined organic layers were washed twice with a saturated aqueous solution of NaHCO₃ and dried over Na₂SO₄, filtered and concentrated under vacuum. Silica gel chromatography purification (CH₂Cl₂:CH₃OH 60:1, 30:1, 15:1, 8:1) afforded pure 16a (74% yield).

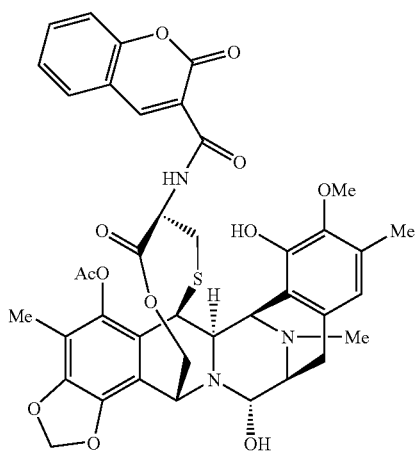

16a

R$_f$: 0.34 (CH₂Cl₂:CH₃OH, 30:1).

¹H-NMR (300 MHz, CDCl₃): δ 9.01 (d, 1H), 8.74 (s, 1H), 7.69-7.62 (m, 2H), 7.45-7.33 (m, 2H), 6.67 (s, 1H), 6.03 (dd, 2H), 5.57 (s, 1H), 5.22 (d, 1H), 4.83 (s, 1H), 4.68-4.66 (m, 1H), 4.53-4.49 (m, 2H), 4.12-4.07 (m, 2H), 3.68 (s, 3H), 3.52-3.49 (m, 1H), 3.23-3.20 (m, 1H), 2.90-2.87 (m, 2H), 2.67-2.63 (m, 1H), 2.28 (s, 3H), 2.13 (s, 6H), 2.08-1.99 (m, 1H), 2.03 (s, 3H).

¹³C-NMR (75 MHz, CDCl₃): δ 169.4, 168.5, 160.7, 160.1, 154.6, 147.9, 146.7, 145.6, 142.7, 141.0, 133.9, 131.3, 129.7, 129.2, 125.1, 122.2, 121.6, 118.5, 118.3, 117.4, 116.6, 115.3, 112.3, 101.8, 81.4, 61.3, 60.1, 58.1, 57.9, 56.1, 54.9, 54.1, 42.1, 41.4, 32.0, 23.8, 20.4, 15.6, 9.6.

MS: 768.7 (M−18+1)⁺.

Example 44

To a solution of 1 equiv. of 15b (37.7 mg) in THF:H₂O (4:1, 0.03 M) 10 equiv. of CuCl were added. The reaction mixture was stirred for 24 h at 23° C. without light. After this time, the reaction was quenched with a saturated aqueous solution of NH₄Cl and diluted and extracted with CH₂Cl₂, the combined organic layers were washed twice with a saturated aqueous solution of NaHCO₃ and dried over Na₂SO₄, filtered and concentrated under vacuum. Silica gel chromatography purification (CH₂Cl₂:CH₃OH 30:1, 20:1) gave pure 16b (77% yield).

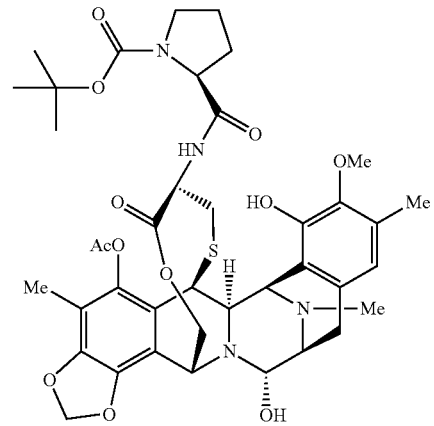

16b

Rf: 0.58 (CH₂Cl₂:CH₃OH, 20:1).

¹H-NMR (300 MHz, CDCl₃): δ 6.54-6.50 (m, 1H), 6.02 (d, 2H), 5.87-5.82 (m, 1H), 5.72-5.68 (m, 1H), 5.14 (d, 1H), 4.79 (s, 1H), 4.60-4.42 (m, 3H), 4.15-4.06 (m, 2H), 3.94-3.90 (m, 1H), 3.81, 3.78 (2s, 3H), 3.51-3.47 (m, 3H), 3.23-3.20 (m, 1H), 2.82-2.80 (m, 2H), 2.31-2.02 (m, 4H), 2.31 (s, 3H), 2.28 (s, 3H), 2.09 (s, 3H), 2.02 (s, 3H), 1.84-1.81 (m, 2H), 1.47, 1.36 (2s, 9H).

MS: 793.7 (M−18+1)⁺.

Example 45

To a solution of 1 equiv. of 15f (140 mg) in THF:H₂O (4:1, 0.03 M) 10 equiv. of CuCl were added. The reaction mixture was stirred for 24 h at 23° C. without light. After this time, the reaction was quenched with a saturated aqueous solution of NaHCO₃ and diluted and extracted with CH₂Cl₂, the combined organic layers were washed twice with a saturated aqueous solution of NaHCO₃ and once with brine and then dried over Na₂SO₄, filtered and concentrated under vacuum. Silica gel chromatography purification (CH₂Cl₂:CH₃OH 50:1, 30:1, 20:1, 10:1, 5:1, 3:1) gave pure 16c (60% yield).

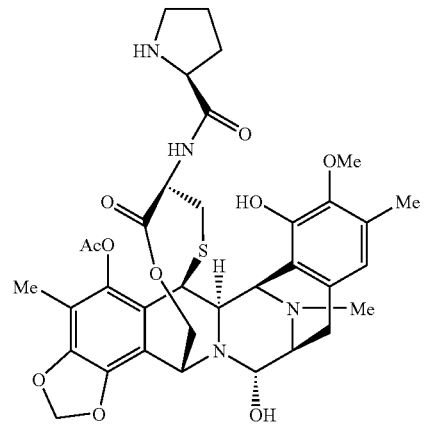

16c

Rf: 0.23 (CH₂Cl₂:CH₃OH, 10:1).

¹H-NMR (300 MHz, CDCl₃): δ 6.91 (bd, 1H), 6.52 (s, 1H), 6.02 (d, 2H), 5.67 (bd, 1H), 5.15 (d, 1H), 4.80 (s, 1H), 4.57-4.54 (m, 1H), 4.49-4.47 (m, 2H), 4.14 (d, 1H), 4.07 (dd, 1H), 3.77 (s, 3H), 3.64-3.58 (m, 1H), 3.52-3.48 (m, 1H), 3.23-3.20 (m, 1H), 3.03-2.98 (m, 2H), 2.83-2.81 (m, 2H), 2.35-2.31 (m,

1H), 2.31 (s, 3H), 2.30 (s, 3H), 2.11-2.02 (m, 2H), 2.09 (s, 3H), 2.02 (s, 3H), 1.83-1.61 (m, 3H).
$^{13}$C-NMR (75 MHz, CDCl$_3$): δ 169.9, 168.8, 147.4, 145.6, 142.9, 141.0, 140.8, 131.6, 128.9, 121.2, 120.7, 118.6, 115.2, 112.2, 101.7, 81.2, 61.2, 60.2, 57.8, 57.8, 56.0, 55.0, 52.2, 42.2, 41.3, 32.8, 23.9, 20.4, 16.0, 9.5.
MS: 711.2 (M+1)$^+$.

Example 46

To a solution of 1 equiv. of 15c (154 mg) in THF:H$_2$O (4:1, 0.03 M) 12 equiv. of CuCl were added. The reaction mixture was stirred for 24 h at 23° C. without light. After this time, the reaction was diluted with CH$_2$Cl$_2$, washed with a saturated aqueous solution of NH$_4$Cl, extracted with CH$_2$Cl$_2$, the combined organic layers were washed twice with a saturated aqueous solution of NaHCO$_3$, and dried over Na$_2$SO$_4$, filtered and concentrated under vacuum. Silica gel chromatography purification (CH$_2$Cl$_2$:CH$_3$OH 40:1, 25:1, 15:1, 10:1) gave pure 16d (94% yield).

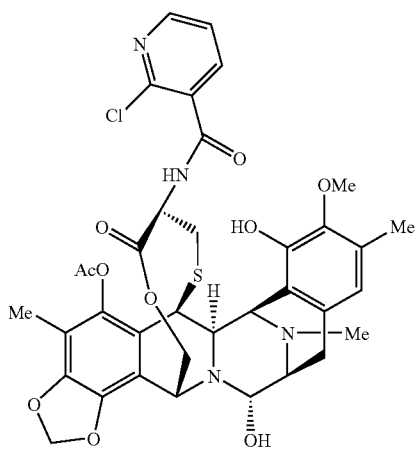

16d

Rf: 0.32 (CH$_2$Cl$_2$:CH$_3$OH, 30:1).
$^1$H-NMR (300 MHz, CDCl$_3$): δ 8.52 (dd, 1H), 7.97 (dd, 1H), 7.38 (dd, 1H), 6.49 (d, 1H), 6.26 (s, 1H), 6.04 (dd, 2H), 5.64 (s, 1H), 5.20 (d, 1H), 4.84-4.76 (m, 1H), 4.81 (s, 1H), 4.49-4.47 (m, 2H), 4.16-4.11 (m, 2H), 3.66 (s, 3H), 3.50-3.47 (m, 1H), 3.22-3.19 (m, 1H), 2.87-2.72 (m, 2H), 2.51-2.48 (m, 1H), 2.30 (s, 3H), 2.22-2.17 (m, 1H), 2.10 (s, 3H), 2.03 (s, 3H), 1.73 (s, 3H).
$^{13}$C-NMR (75 MHz, CDCl$_3$): δ 169.8, 168.6, 164.0, 150.9, 147.6, 147.5, 145.7, 142.8, 141.1, 140.9, 139.2, 131.3, 129.2, 122.5, 120.9, 120.6, 118.2, 115.2, 112.5, 101.8, 81.4, 61.6, 60.1, 57.7, 57.6, 56.0, 54.8, 53.2, 42.2, 41.3, 32.2, 23.6, 20.5, 15.2, 9.6
MS: 735.3 (M−18+1)$^+$.

Example 47

To a solution of 1 equiv. of 15d (30.1 mg) in THF:H$_2$O (4:1, 0.03 M) 10 equiv. of CuCl were added. The reaction was stirred for 24 h at 23° C. without light. After this time, the reaction was diluted with CH$_2$Cl$_2$, washed with a saturated aqueous solution of NH$_4$Cl, twice with a saturated aqueous solution of NaHCO$_3$, the aqueous layers were extracted with CH$_2$Cl$_2$, and the combined organic layers were dried over Na$_2$SO$_4$, filtered and concentrated under vacuum. Silica gel chromatography purification (CH$_2$Cl$_2$:CH$_3$OH 30:1, 10:1) gave pure 16e (88% yield).

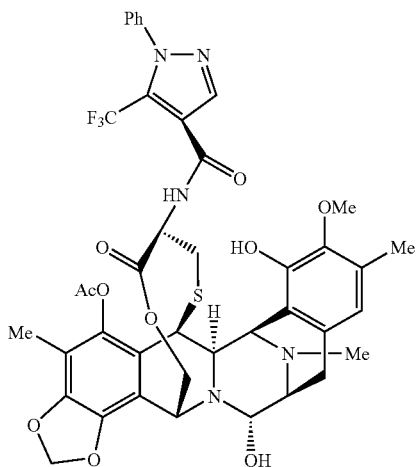

16e

Rf: 0.37 (CH$_2$Cl$_2$:CH$_3$OH, 30:1).
$^1$H NMR (300 MHz, CDCl$_3$): δ 7.82 (s, 1H), 7.54-7.44 (m, 5H), 6.45 (s, 1H), 6.17 (d, 1H), 6.03 (dd, 2H), 5.72 (bp, 1H), 5.20 (d, 1H), 4.81 (s, 1H), 4.73-4.69 (m, 1H), 4.50-4.49 (m, 2H), 4.15-4.10 (m, 2H), 3.69 (s, 3H), 3.51 (d, 1H), 3.24-3.22 (m, 1H), 2.91-2.77 (m, 2H), 2.56-2.51 (m, 1H), 2.29 (s, 3H), 2.17-2.12 (m, 1H), 2.12 (s, 3H), 2.03 (s, 3H), 2.02 (s, 3H).
$^{13}$C-NMR (75 MHz, CDCl$_3$): δ 170.0, 168.5, 159.8, 147.7, 145.7, 142.9, 141.1, 140.8, 139.3, 139.0, 131.5, 129.9, 129.2, 129.1, 125.7, 120.9, 120.5, 118.5, 115.1, 112.6, 101.8, 81.4, 61.7, 60.1, 57.7, 57.7, 56.0, 54.9, 53.0, 42.1, 41.3, 32.4, 23.7, 20.4, 15.3, 9.6.
MS: 834.3 (M−18+1)$^+$.

Example 48

To a solution of 1 equiv. of 15e (30.1 mg) in THF:H$_2$O (4:1, 0.03 M) 10 equiv. of CuCl were added. The reaction was stirred for 24 h at 23° C. without light. After this time, the reaction was diluted with CH$_2$Cl$_2$, washed with a saturated aqueous solution of NH$_4$Cl, twice with a saturated aqueous solution of NaHCO$_3$, the aqueous layers were extracted with CH$_2$Cl$_2$, and the combined organic layers were dried over Na$_2$SO$_4$, filtered and concentrated under vacuum. Silica gel chromatography purification (CH$_2$Cl$_2$:CH$_3$OH 30:1, 10:1) gave pure 16f (88% yield).

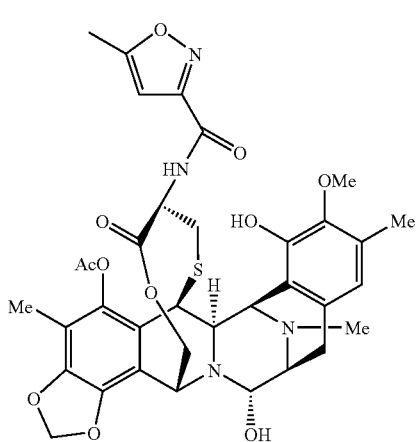

16f

Rf: 0.37 (CH$_2$Cl$_2$:CH$_3$OH, 30:1).

$^1$H-NMR (300 MHz, CDCl$_3$): δ 7.82 (s, 1H), 7.54-7.44 (m, 5H), 6.45 (s, 1H), 6.17 (d, 1H), 6.03 (dd, 2H), 5.72 (bp, 1H), 5.20 (d, 1H), 4.81 (s, 1H), 4.73-4.69 (m, 1H), 4.50-4.49 (m, 2H), 4.15-4.10 (m, 2H), 3.69 (s, 3H), 3.51 (d, 1H), 3.24-3.22 (m, 1H), 2.91-2.77 (m, 2H), 2.56-2.51 (m, 1H), 2.29 (s, 3H), 2.17-2.12 (m, 1H), 2.12 (s, 3H), 2.03 (s, 3H), 2.02 (s, 3H).

$^{13}$C-NMR (75 MHz, CDCl$_3$): δ 170.0, 168.5, 159.8, 147.7, 145.7, 142.9, 141.1, 140.8, 139.3, 139.0, 131.5, 129.9, 129.2, 129.1, 125.7, 120.9, 120.5, 118.5, 115.1, 112.6, 101.8, 81.4, 61.7, 60.1, 57.7, 57.7, 56.0, 54.9, 53.0, 42.1, 41.3, 32.4, 23.7, 20.4, 15.3, 9.6.

MS: 834.3 (M−18+1)$^+$.

Cytotoxic Assay

The compounds of the present invention were tested according to the protocol described below.

A colorimetric type of assay, using sulforhodamine B (SRB) reaction has been adapted for a quantitative measurement of cell growth and viability (following the technique described by Skehan P et al. J. Natl. Cancer Inst. 1990, 82, 1107-1112).

This form of assay employs 96-well cell culture microplates of 9 mm diameter (Faircloth et al. Methods in cell science, 1988, 11(4), 201-205; Mosmann et al, Journal of. Immunological. Methods, 1983, 65(1-2), 55-63). Most of the cell lines are obtained from American Type Culture Collection (ATCC) derived from different human cancer types. Cells are maintained in RPMI 1640 10% FBS, supplemented with 0.1 g/L penicillin and 0.1 g/l streptomycin sulfate and then incubated at 37° C., 5% CO$_2$ and 98% humidity. For the experiments, cells were harvested from subconfluent cultures using trypsin and resuspended in fresh medium before counting and plating.

Cells were seeded in 96 well microtiter plates at 5×10$^3$ cells per well in aliquots of 195 µL medium, and allowed to attach to the plate surface for 18 hours in drug free medium. Afterwards, samples are in aliquots of 5 µL in a ranging from 10 to 10-8 µg/mL dissolved in DMSO/ETOH (0.2% in PS buffer). After 48 hours exposure, the antitumor effect are measured by the SRB method: cells are fixed by adding 50 µL of cold 50% (w/v) trichloroacetic acid and incubating for 60 minutes at 4° C. Plates are washed with deionised water and dried. 100 µL of SRB solution (0.4% w/v in 1% acetic acid) is added to each microtiter well and incubated for 10 minutes at room temperature. Unbound SRB is removed by washing with 1% acetic acid. Plates are air-dried and bound stain is solubilized with Tris Buffer. Optical densities are read on an automated spectrophotometric plate reader at a single wavelength of 490 nm.

The values for mean ±SD of data from triplicate wells are calculated. GI$_{50}$ (concentration that produces 50% growth inhibition) parameter was calculated (NCI algorithm) by automatic interpolation.

The results are shown in Table below.

| Compound | GI$_{50}$ (Molar) | | | |
| --- | --- | --- | --- | --- |
| | A549 | HT29 | MEL-28 | DU-14S |
| 15a | 2.83E−09 | 4.38E−09 | 3.23E−09 | 4.38E−09 |
| 15b | 7.32E−09 | 3.66E−09 | | |
| 15c | 1.80E−09 | 2.93E−09 | 1.21E−09 | 4.68E−10 |
| 15d | 1.46E−08 | 1.01E−08 | | |
| 15e | 5.77E−09 | 5.36E−09 | 2.58E−09 | 3.84E−09 |
| 15f | 2.78E−09 | 2.78E−10 | | |
| 16a | 2.94E−09 | 3.94E−09 | 3.02E−09 | 4.73E−09 |

-continued

| Compound | GI$_{50}$ (Molar) | | | |
| --- | --- | --- | --- | --- |
| | A549 | HT29 | MEL-28 | DU-14S |
| 16b | 1.23E−09 | 1.23E−09 | 1.11E−09 | 3.70E−10 |
| 16c | 5.63E−09 | 4.22E−11 | 2.81E−10 | 1.13E−09 |
| 16d | 1.33E−06 | 1.33E−05 | 2.50E−09 | 2.16E−09 |
| 16e | 3.51E−08 | 3.86E−08 | 2.98E−08 | 2.72E−08 |
| 16f | 3.47E−09 | 4.30E−09 | 5.13E−09 | 3.40E−09 |

What is claimed is:

1. A compound of formula (XVIIb):

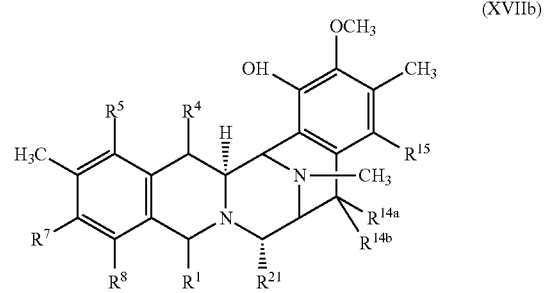

(XVIIb)

wherein
R$^1$ and R$^4$ together form a group of formula (VIa) or (VIb):

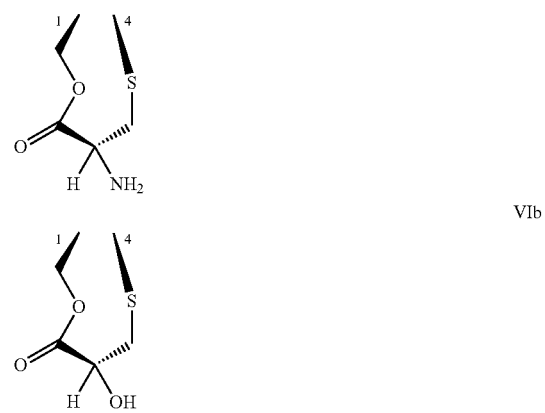

VIa

VIb wherein the —CHNH$_2$ in formula (.VIa) is replaced by a group
CHNH—CO—R$^a$, or the —CHOH group in formula (VIb) is replaced by a group —CHO—CO—R$^a$, wherein R$^a$ is:
(i) aromatic heterocyclyl; or
(ii) partially saturated heterocyclyl; or
(iii) completely saturated heterocyclyl; and
each of which is optionally substituted with one or more substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocycly-loxy, alkyl, haloalkyl, and amino;
R$^5$ is H, —OH or O-acyl, wherein the acyl group is of formula —CO—R$^{aa}$, wherein R$^{aa}$ is alkyl, alkoxy, alkenyl, arylalkyl, aryl, arylalkylene, amino acid, aromatic heterocyclyl, partially saturated heterocyclyl, or completely saturated heterocyclyl, each of which is optionally substituted with one or more substituents selected from the group consisting of halo, cyano, nitro, carboxyalkyl, alkoxy, haloalkoxy, aryl, aryloxy, heterocyclyl, heterocyclyloxy, alkyl, and amino;

$R^7$ is —OCH$_3$ and $R^8$ is —OH or $R^7$ and $R^8$ together form a group —O—CH$_2$—O—;

$R^{14a}$ and $R^{14b}$ are both —H or one is —H and the other is —OH, —OCH$_3$ or —OCH$_2$CH$_3$, or $R^{14a}$ and $R^{14b}$ together form a keto group;

$R^{15}$ is —H or —OH;

$R^{21}$ is —H, —OH or —CN, wherein each of aryl and aryloxy, independently, contain 1 to 3 separate or fused rings and from 6 to 18 carbon ring atoms, and wherein each of heterocyclyl and heterocyclyloxy independently contain one, two or three heteroatoms selected from N, O or S atoms, and derivatives where the group —NCH$_3$ at the 12-position is replaced by —NH or —NCH$_2$CH$_3$; or a pharmaceutically acceptable salt thereof.

2. The compound of claim 1, wherein $R^a$ is aromatic heterocyclyl, which is optionally substituted with one or more substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

3. The compound of claim 1, wherein $R^a$ is completely saturated heterocyclyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

4. The compound of claim 1, wherein $R^1$ and $R^4$ together form a group of formula (VIa), wherein the —CHNH$_2$ in formula (VIa) is replaced by a group —CHNH—CO—$R^a$.

5. The compound of claim 4, wherein $R^a$ is aromatic heterocyclyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

6. The compound of claim 4, wherein $R^a$ is completely saturated heterocyclyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

7. The compound of claim 1, wherein $R^5$ is —O—CO—$R^{aa}$.

8. The compound of claim 7, wherein $R^{aa}$ is alkyl, haloalkyl, alkoxyalkyl, haloalkoxyalkyl, arylalkylene, haloalkylarylalkylene, arylalkyl, aryl, aryl-aryl, haloaryl, nitroaryl, alkenyl, aromatic heterocyclyl, partially saturated heterocyclyl, completely saturated heterocyclyl, or amino acid.

9. The compound of claim 1, wherein $R^{aa}$ is alkyl.

10. The compound of claim 9, wherein $R^{aa}$ is CH$_3$.

11. The compound of claim 1, wherein $R^7$ and $R^8$ together form a group —O—CH$_2$—O—.

12. The compound of claim 1, wherein $R^{14a}$ and $R^{14b}$ are hydrogen.

13. The compound of claim 1, wherein $R^{15}$ is hydrogen.

14. The compound of claim 1, wherein $R^{21}$ is —OH.

15. The compound of claim 1, wherein $R^{21}$ is —CN.

16. The compound of claim 1, wherein:

$R^1$ and $R^4$ together form a group of formula (VIa), wherein the —CHNH$_2$ in formula (VIa) is replaced by a group —CHNH—CO—$R^a$; and $R^5$ is —O—CO—$R^{aa}$.

17. The compound of claim 16, wherein $R^a$ is aromatic heterocyclyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyloxy, aromatic heterocyclyloxy, partially saturated heterocyclyloxy, completely saturated heterocyclyloxy, alkyl, haloalkyl, and amino.

18. The compound of claim 17, wherein $R^a$ is coumarinyl.

19. The compound of claim 17, wherein $R^a$ is pyridinyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

20. The compound of claim 17, wherein $R^a$ is pyrazolyl or isoxazolyl, each of which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

21. The compound of claim 16, wherein $R^a$ is completely saturated heterocyclyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

22. The compound of claim 21, wherein $R^a$ is pyrrolidinyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

23. The compound of claim 16, wherein $R^{aa}$ is alkyl.

24. The compound of claim 23, wherein $R^{aa}$ is CH$_3$.

25. The compound of claim 16, wherein $R^7$ and $R^8$ together form a group —O—CH$_2$—O—, and each of $R^{14a}$, $R^{14b}$, and $R^{15}$ is hydrogen.

26. The compound of claim 16, wherein $R^{21}$ is —OH.

27. The compound of claim 16, wherein $R^{21}$ is —CN.

28. The compound of claim 1, wherein:

$R^1$ and $R^4$ together form a group of formula (VIa), wherein the —CHNH$_2$ in formula (VIa) is replaced by a group —CHNH—CO—$R^a$, wherein $R^a$ is aromatic heterocyclyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino;

$R^5$ is —O—CO—$R^{aa}$, wherein $R^{aa}$ is alkyl;

$R^7$ and $R^8$ together form a group —O—CH$_2$—O—;

each of $R^{14a}$, $R^{14b}$, and $R^{15}$ is hydrogen; and $R^{21}$ is —OH or —CN.

29. The compound of claim 28, wherein $R^a$ is coumarinyl.

30. The compound of claim 28, wherein $R^a$ is pyridinyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

31. The compound of claim 28, wherein $R^a$ is pyrazolyl or isoxazolyl, each of which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

32. The compound of claim 1, wherein:

$R^1$ and $R^4$ together form a group of formula (VIa), wherein the —CHNH$_2$ in formula (VIa) is replaced by a group —CHNH—CO—$R^a$, wherein $R^a$ is completely saturated heterocyclyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino;

$R^5$ is —O—CO—$R^{aa}$, wherein $R^{aa}$ is alkyl;

$R^7$ and $R^8$ together form a group —O—CH$_2$—O—;

each of $R^{14a}$, $R^{14b}$, and $R^{15}$ is hydrogen; and $R^{21}$ is —OH or —CN.

33. The compound of claim 32, wherein $R^a$ is pyrrolidinyl, which is optionally substituted with one or more substituents substituents selected from the group consisting of halo, cyano, nitro, carboxyalkyl, alkoxy, aryl, aryloxy, aromatic heterocyclyl, partially saturated heterocyclyl, completely saturated heterocyclyl, aromatic heterocyclyloxy, partially saturated heterocyclyloxy, completely saturated heterocyclyloxy, alkyl, haloalkyl, and amino.

34. The compound of claim 1, wherein the compound has the formula:

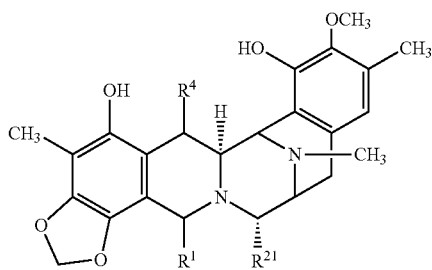

wherein $R^1$, $R^4$, and $R^{21}$ are as defined in claim 1.

35. The compound of claim 1, wherein the compound is:

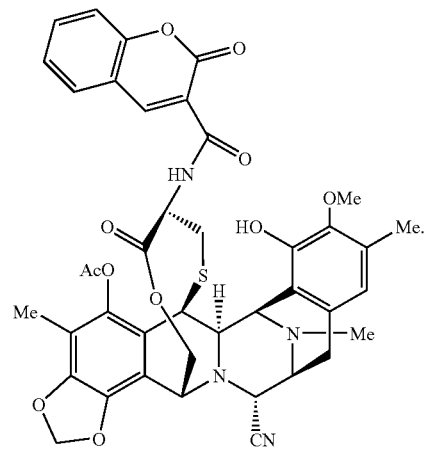

36. The compound of claim 1, wherein the compound is:

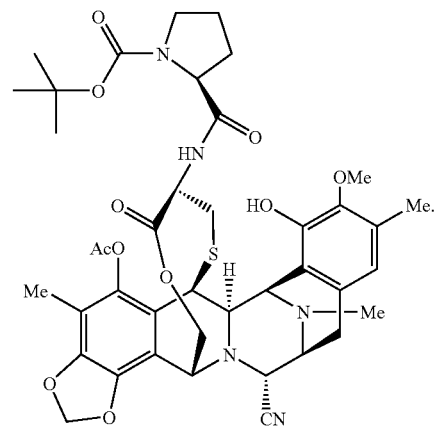

37. The compound of claim 1, wherein the compound is:

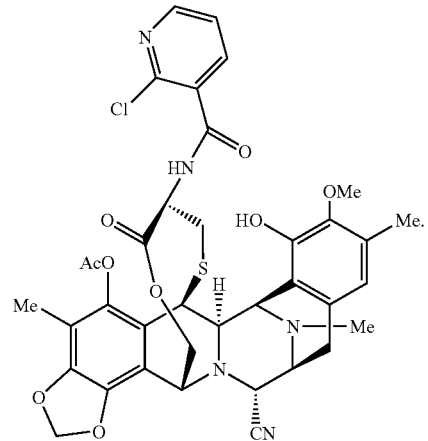

38. The compound of clim 1, wherein the compound is:
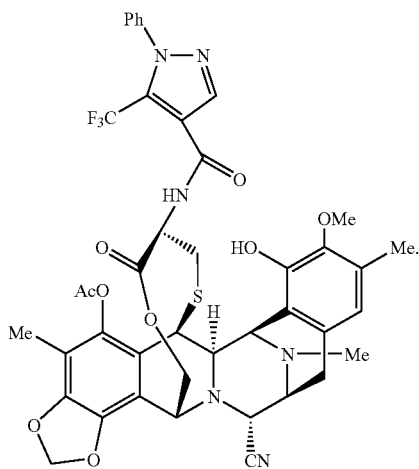
39. The compound of claim 1, wherein the compound is:
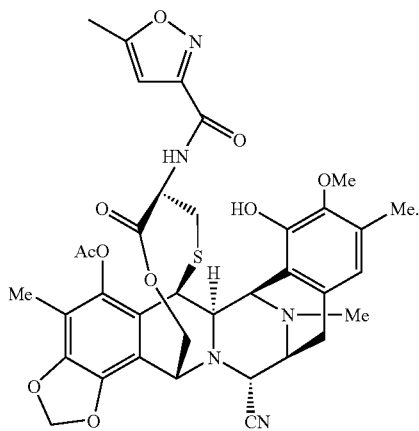
40. The compound of claim 1, wherein the compound is:
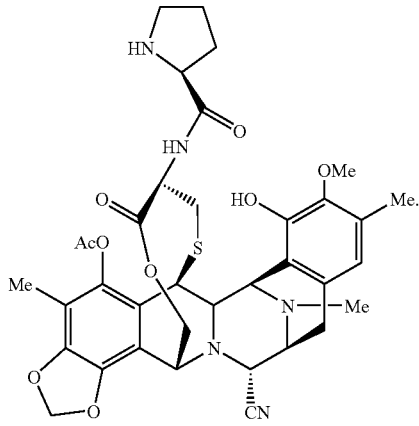
41. The compound of claim 1, wherein the compound is:
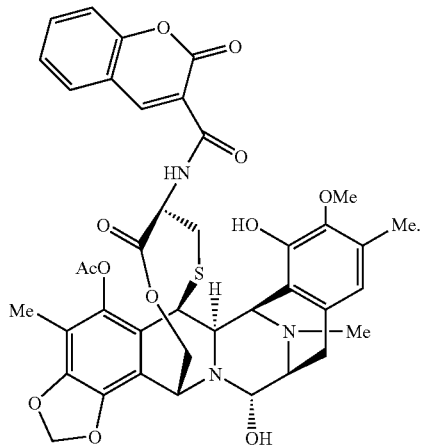
42. The compound of claim 1, wherein the compound is:
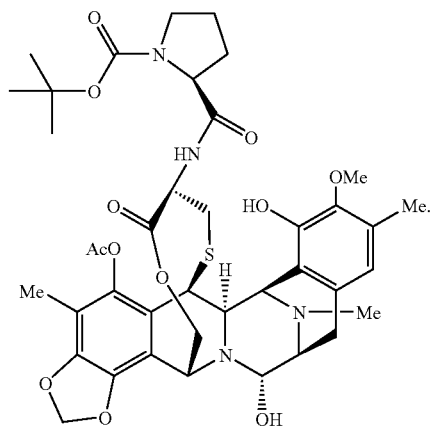

43. The compound of claim 1, wherein the compound is:

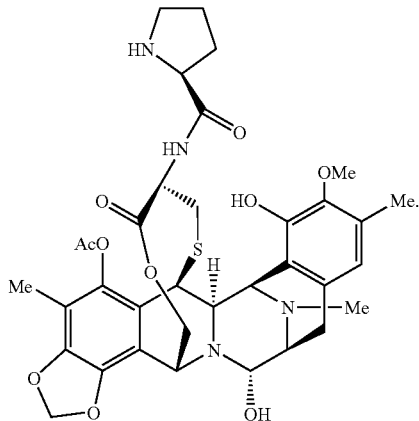

44. The compound of claim 1, wherein the compound is:

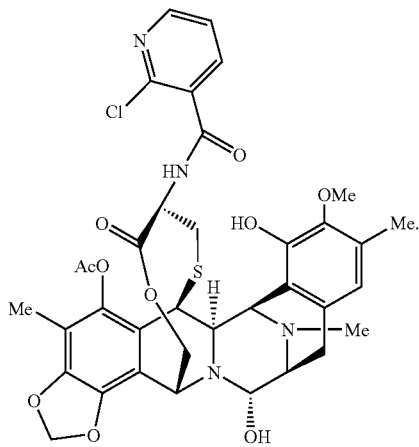

45. The compound of claim 1, wherein the compound is:

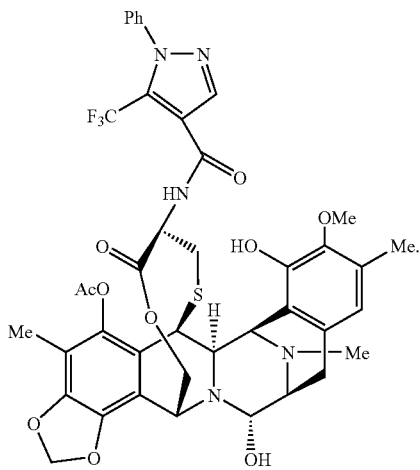

46. The compound of claim 1, wherein the compound is:

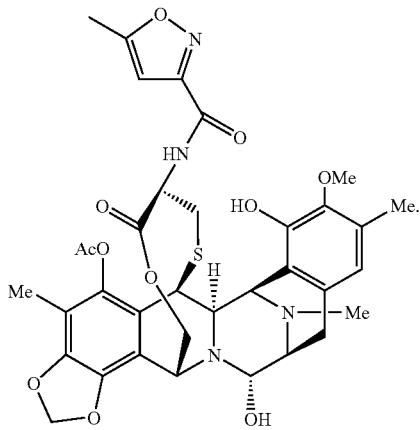

47. A pharmaceutical composition comprising a compound according to claim 1 or a pharmaceutically acceptable salt thereof, together with a pharmaceutically acceptable carrier or diluent.

* * * * *